United States Patent
Ito et al.

(10) Patent No.: US 10,580,999 B2
(45) Date of Patent: Mar. 3, 2020

(54) CONDENSED CYCLIC COMPOUND AND AN ORGANIC LIGHT-EMITTING DEVICE INCLUDING THE SAME

(71) Applicant: SAMSUNG DISPLAY CO., LTD., Yongin-si, Gyeonggi-Do (KR)

(72) Inventors: Naoyuki Ito, Yongin-si (KR); Seulong Kim, Yongin-si (KR); Younsun Kim, Yongin-si (KR); Dongwoo Shin, Yongin-si (KR); Jungsub Lee, Yongin-si (KR); Jino Lim, Yongin-si (KR)

(73) Assignee: SAMSUNG DISPLAY CO., LTD., Yongin-si, Gyeonggi-do (KR)

( * ) Notice: Subject to any disclaimer, the term of this patent is extended or adjusted under 35 U.S.C. 154(b) by 54 days.

(21) Appl. No.: 15/399,155

(22) Filed: Jan. 5, 2017

(65) Prior Publication Data
US 2017/0194571 A1    Jul. 6, 2017

(30) Foreign Application Priority Data

| Jan. 5, 2016 | (KR) | 10-2016-0001115 |
| Jan. 5, 2016 | (KR) | 10-2016-0001122 |
| Jan. 20, 2016 | (KR) | 10-2016-0006995 |
| Jan. 20, 2016 | (KR) | 10-2016-0006996 |

(51) Int. Cl.
| H01L 51/54 | (2006.01) |
| C09K 11/06 | (2006.01) |
| H01L 51/00 | (2006.01) |
| C07D 307/77 | (2006.01) |
| C09K 11/02 | (2006.01) |
| C07D 333/50 | (2006.01) |
| C07D 307/91 | (2006.01) |
| C07D 493/04 | (2006.01) |
| C07D 495/04 | (2006.01) |
| C07D 405/10 | (2006.01) |
(Continued)

(52) U.S. Cl.
CPC ........ *H01L 51/0073* (2013.01); *C07D 307/77* (2013.01); *C07D 307/91* (2013.01); *C07D 333/50* (2013.01); *C07D 405/10* (2013.01); *C07D 493/04* (2013.01); *C07D 495/04* (2013.01); *C09K 11/025* (2013.01); *C09K 11/06* (2013.01); *H01L 51/006* (2013.01); *H01L 51/0052* (2013.01); *H01L 51/0058* (2013.01); *H01L 51/0074* (2013.01); *H01L 51/5265* (2013.01); *C09K 2211/1007* (2013.01); *C09K 2211/1011* (2013.01); *C09K 2211/1014* (2013.01); *H01L 51/0054* (2013.01); *H01L 51/5012* (2013.01); *H01L 51/5016* (2013.01); *H01L 51/5056* (2013.01); *H01L 51/5072* (2013.01); *H01L 51/5206* (2013.01); *H01L 51/5221* (2013.01)

(58) Field of Classification Search
CPC .. C07D 307/77; C07D 307/91; C07D 333/50; C07D 405/00; C07D 405/10; C07D 493/00; C07D 493/04; C07D 495/00; C07D 495/02; C07D 495/04; C09K 11/025; C09K 11/06; C09K 2211/00; C09K 2211/10; C09K 2211/1011; C09K 2211/1014; C09K 2211/1007; H01L 51/0032; H01L 51/005; H01L 51/0052; H01L 51/0054; H01L 51/0058; H01L 51/006; H01L 51/0072; H01L 51/0073; H01L 51/0074; H01L 51/50; H01L 51/5012; H01L 51/5016; H01L 51/5056; H01L 51/5072
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS

| 7,839,074 B2 | 11/2010 | Ikeda et al. |
| 8,241,763 B2 | 8/2012 | Buesing et al. |
| 2006/0043858 A1 | 3/2006 | Ikeda et al. |
(Continued)

FOREIGN PATENT DOCUMENTS

| KR | 10-2008-0049770 | 6/2008 |
| KR | 10-2008-0109000 | 12/2008 |
(Continued)

OTHER PUBLICATIONS

Machine translation of KR2013-0075982 (Year: 2013).*
(Continued)

*Primary Examiner* — Andrew K Bohaty
(74) *Attorney, Agent, or Firm* — F. Chau & Associates, LLC

(57) ABSTRACT

A condensed cyclic compound represented by Formula 1 and an organic light-emitting device including the same.

[Formula 1]

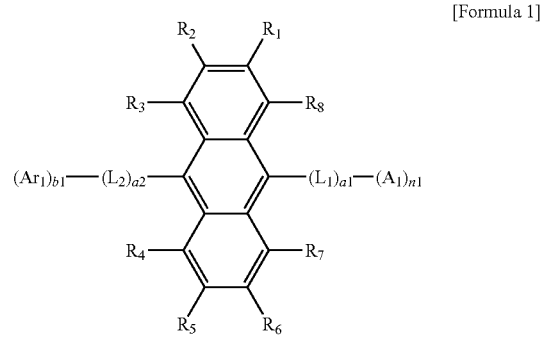

19 Claims, 4 Drawing Sheets

(51) Int. Cl.
  *H01L 51/52* (2006.01)
  *H01L 51/50* (2006.01)

(56) References Cited

U.S. PATENT DOCUMENTS

| | | |
|---|---|---|
| 2008/0193797 A1 | 8/2008 | Heil et al. |
| 2009/0261717 A1 | 10/2009 | Buesing et al. |
| 2010/0032658 A1 | 2/2010 | Lee et al. |
| 2011/0156016 A1 | 6/2011 | Kawamura et al. |
| 2012/0138914 A1* | 6/2012 | Kawamura .......... C07D 307/79 257/40 |
| 2013/0069523 A1 | 3/2013 | Matsuura et al. |
| 2014/0332793 A1 | 11/2014 | Park et al. |
| 2015/0372237 A1 | 12/2015 | Kawamura et al. |

FOREIGN PATENT DOCUMENTS

| | | |
|---|---|---|
| KR | 10-2009-0065201 | 6/2009 |
| KR | 10-2010-0007780 | 1/2010 |
| KR | 10-2011-0043625 | 4/2011 |
| KR | 10-2011-0047278 | 5/2011 |
| KR | 10-2012-0003692 | 1/2012 |
| KR | 10-2012-0038402 | 4/2012 |
| KR | 10-2013-0075982 | 7/2013 |
| KR | 20130075982 A * | 7/2013 |
| KR | 10-2014-0049186 | 4/2014 |
| KR | 10-2015-0128583 | 11/2015 |
| WO | 2010137285 | 12/2010 |
| WO | 2014061963 | 4/2014 |

OTHER PUBLICATIONS

Office Action for U.S. Appl. No. 15/399,255 dated Apr. 18, 2018 in related application.
Notice of Allowance issued in corresponding U.S. Appl. No. 15/399,255 dated Sep. 18, 2019.
Office Action issued in corresponding U.S. Appl. No. 15/399,414 dated May 2, 2019.
Office Action issued in corresponding U.S. Appl No. 15/399,414 dated Sep. 26, 2019.
Office Action issued in corresponding U.S. Appl. No. 16/399,349 dated Sep. 25, 2019.

* cited by examiner

| 190 |
|---|
| 150 |
| 110 |

| 190 |
|---|
| 150 |
| 110 |
| 210 |

| 220 |
|---|
| 190 |
| 150 |
| 110 |

| 220 |
|-----|
| 190 |
| 150 |
| 110 |
| 210 |

CONDENSED CYCLIC COMPOUND AND AN ORGANIC LIGHT-EMITTING DEVICE INCLUDING THE SAME

CROSS-REFERENCE TO RELATED APPLICATION

This application claims the benefit of Korean Patent Application Nos.: 10-2016-0006996, filed on Jan. 20, 2016; 10-2016-0001122, filed on Jan. 5, 2016; 10-2016-0001115, filed on Jan. 5, 2016; 10-2016-0006995, filed on Jan. 20, 2016 in the Korean Intellectual Property Office. The above-referenced disclosures are incorporated by reference herein.

TECHNICAL FIELD

Exemplary embodiments of the present invention relate to a condensed cyclic compound, and more particularly to an organic light-emitting device including the same.

DISCUSSION OF RELATED ART

Organic light-emitting devices may be self-emission devices. Organic light-emitting devices may produce full-color images. Organic light-emitting devices may have relatively wide viewing angles, relatively high contrast ratios, and relatively short response times, and increased brightness, driving voltage, and response speed characteristics.

Organic light-emitting devices may include a first electrode disposed on a substrate. Organic light-emitting devices may include a hole transport region, an emission layer, an electron transport region, and a second electrode sequentially disposed on the first electrode. Holes provided from the first electrode may move toward the emission layer through the hole transport region. Electrons provided from the second electrode may move toward the emission layer through the electron transport region. Carriers, such as holes and electrons, may recombine in the emission layer to produce excitons. The excitons may transition from an excited state to a ground state, thus generating light.

SUMMARY

One or more exemplary embodiments of the present invention may include a condensed cyclic compound and an organic light-emitting device including the same.

According to an exemplary embodiment of the present invention, a condensed cyclic compound is represented by Formula 1:

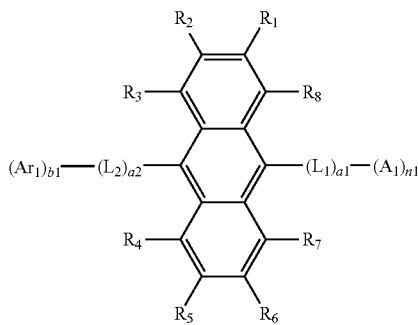

<Formula 1>

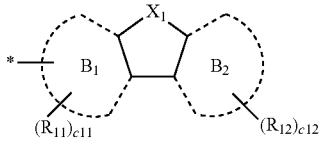

<Formula 1-1>

In Formulae 1 and 1-1, $A_1$ is selected from groups represented by Formula 1-1, n1 is an integer selected from 1 to 5, $X_1$ is selected from oxygen (O) and sulfur (S), ring $B_1$ and ring $B_2$ are each independently selected from a $C_7$-$C_{60}$ aromatic ring and a $C_1$-$C_{60}$ heteroaromatic ring, $L_1$ and $L_2$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$heteroarylene group, a substituted or unsubstituted divalent non-aromatic condensed polycyclic group, and a substituted or unsubstituted divalent non-aromatic condensed heteropolycyclic group, a1 is an integer selected from 1 to 3, a2 is an integer selected from 0 to 3, $Ar_1$ is selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, b1 is be an integer selected from 1 to 5,

* indicates a binding site to a neighboring atom, $R_1$ to $R_8$, $R_{11}$, and $R_{12}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), c11 is an integer selected from 0 to 7, c12 is an integer selected from 0 to 8, at least one substituent selected from the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$), a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$), and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_6$-$C_{60}$ aryl group substituted with a $C_6$-$C_{60}$ aryl group, a terphenyl group, a $C_1$-$C_{60}$ heteroaryl group, a $C_1$-$C_{60}$ heteroaryl group substituted with a $C_1$-$C_{60}$ alkyl group, a $C_1$-$C_{60}$ heteroaryl group substituted with a $C_6$-$C_{60}$ aryl group, a monovalent non-aromatic condensed polycyclic group, and a monovalent non-aromatic condensed heteropolycyclic group.

According to an exemplary embodiment of the present invention, an organic light-emitting device includes a first electrode; a second electrode facing the first electrode; and an organic layer disposed between the first electrode and the second electrode. The organic layer includes an emission layer. The organic layer includes at least one of the condensed cyclic compounds represented by Formula 1.

BRIEF DESCRIPTION OF THE DRAWINGS

The above and other features of the present invention will become more apparent by describing in detail exemplary embodiments thereof, with reference to the accompanying drawings, in which:

FIG. 1 is a schematic cross-sectional diagram illustrating an organic light-emitting device according to an exemplary embodiment of the present invention;

FIG. 2 is a schematic cross-sectional diagram illustrating an organic light-emitting device according to an exemplary embodiment of the present invention;

FIG. 3 is a schematic cross-sectional diagram illustrating an organic light-emitting device according to an exemplary embodiment of the present invention; and FIG. 4 is a schematic cross-sectional diagram illustrating an organic light-emitting device according to an exemplary embodiment of the present invention.

DETAILED DESCRIPTION OF THE EMBODIMENTS

A condensed cyclic compound according to an exemplary embodiment of the present invention may be represented by Formula 1:

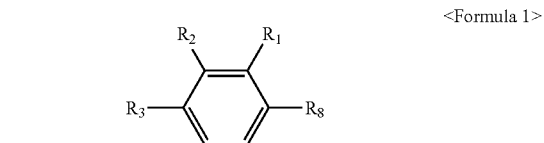

<Formula 1>

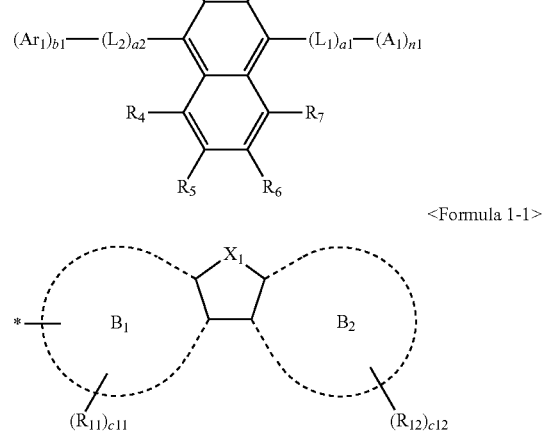

<Formula 1-1>

In Formula 1, $A_1$ may be selected from groups represented by Formula 1-1.

n1 in Formula 1 may be an integer selected from 1 to 5. n1 may indicate the number of $A_1(s)$. When n1 is 2 or greater, at least $A_1(s)$ may be the same as or different from each other. According to an exemplary embodiment of the present invention, n1 may be 1 or 2. According to an exemplary embodiment of the present invention, n1 may be 1. However, exemplary embodiments of the present invention are not limited thereto.

In Formula 1-1, ring $B_1$ and ring $B_2$ may each independently be a $C_7$-$C_{60}$aromtic ring or a $C_1$-$C_{60}$heteroaromatic ring.

According to an exemplary embodiment of the present invention, ring $B_1$ and ring $B_2$ in Formula 1-1 may each independently be selected from a naphthalene group, a heptalene group, a phenalene group, a phenanthrene group, an anthracene group, a triphenylene group, a pyrene group, a chrysene group, a naphthacene group, a picene group, a perylene group, a pentaphene group, a quinoline group, an isoquinoline group, a quinoxaline group, a quinazoline group, a cinnoline group, a naphthyridine group, an acridine group, and a phenanthroline group.

According to an exemplary embodiment of the present invention, ring $B_1$ and ring $B_2$ may each independently be selected from a naphthalene group and a phenanthrene group.

In Formula 1-1, $X_1$ may be selected from oxygen (O) and sulfur (S).

In Formula 1, $A_1$ may be selected from groups represented by Formulae 1-1(1) to 1-1(20):

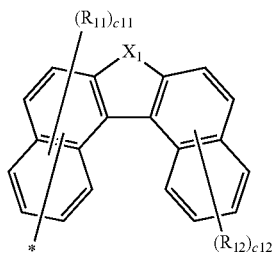

Formula 1-1(1)

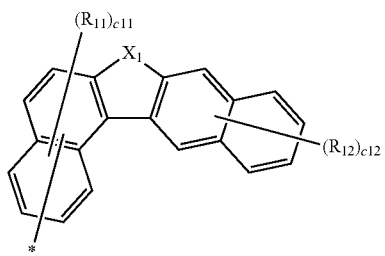

Formula 1-1(2)

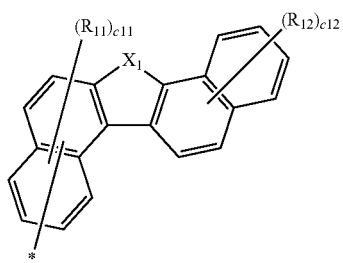

Formula 1-1(3)

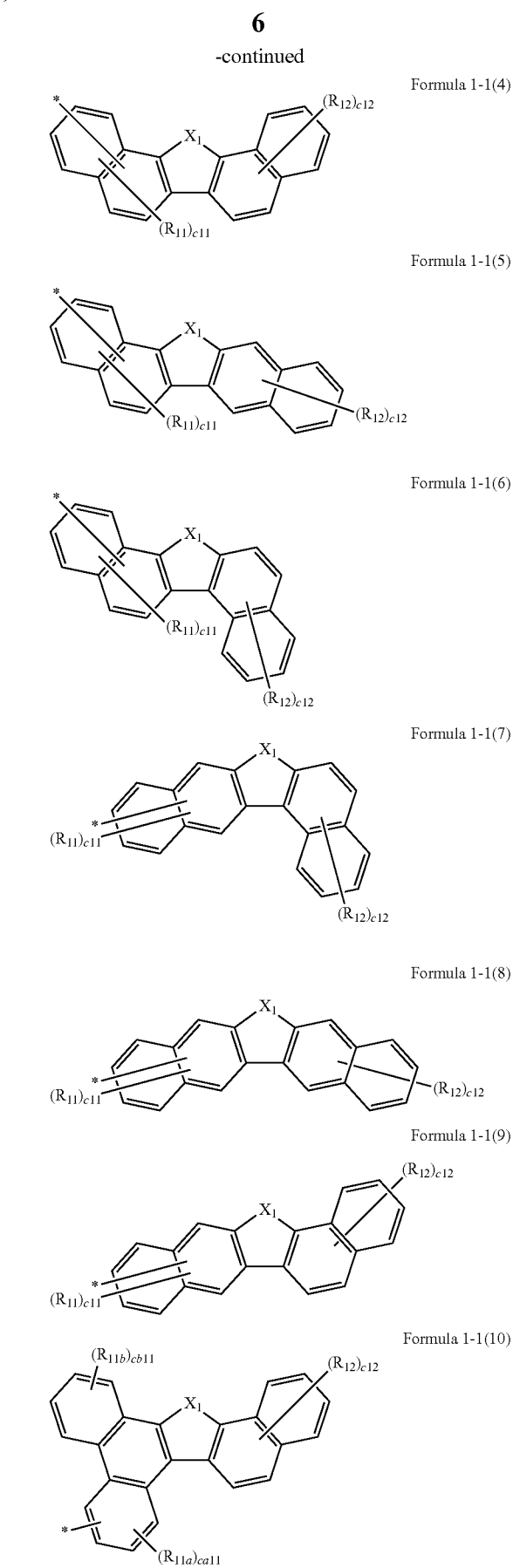

Formula 1-1(11)
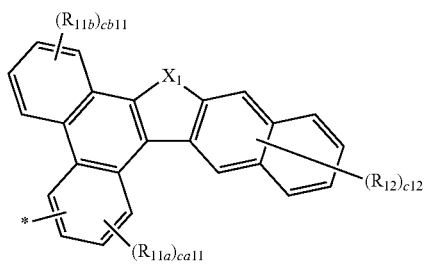
Formula 1-1(12)
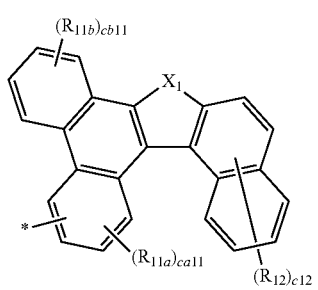
Formula 1-1(13)
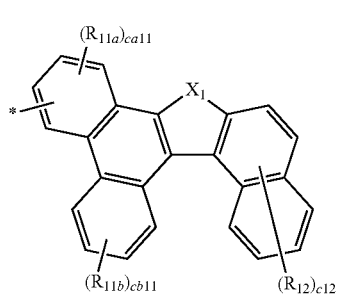
Formula 1-1(14)
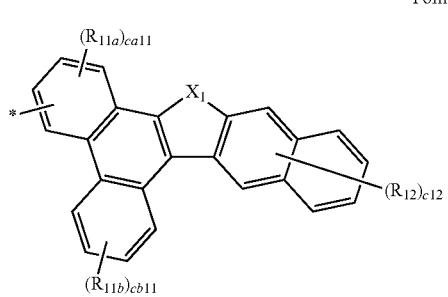
Formula 1-1(15)
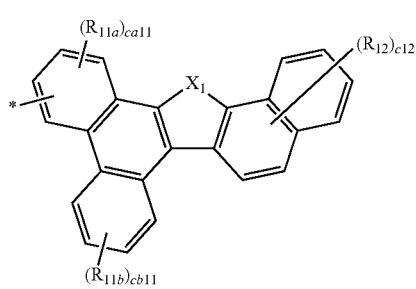
Formula 1-1(16)
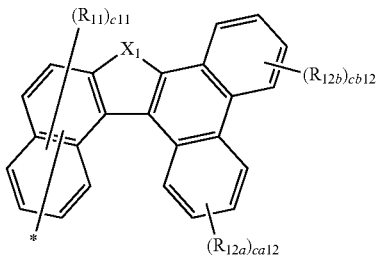
Formula 1-1(17)
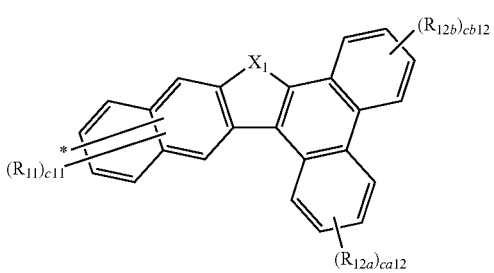
Formula 1-1(18)
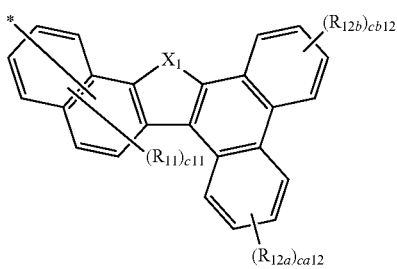
Formula 1-1(19)
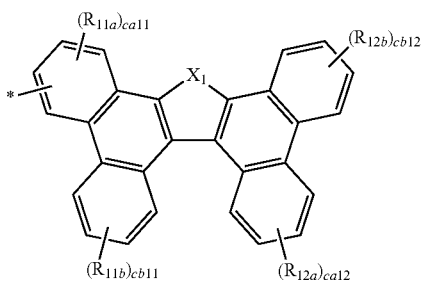
Formula 1-1(20)
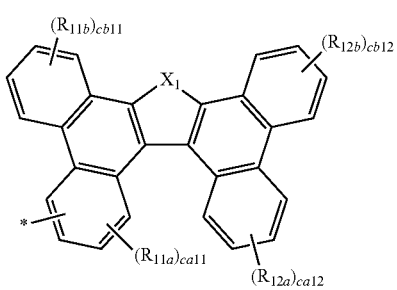
In Formulae 1-1(1) to 1-1(20), $X_1$, $R_{11}$, R12, c11, c12, and * may each independently be the same as defined herein, $R_{11a}$ and $R_{11b}$ may each independently be the same as defined herein with respect to $R_{11}$, $R_{12a}$ and $R_{12b}$ may each independently be the same as defined herein with respect to with $R_{12}$, ca11 may be an integer selected from 0 to 3, and ca12, cb11, and cb12 may each independently be an integer selected from 0 to 4.

In Formula 1, $L_1$ and $L_2$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

For example, $L_1$ and $L_2$ in Formula 1 may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si$(Q_{31})(Q_{32})(Q_{33})$.

$Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

According to an exemplary embodiment of the present invention, $L_1$ and $L_2$ may each independently be selected from groups represented by Formulae 3-1 to 3-41:

Formula 3-1

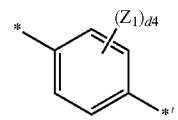

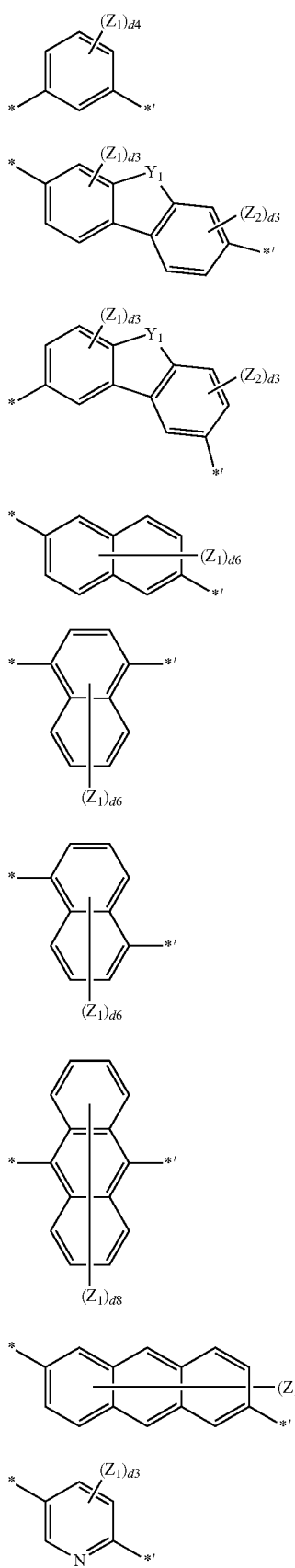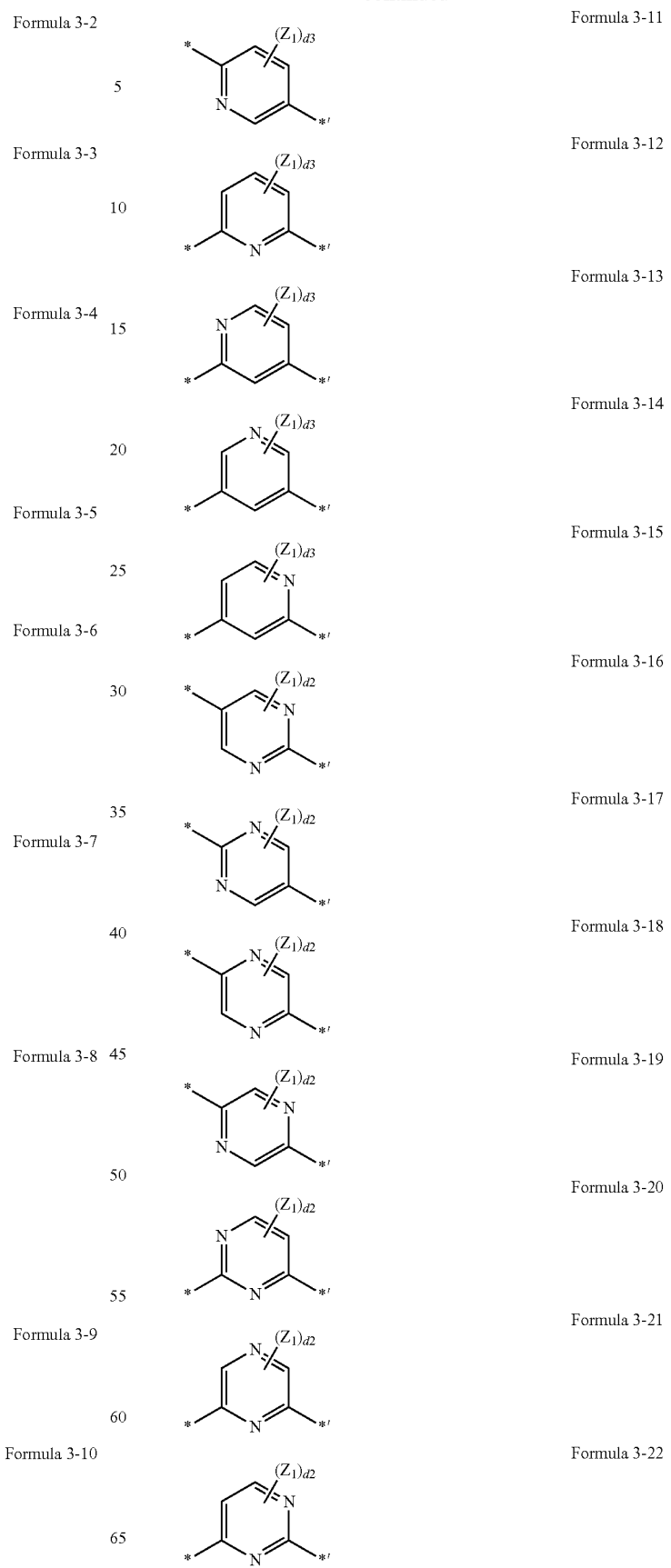

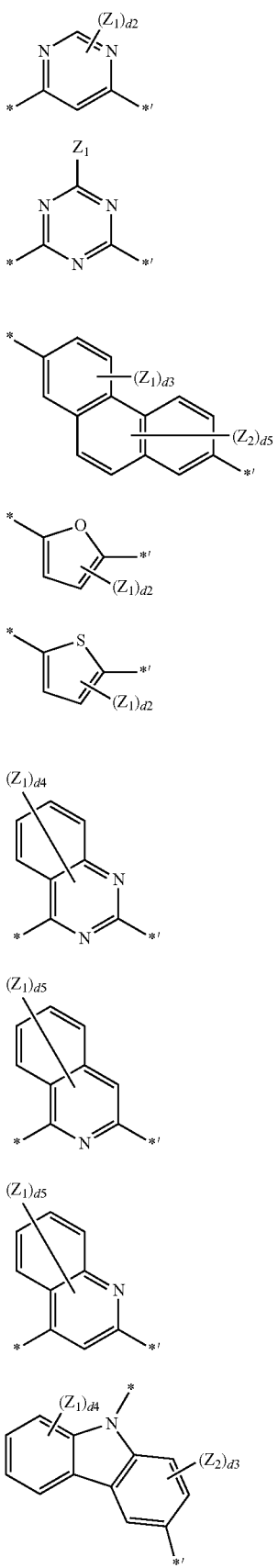
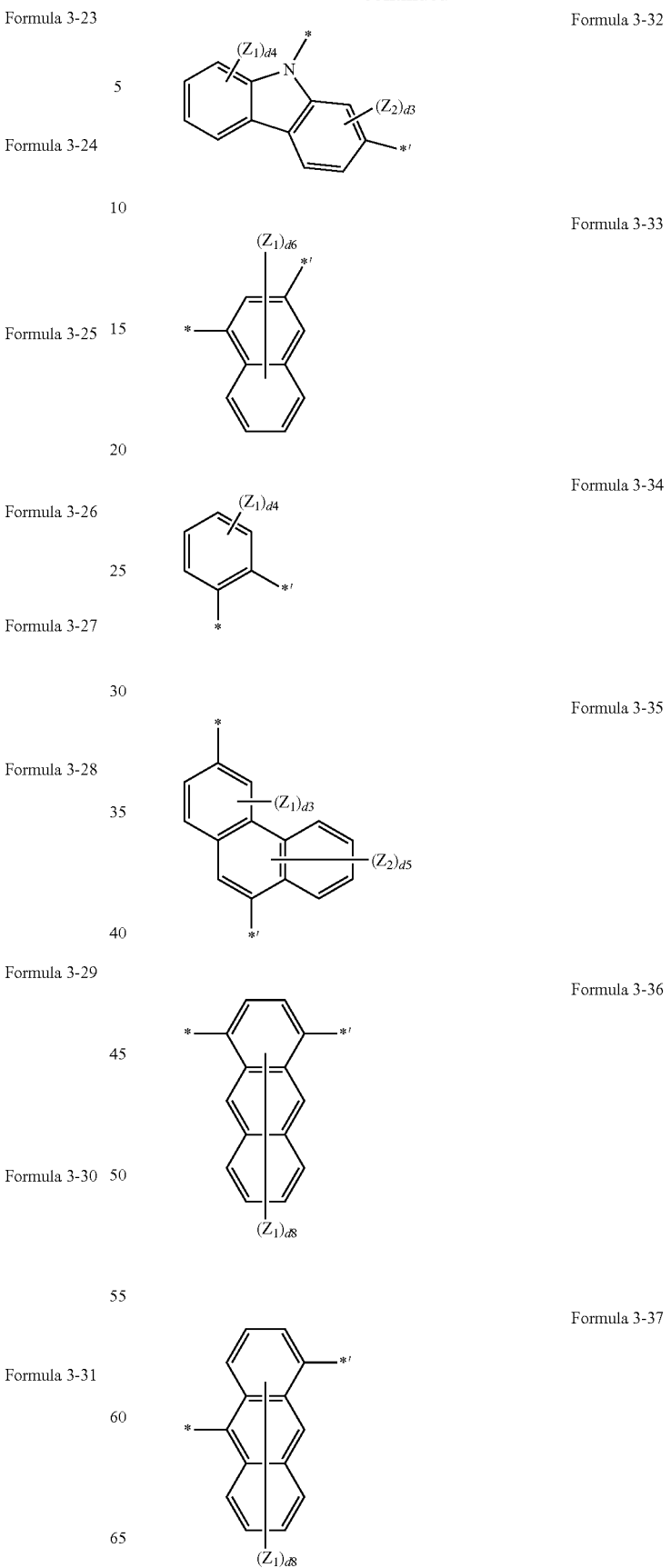
Formula 3-23
Formula 3-24
Formula 3-25
Formula 3-26
Formula 3-27
Formula 3-28
Formula 3-29
Formula 3-30
Formula 3-31
Formula 3-32
Formula 3-33
Formula 3-34
Formula 3-35
Formula 3-36
Formula 3-37

-continued

Formula 3-38
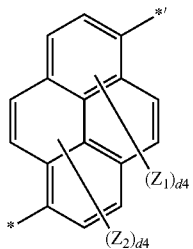

Formula 3-39
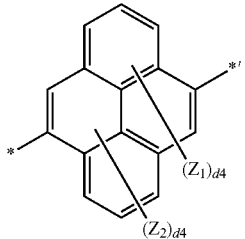

Formua 3-40
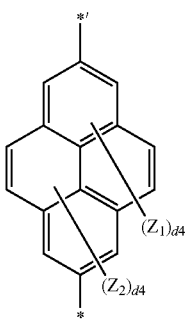

Formula 3-41
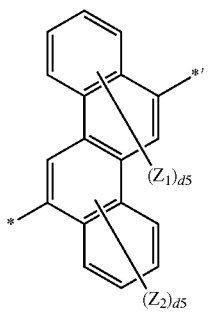

In Formulae 3-1 to 3-41,
$Y_1$ may be O, S, $C(Z_3)(Z_4)$, $N(Z_5)$, or $Si(Z_6)(Z_7)$,
$Z_1$ to $Z_7$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a dibenzofuranyl group, a dibenzothiophenyl group, a triazinyl group, a benzimidazolyl group, a phenanthrolinyl group, and —Si$(Q_{31})(Q_{32})(Q_{33})$,
$Q_{31}$ to $Q_{33}$ may each independently be selected from a $C_1$-$C_{10}$ alkyl group, a alkoxy group, a phenyl group, a biphenyl group, a terphenyl group, and a naphthyl group, d2 may be an integer selected from 1 and 2,
d3 may be an integer selected from 1 to 3,
d4 may be an integer selected from 1 to 4,
d5 may be an integer selected from 1 to 5,
d6 may be an integer selected from 1 to 6,
d8 may be an integer selected from 1 to 8, and
\* and \*' may each independently indicate a binding site to a neighboring atom.

According to an exemplary embodiment of the present invention, $L_1$ and $L_2$ may each independently be selected from groups represented by Formulae 4-1 to 4-35:

Formula 4-1
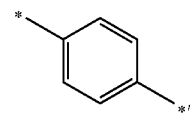

Formula 4-2
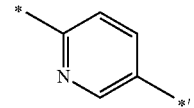

Formula 4-3
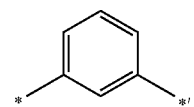

Formula 4-4
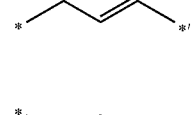

Formula 4-5
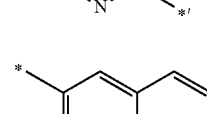

Formula 4-6
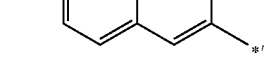

Formula 4-7
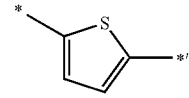

Formula 4-8
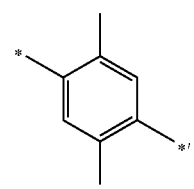

Formula 4-9

Formula 4-10

Formula 4-11

Formula 4-12

Formula 4-13

Formula 4-14

Formula 4-15

Formula 4-16

Formula 4-17

Formula 4-18

Formula 4-19

Formula 4-20

Formula 4-21

Formula 4-22

Formula 4-23

Formula 4-24

-continued

Formula 4-25

Formula 4-26

Formula 4-27

Formula 4-28

Formula 4-29

Formula 4-30

Formula 4-31

Formula 4-32

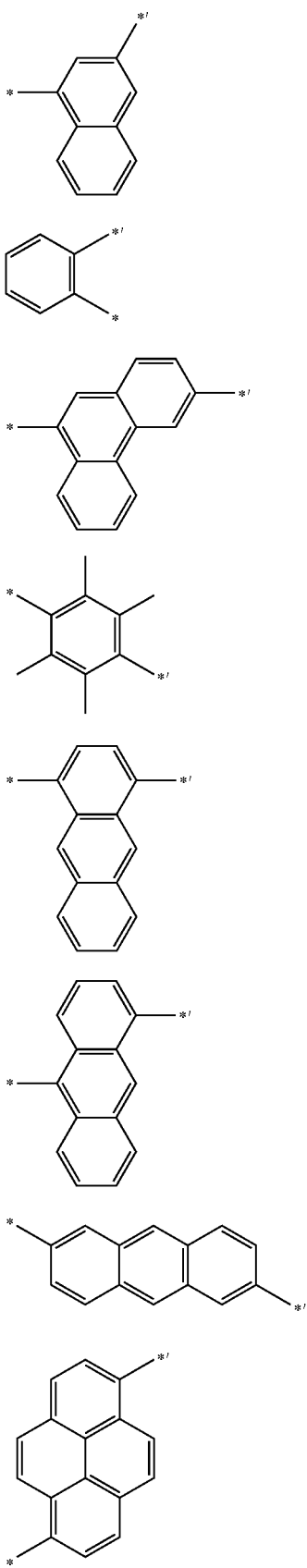

-continued

Formula 4-33

Formula 4-34

Formula 4-35

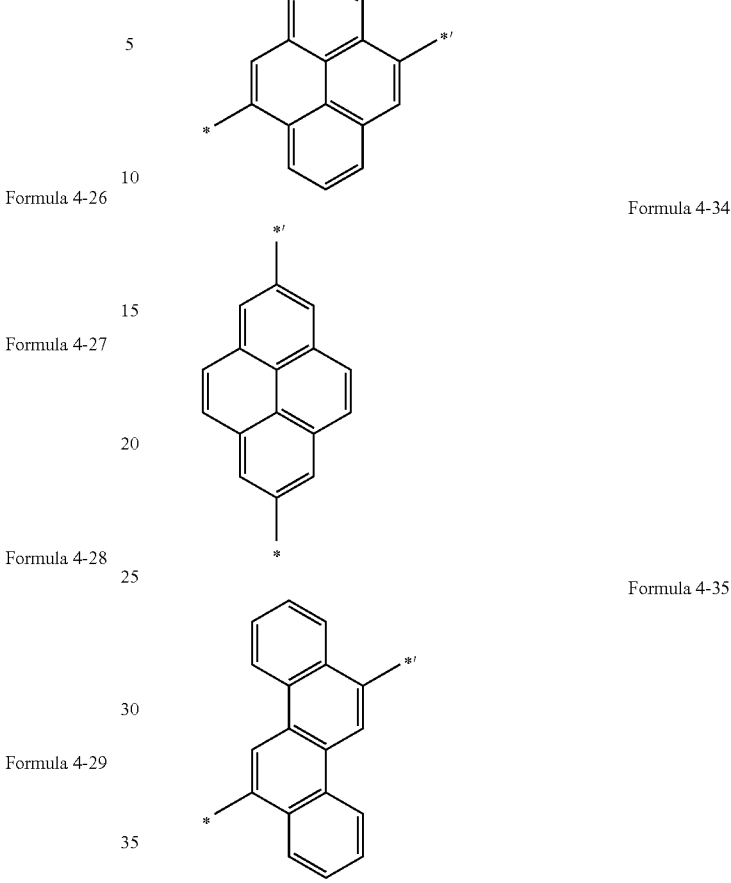

In Formulae 4-1 to 4-35, * and *' may each independently indicate a binding site to a neighboring atom.

In Formula 1, a1 may be an integer selected from 1 to 3, and a2 may be an integer selected from 0 to 3. a1 may indicate the number of $L_1$(s). When a1 is 2 or greater, at least two $L_1$(s) may be the same as or different from each other. a2 may be the same as a1 and the structures of Formulae 1 and 2.

According to an exemplary embodiment of the present invention, in Formula 1, a1 may be an integer selected from 1 and 2. According to an exemplary embodiment of the present invention, a1 may be 1. According to an exemplary embodiment of the present invention, in Formula 1, a2 may be an integer selected from 0 and 1; however, exemplary embodiments of the present invention are not limited thereto.

In Formula 1, $Ar_1$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, $Ar_1$ in Formula 1 may be selected from:
a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, a benzothiazolyl group, an isobenzothiazolyl group, a benzoxazolyl group, an isobenzoxazolyl group, a triazolyl group, a tetrazolyl group, an oxadiazolyl group, a triazinyl group, a benzocarbazolyl group, a dibenzocarbazolyl group, a thiadiazolyl group, an imidazopyridinyl group, and an imidazopyrimidinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, a benzothiazolyl group, an isobenzothiazolyl group, a benzoxazolyl group, an isobenzoxazolyl group, a triazolyl group, a tetrazolyl group, an oxadiazolyl group, a triazinyl group, a benzocarbazolyl group, a dibenzocarbazolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$).

$Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

According to an exemplary embodiment of the present invention, $Ar_1$ may be selected from groups represented by Formulae 5-1 to 5-79:

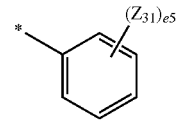

Formula 5-1

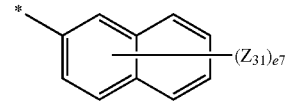

Formula 5-2

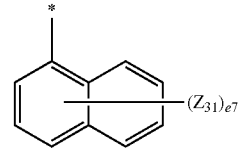

Formula 5-3

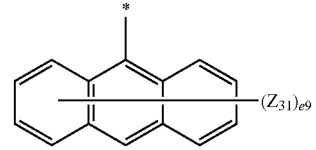

Formula 5-4

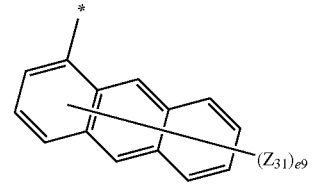

Formula 5-5

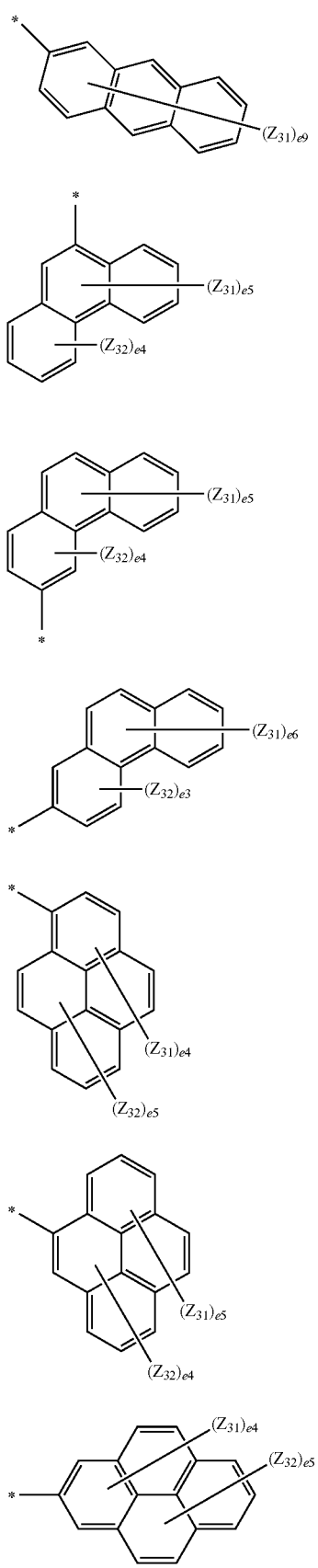
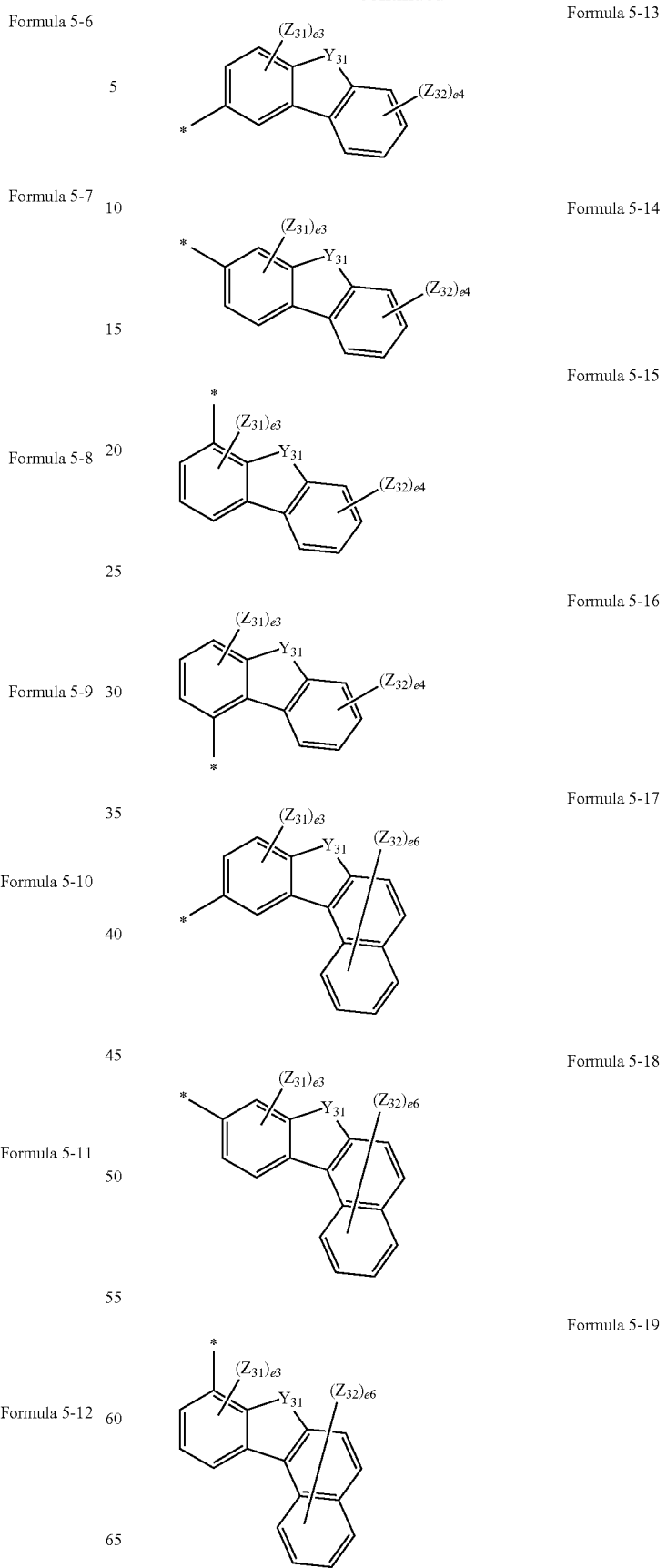

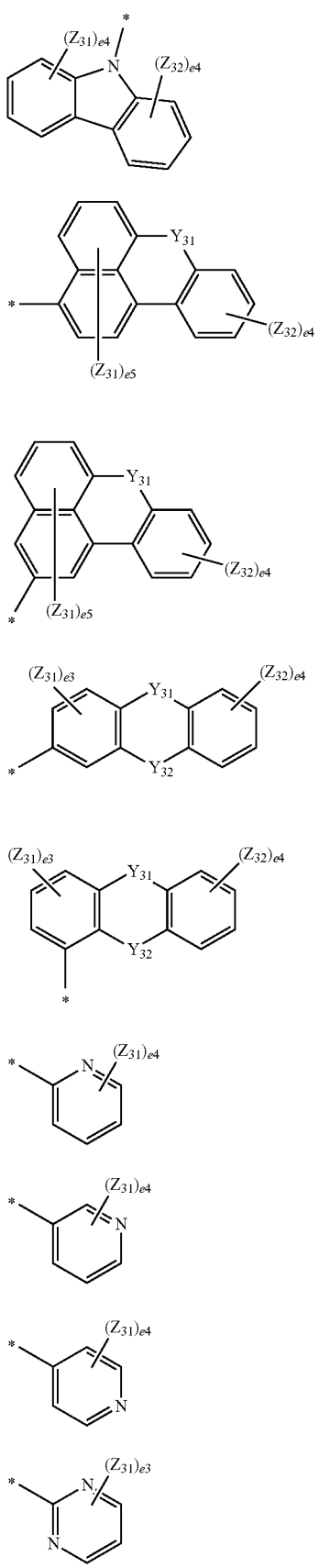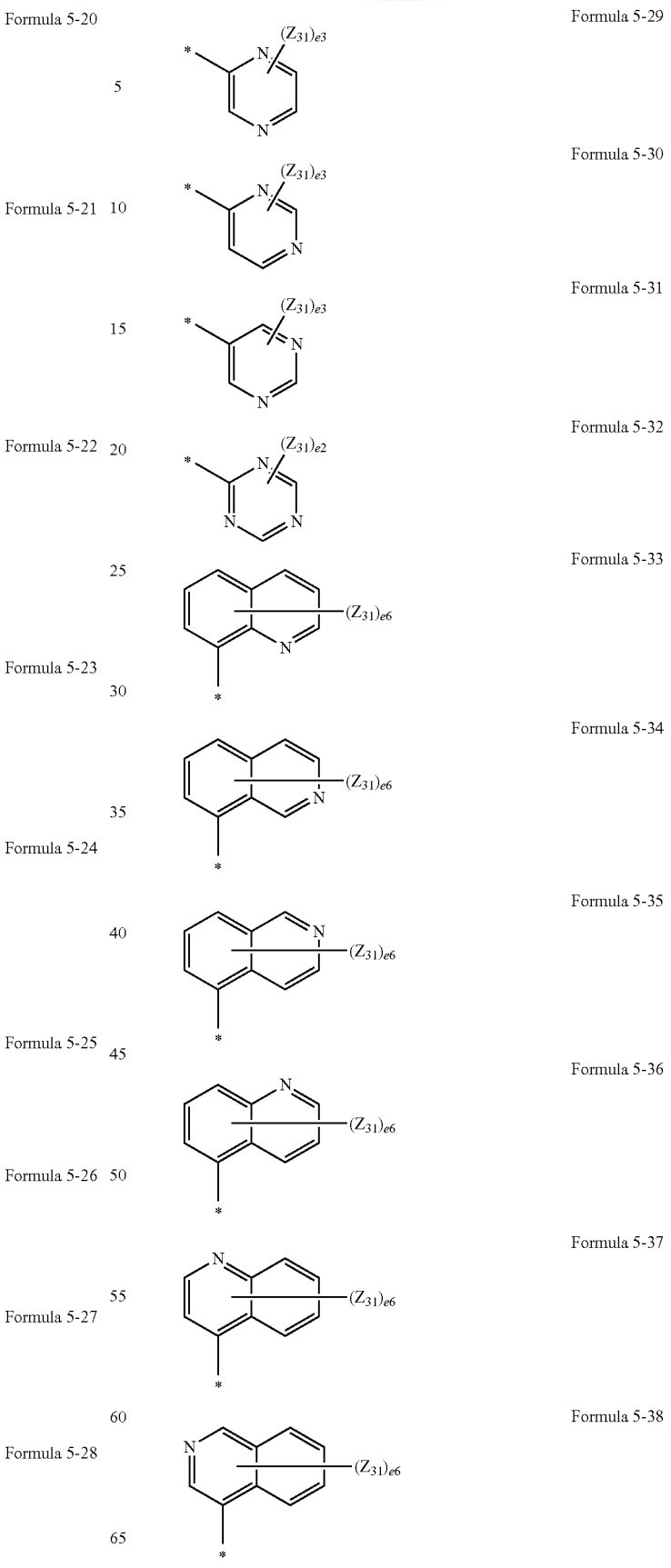

Formula 5-39
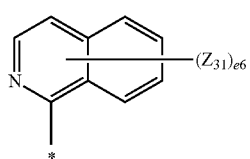
Formula 5-40
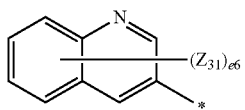
Formula 5-41
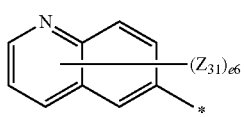
Formula 5-42
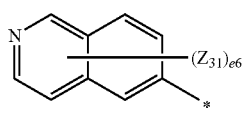
Formula 5-43
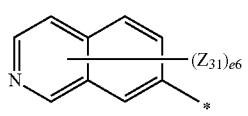
Formula 5-44
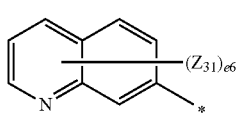
Formula 5-45
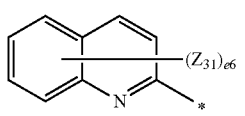
Formula 5-46
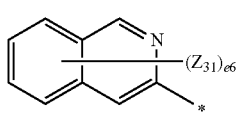
Formula 5-47
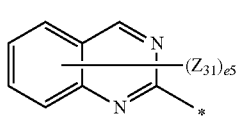
Formula 5-48
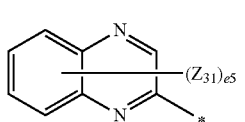
Formula 5-49
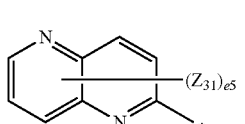
Formula 5-50
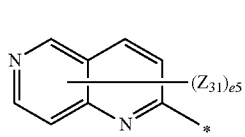
Formula 5-51
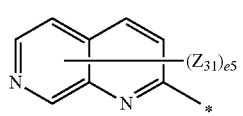
Formula 5-52
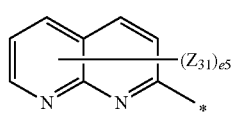
Formula 5-53
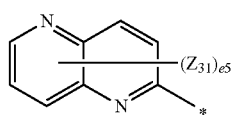
Formula 5-54
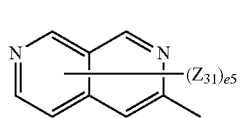
Formula 5-55
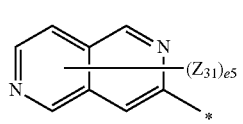
Formula 5-56
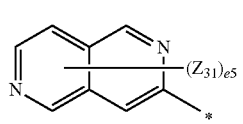
Formula 5-57
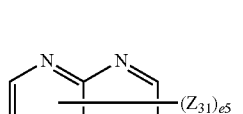
Formula 5-58
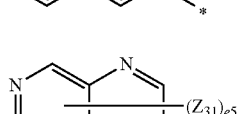
Formula 5-59
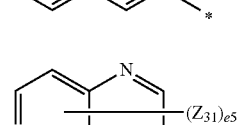
Formula 5-60
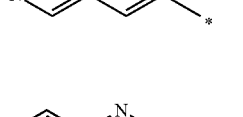
Formula 5-61
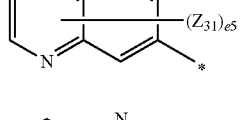
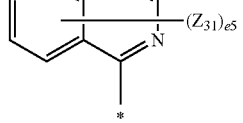

-continued

Formula 5-62
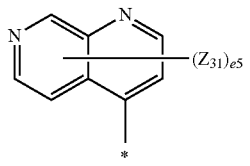

Formula 5-63
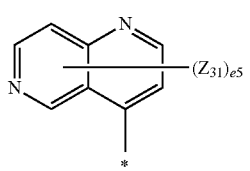

Formula 5-64
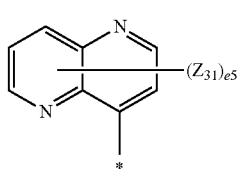

Formula 5-65

Formula 5-66

Formula 5-67
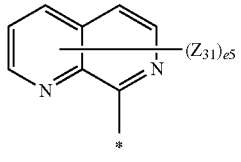

Formula 5-68
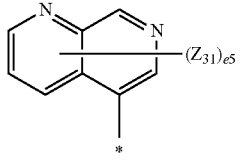

Formula 5-69
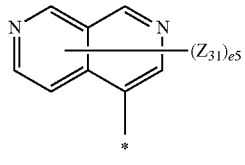

Formula 5-70
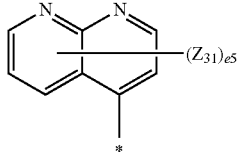

-continued

Formula 5-71
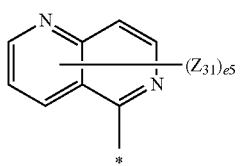

Formula 5-72
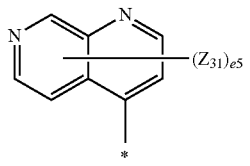

Formula 5-73
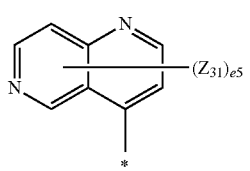

Formula 5-74
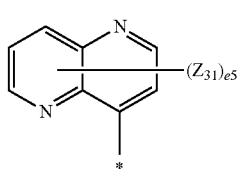

Formula 5-75
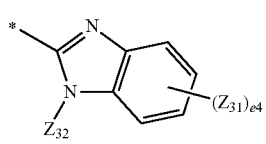

Formula 5-76
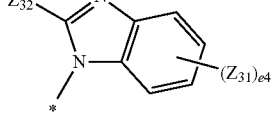

Formula 5-77
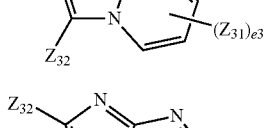

Formula 5-78
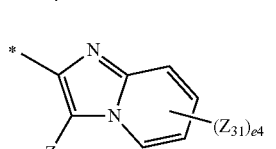

Formula 5-79
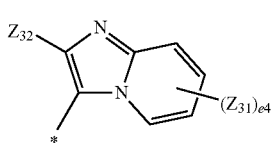

In Formulae 5-1 to 5-79, $Y_{31}$ and $Y_{32}$ may each independently be O, S, $C(Z_{33})(Z_{34})$, $N(Z_{35})$, or $Si(Z_{36})(Z_{37})$, $Z_{31}$ to $Z_{37}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a dibenzofuranyl group, a dibenzothiophenyl group, a benzimidazolyl group, a phenanthrolinyl group, a triazinyl group, and —Si($Q_{31}$)($Q_{32}$)($Q_{33}$), $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, e2 may be an integer selected from 1 and 2,
e3 may be an integer selected from 1 to 3,
e4 may be an integer selected from 1 to 4,
e5 may be an integer selected from 1 to 5,
e6 may be an integer selected from 1 to 6,
e8 may be an integer selected from 1 to 8, and
* may indicate a binding site to a neighboring atom.

According to an exemplary embodiment of the present invention, $Ar_1$ may be selected from groups represented by Formulae 6-1 to 6-44:

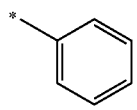
Formula 6-1

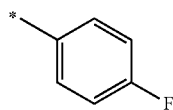
Formula 6-2

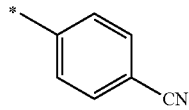
Formula 6-3

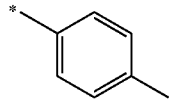
Formula 6-4

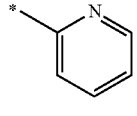
Formula 6-5

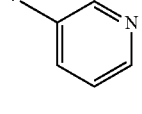
Formula 6-6

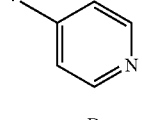
Formula 6-7

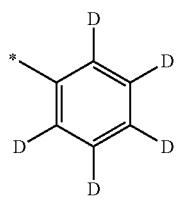
Formula 6-8

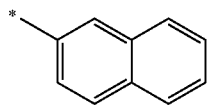
Formula 6-9

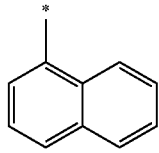
Formula 6-10

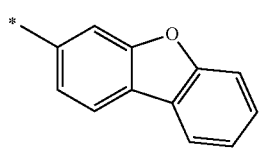
Formula 6-11

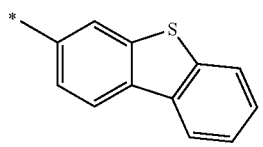
Formula 6-12

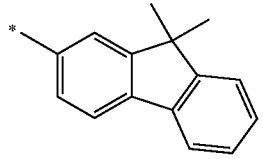
Formula 6-13

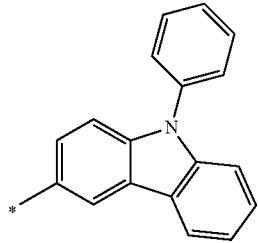
Formula 6-14

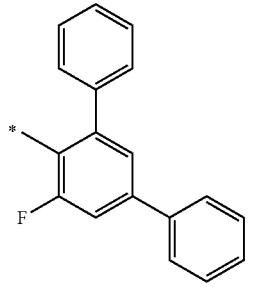
Formula 6-15

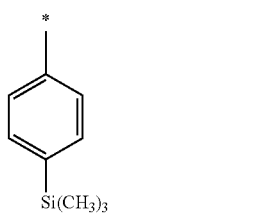
Formula 6-16

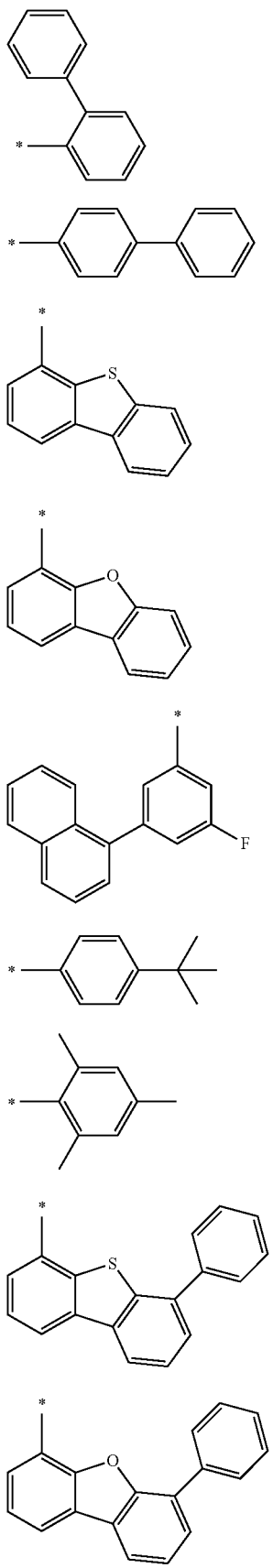
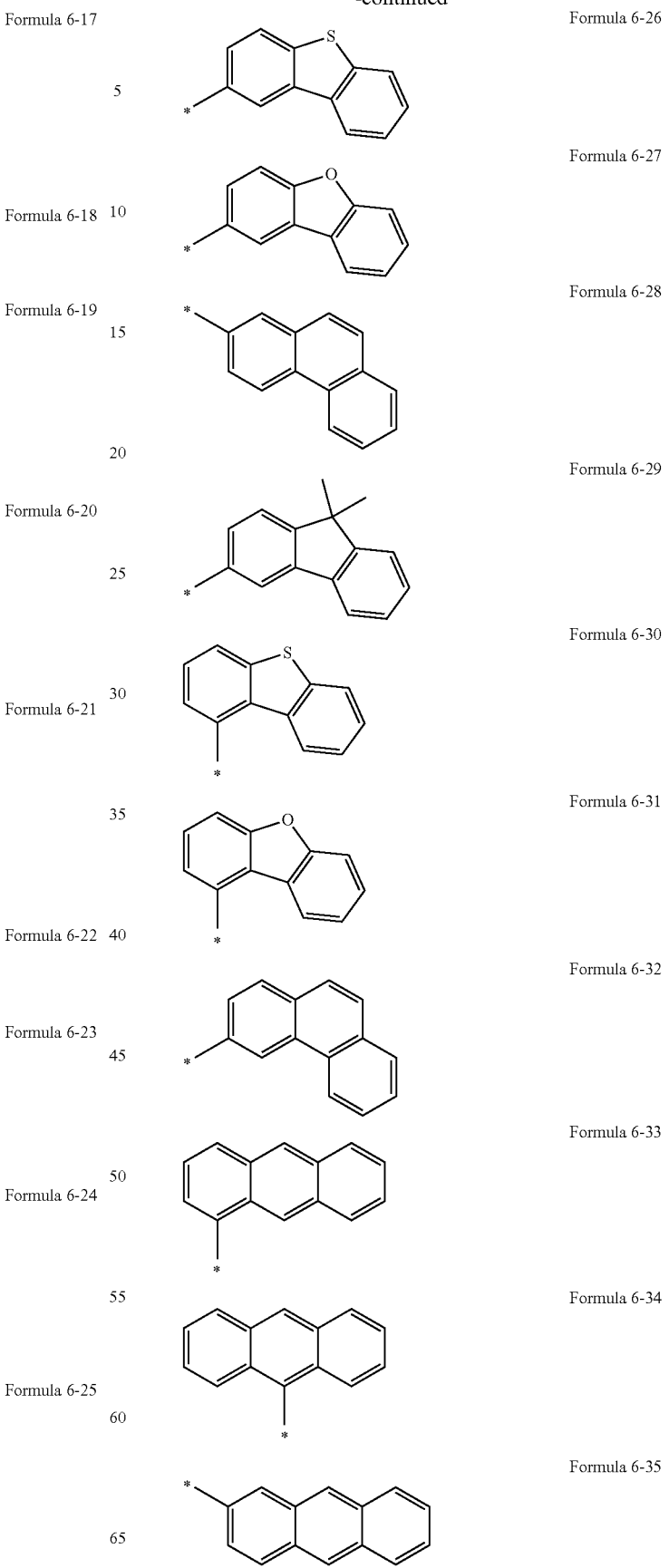

-continued

Formula 6-36
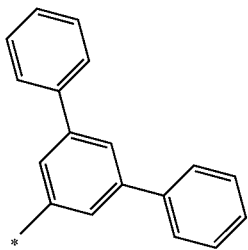

Formula 6-37
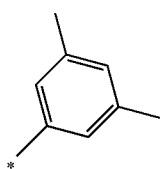

Formula 6-38
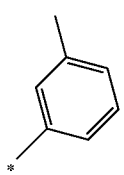

Formula 6-39
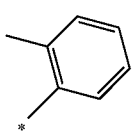

Formula 6-40
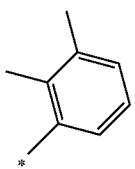

Formula 6-41
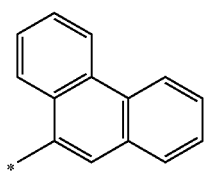

Formula 6-42
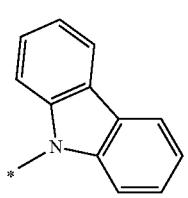

Formula 6-43
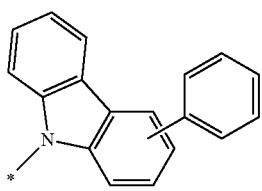

Formula 6-44
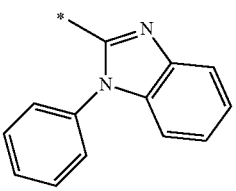

In Formulae 6-1 to 6-44, * may indicate a binding site to a neighboring atom.

In Formula 1, b1 may be an integer selected from 1 to 5. b1 may indicate the number of $Ar_1$(s). When b1 is 2 or greater, at least two $Ar_1$ (s) may be the same as or different from each other. According to an exemplary embodiment of the present invention, b1 may be 1 or 2. According to an exemplary embodiment of the present invention, b1 may be 1. However, exemplary embodiments of the present invention are not limited thereto.

In Formulae 1 and 2, $R_1$ to $R_8$, $R_{11}$, and $R_{12}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$).

According to an exemplary embodiment of the present invention, $R_1$ to $R_8$, $R_{11}$, and $R_{12}$ in Formulae 1 and 2 may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$).

According to an exemplary embodiment of the present invention, $R_1$ to $R_8$, $R_{11}$, and $R_{12}$ in Formulae 1 and 2 may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, and a hydrazono group;

a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, or an imidazopyrimidinyl group;

a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, an imidazopyrimidinyl group, and —Si($Q_{31}$)($Q_{32}$)($Q_{33}$), and —Si($Q_1$)($Q_2$)($Q_3$).

$Q_1$ to $Q_3$ and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

According to an exemplary embodiment of the present invention, $R_1$ to $R_8$, $R_{11}$, and $R_{12}$ in Formula 1 may each independently be selected from hydrogen, deuterium, —F, —Cl, —Br, —I, a hydroxyl group, a cyano group, a nitro group, an amidino group, a hydrazino group, a hydrazono group, a $C_1$-$C_{10}$ alkyl group, and a $C_1$-$C_{10}$ alkoxy group;

a $C_1$-$C_{10}$ alkyl group and a $C_1$-$C_{10}$ alkoxy group, each substituted with at least one selected from deuterium, —F, —Cl, —Br, —I, a hydroxyl group, a cyano group, a nitro group, an amidino group, a hydrazino group, and a hydrazono group;

a phenyl group, a biphenyl group, a terphenyl group, a naphthyl group, a pyridinyl group, a pyrimidinyl group, and a triazinyl group; and a phenyl group, a naphthyl group, a pyridinyl group, a pyrimidinyl group, and a triazinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, and a triazinyl group.

In Formula 1-1, c11 may be an integer selected from 0 to 7, and c12 may be an integer selected from 0 to 8. c11 may indicate the number of $R_{11}$(s). When c11 is 2 or greater, at least two $R_{11}$(s) may be the same as or different from each other. C12 may be the same as c11 and the structures of Formula 1.

According to an exemplary embodiment of the present invention, c11 and c12 in Formula 1-1 may each independently be an integer selected from 1 and 2. According to an exemplary embodiment of the present invention, c11 and c12 in Formula 1-1 may each independently be 1. However, exemplary embodiments of the present invention are not limited thereto.

According to an exemplary embodiment of the present invention, the condensed cyclic compound represented by Formula 1 may be represented by at least one of Formulae 1A to 1T:

<Formula 1A>

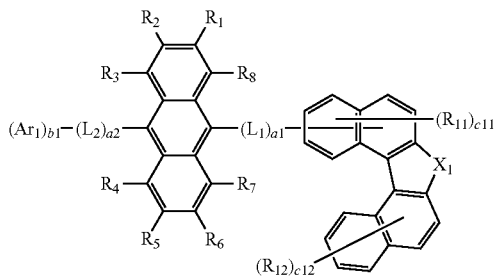

<Formula 1B>

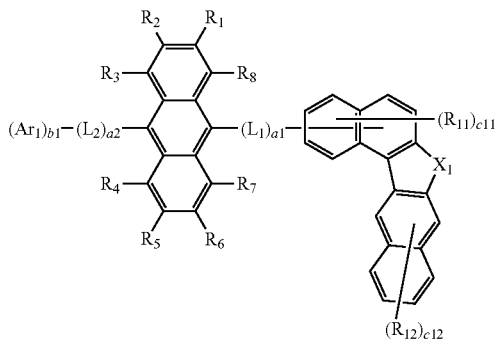

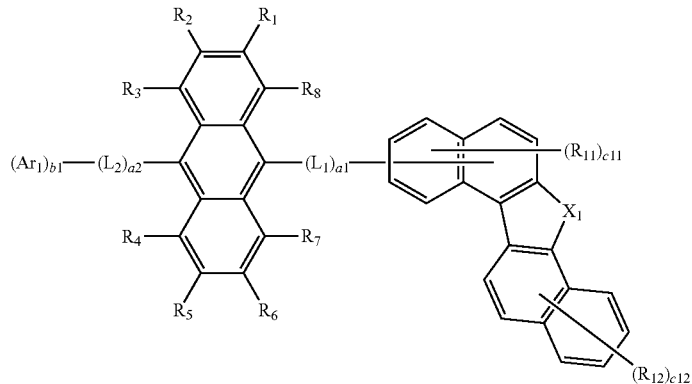
<Formula 1C>
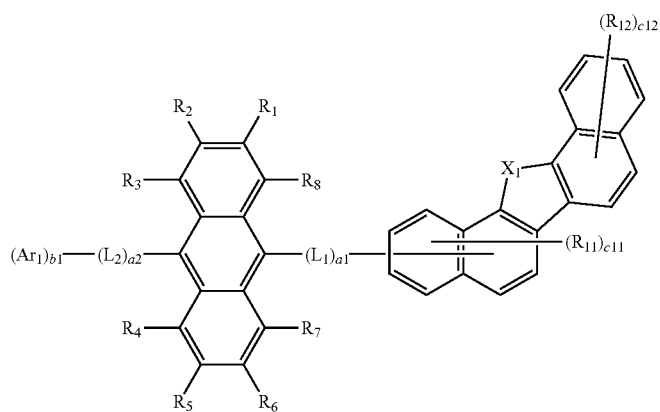
<Formula 1D>
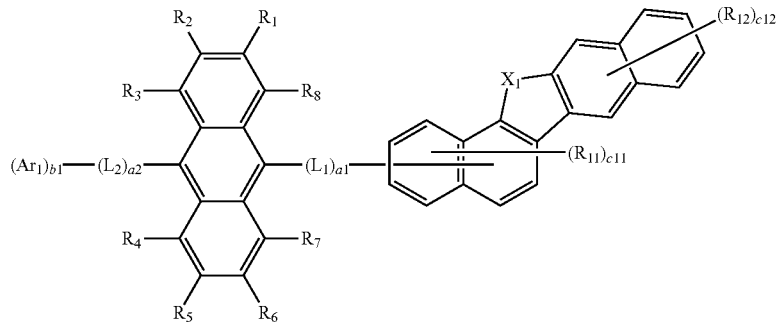
<Formula 1E>
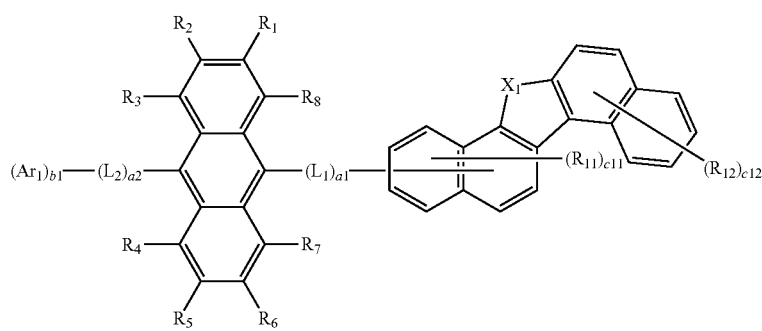
<Formula 1F>

-continued
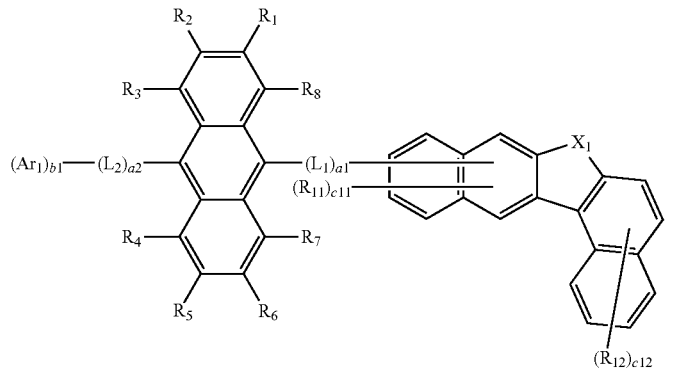
<Formula 1G>
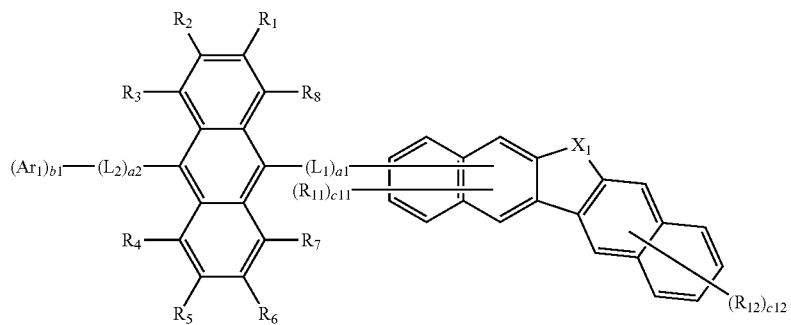
<Formula 1H>
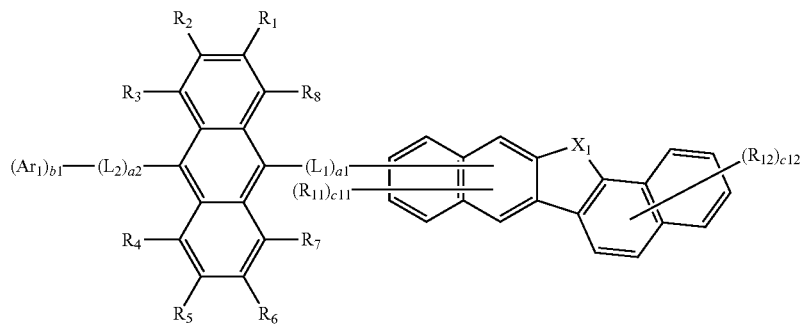
<Formula 1I>
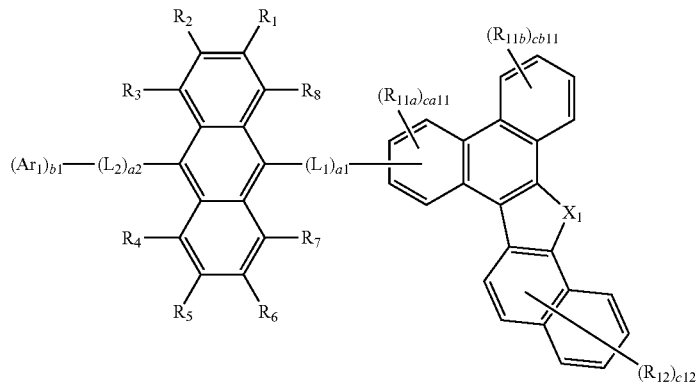
<Formula 1J>

-continued
<Formula 1K>
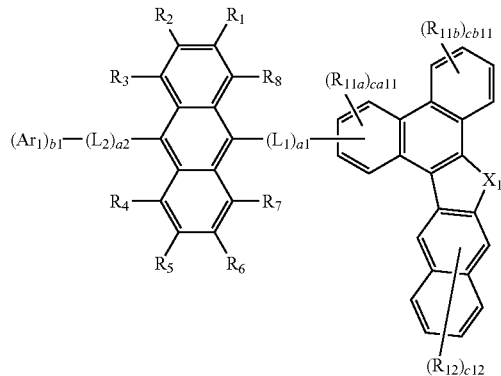
<Formula 1L>
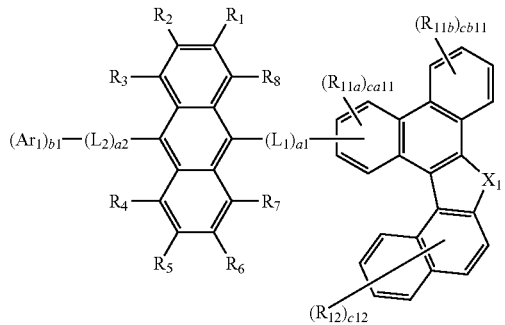
<Formula 1M>
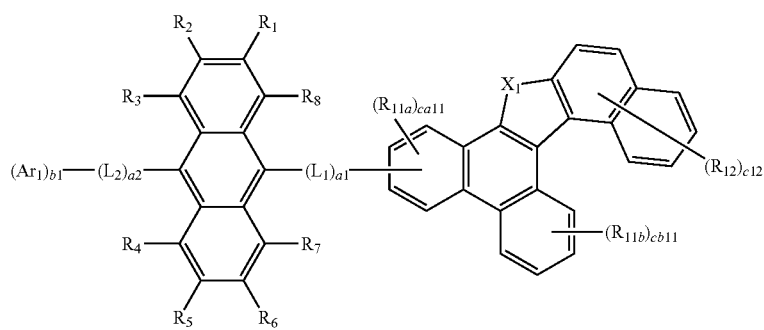
<Formula 1N>
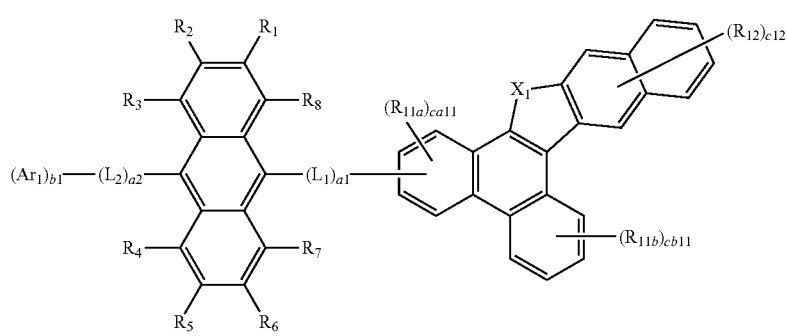
<Formula 1O>
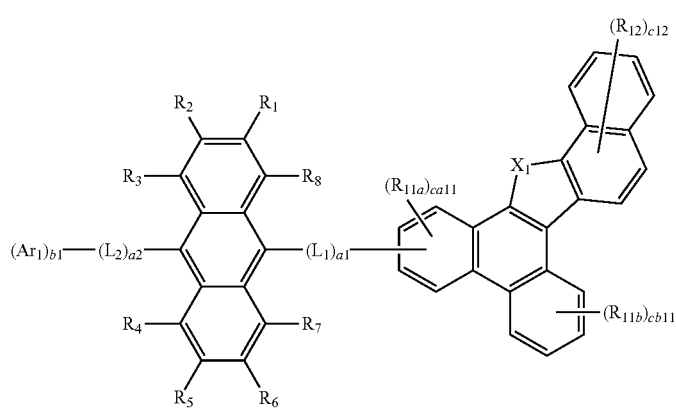

<Formula 1P>
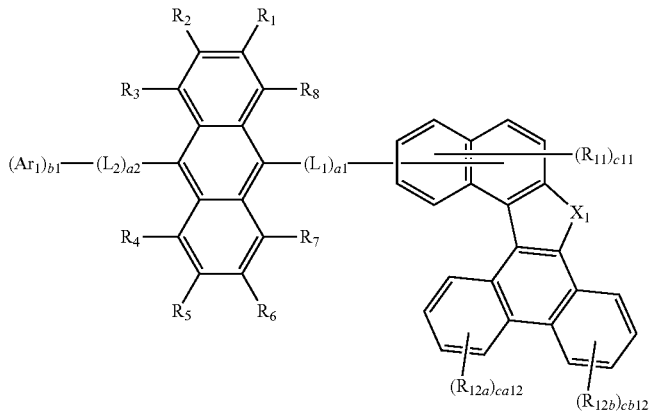
<Formula 1Q>
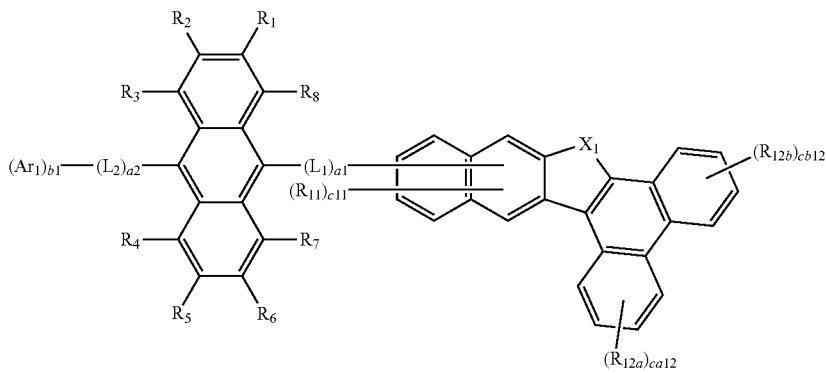
<Formula 1R>
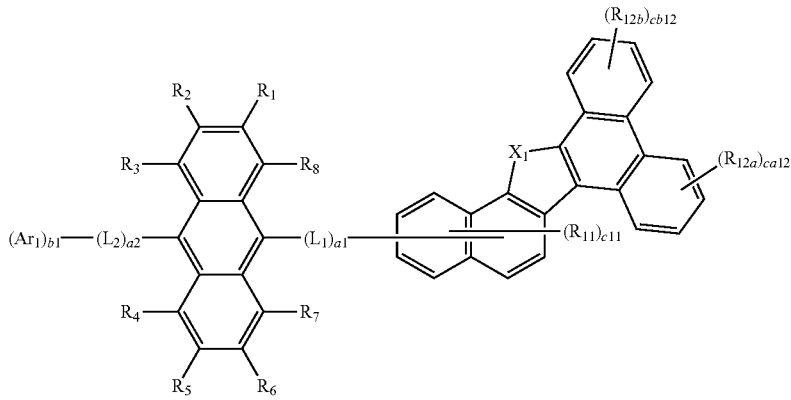
<Formula 1S>
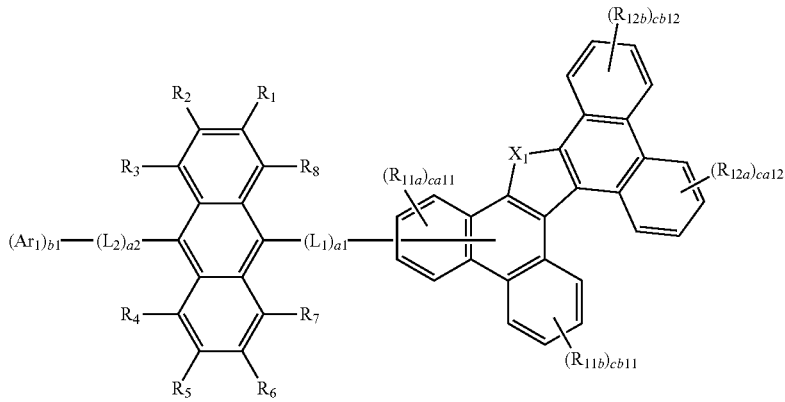

-continued

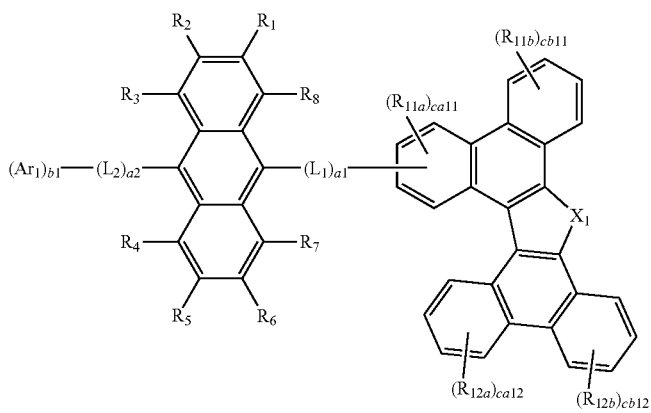
<Formula 1T>

In Formulae 1A to 1T, $X_1$, $L_1$, $L_2$, a1, a2, $Ar_1$, b1, $R_1$ to $R_8$, $R_{11}$, $R_{12}$, c11, and c12 may each independently be the same as defined herein, $R_{11a}$ and $R_{11b}$ may each independently be the same as described herein with respect to $R_{11}$, $R_{12a}$ and $R_{12b}$ may each independently be the same as described herein with respect to $R_{12}$, ca11 may be an integer selected from 0 to 3, and ca12, cb11, and cb12 may each independently be an integer selected from 0 to 4.

According to an exemplary embodiment of the present invention, the condensed cyclic compound represented by Formula 1 may be represented by at least one of Formulae 1A(1) to 1T(1):

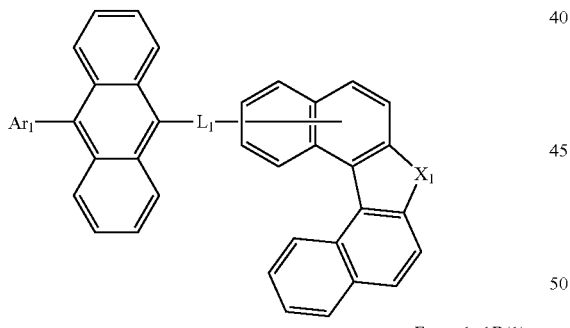
<Formula 1A(1)>

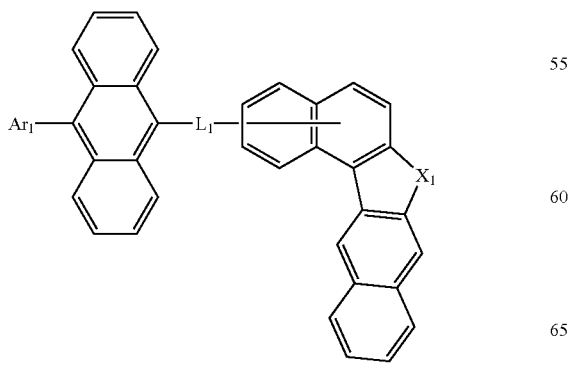
<Formula 1B(1)>

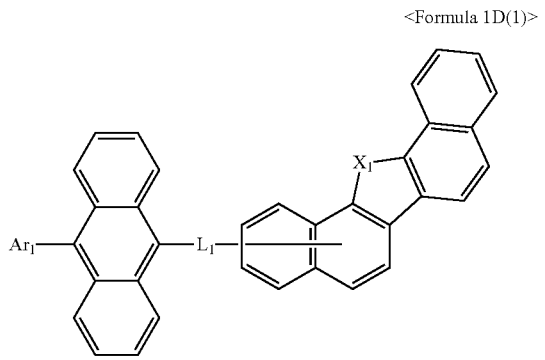
<Formula 1C(1)>

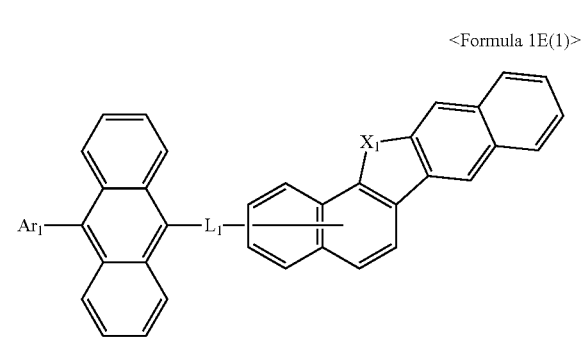
<Formula 1D(1)>

<Formula 1E(1)>

<Formula 1F(1)>
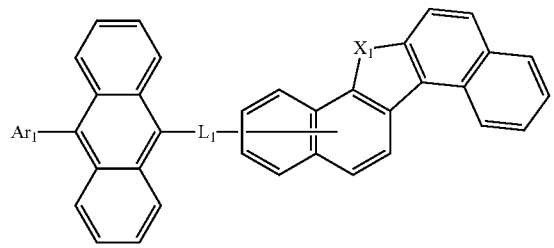
<Formula 1G(1)>
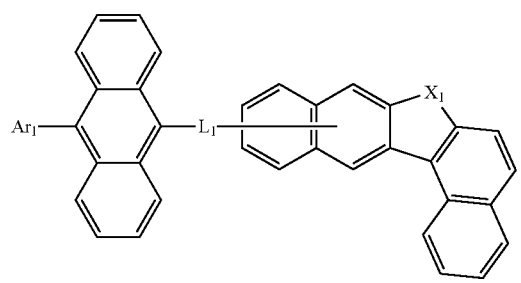
<Formula 1H(1)>
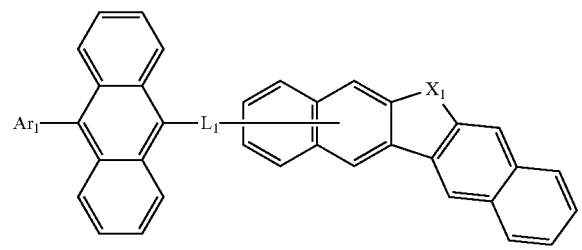
<Formula 1I(1)>
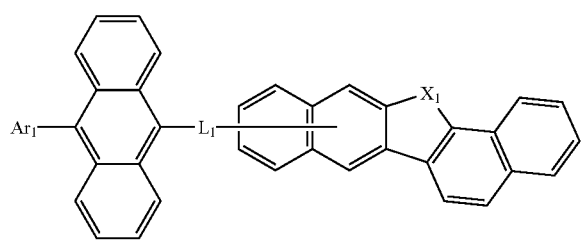
<Formula 1J(1)>
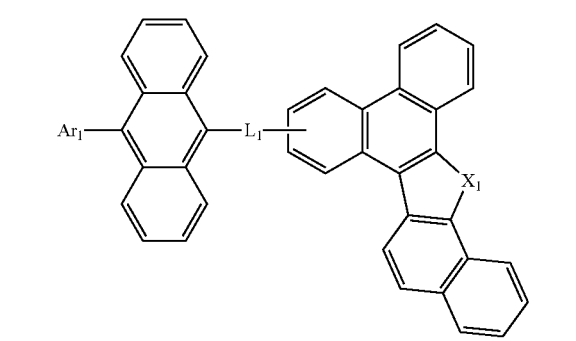
<Formula 1K(1)>
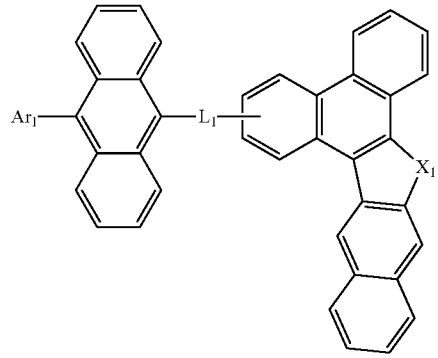
<Formula 1L(1)>
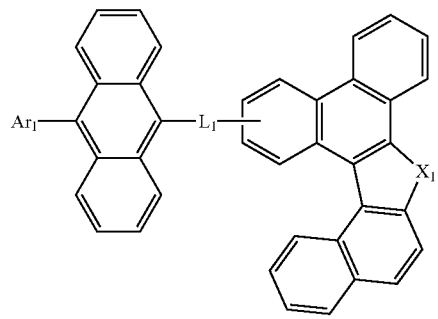
<Formula 1M(1)>
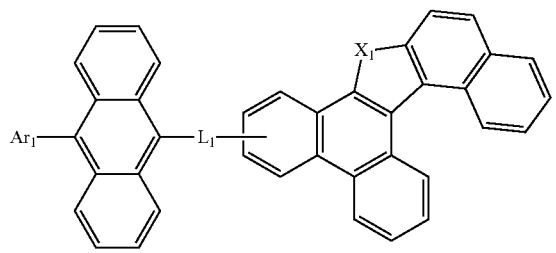
<Formula 1N(1)>
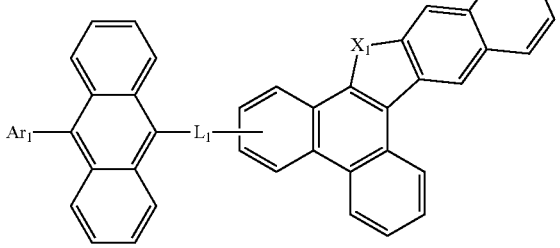
<Formula 1O(1)>
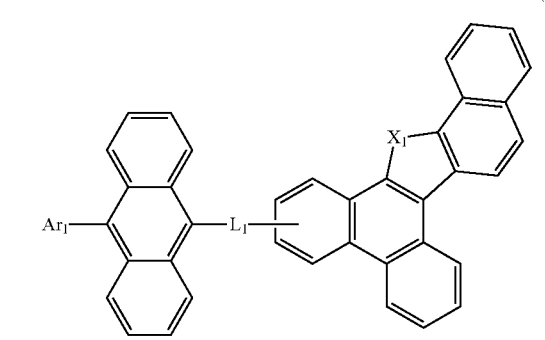

<Formula 1P(1)>

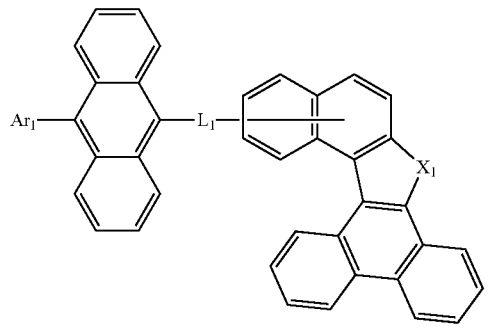

<Formula 1S(1)>

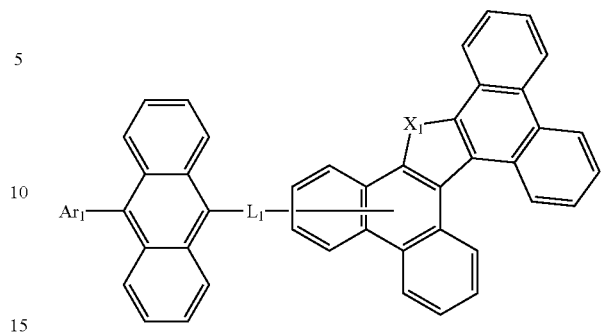

<Formula 1Q(1)>

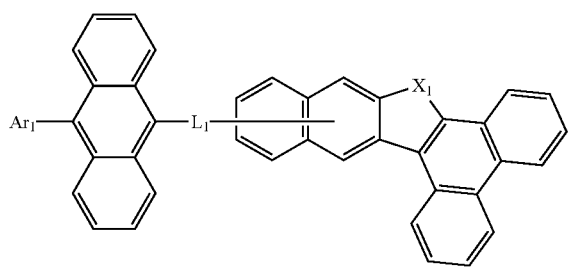

<Formula 1T(1)>

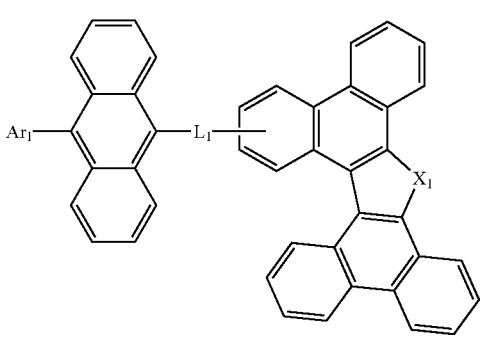

<Formula 1R(1)>

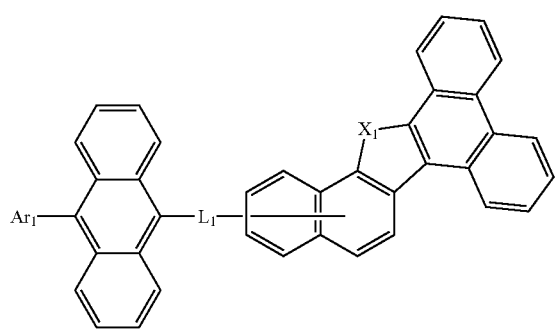

In Formulae 1A(1) to 1T(1), $X_1$, $L_1$, and $Ar_1$ may each independently be the same as described herein.

For example, in Formulae 1A(1) to 1T(1), $X_1$ may be selected from oxygen (O) and sulfur (S), $L_1$ and $L_2$ may each independently be selected from groups represented by Formulae 4-1 to 4-35, and $Ar_1$ may be selected from groups represented by Formulae 6-1 to 6-44.

The condensed cyclic compound represented by Formula 1 may be at least one selected from the compounds below:

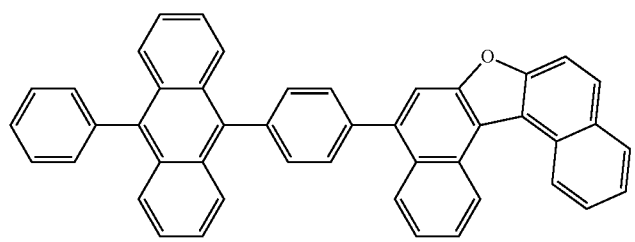

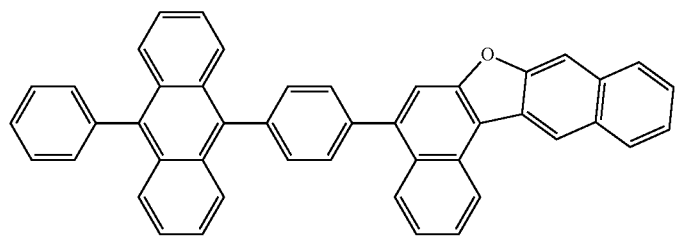

-continued
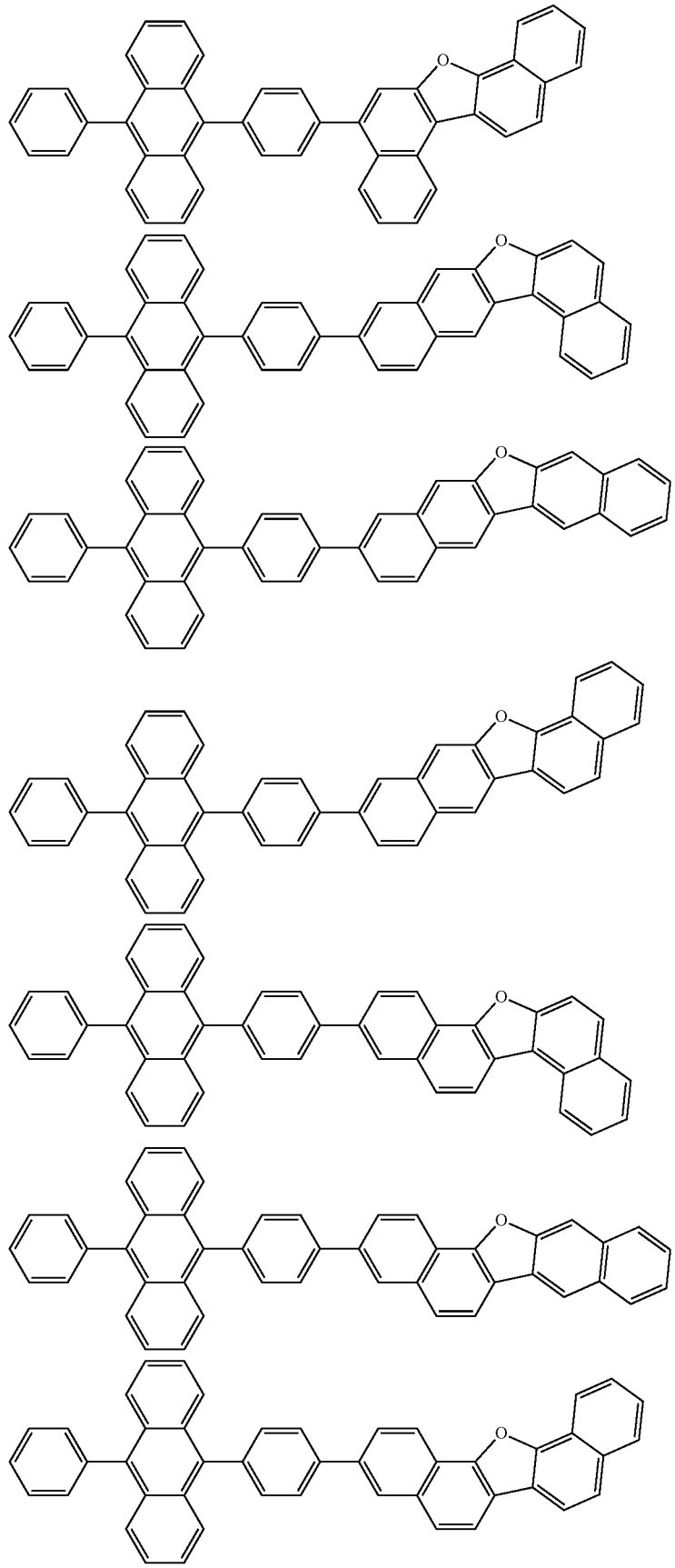

-continued
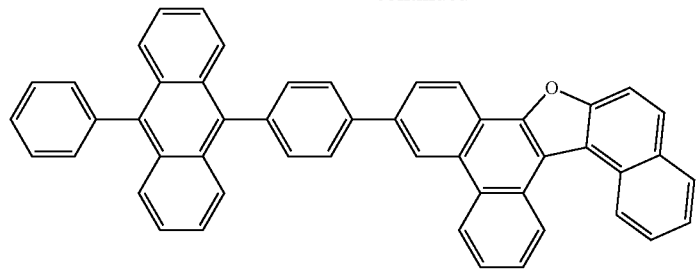
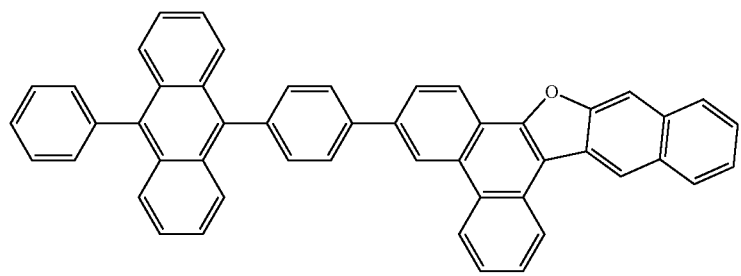
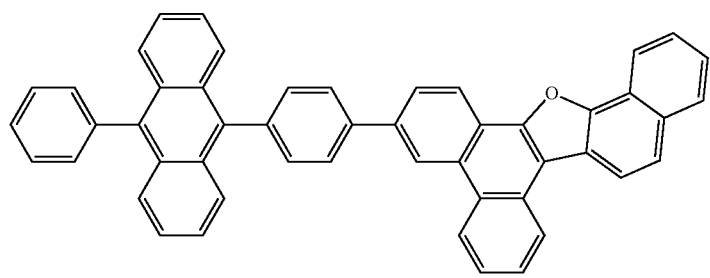
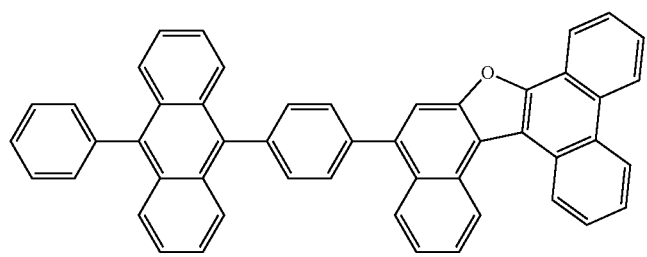
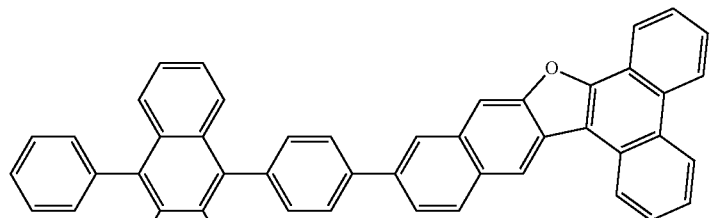
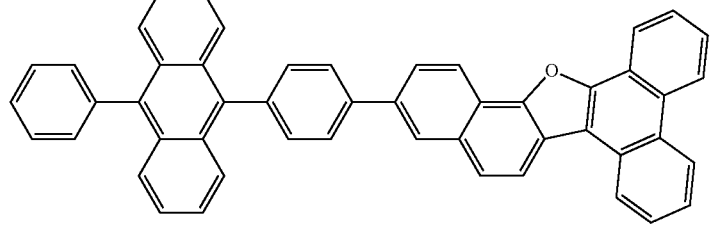

-continued
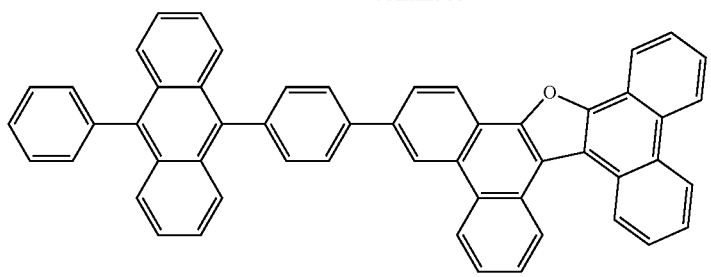
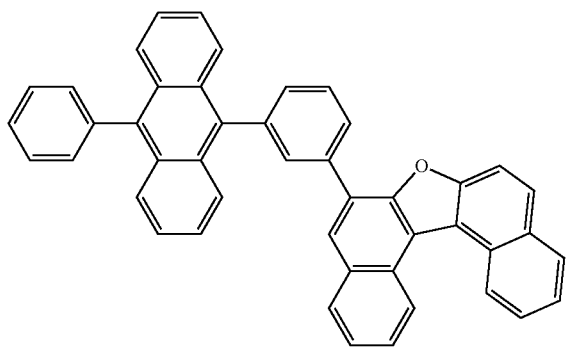
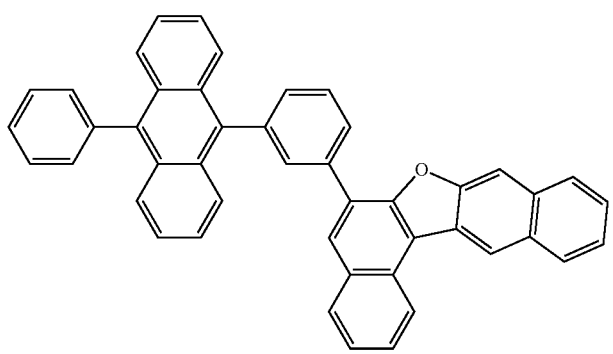
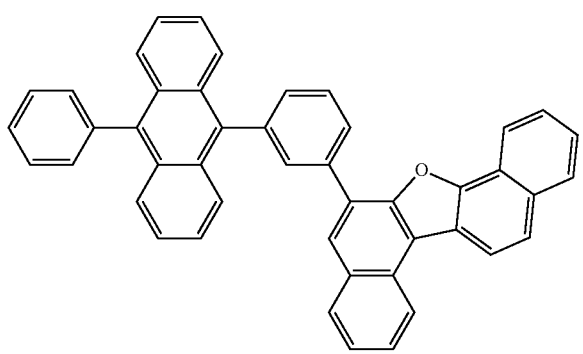
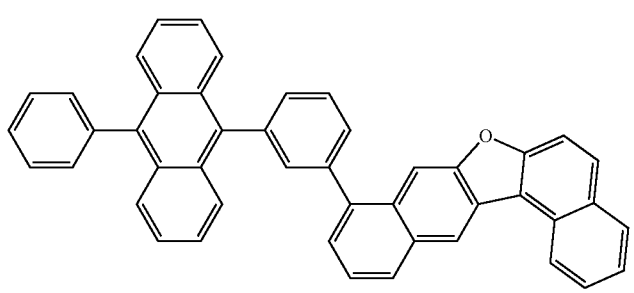

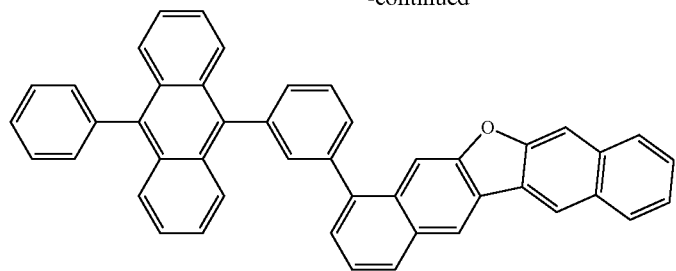
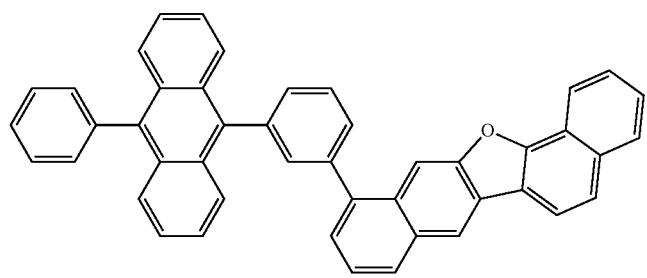
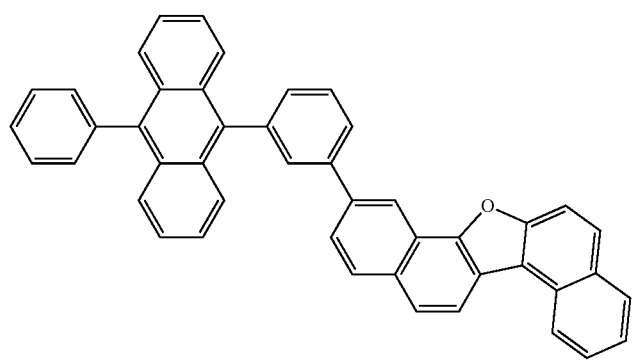
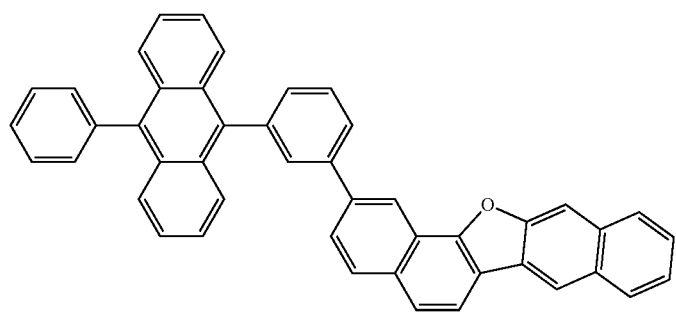
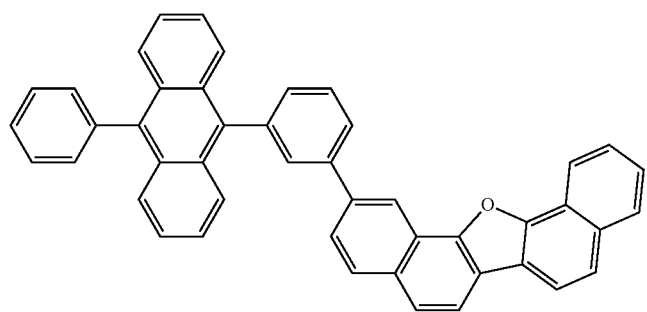

-continued
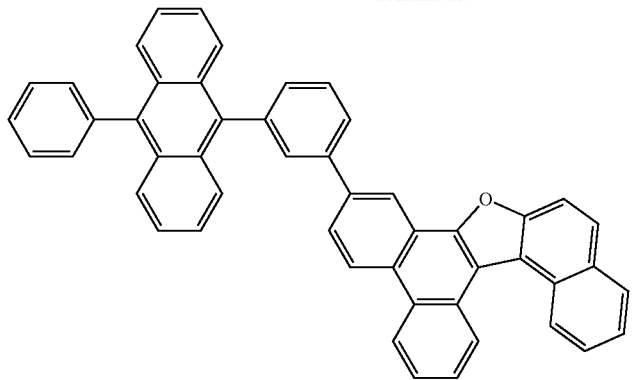
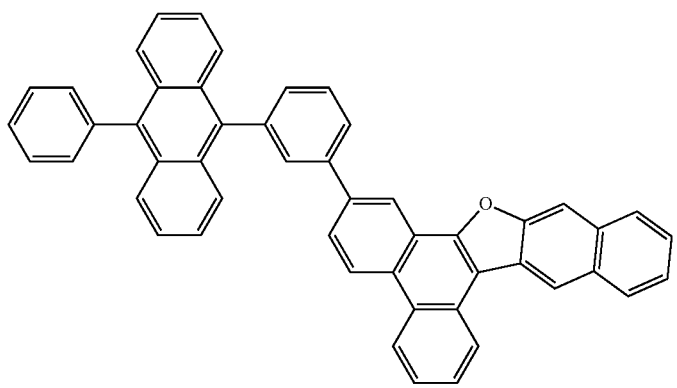
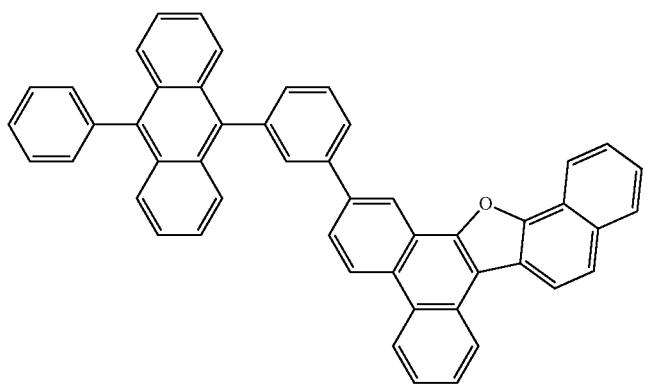
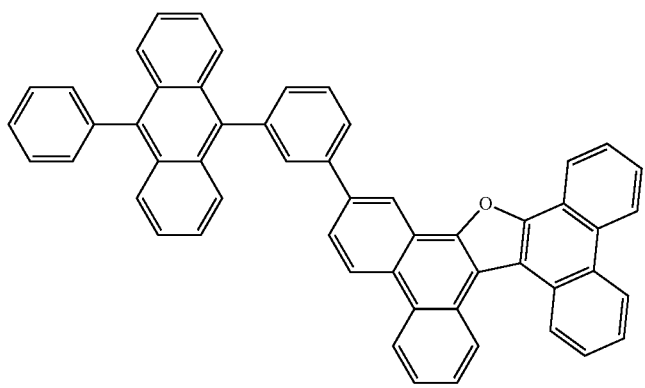

-continued
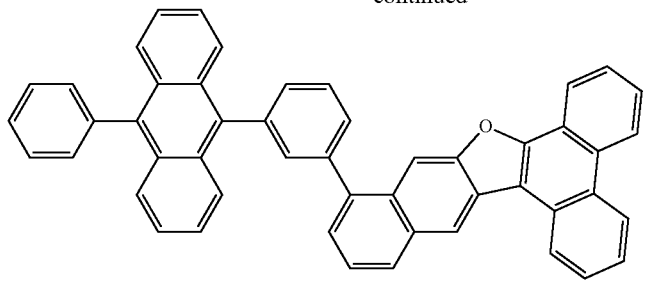
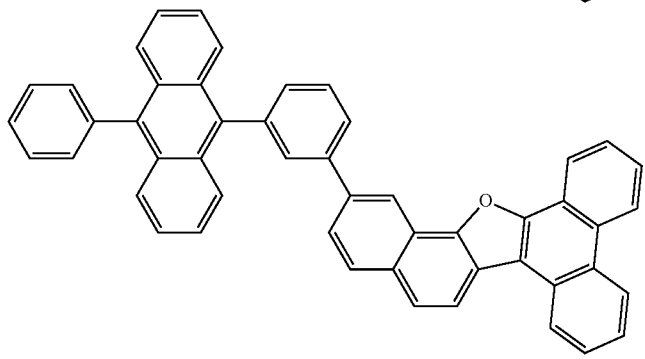
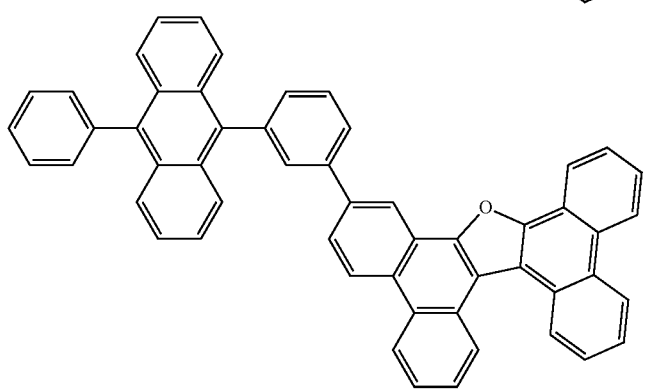
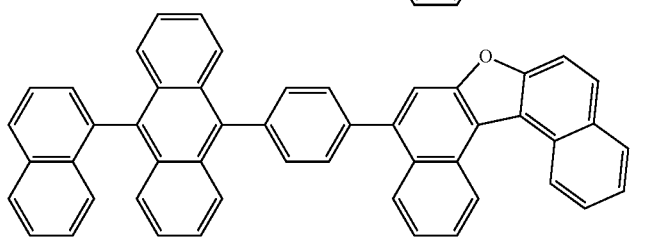
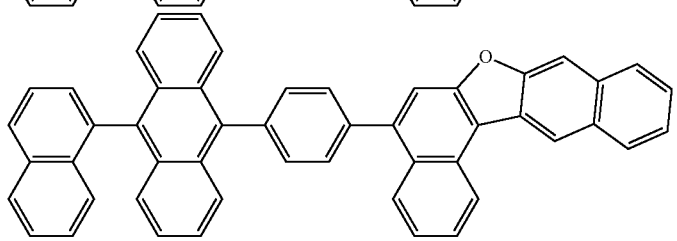
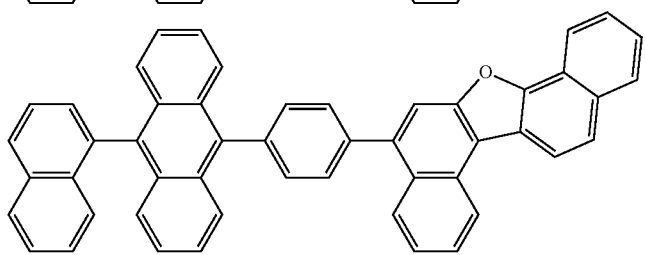

-continued
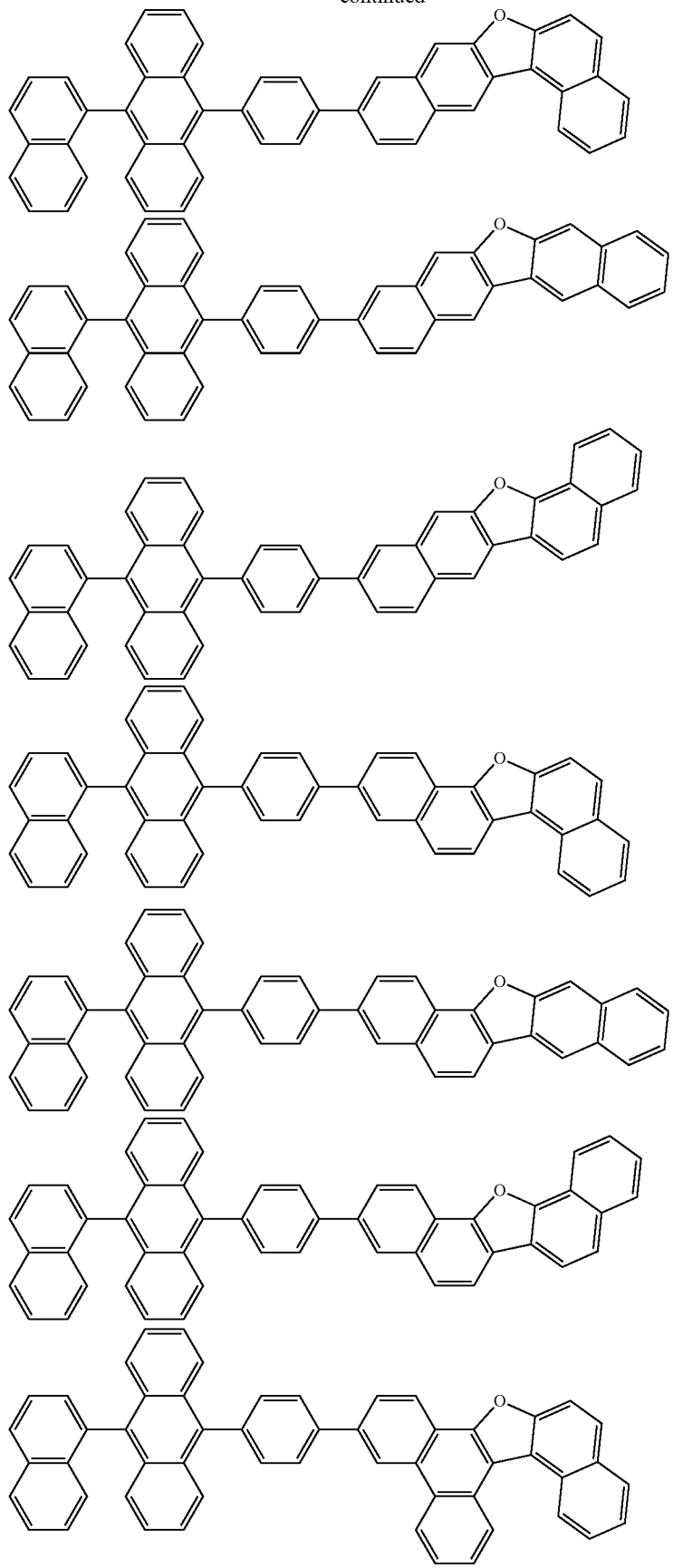

-continued
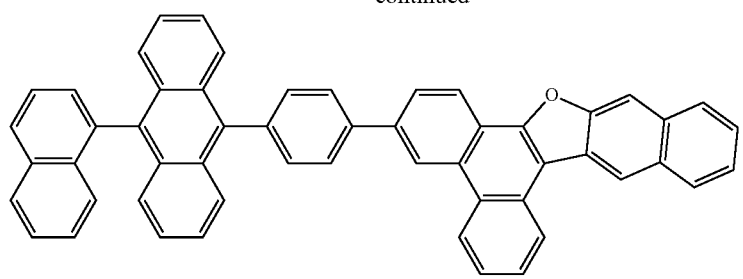
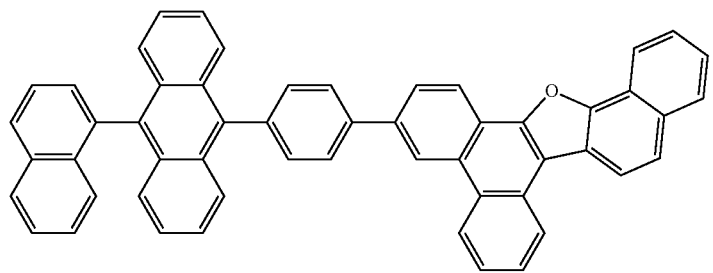
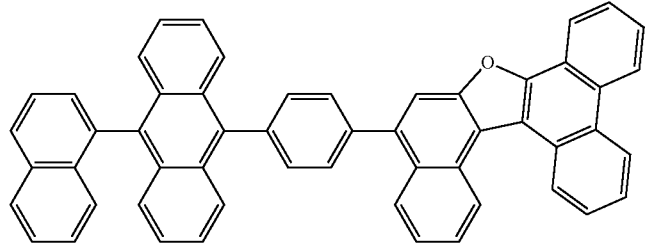
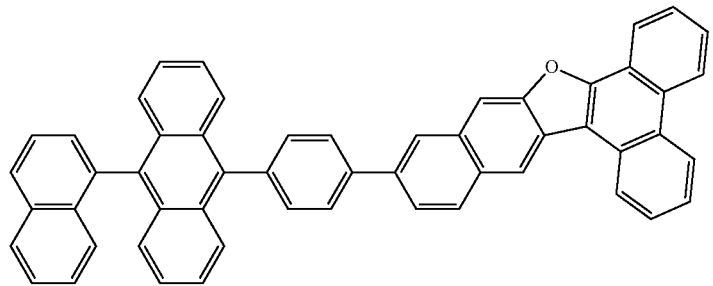
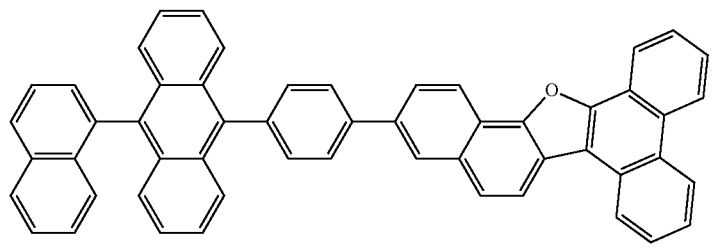
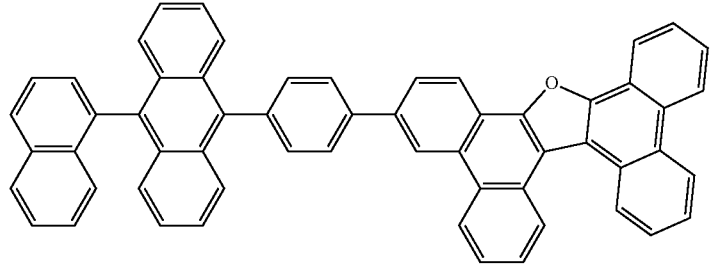

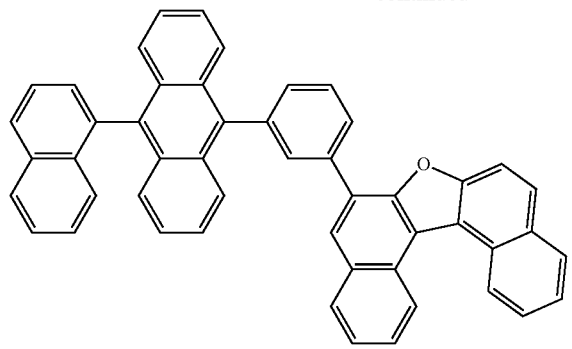
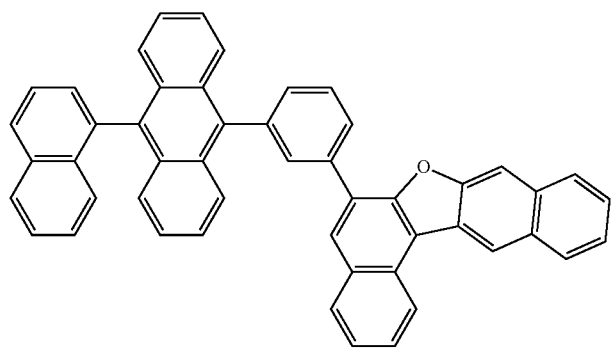
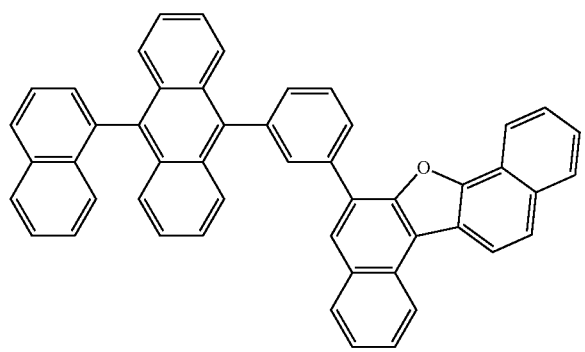
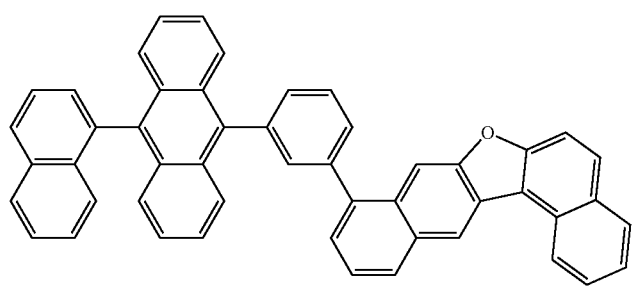
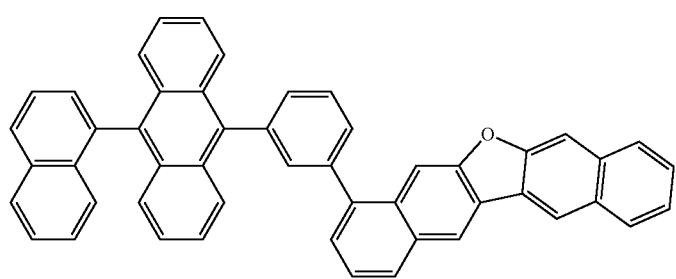

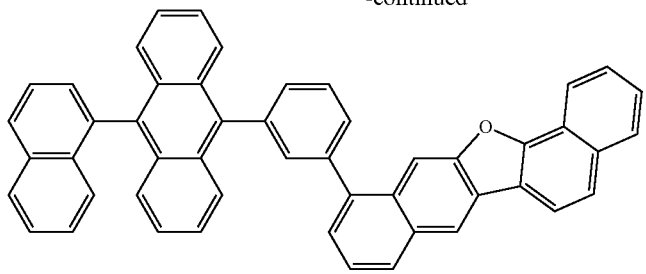

-continued
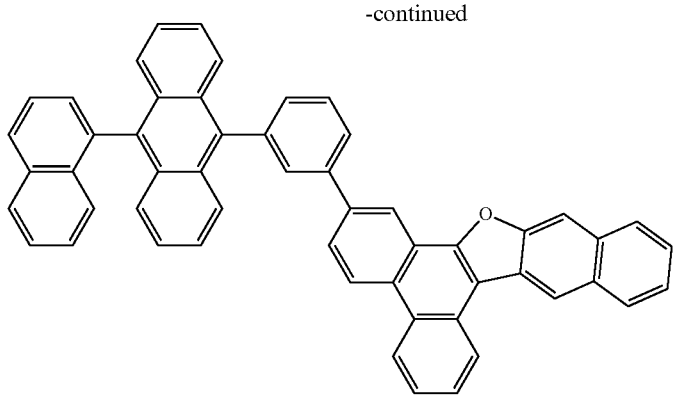
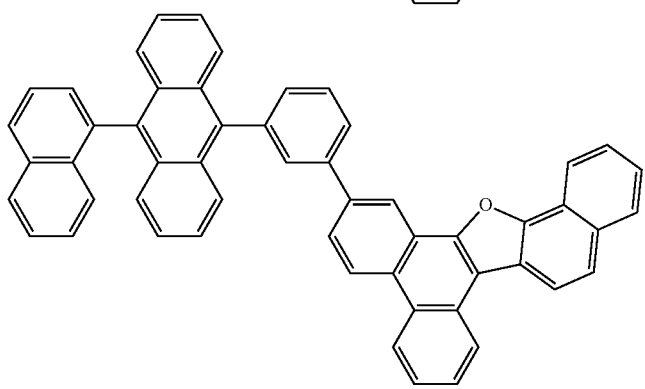
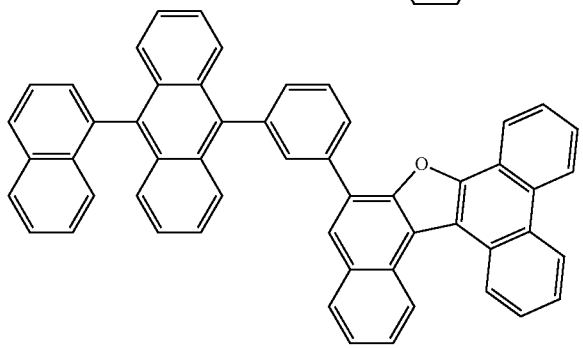
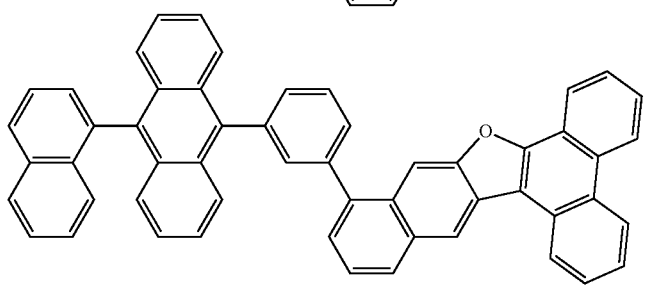
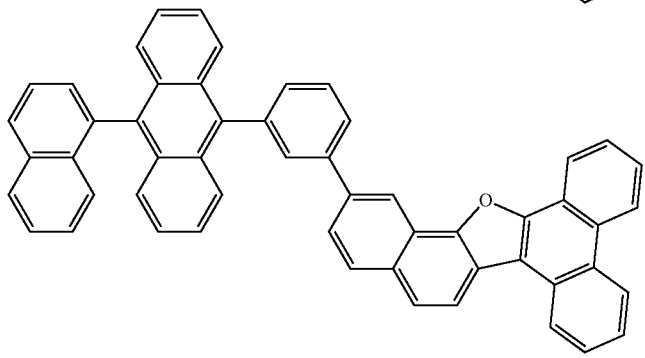

-continued
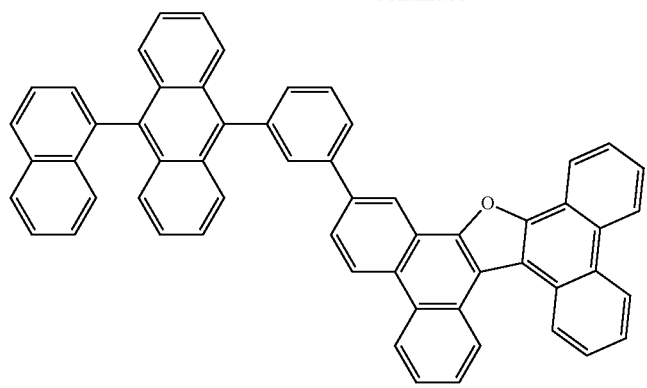
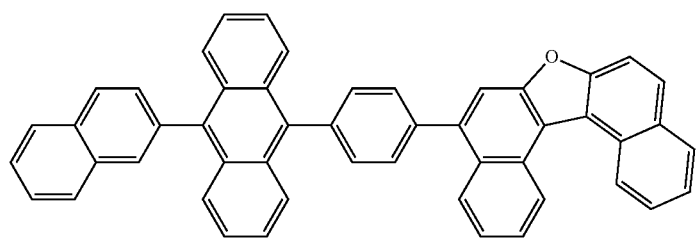
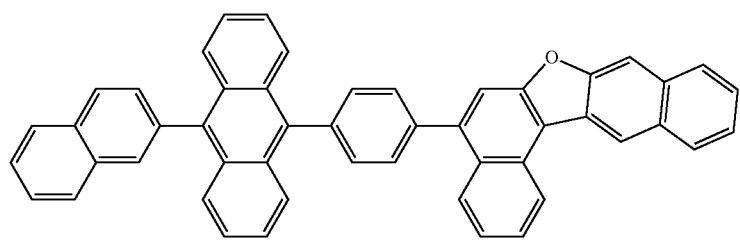
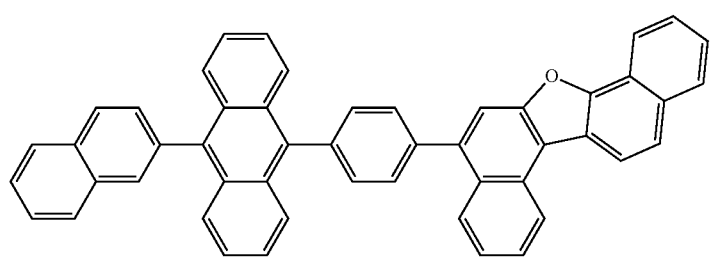
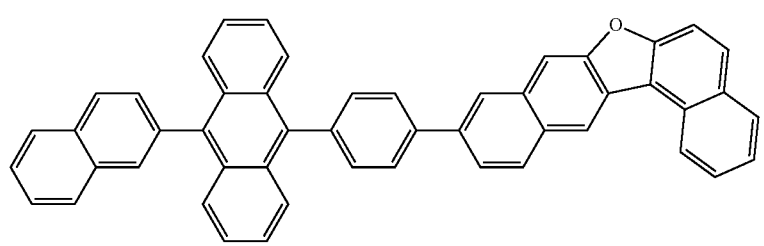
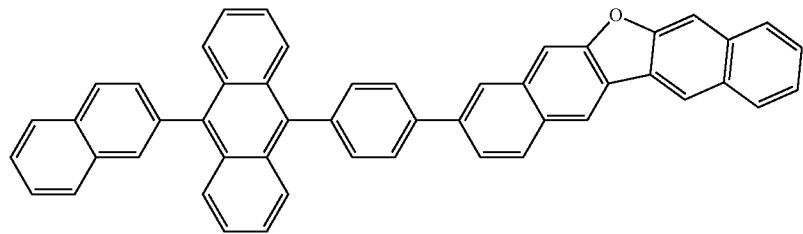

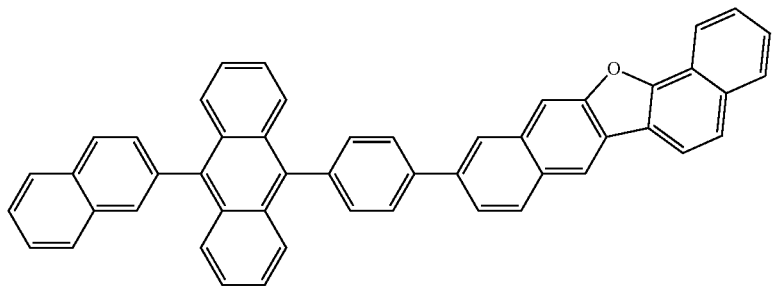
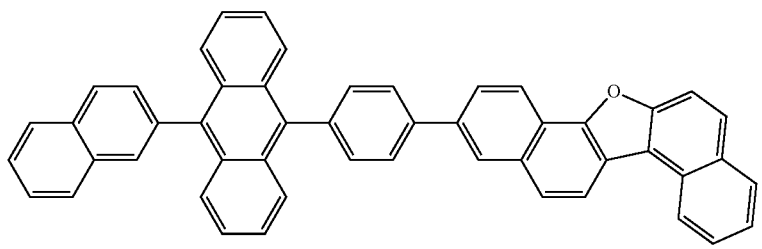
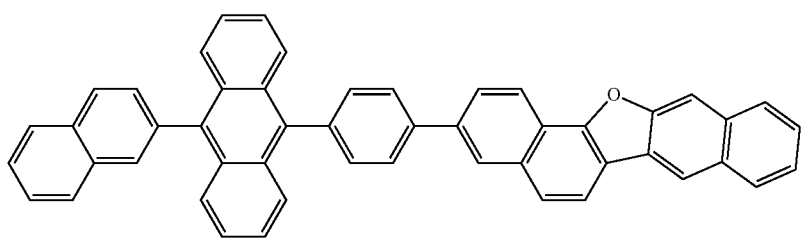
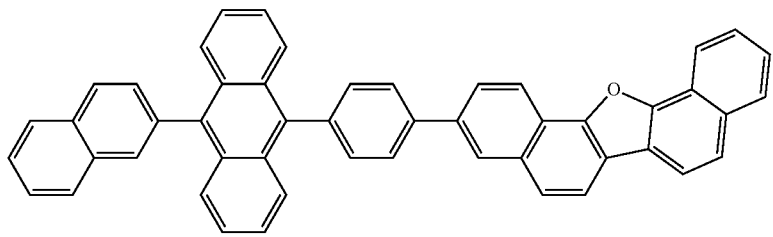
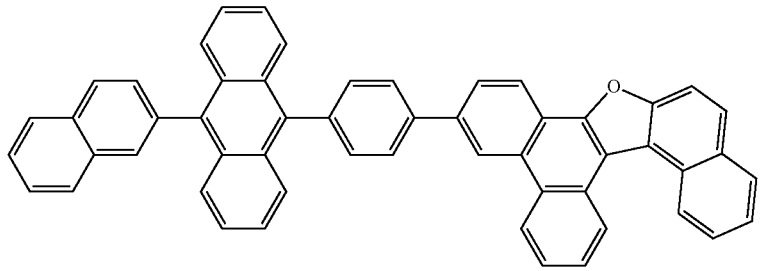
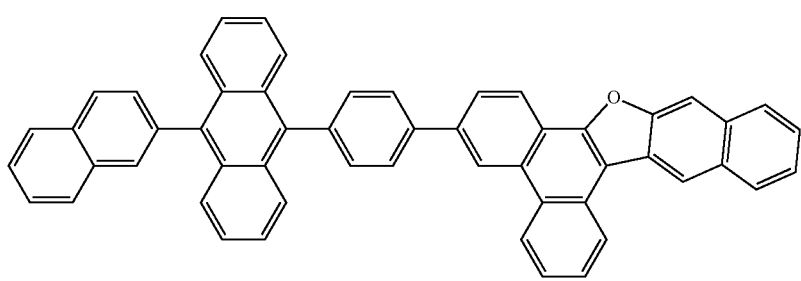

-continued
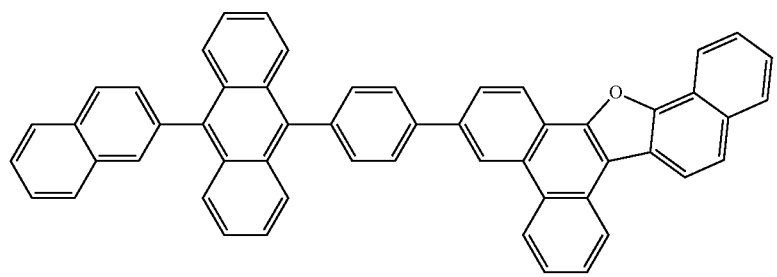
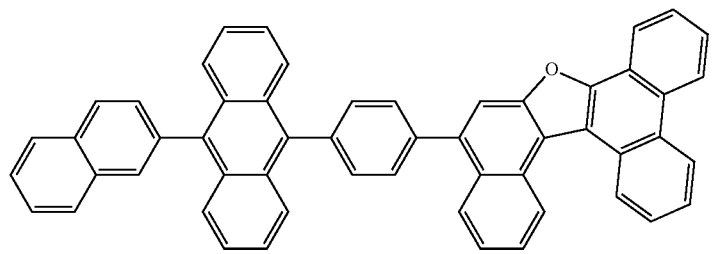
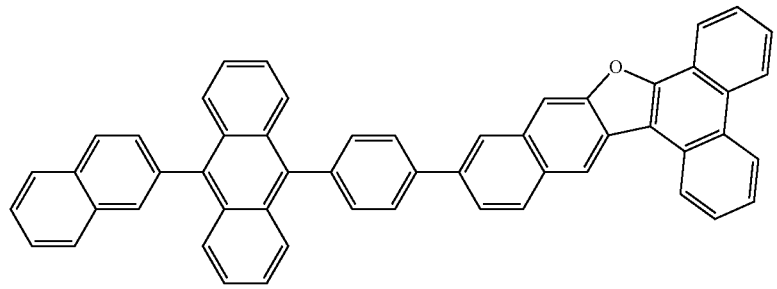
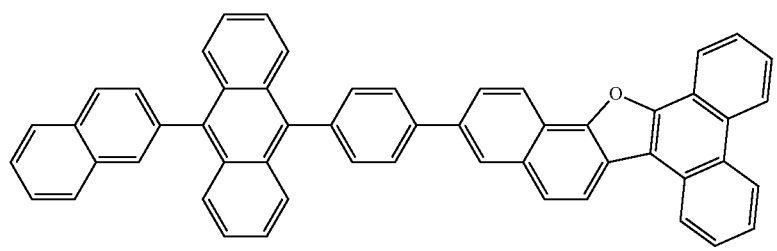
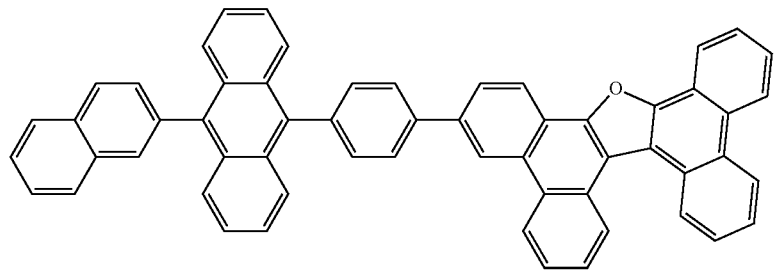
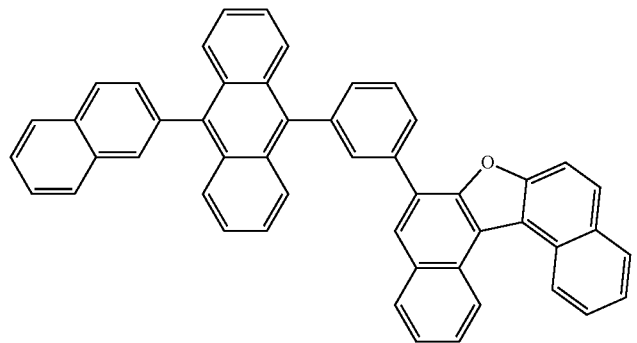

-continued
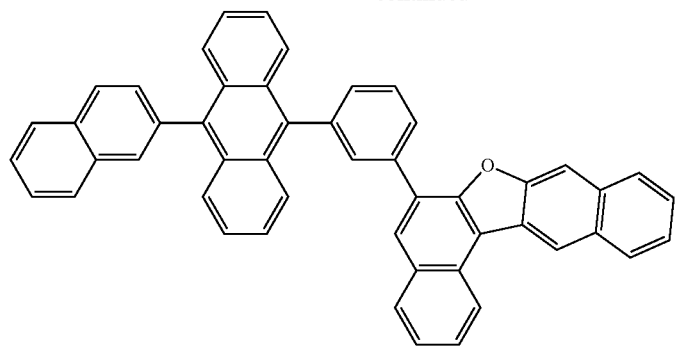
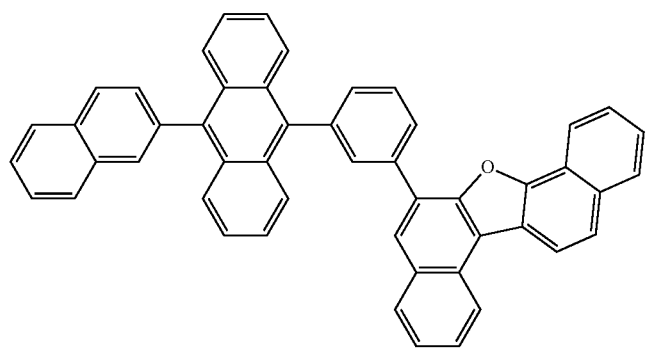
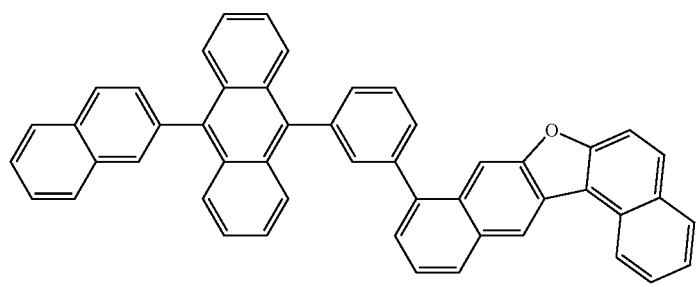
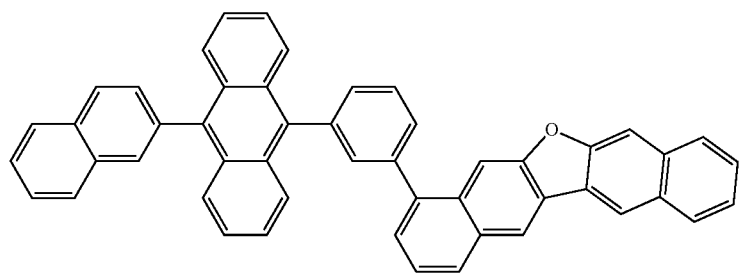
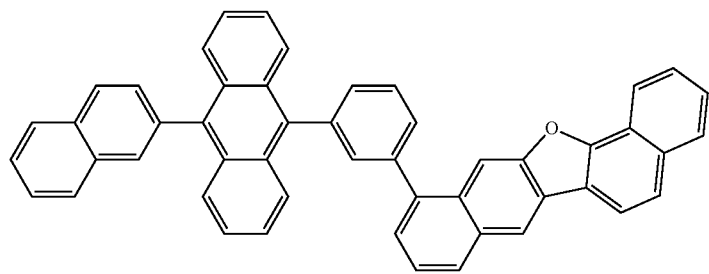

-continued
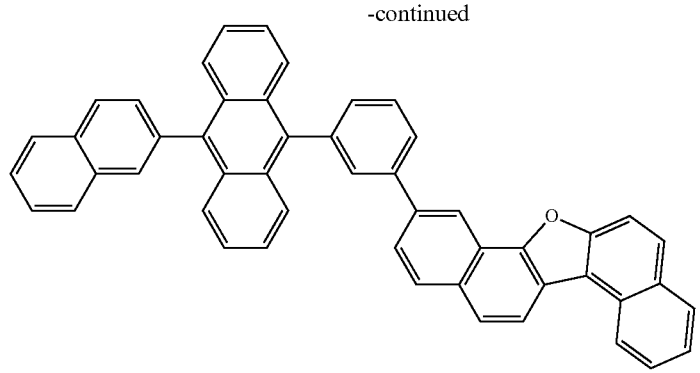
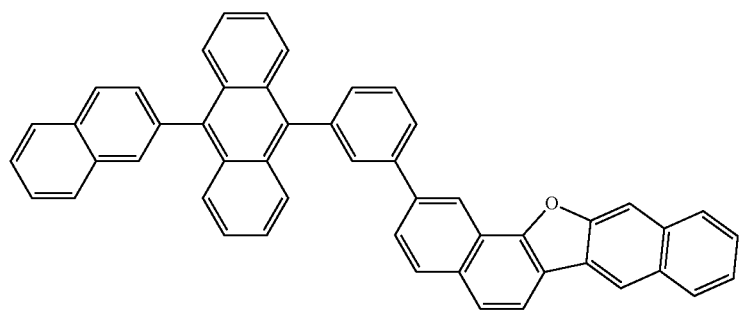
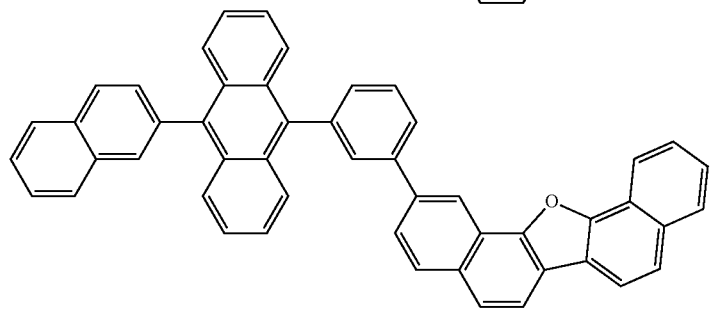
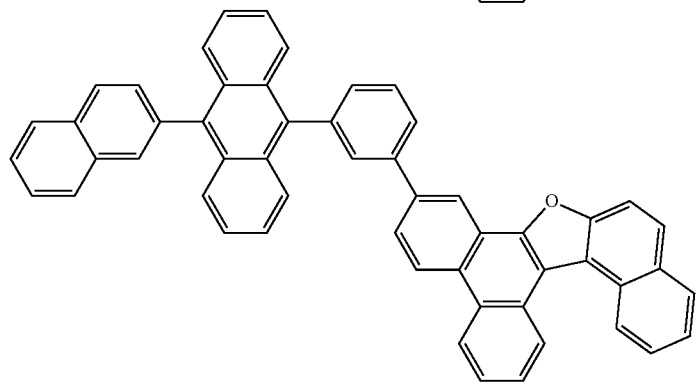
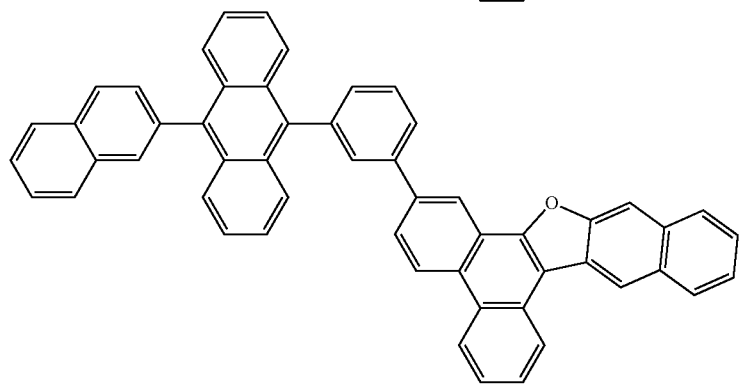

-continued
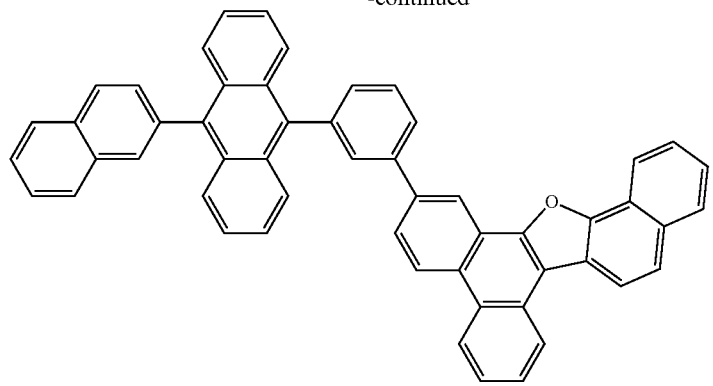
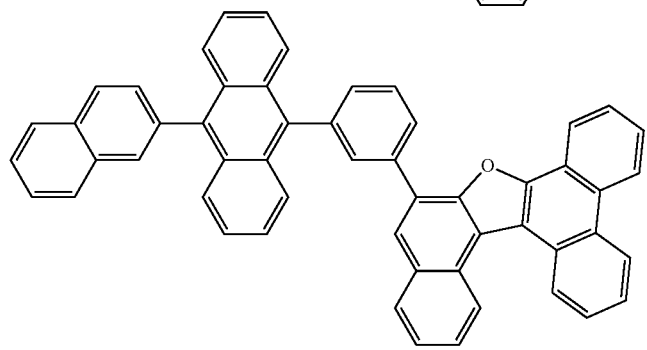
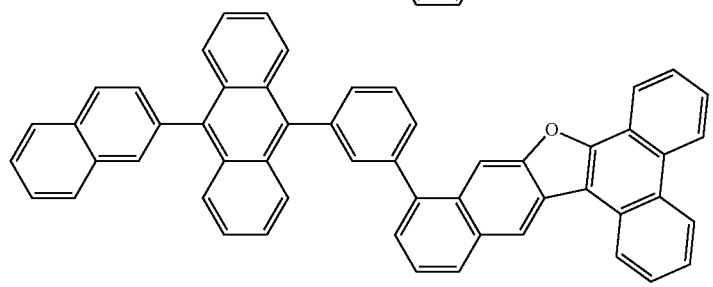
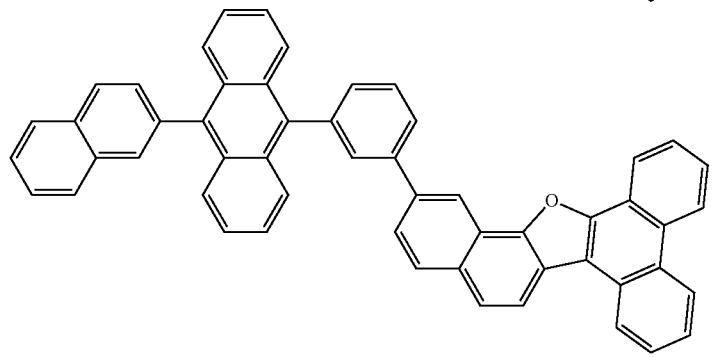
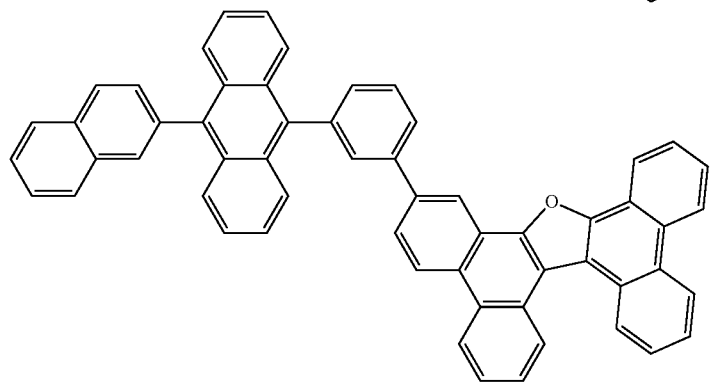

-continued
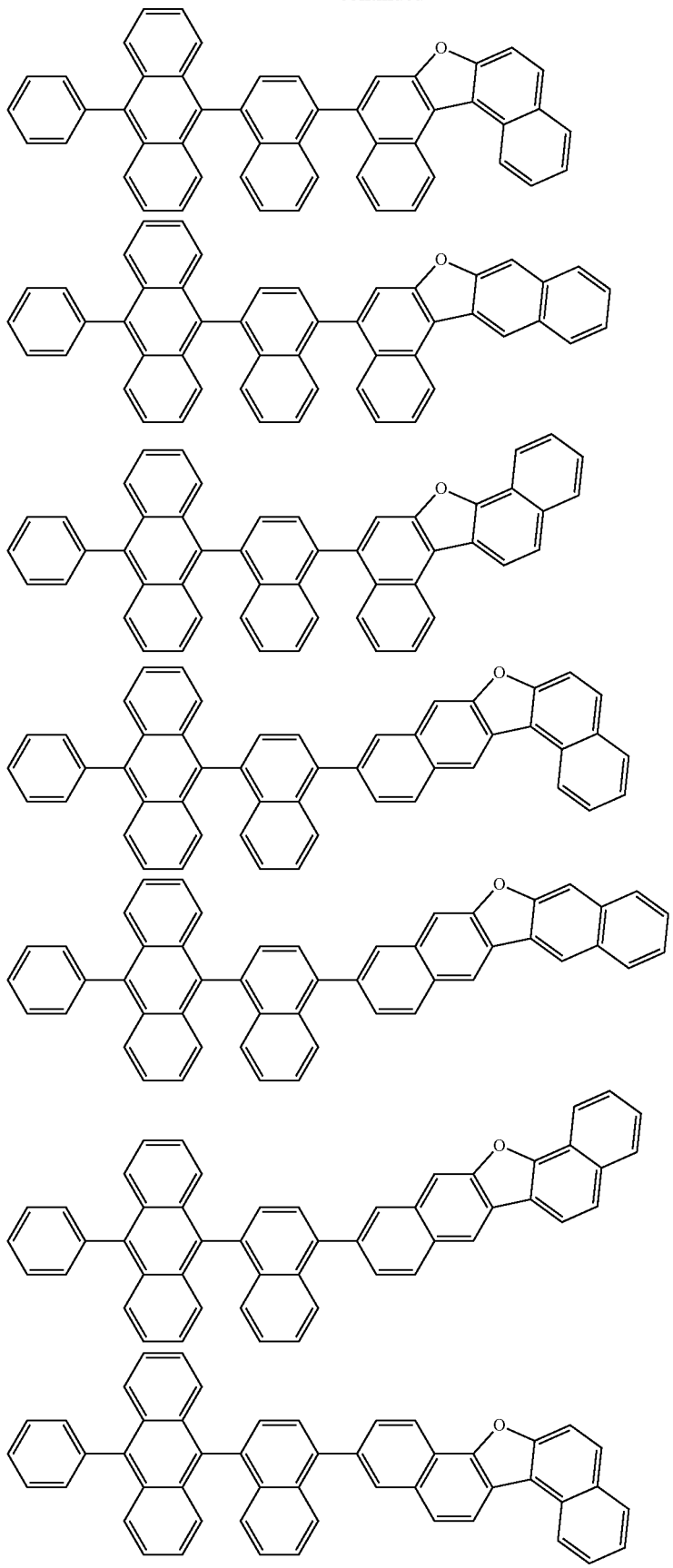

-continued
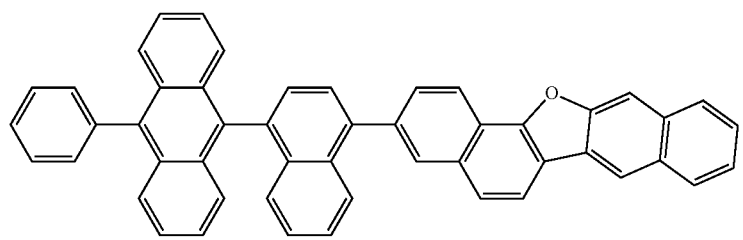
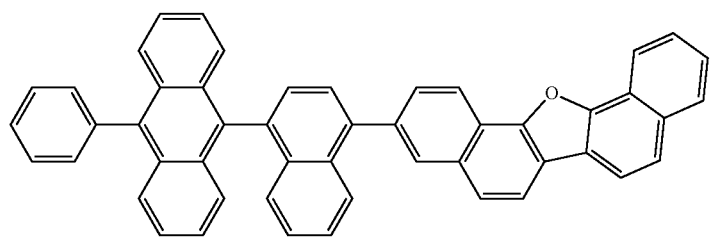
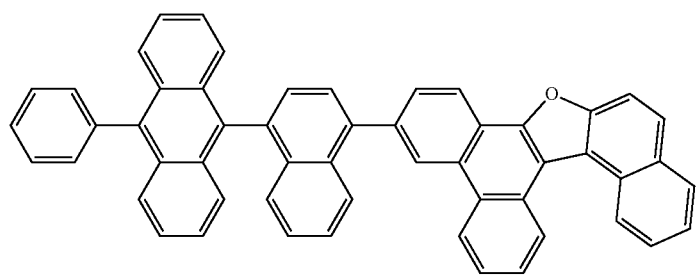
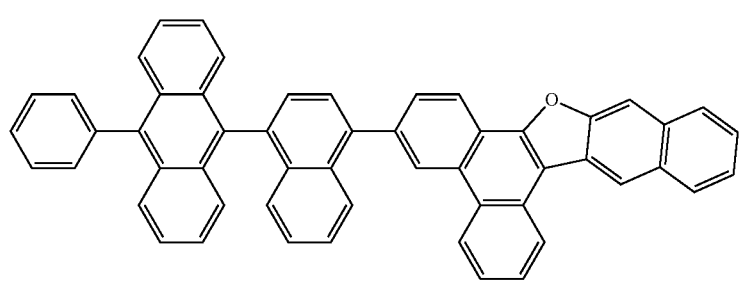
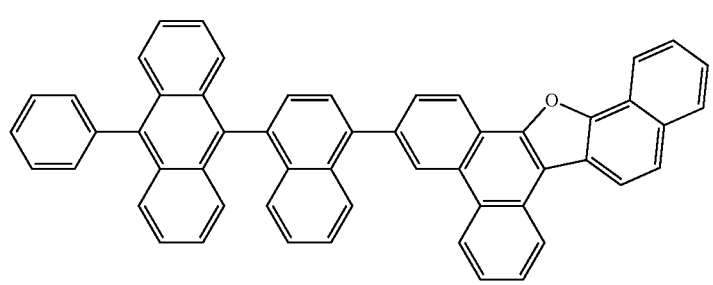
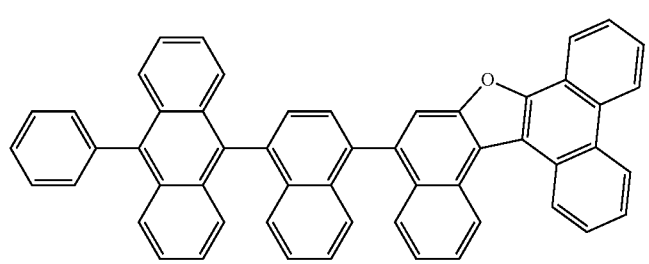

-continued
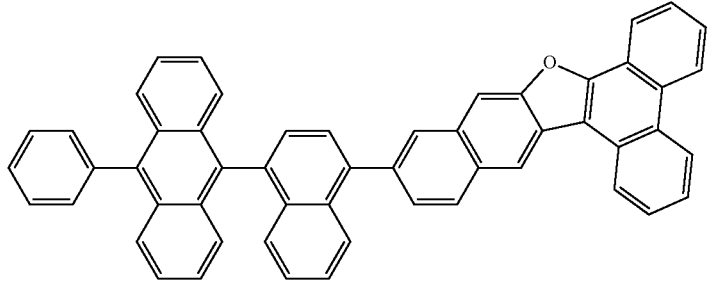
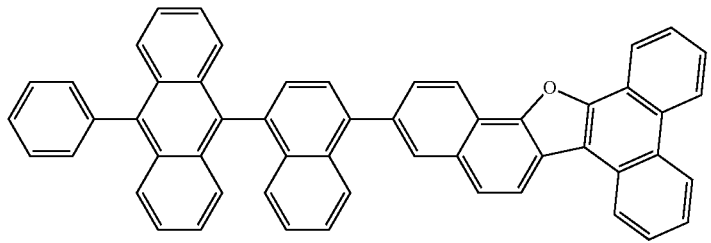
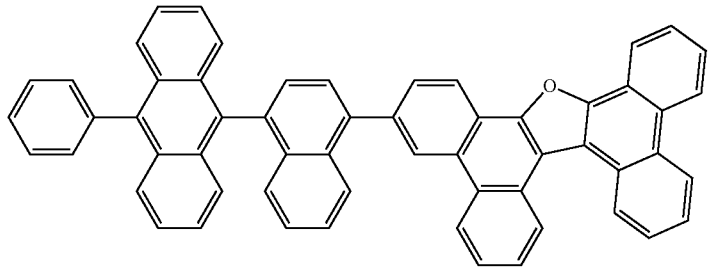
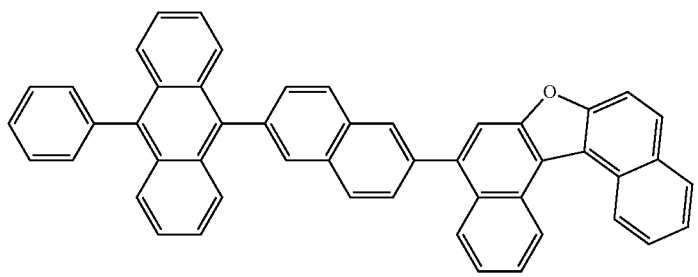
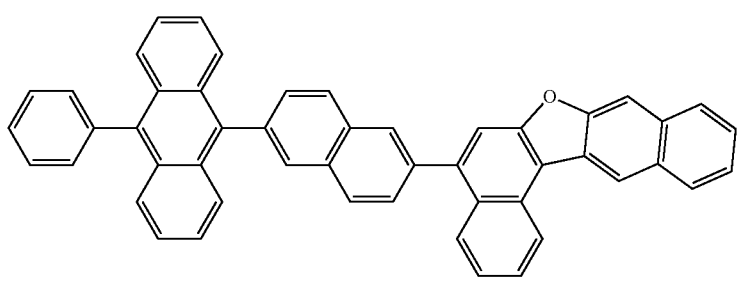
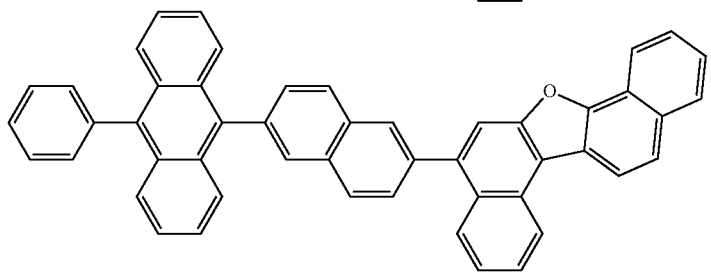

-continued
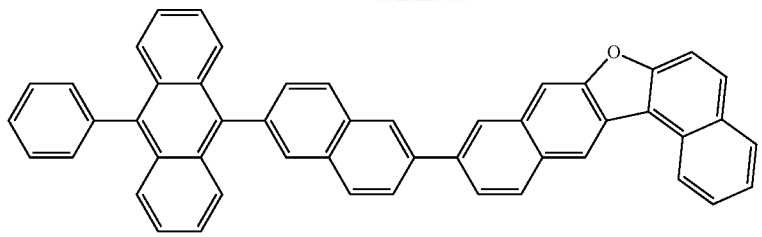
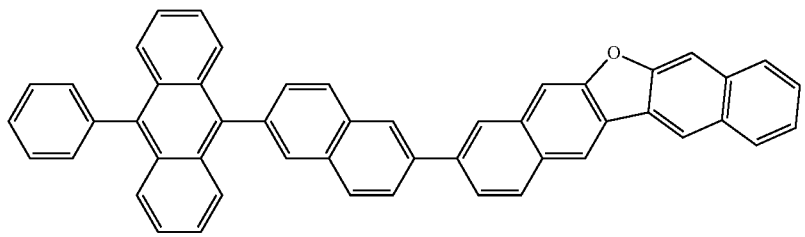
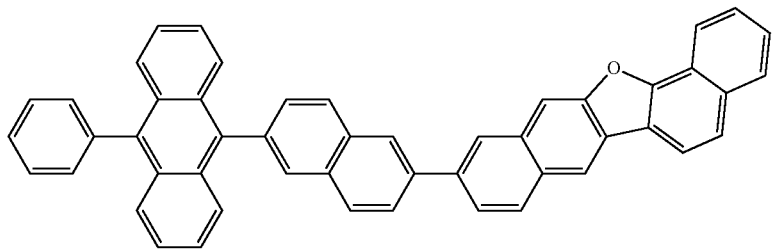
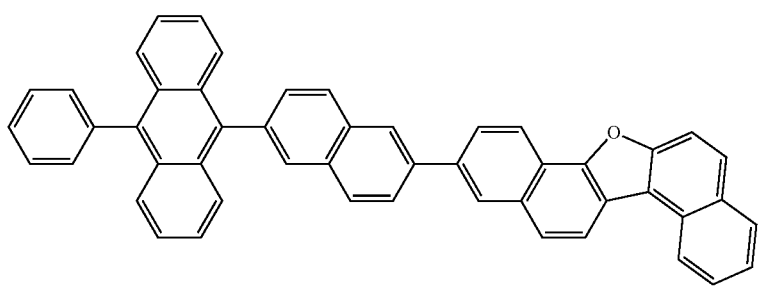
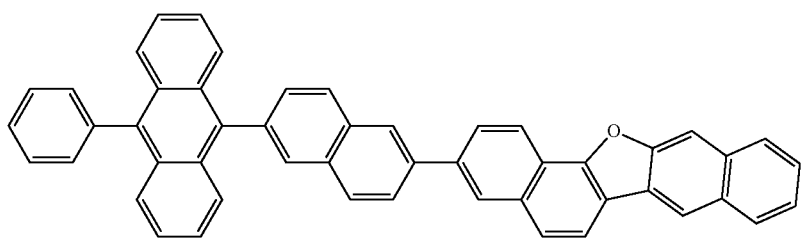
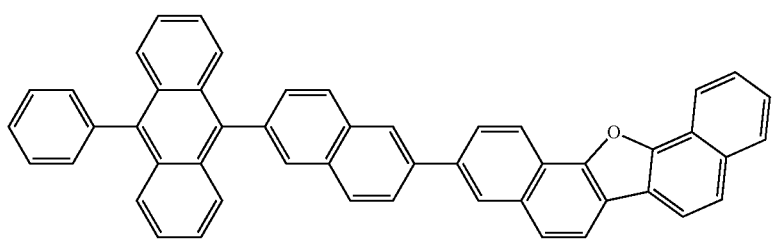

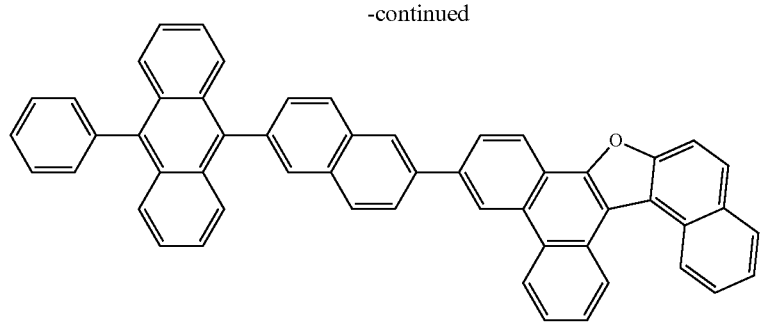
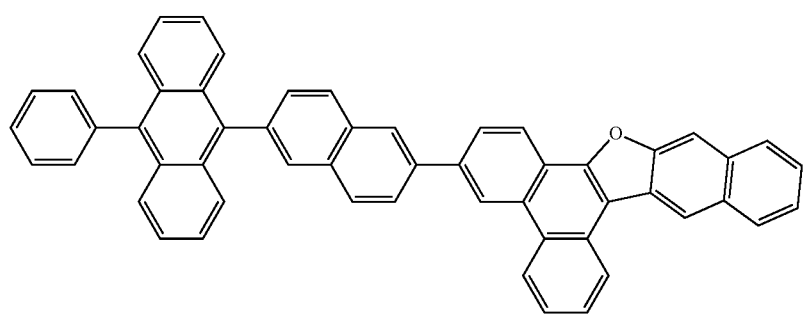
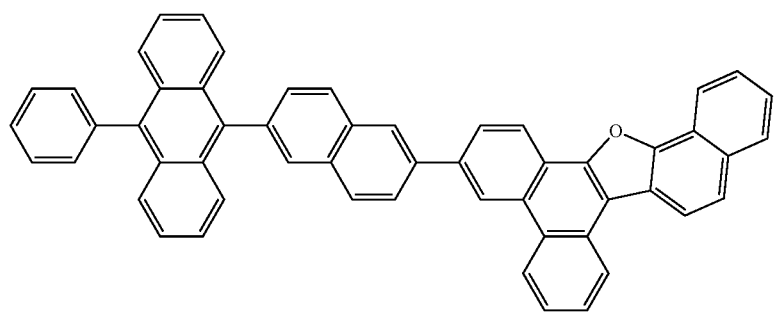
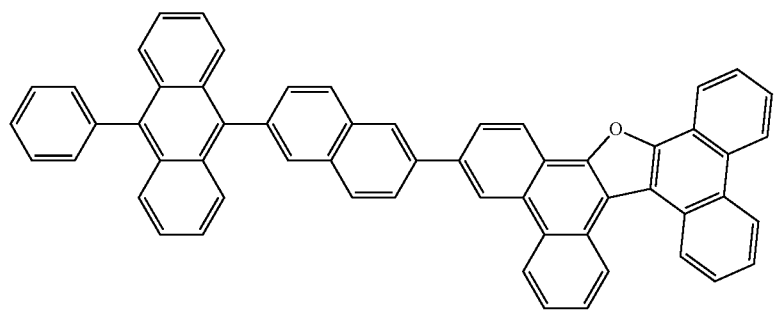
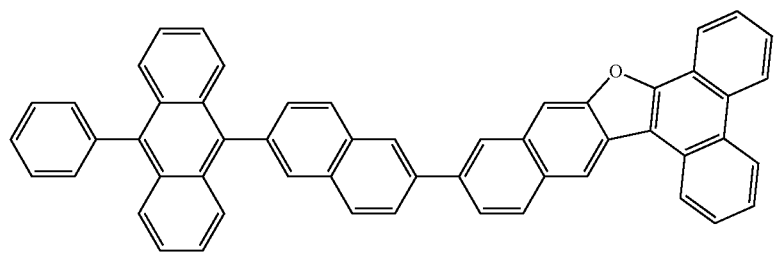

-continued
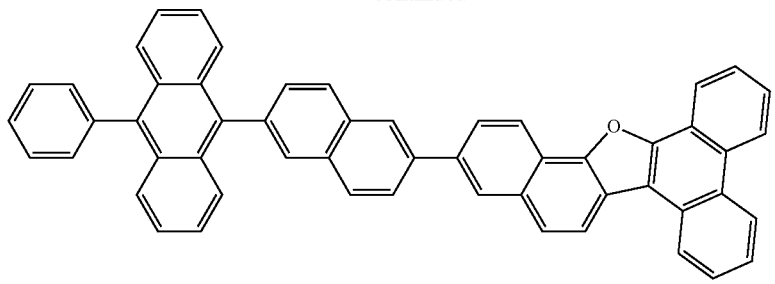
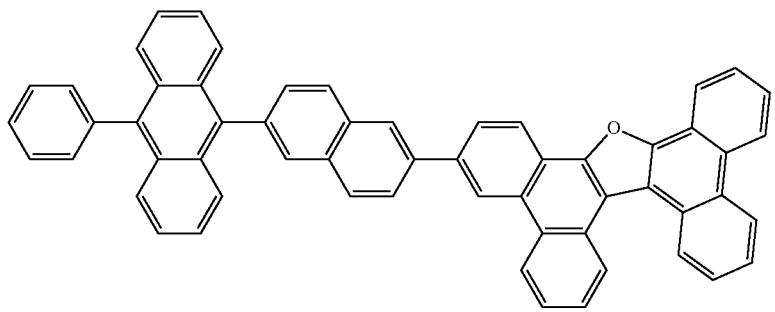
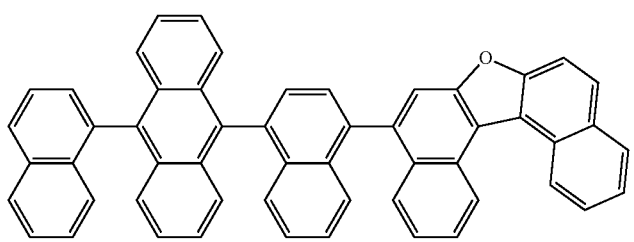
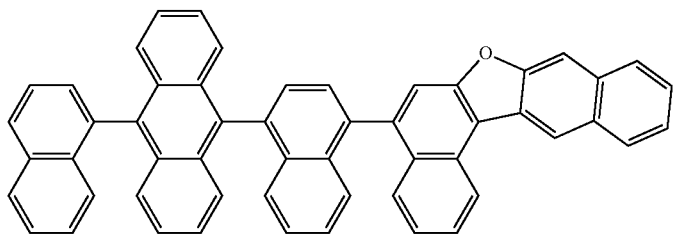
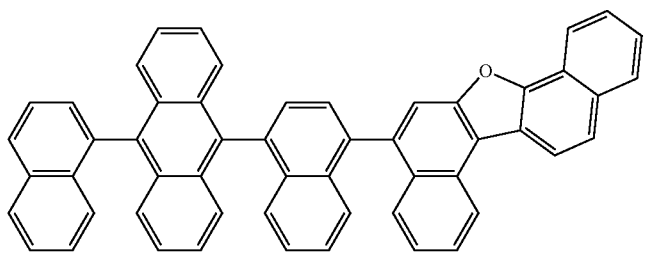
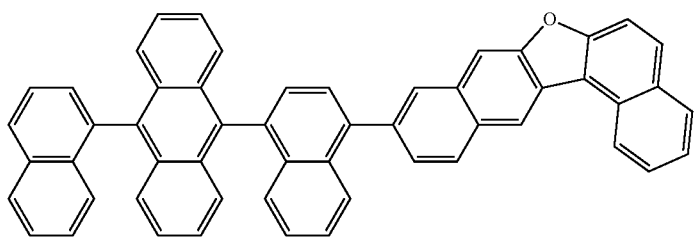

-continued
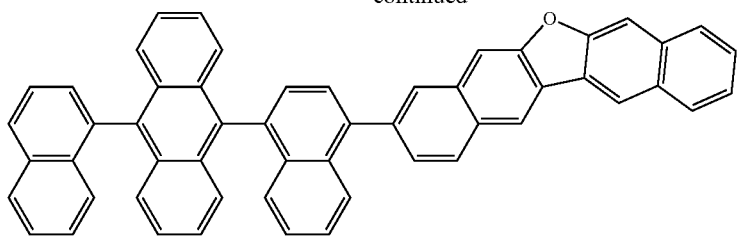
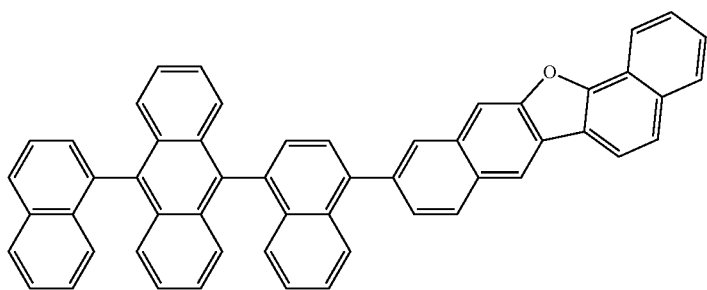
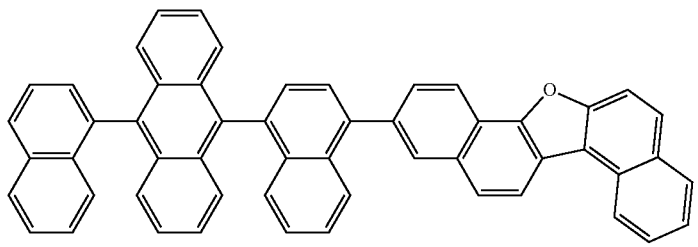
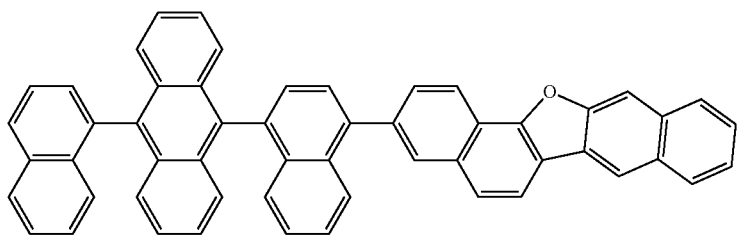
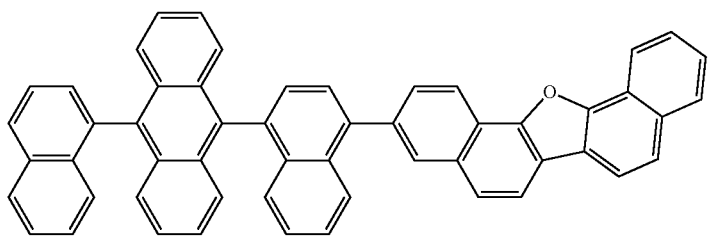
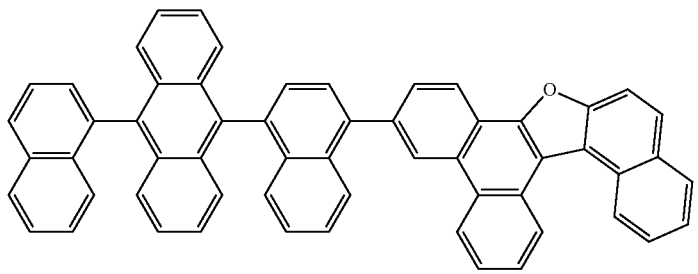

-continued
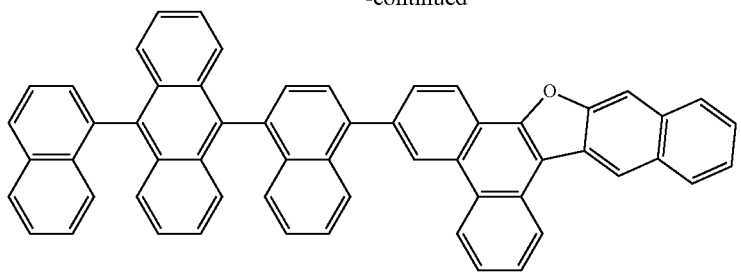
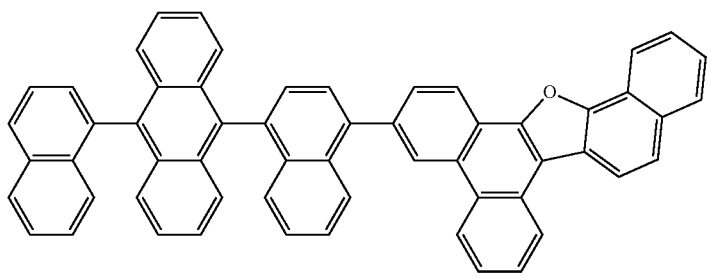
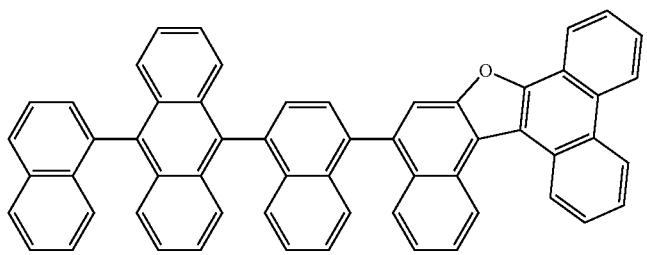
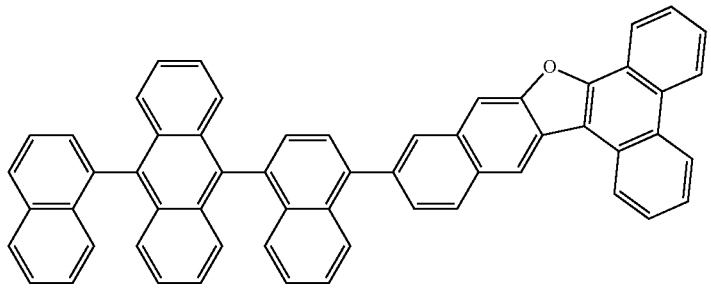
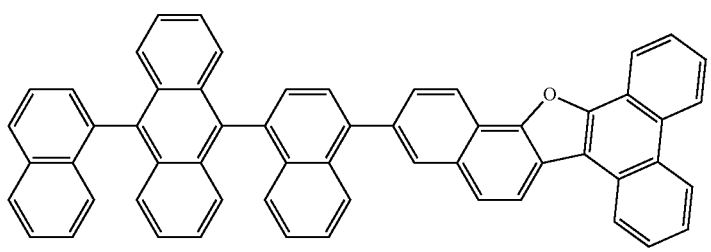
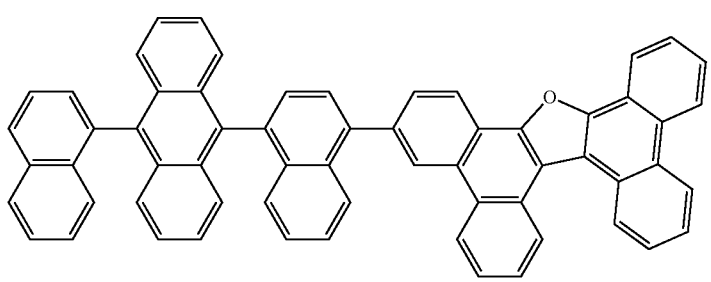

-continued
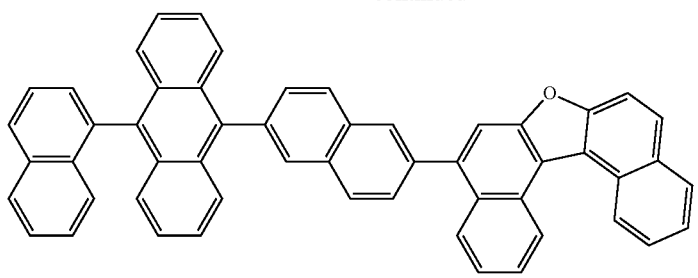
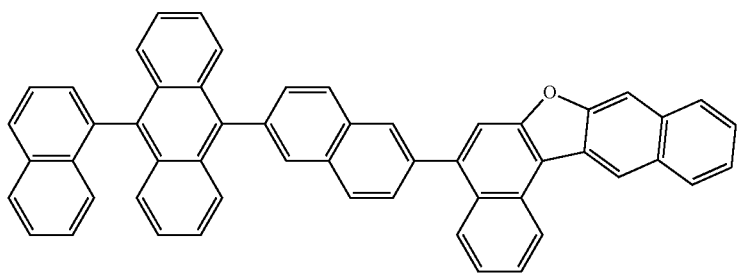
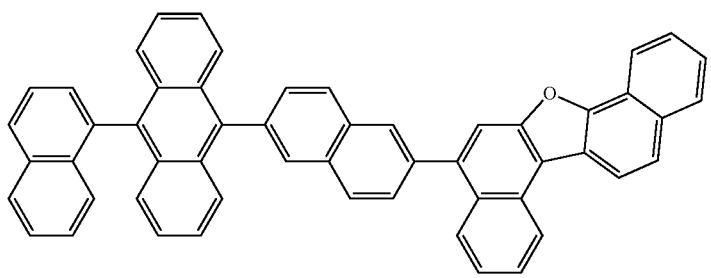
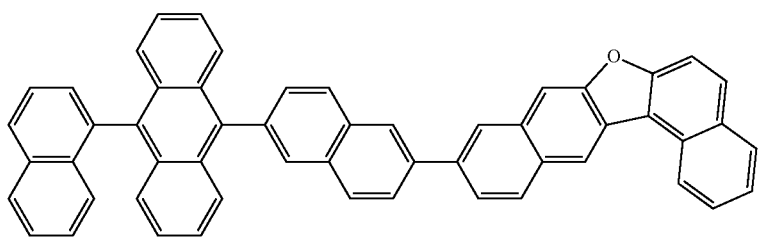
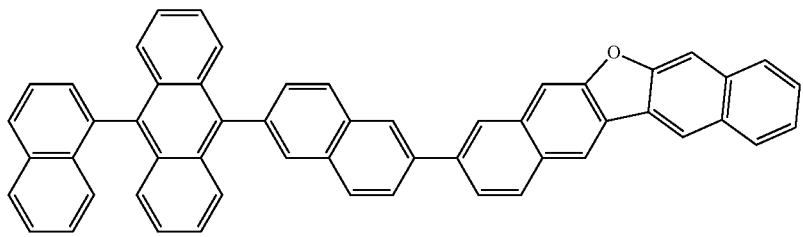
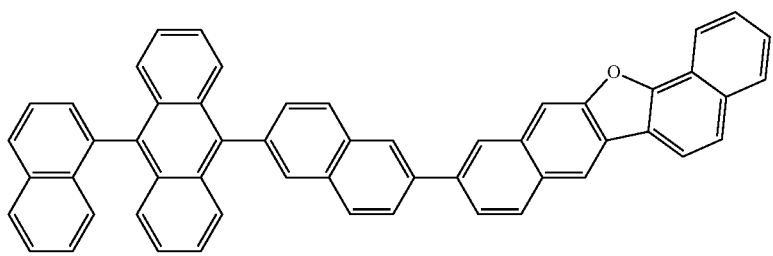

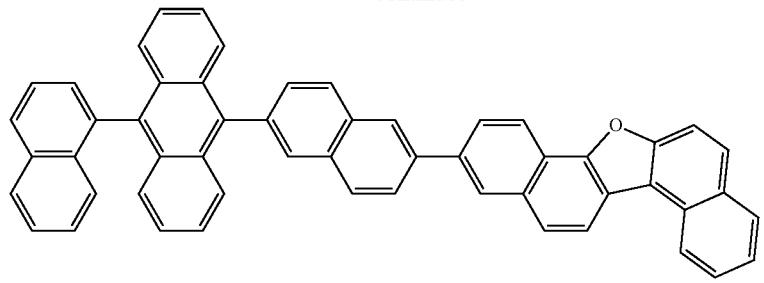
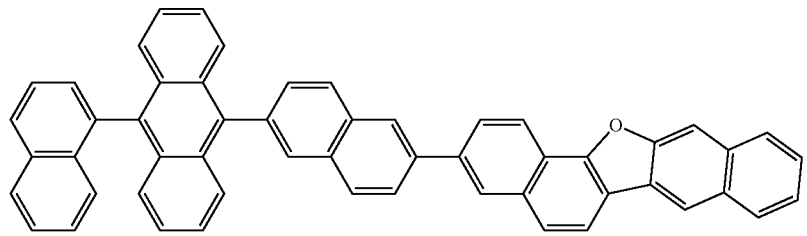
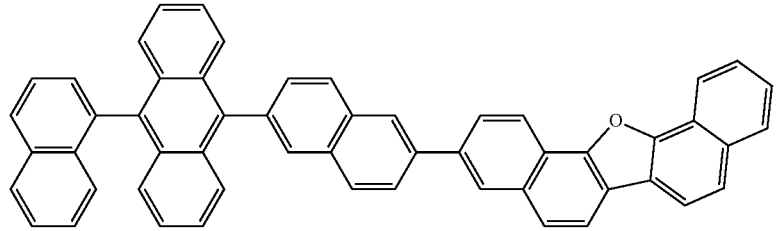
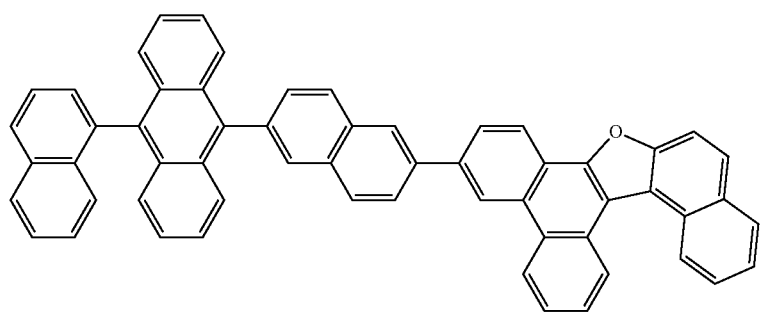
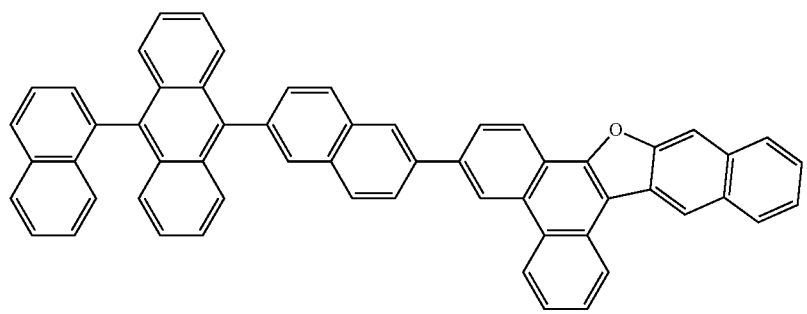
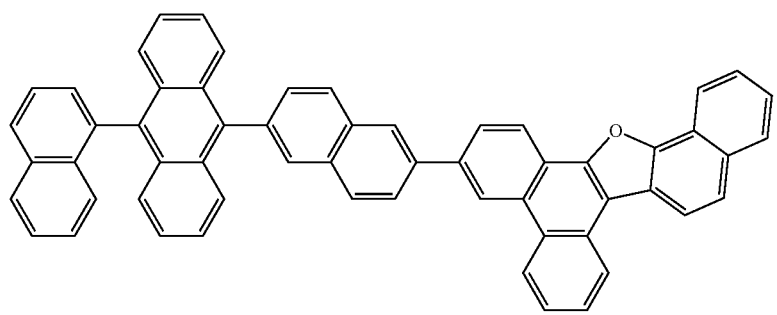

-continued
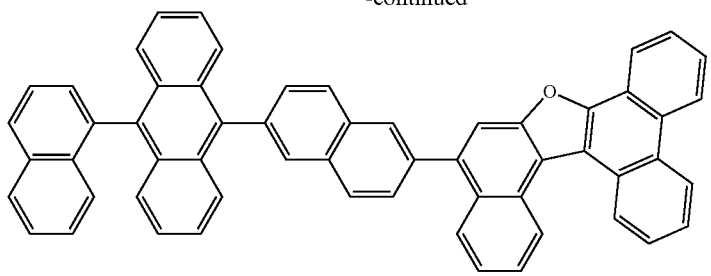
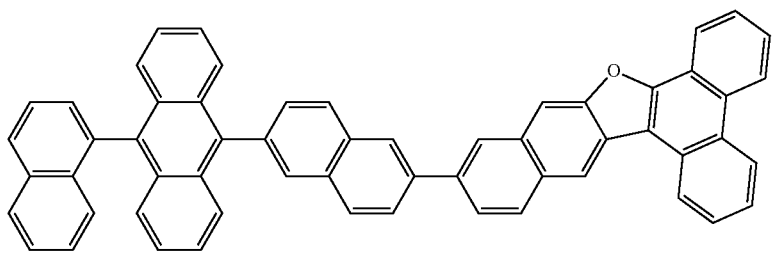
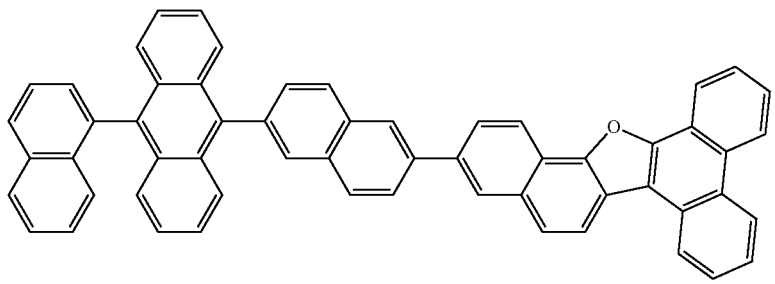
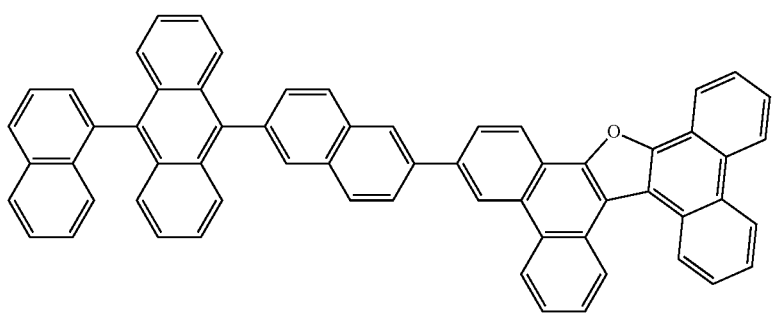
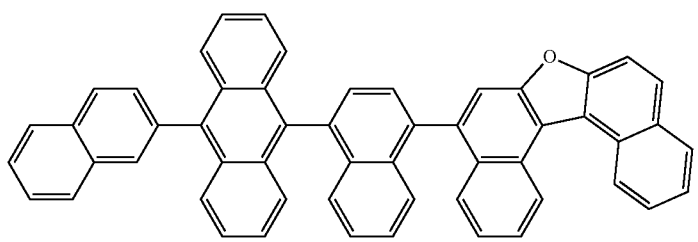
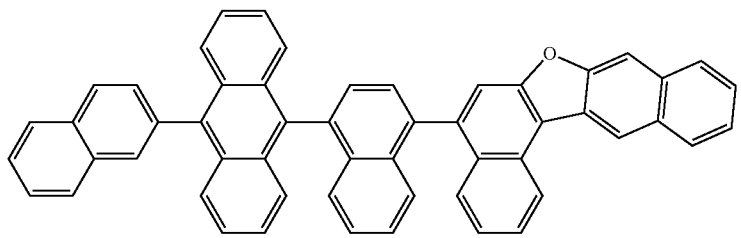

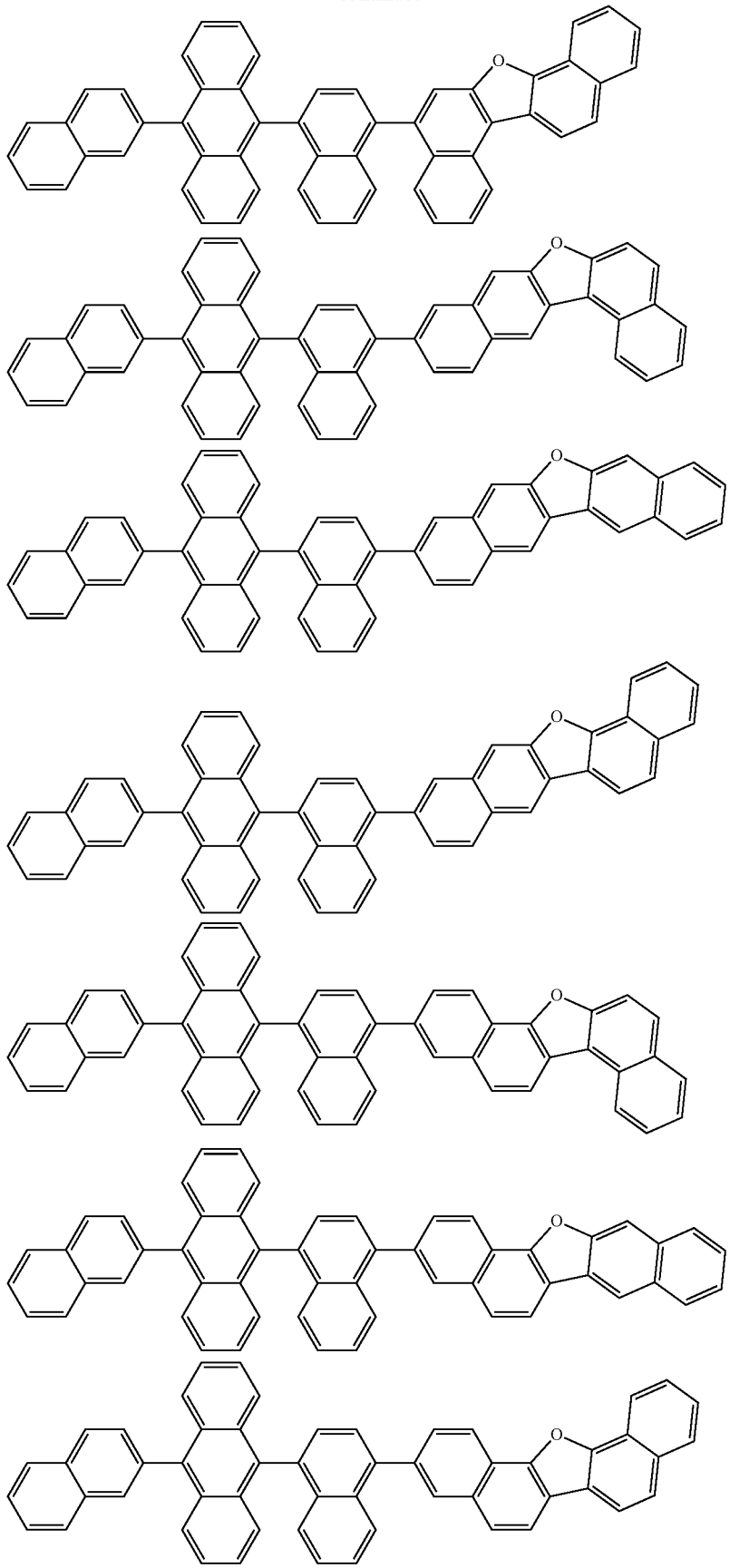

-continued
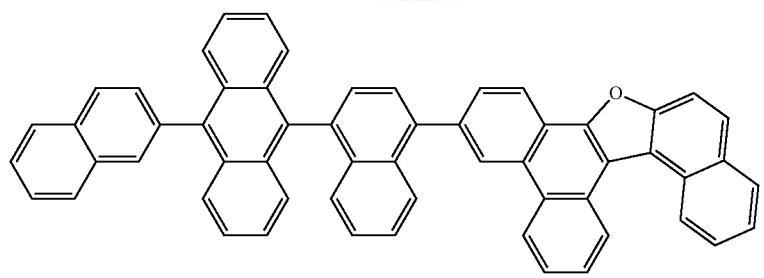
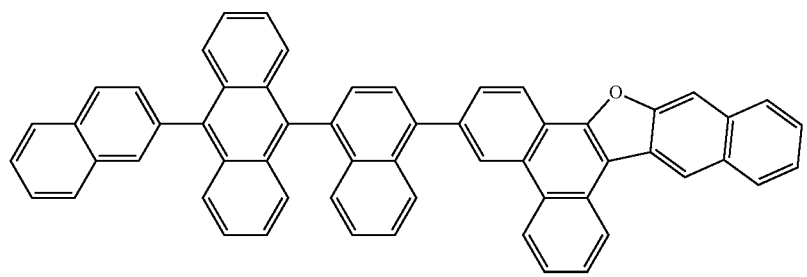
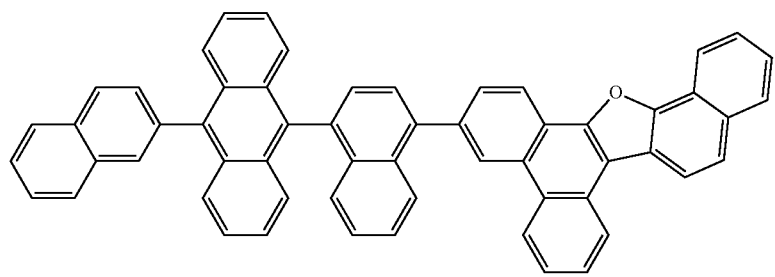
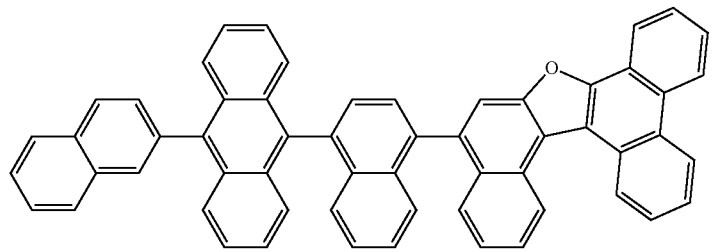
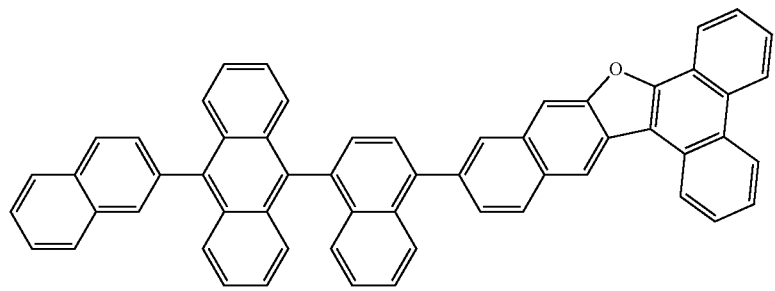
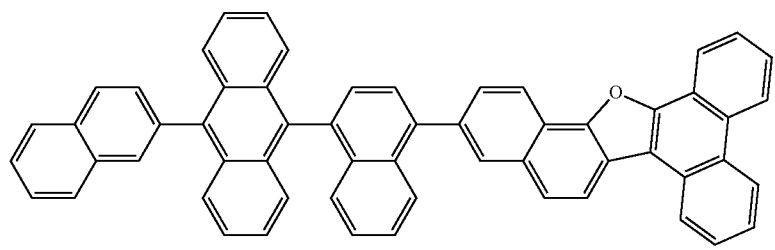

-continued
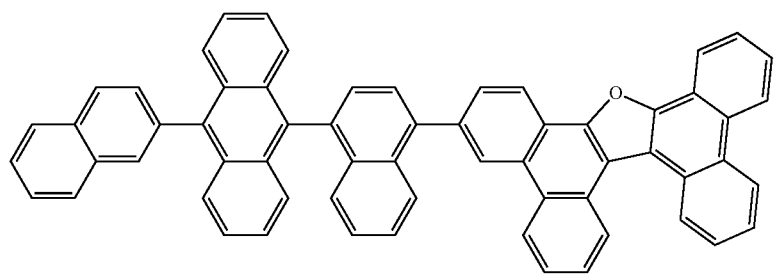
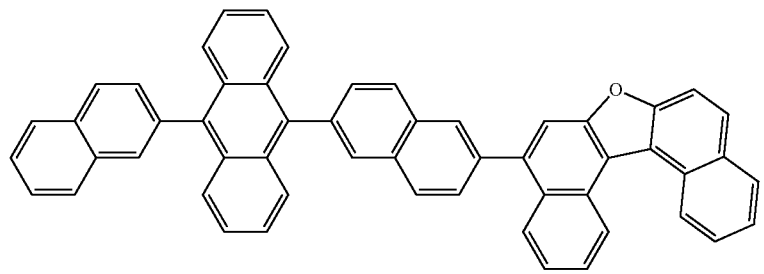
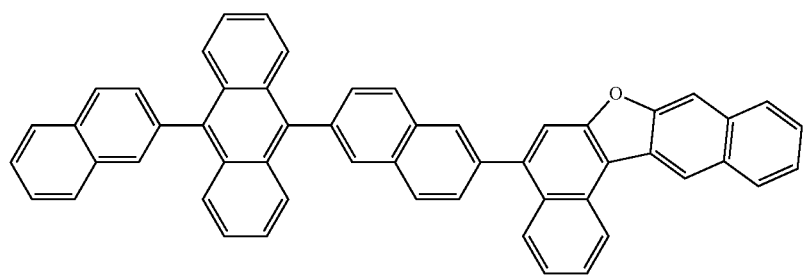
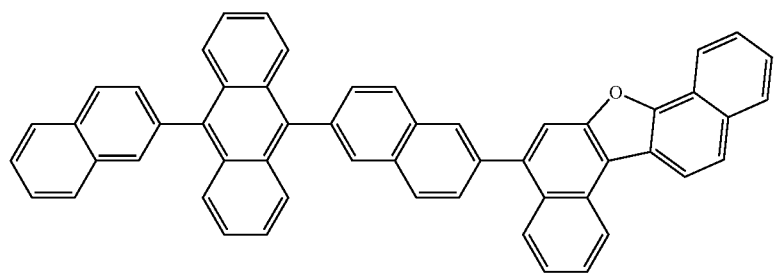
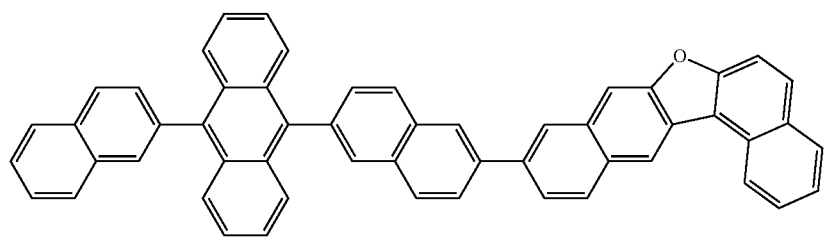
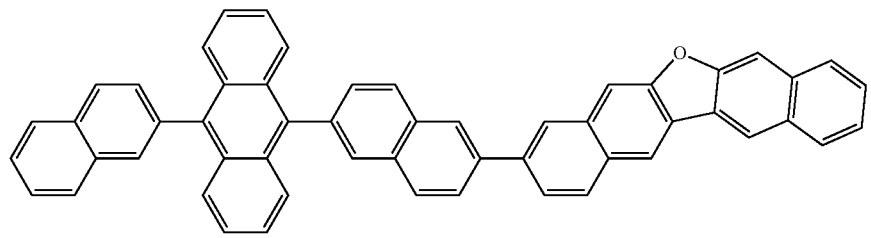

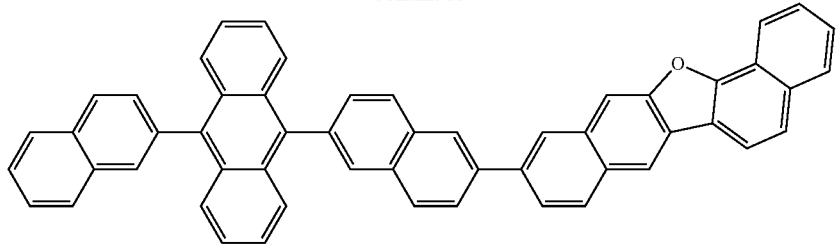
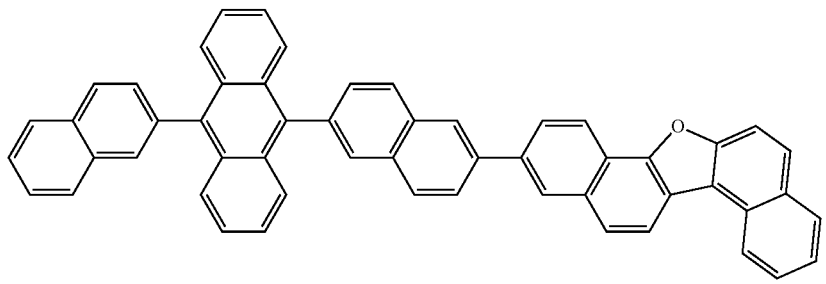
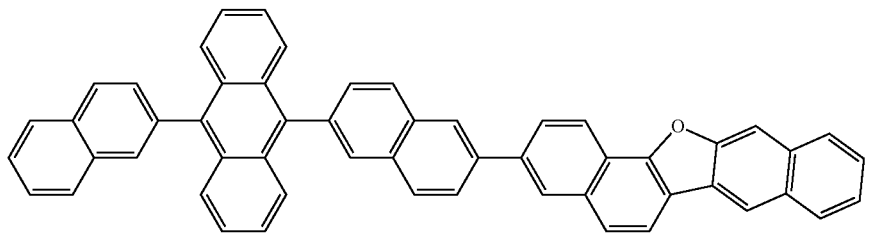
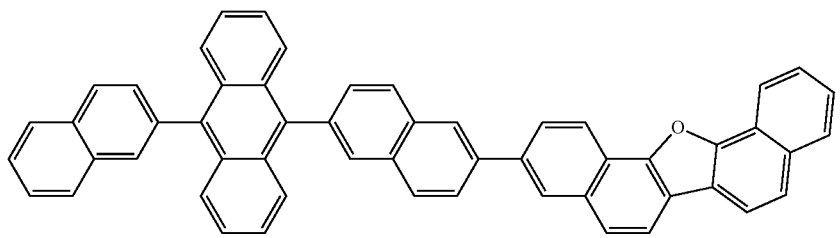
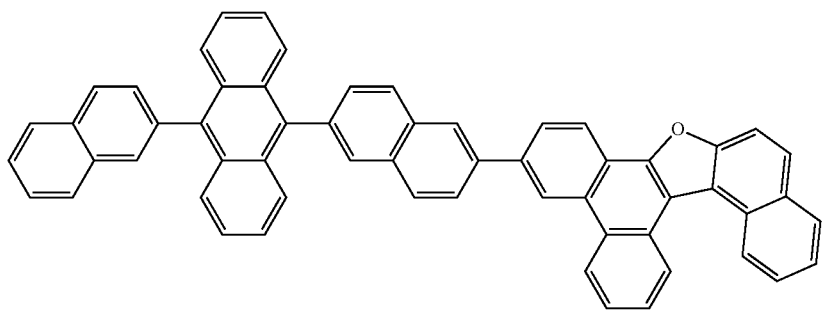
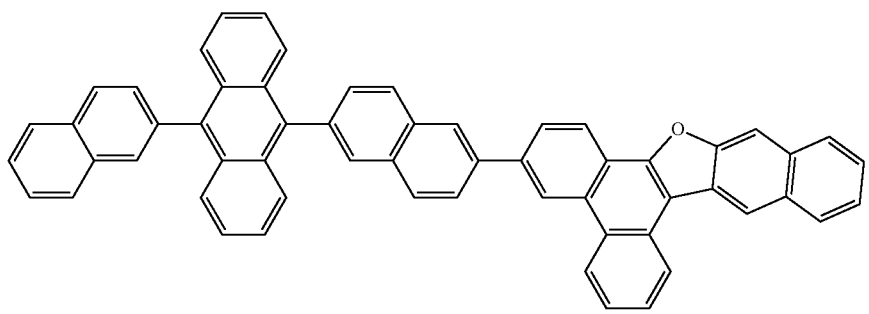

-continued
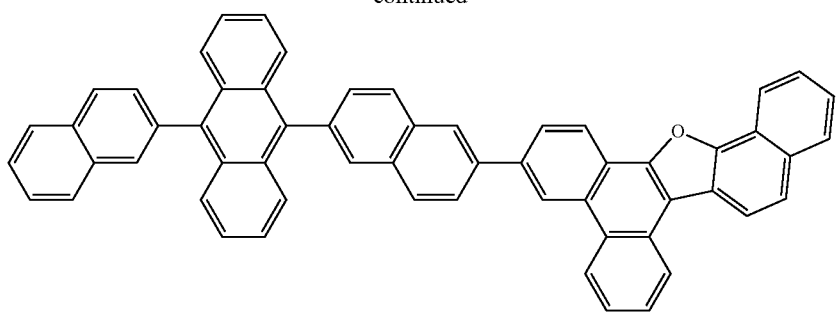
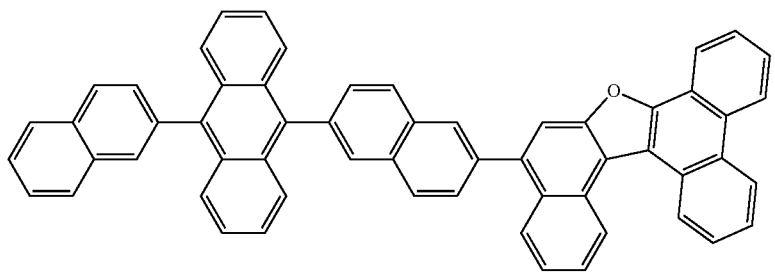
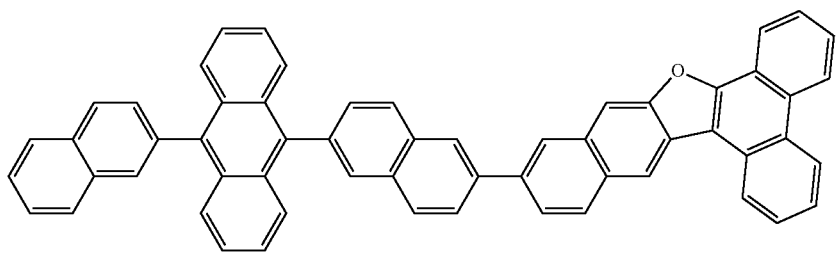
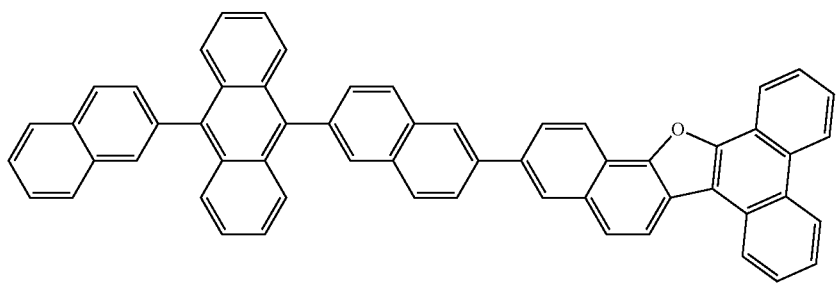
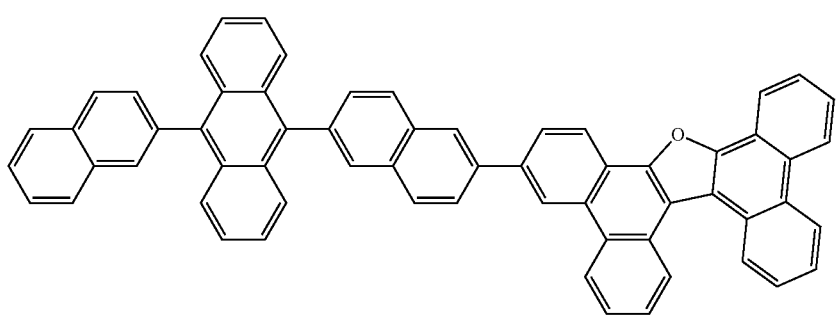

-continued
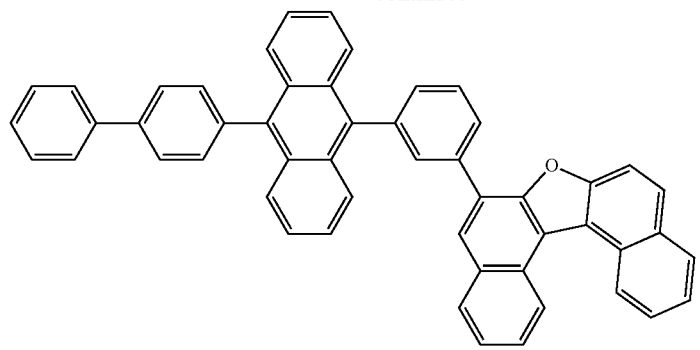
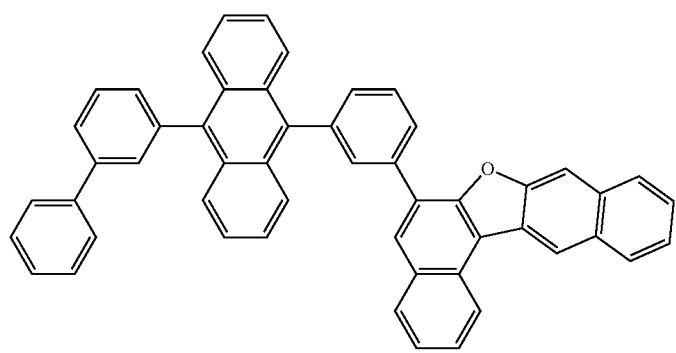
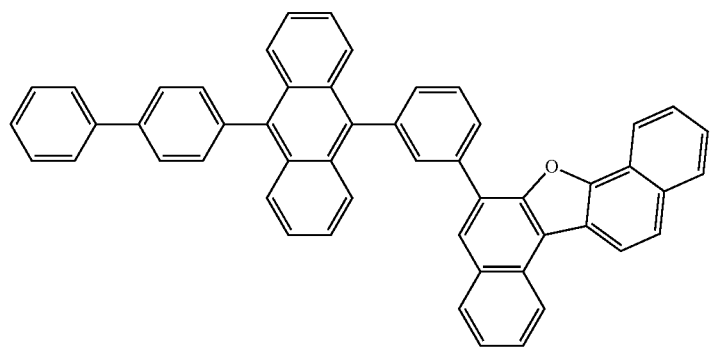
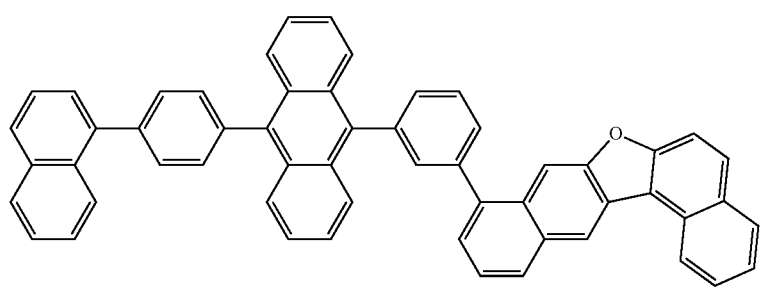
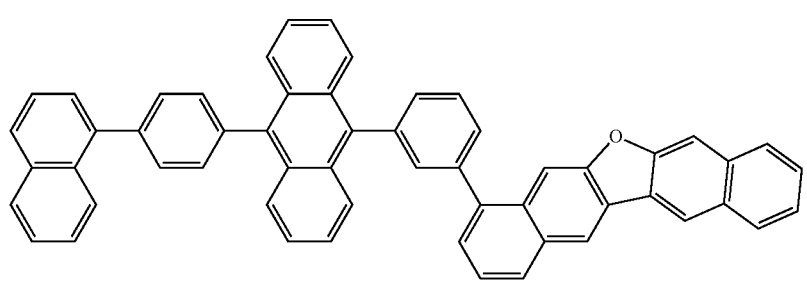

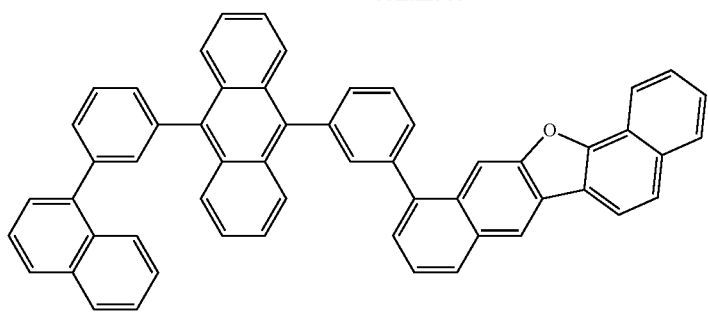
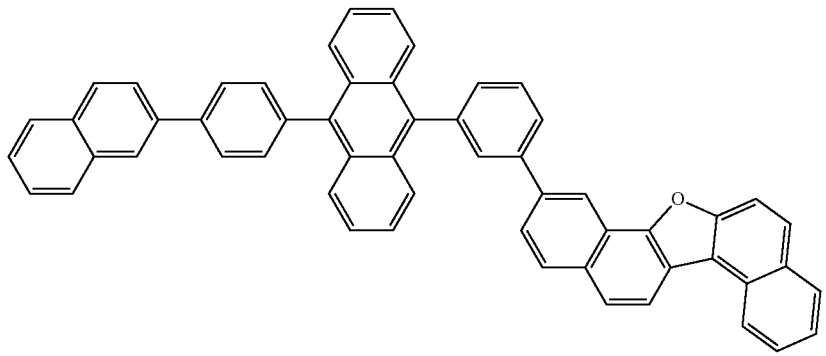
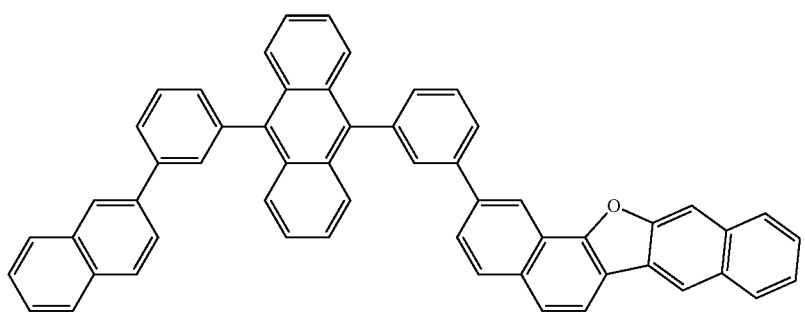
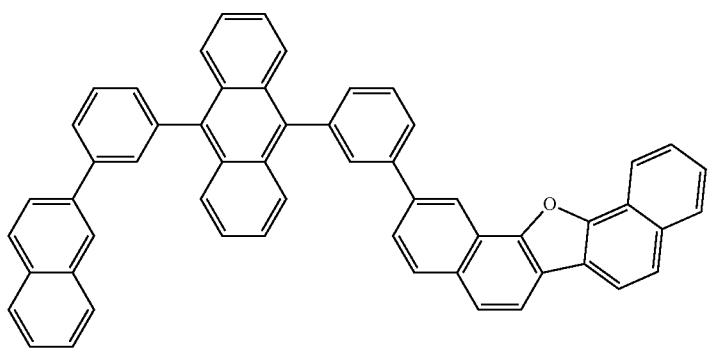
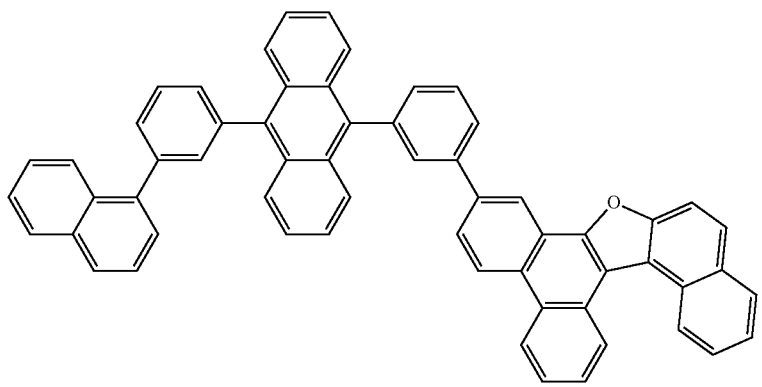

-continued
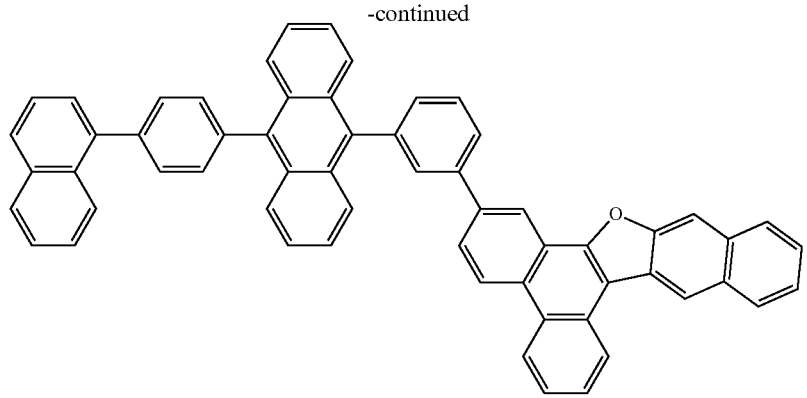
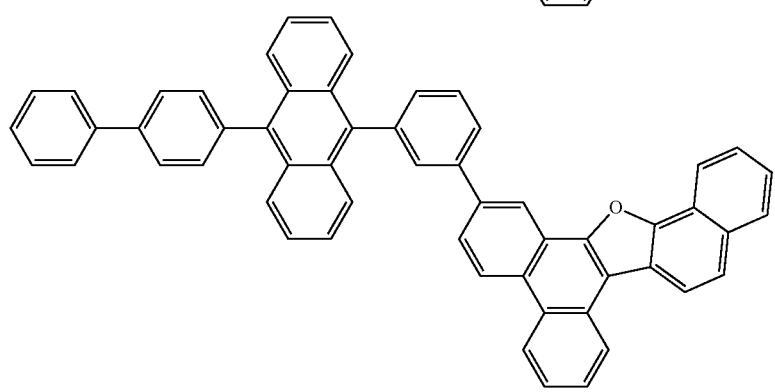
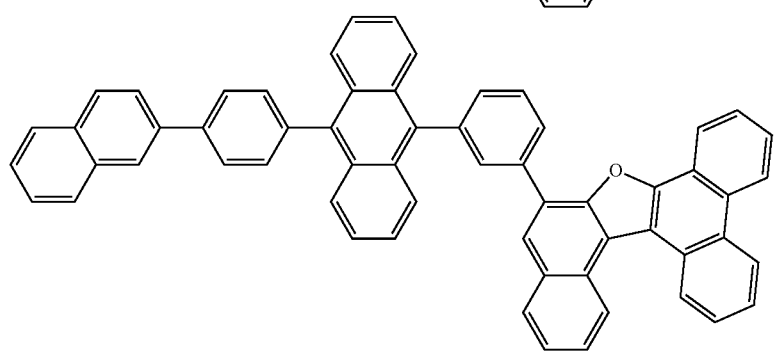
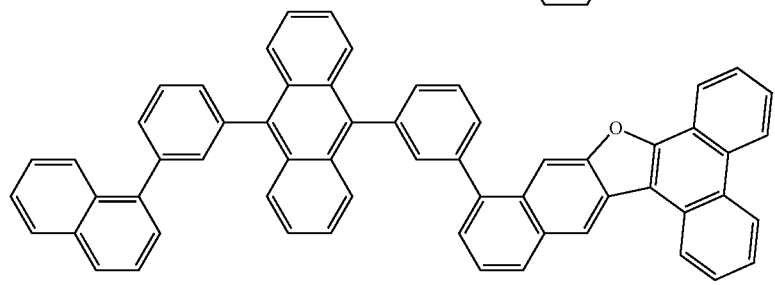
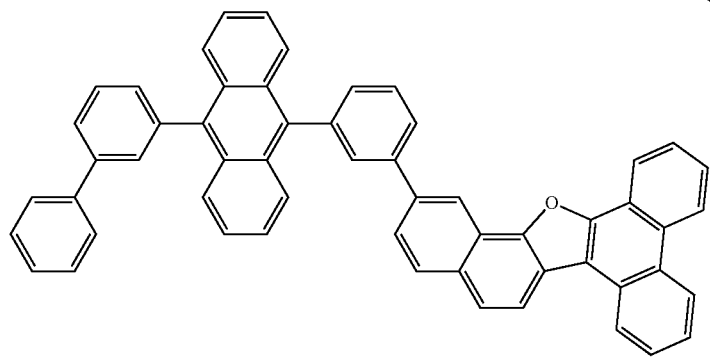

-continued
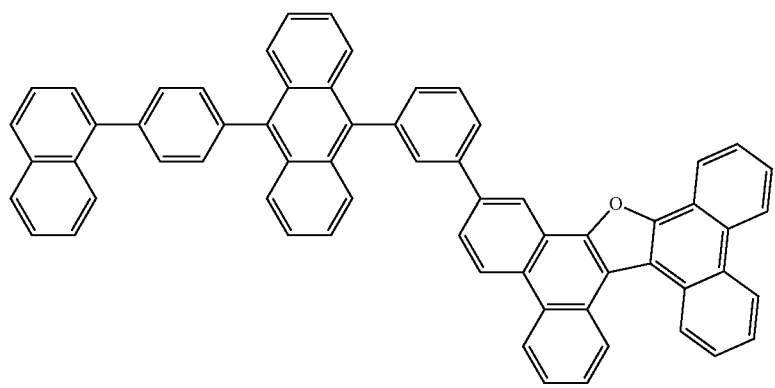
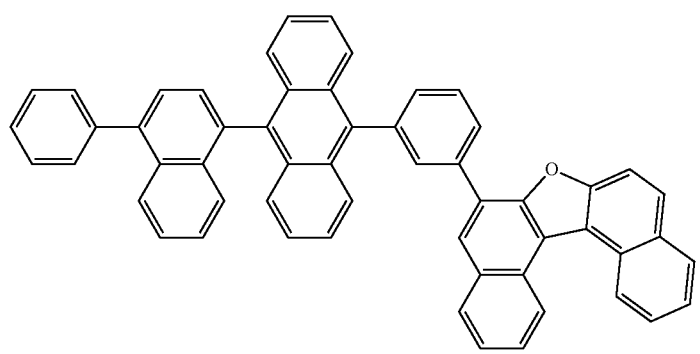
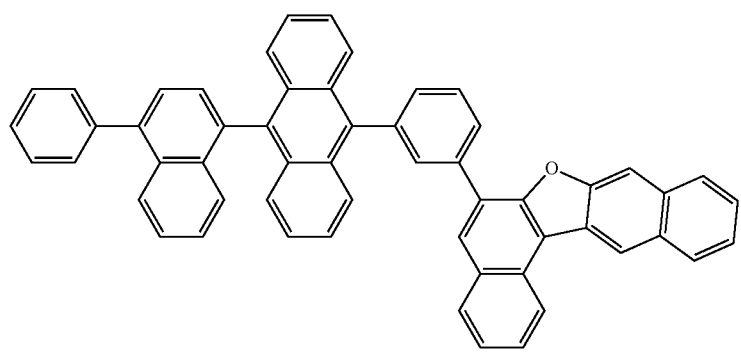
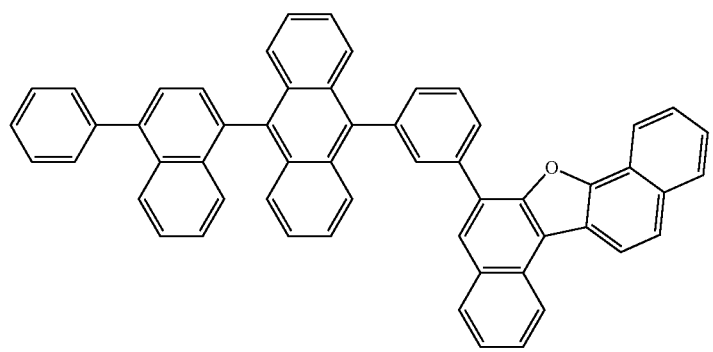
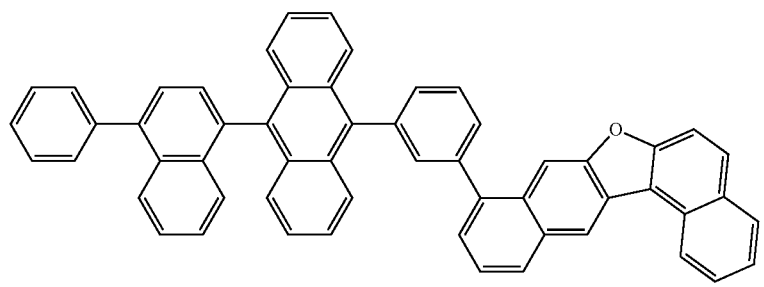

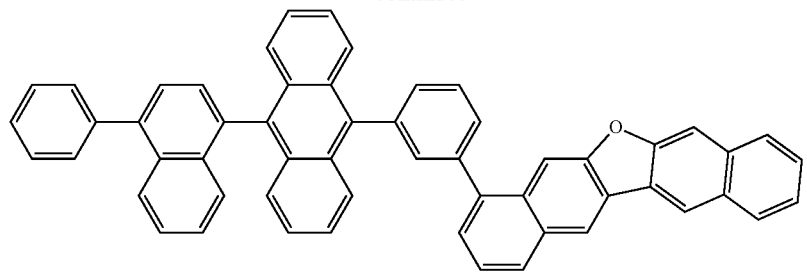
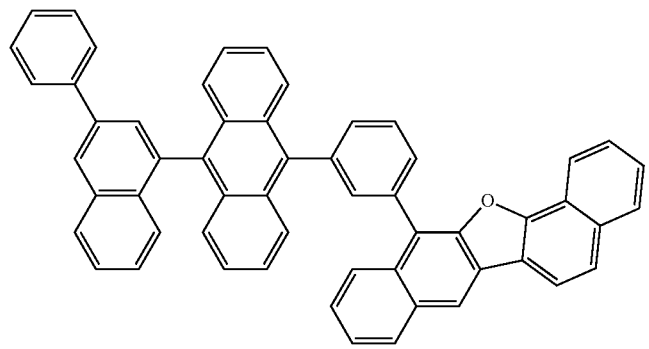
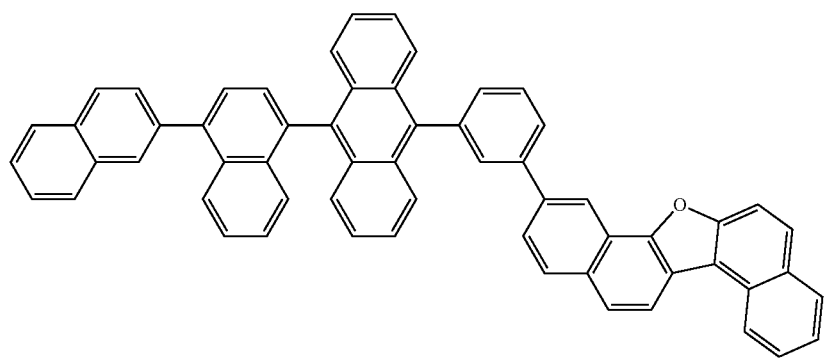
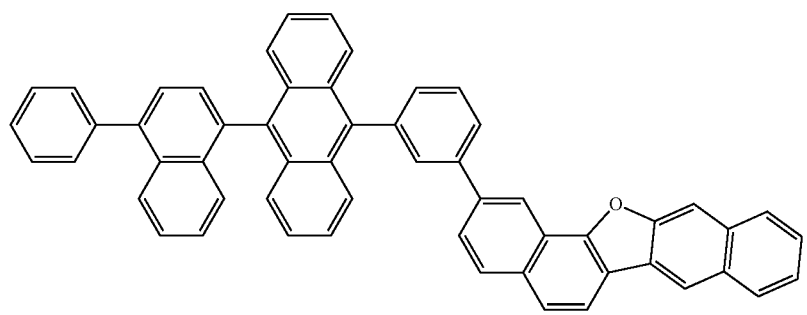
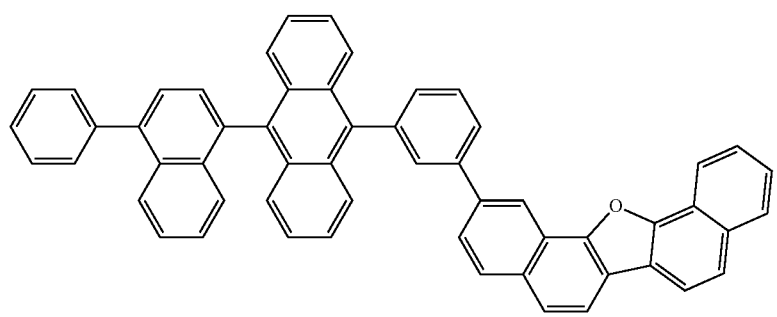

-continued
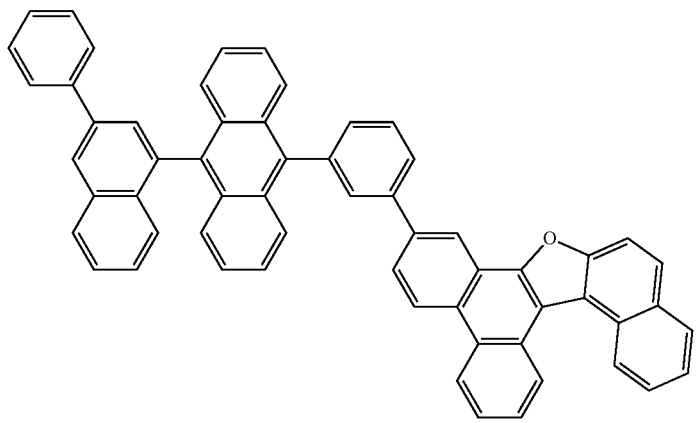
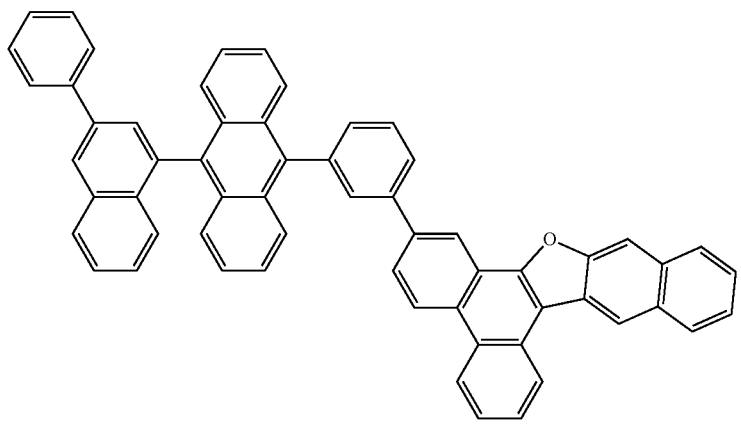
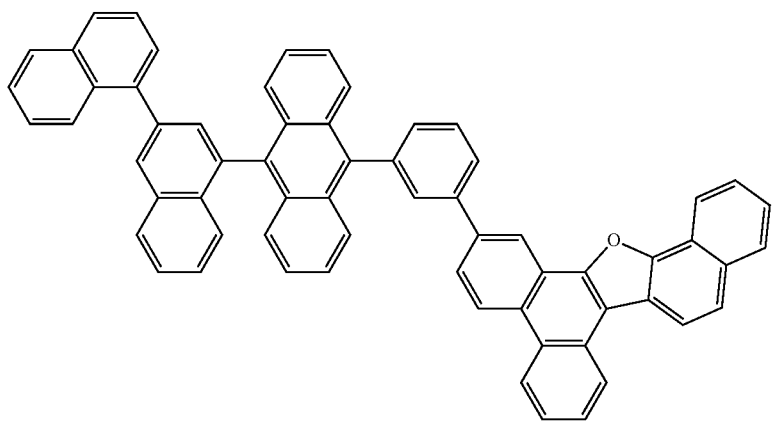
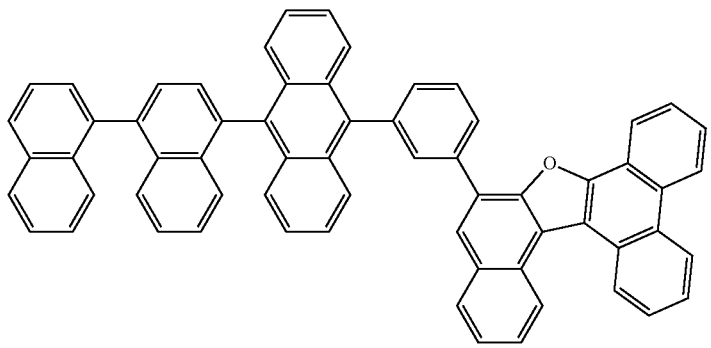

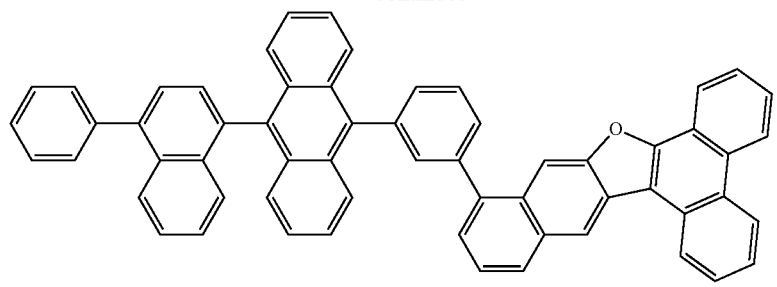
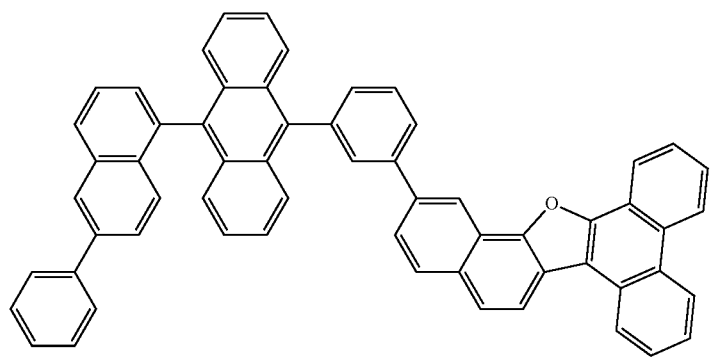
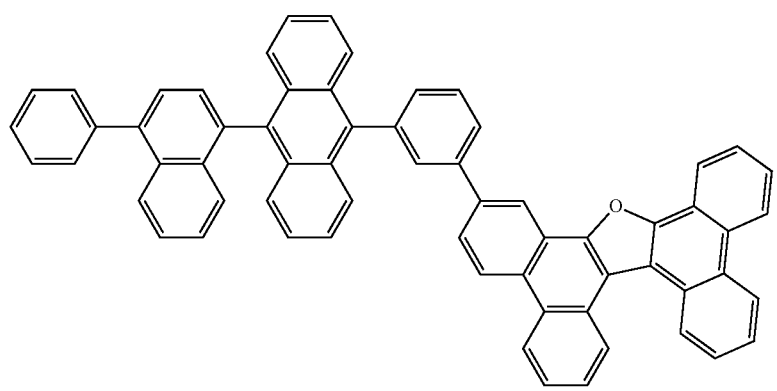
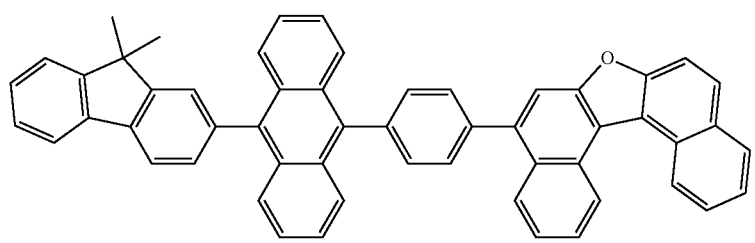
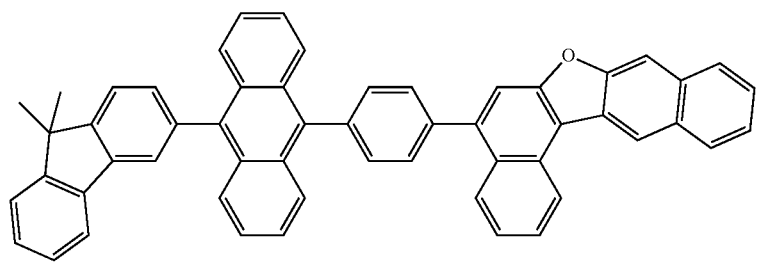

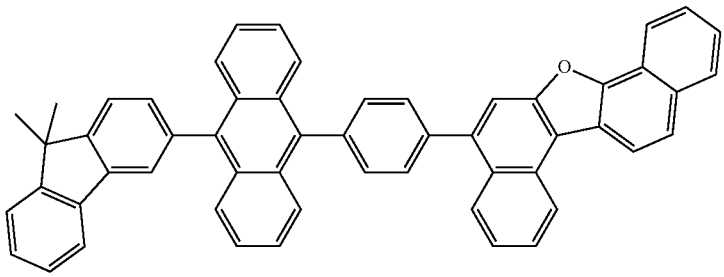
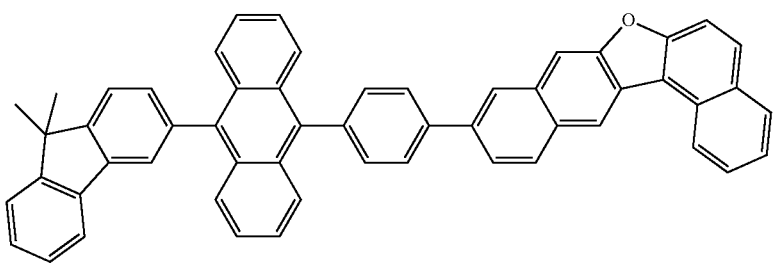
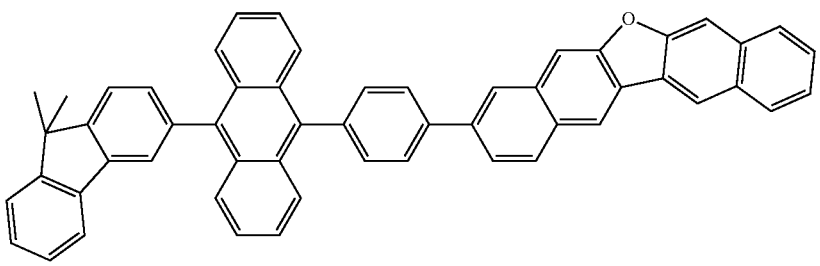
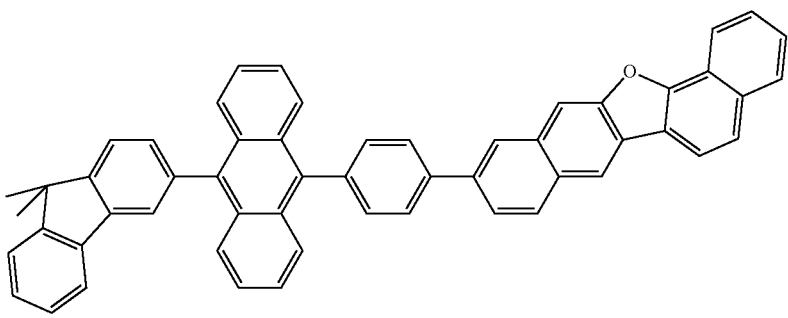
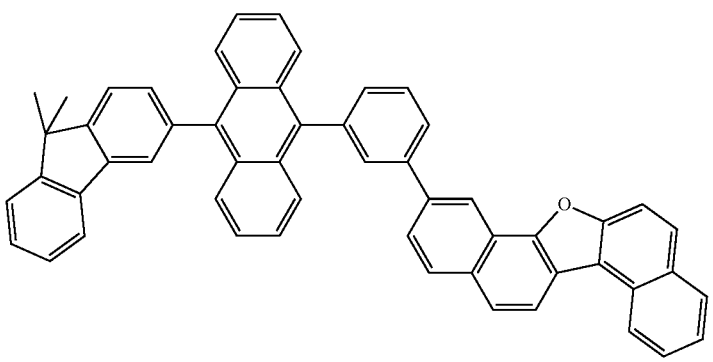

-continued
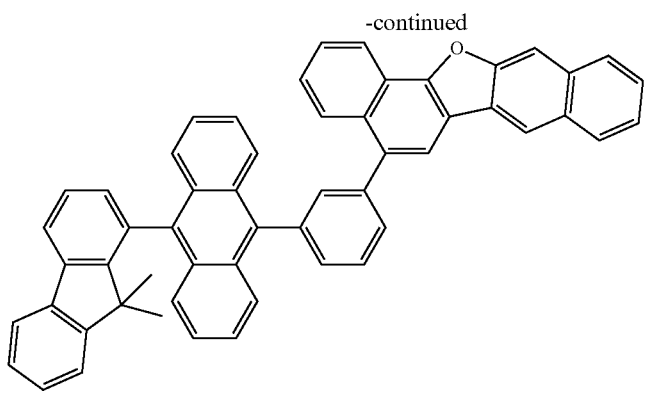
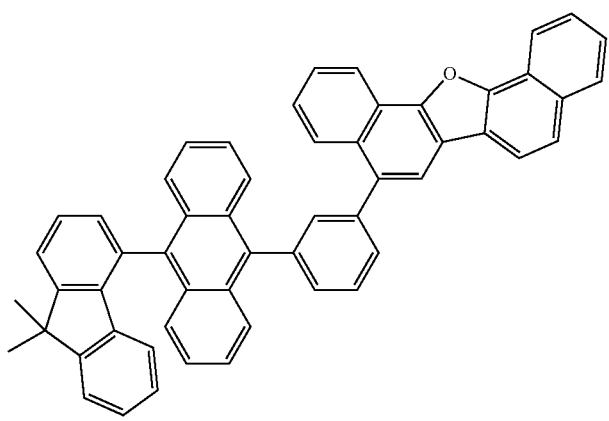
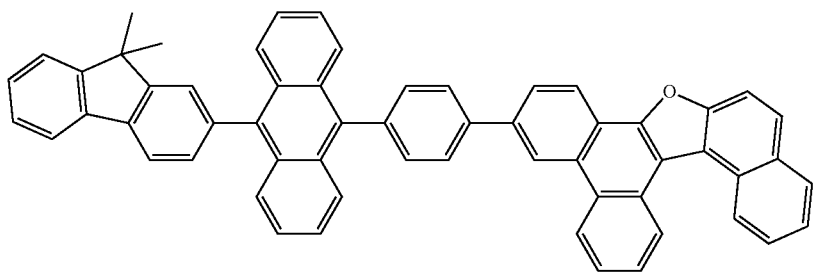
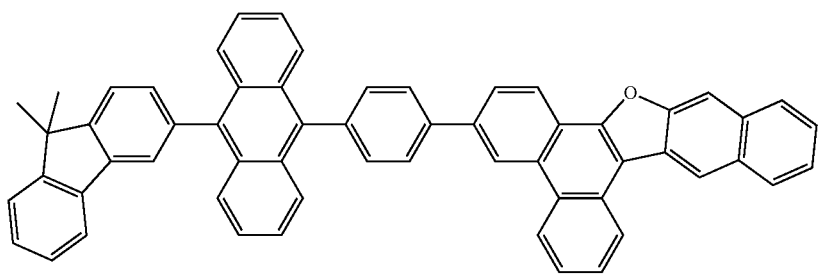
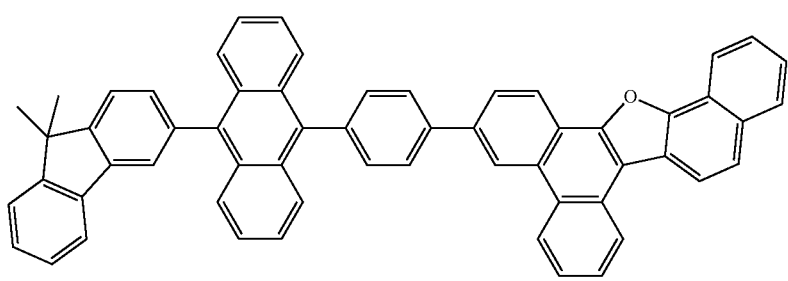

-continued
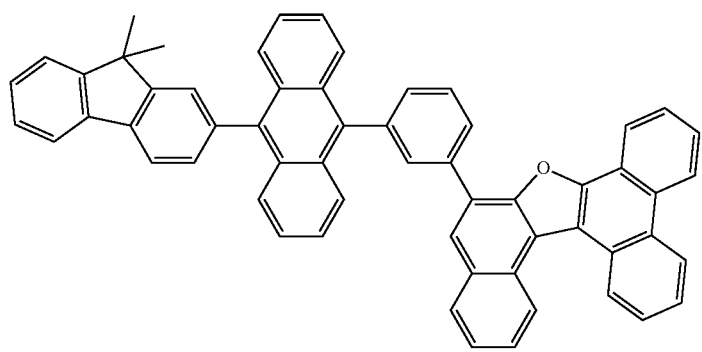
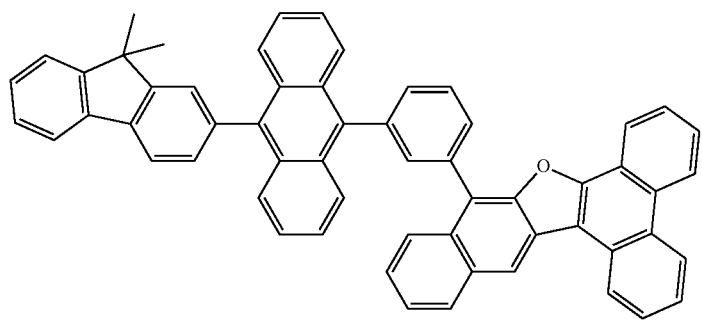
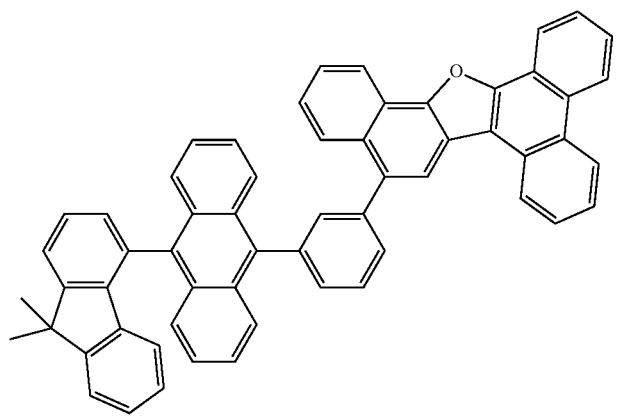
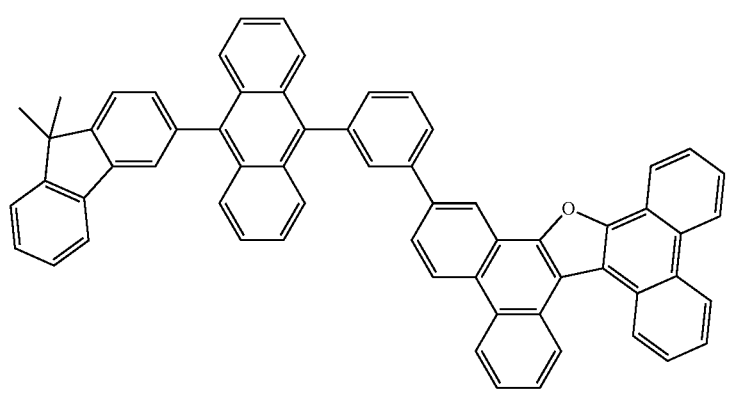
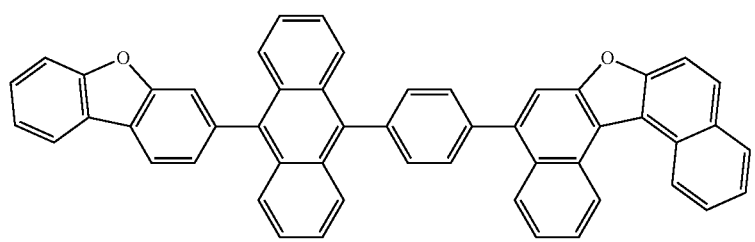

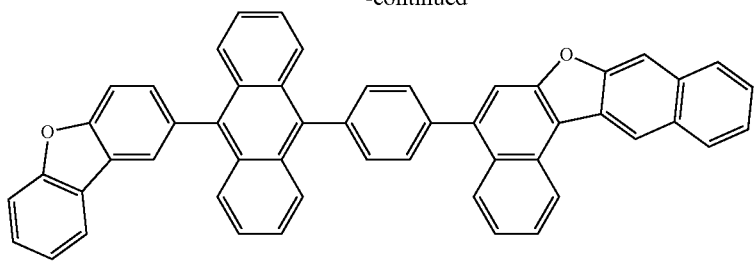
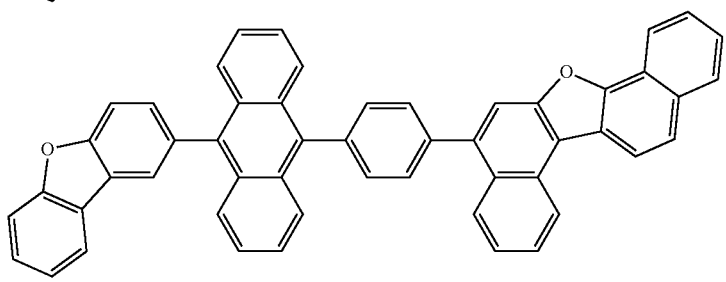
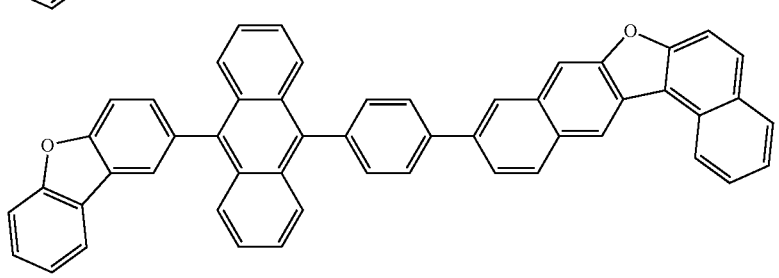
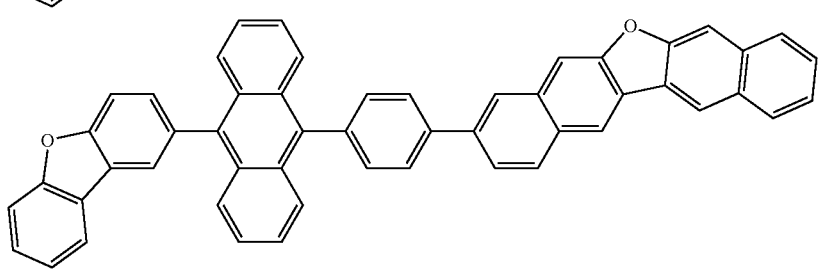
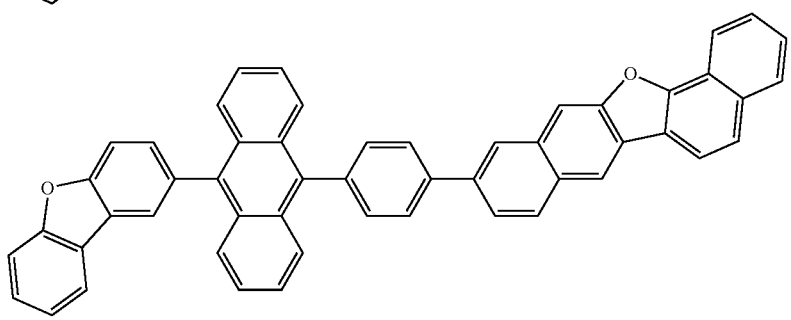
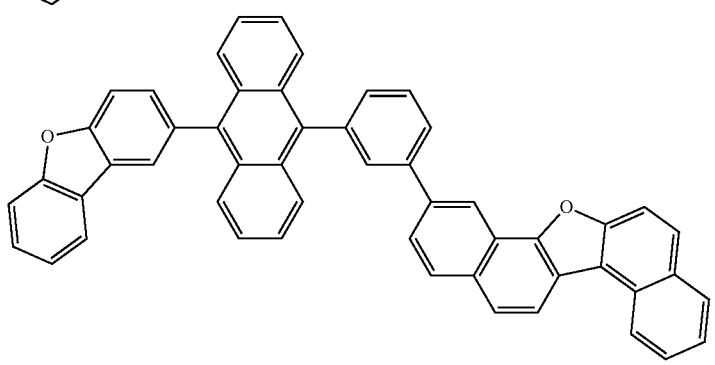

-continued
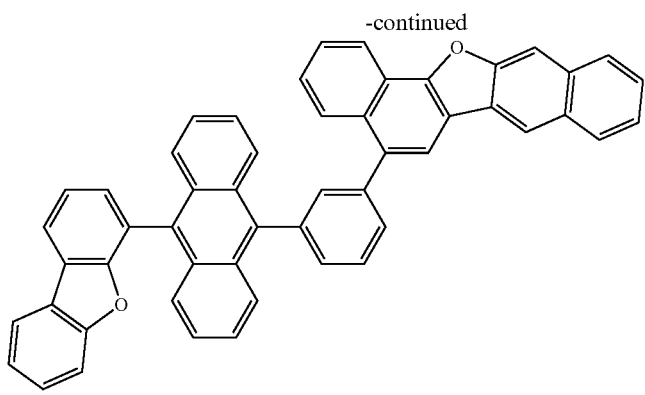
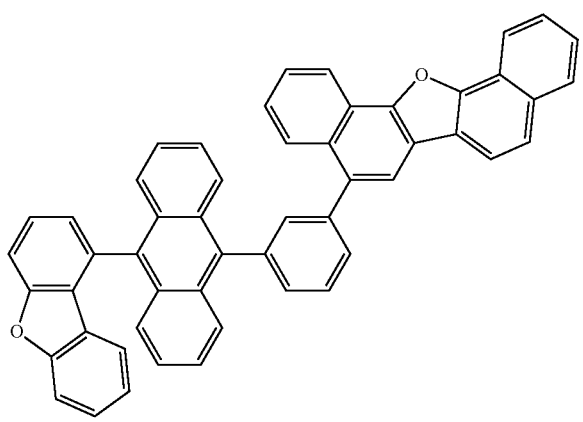
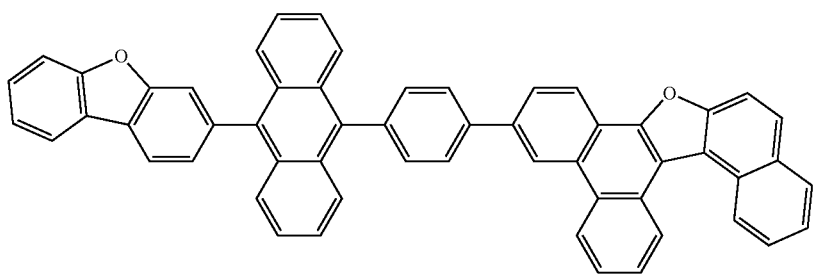
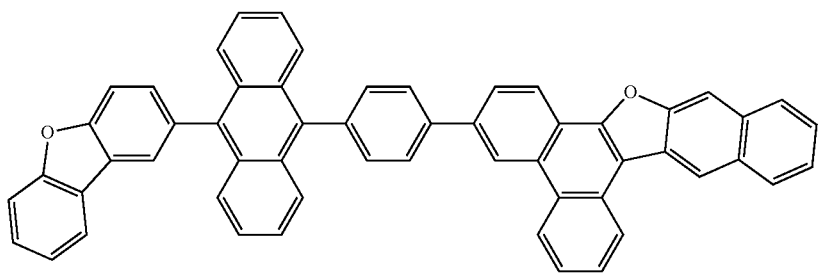
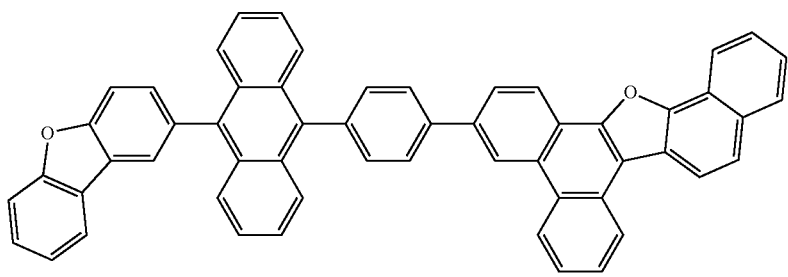

-continued
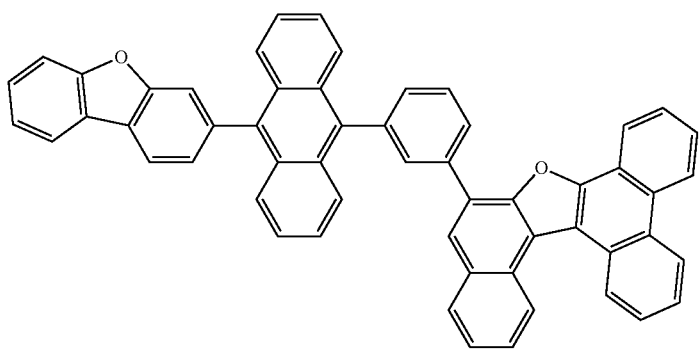

-continued
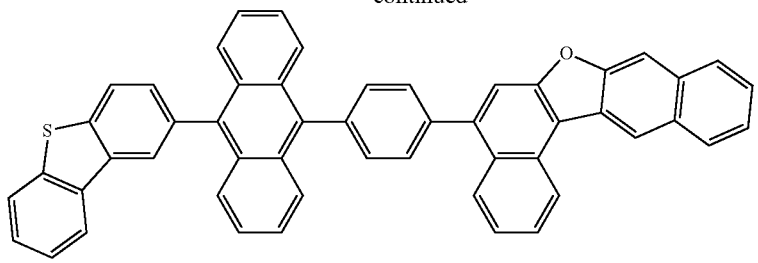
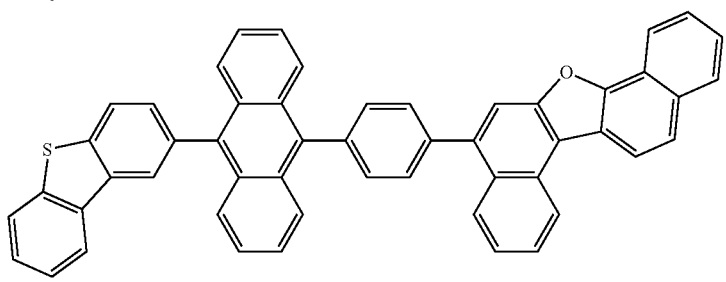
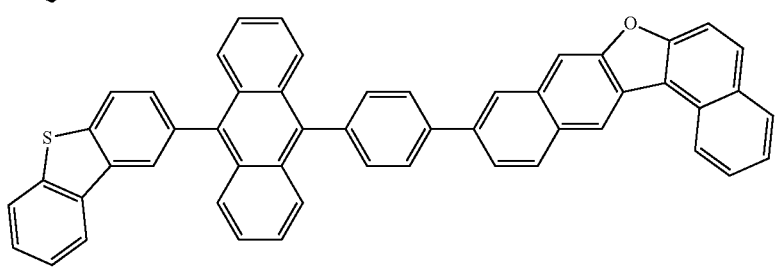
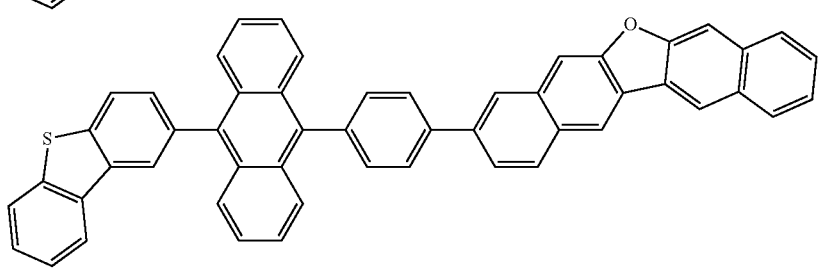
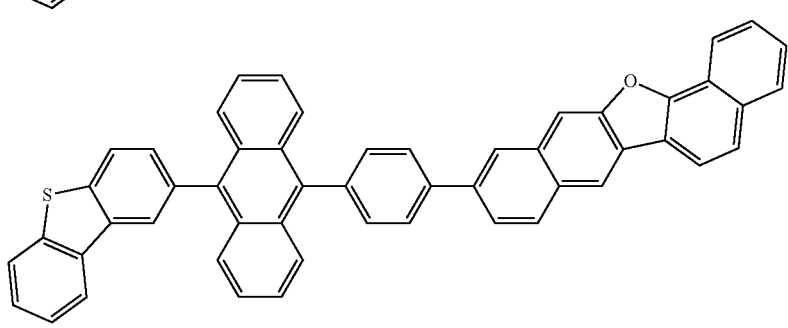
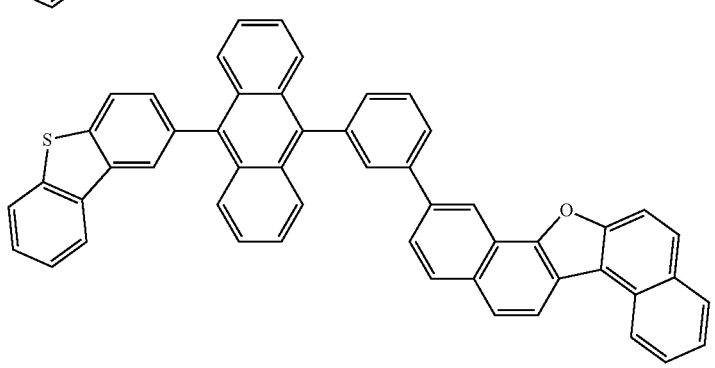

-continued
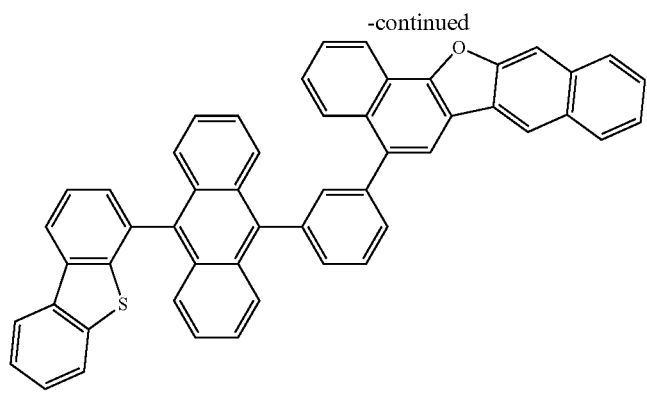
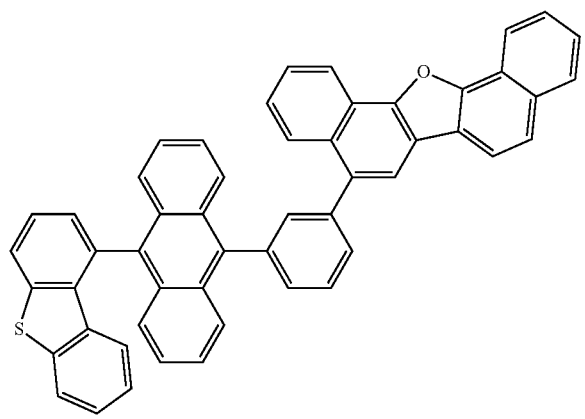
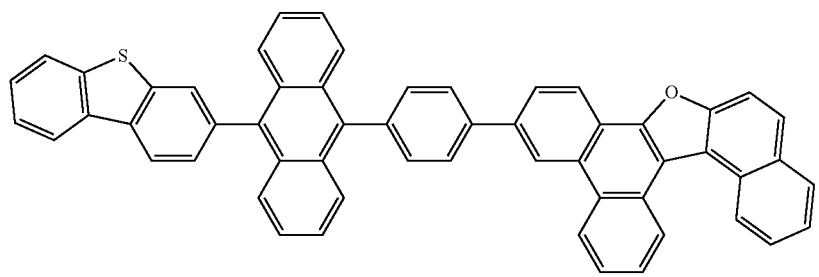
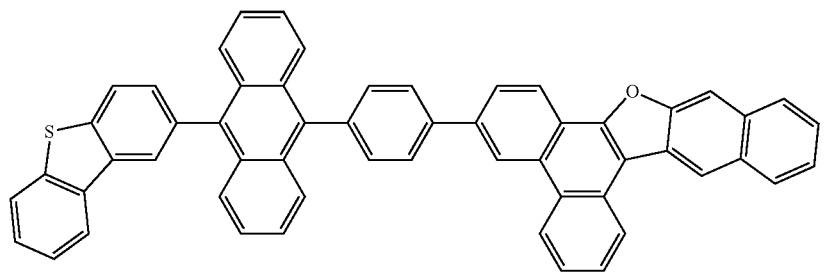
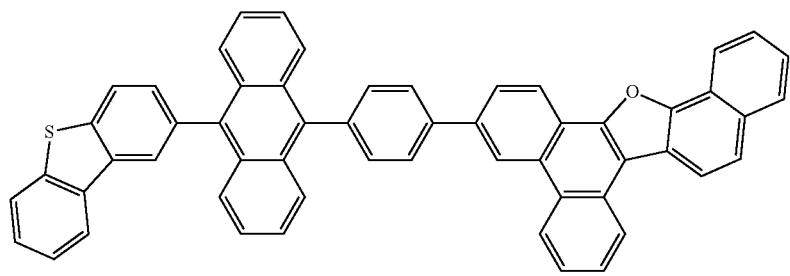

-continued
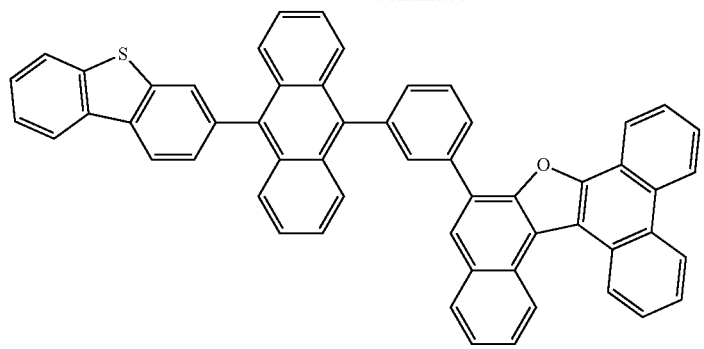
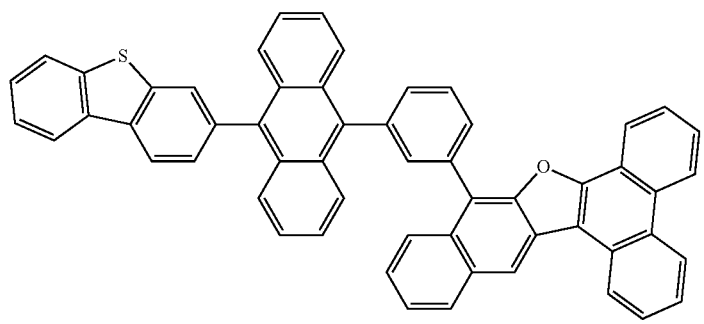
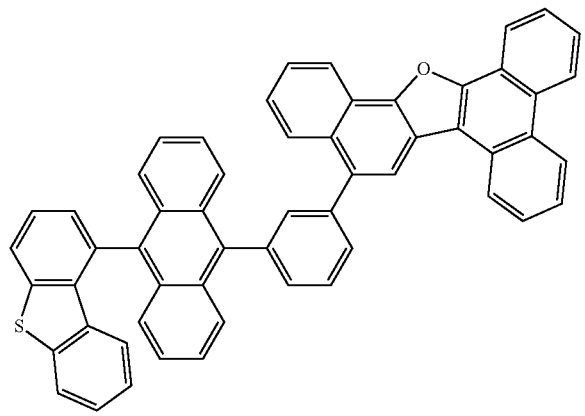
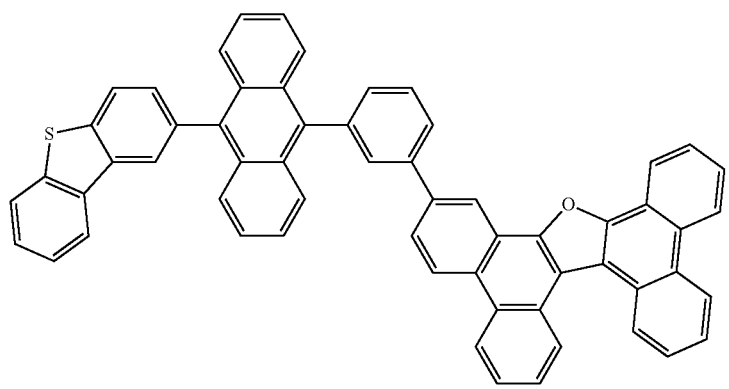

-continued
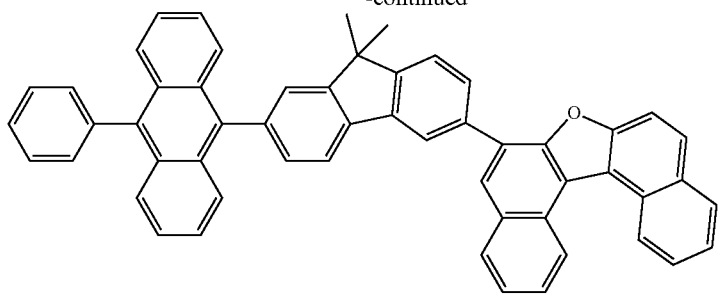
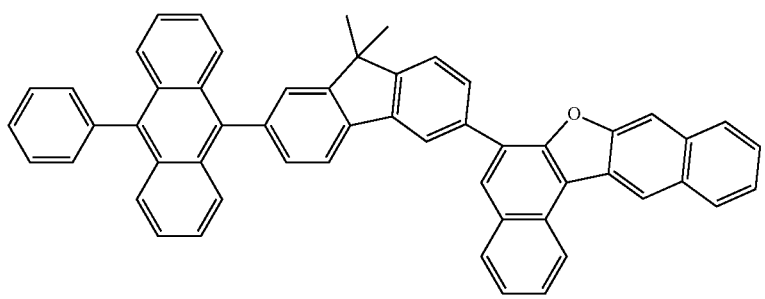
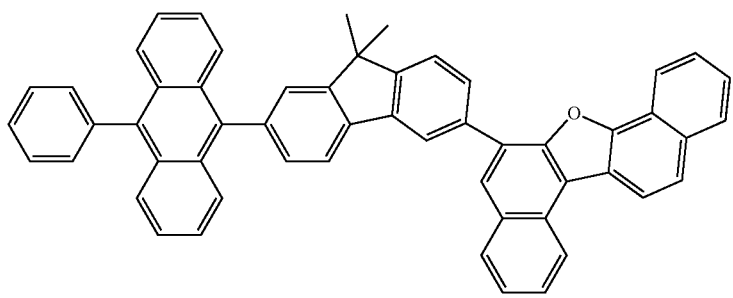
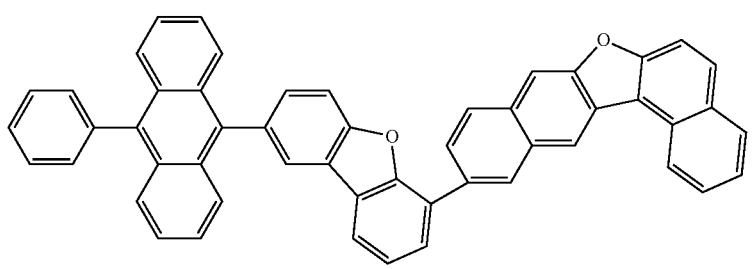
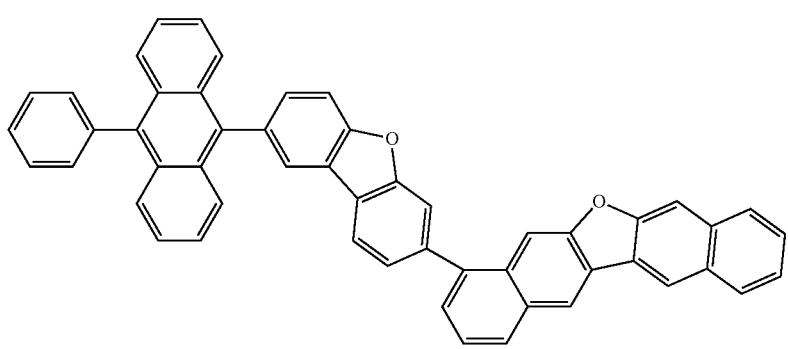

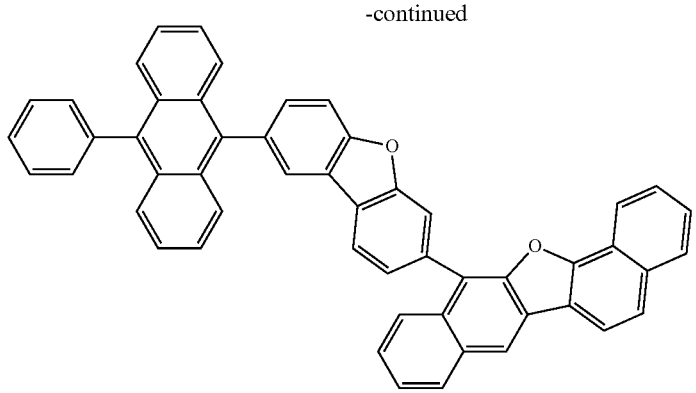
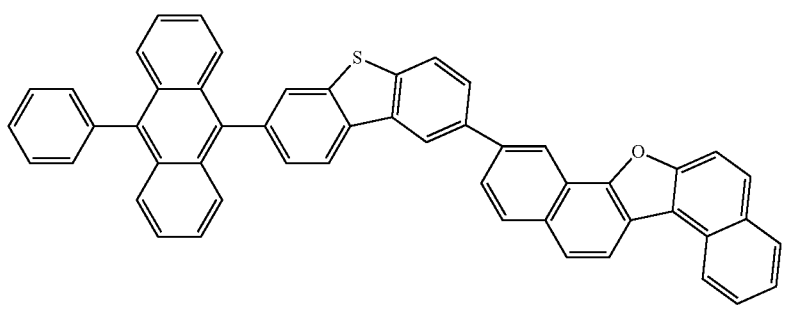
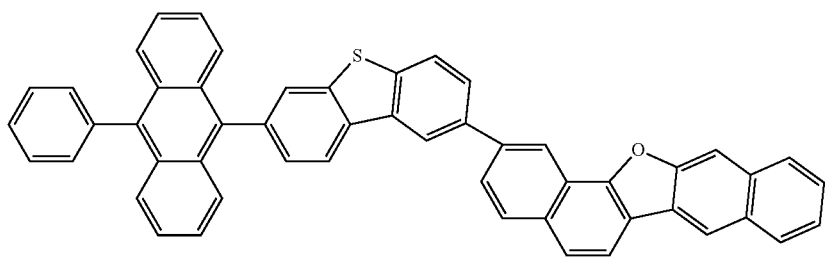
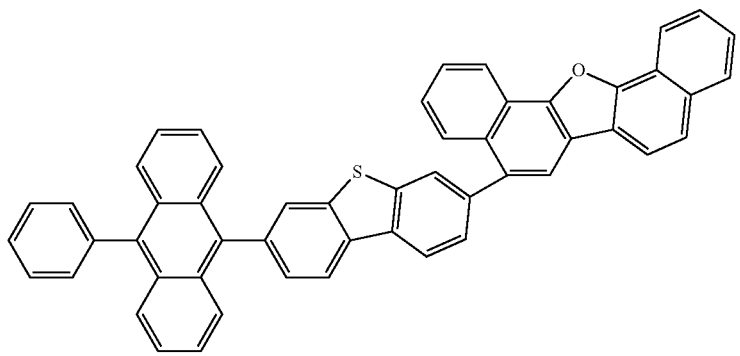
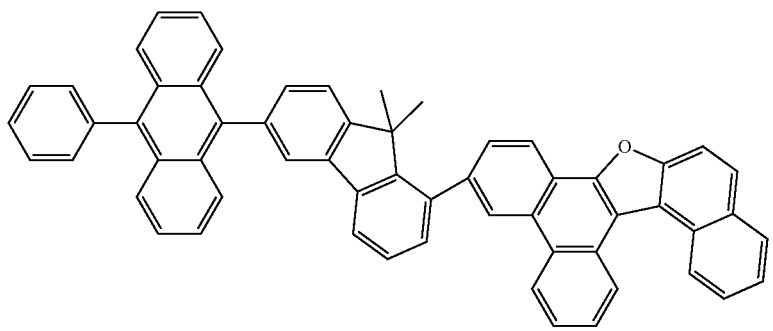

-continued
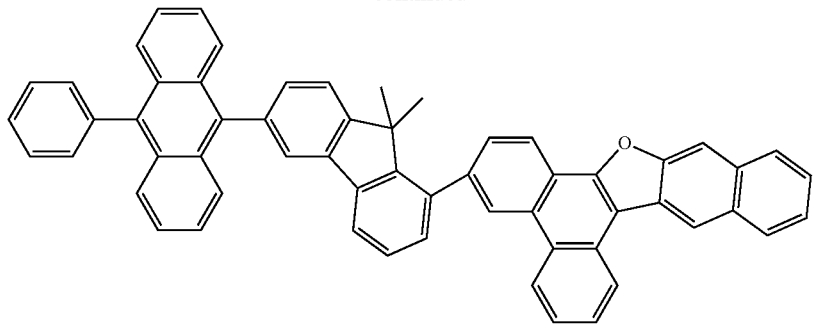
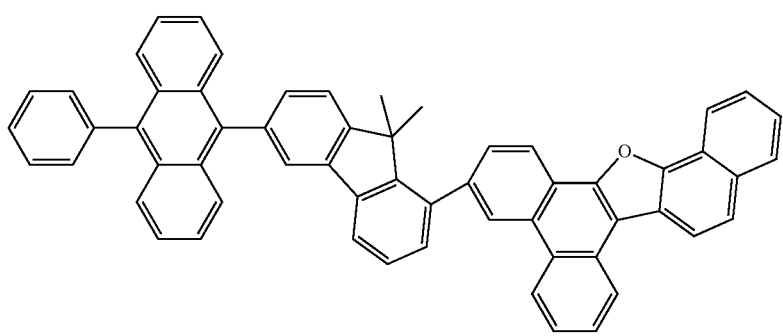
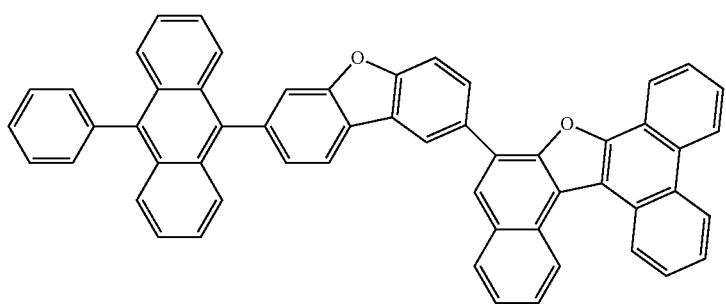

-continued
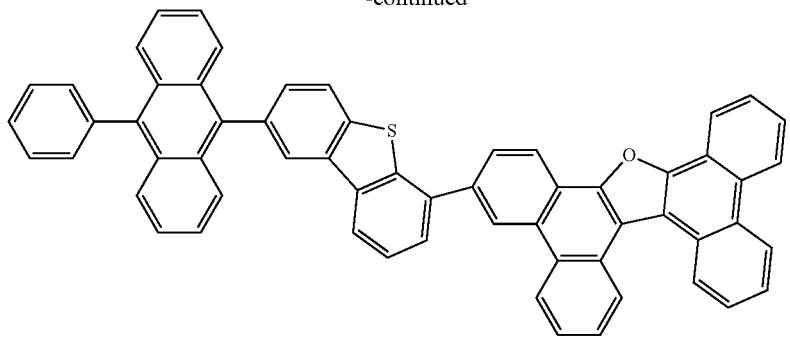
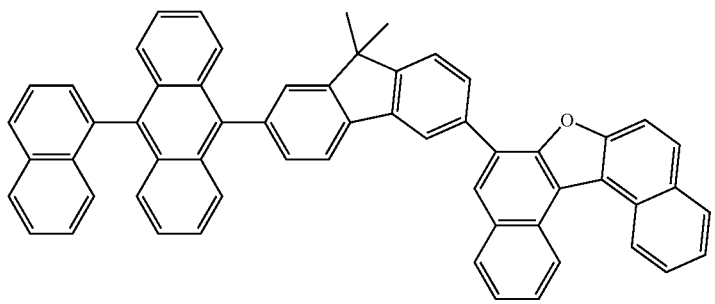
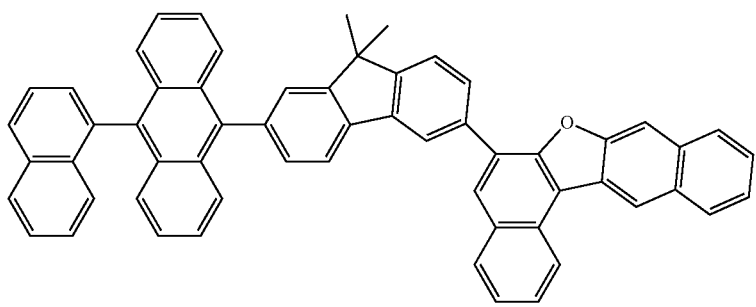
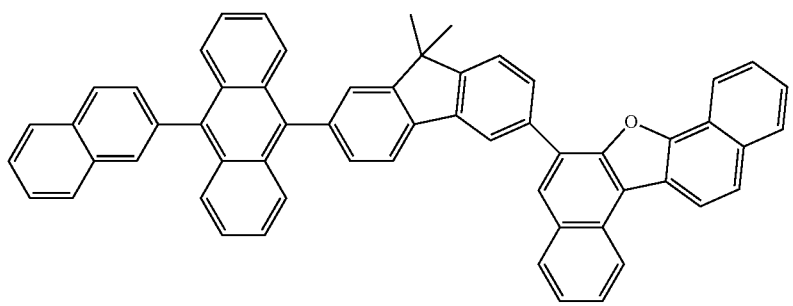
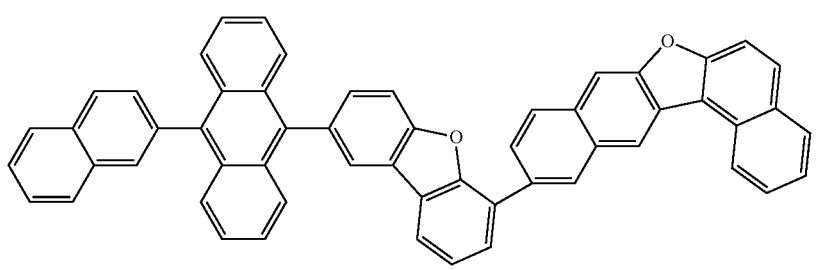

-continued
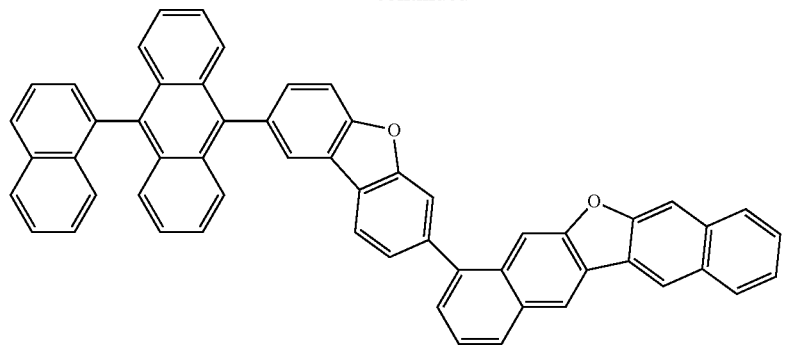
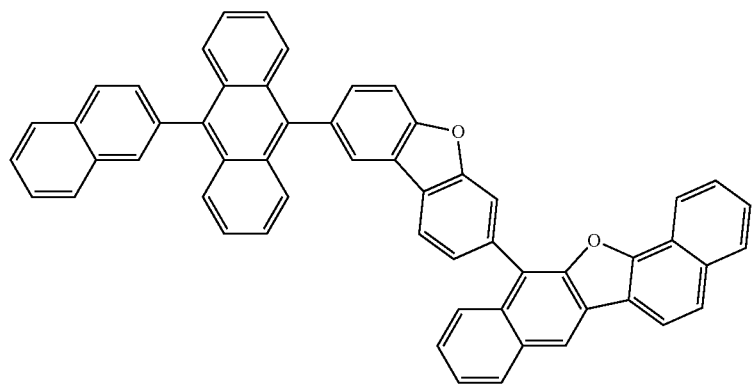
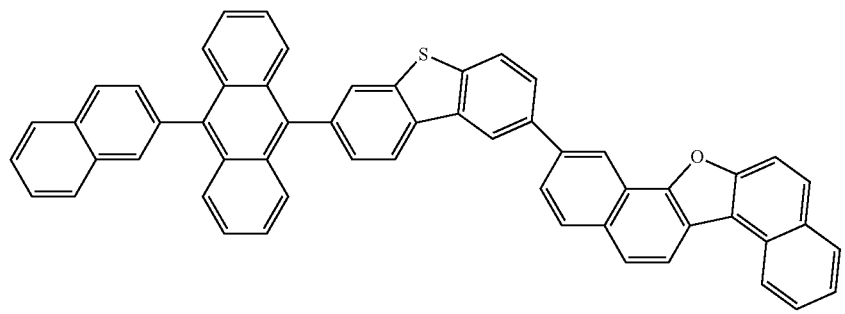
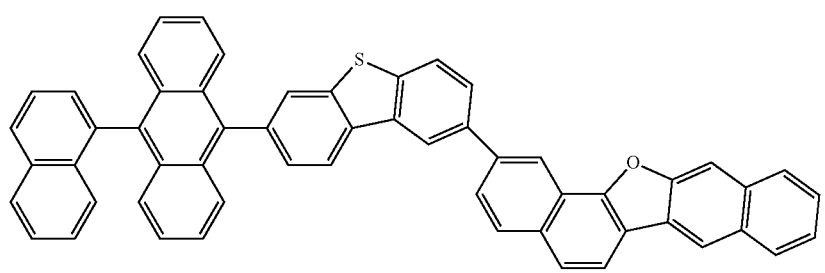
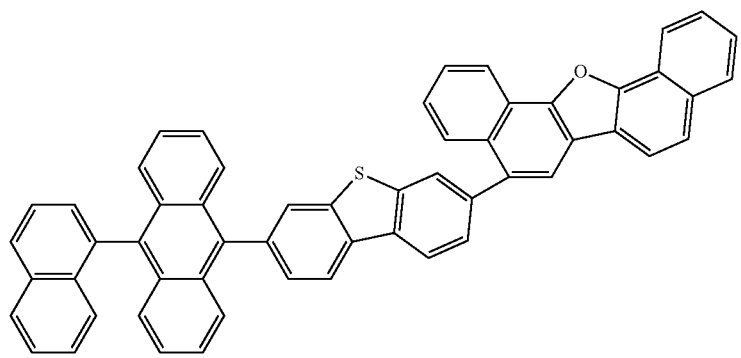

-continued
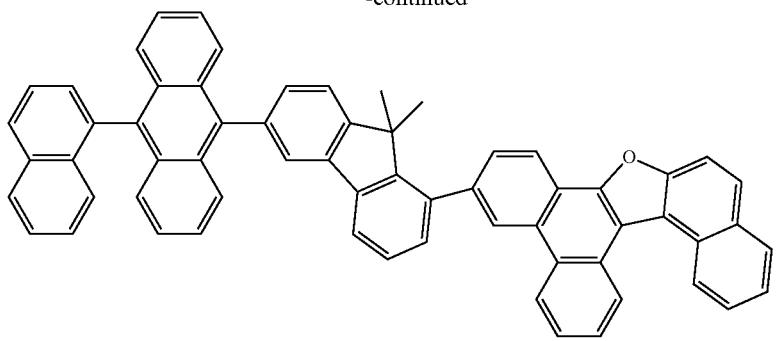
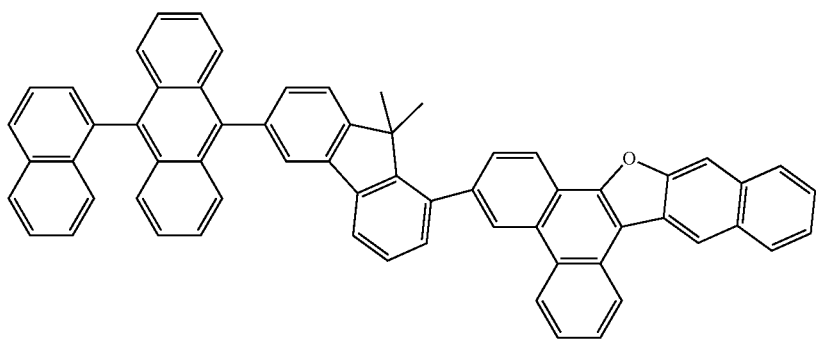
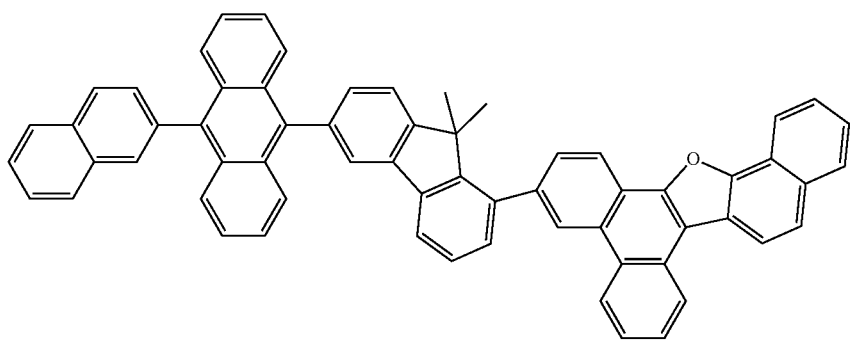
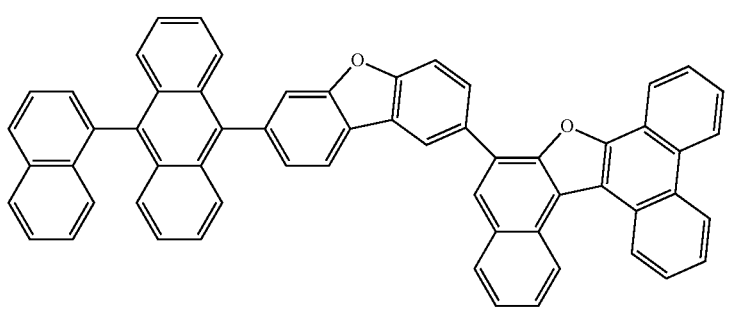
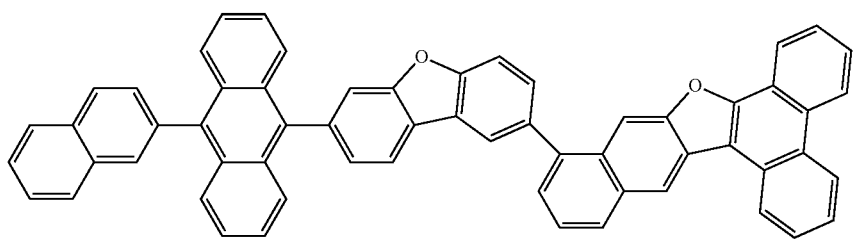

-continued
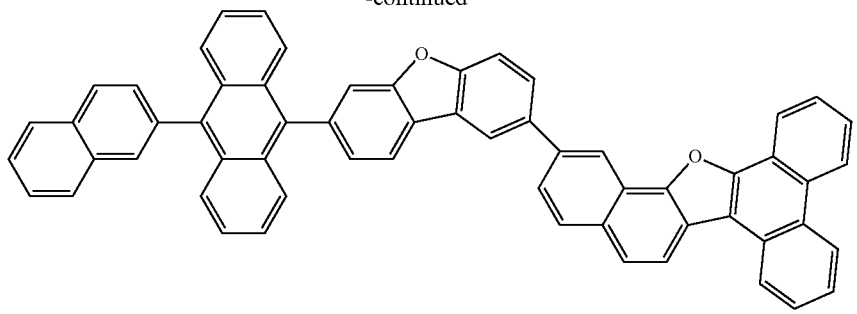
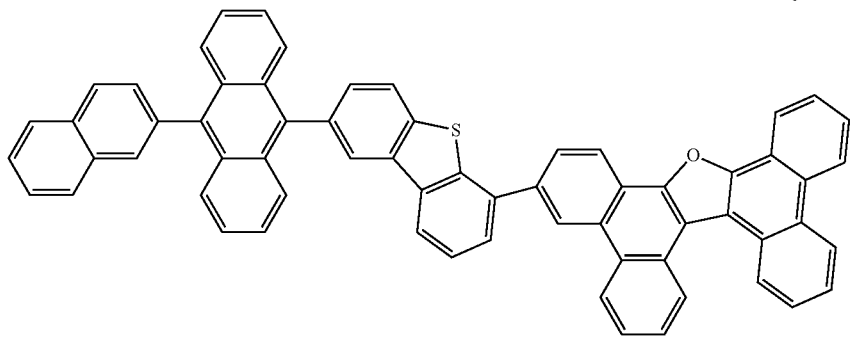
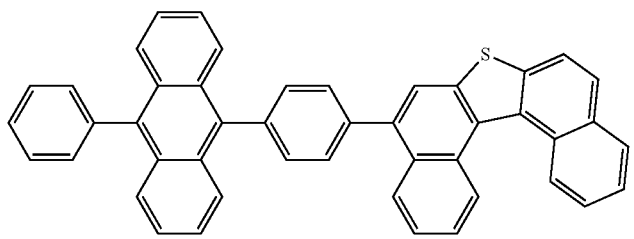
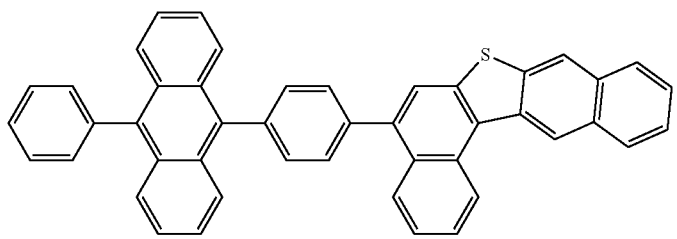
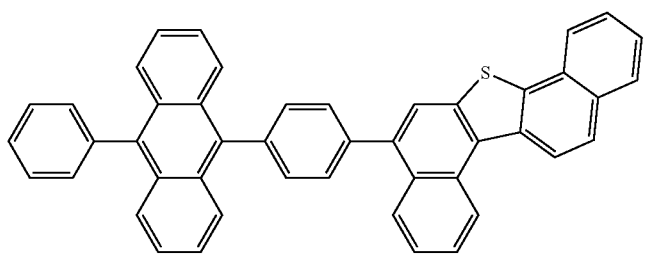
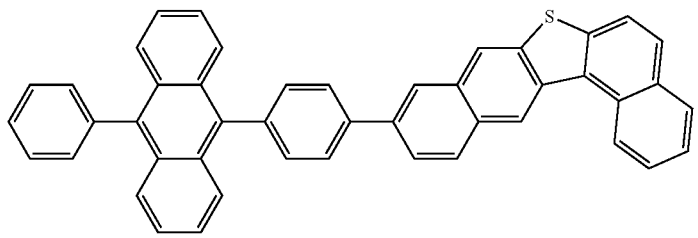

-continued
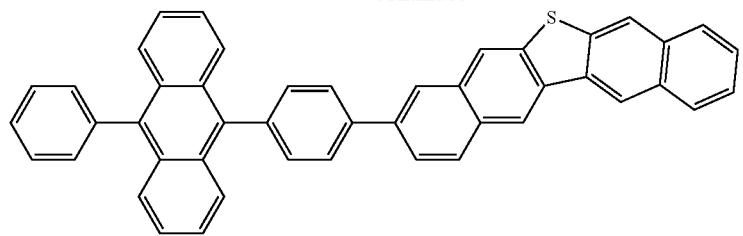
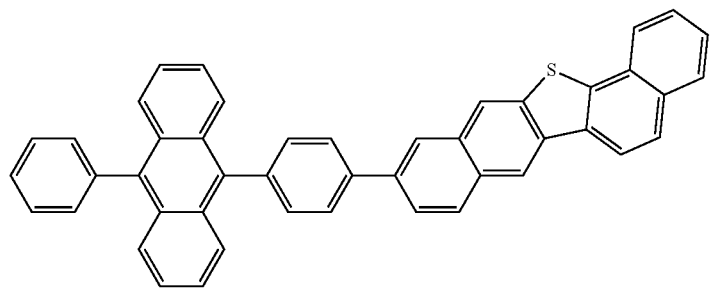
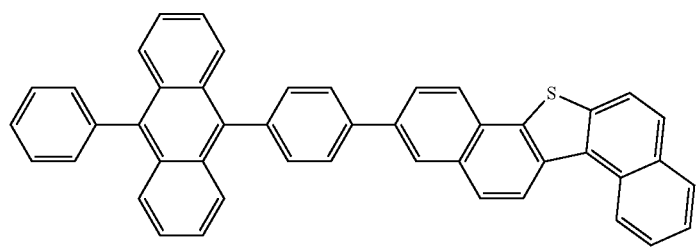
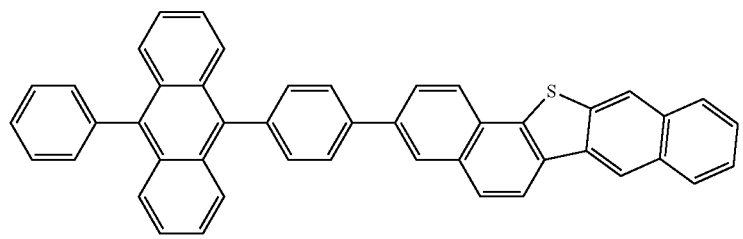
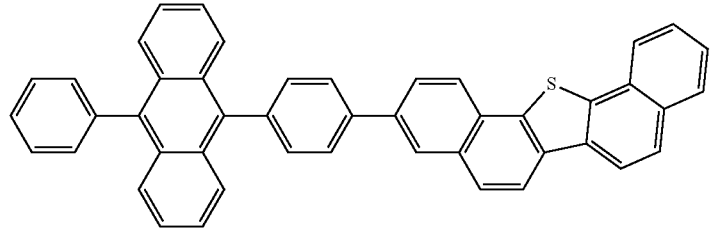
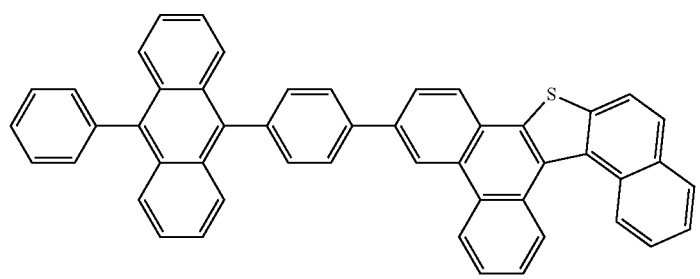

-continued
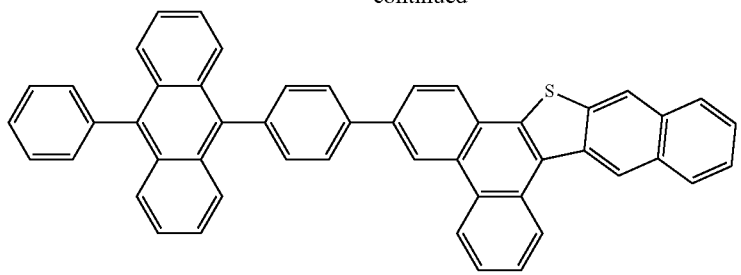
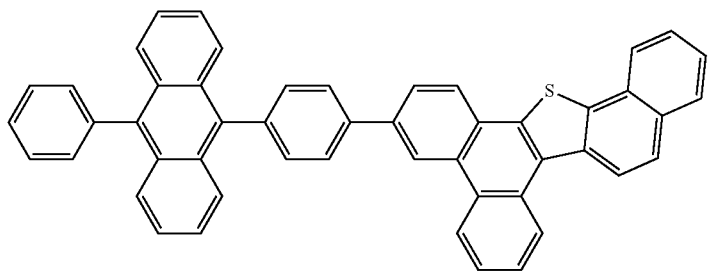
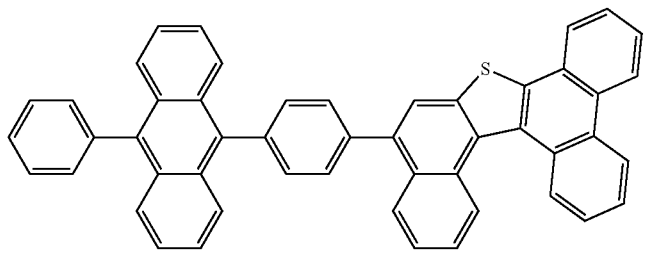
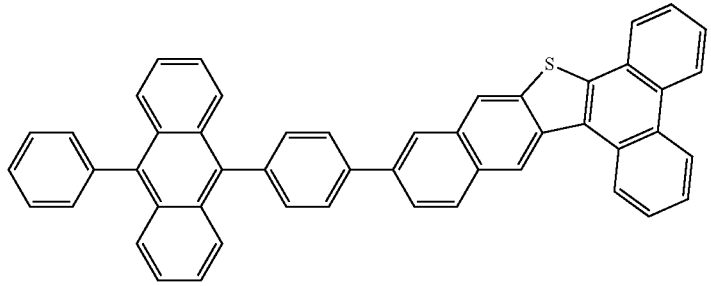
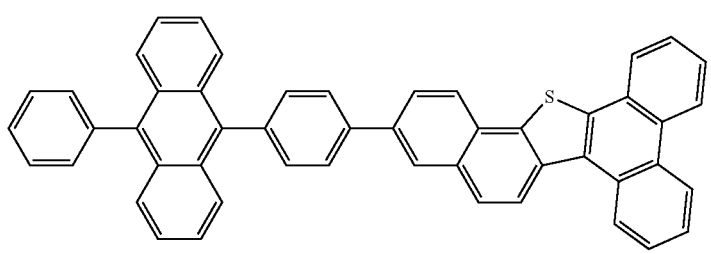
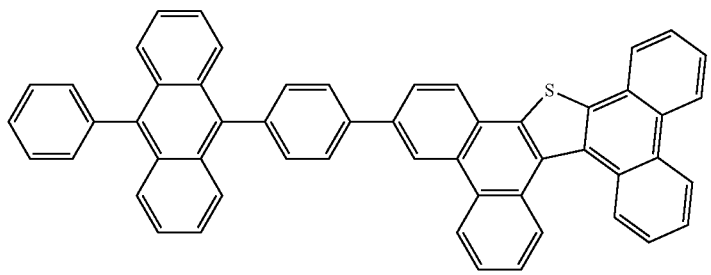

-continued
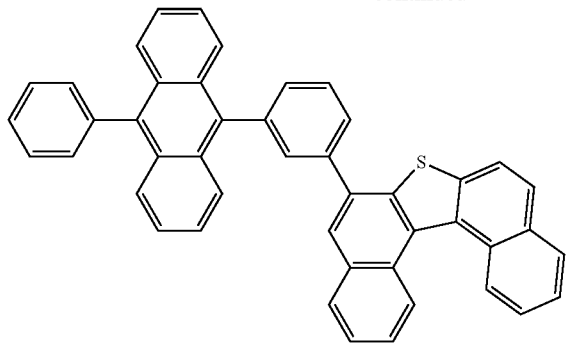
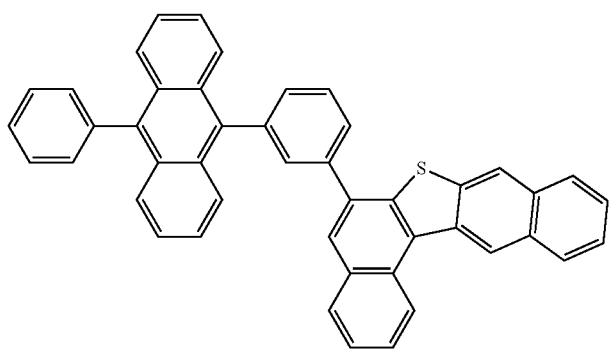
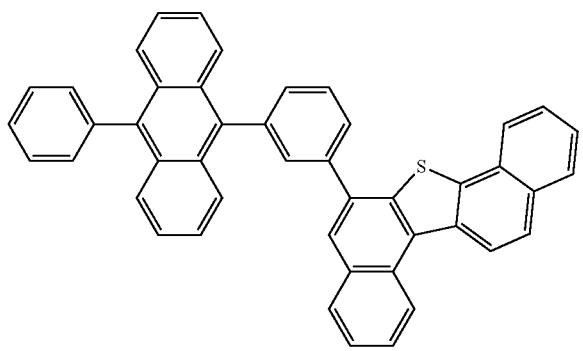
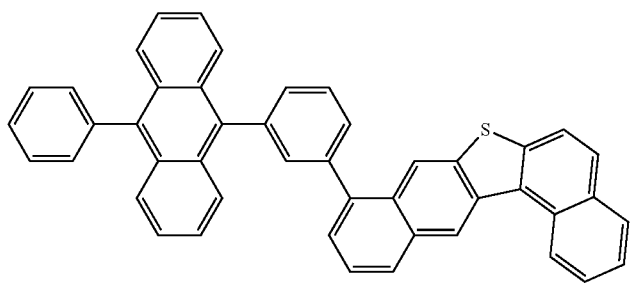
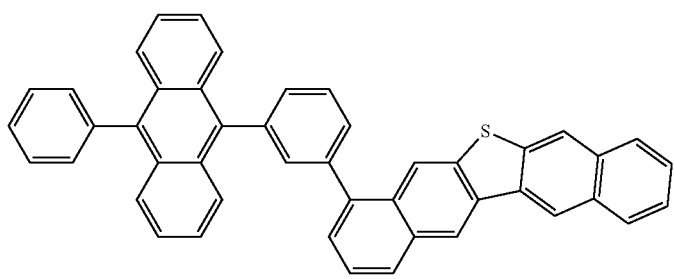

-continued
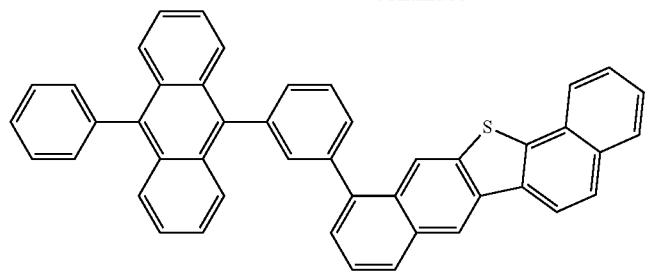
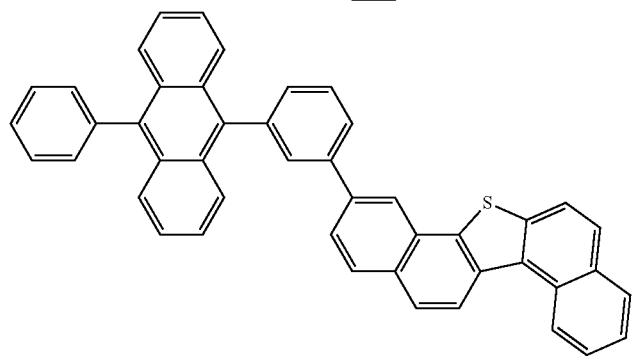
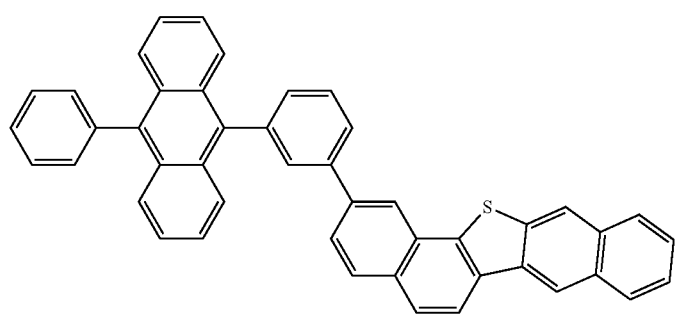
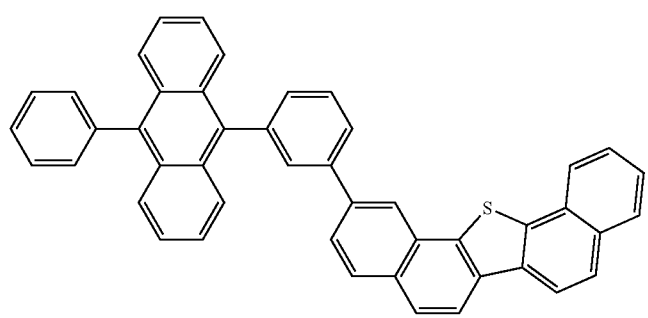
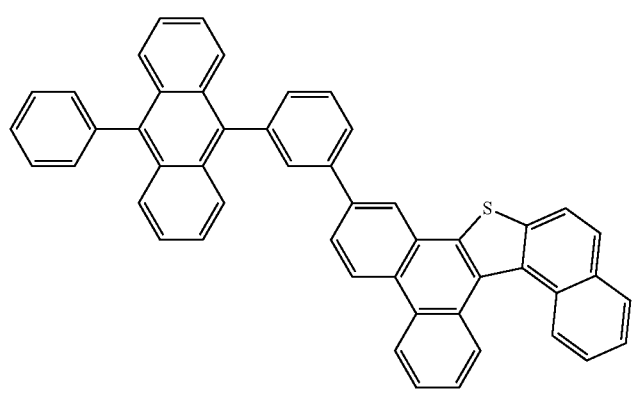

-continued
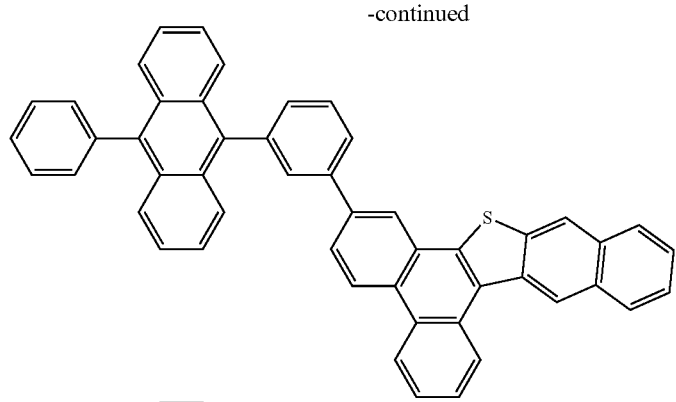
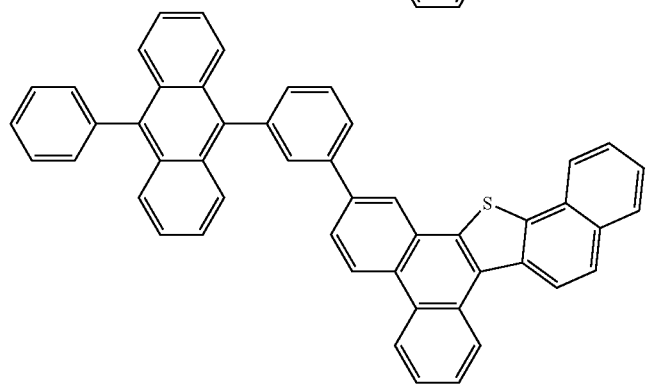
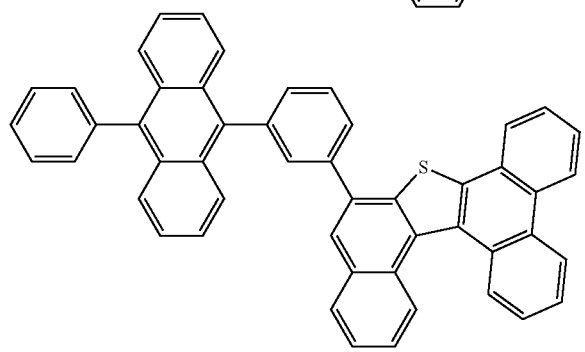
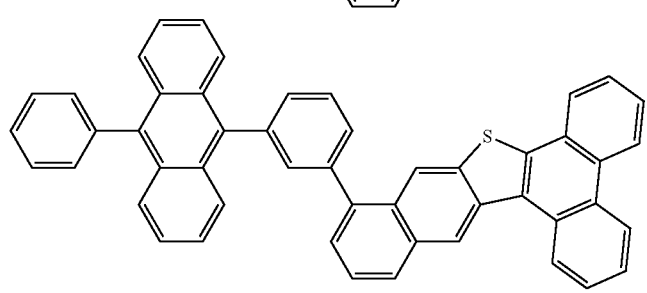
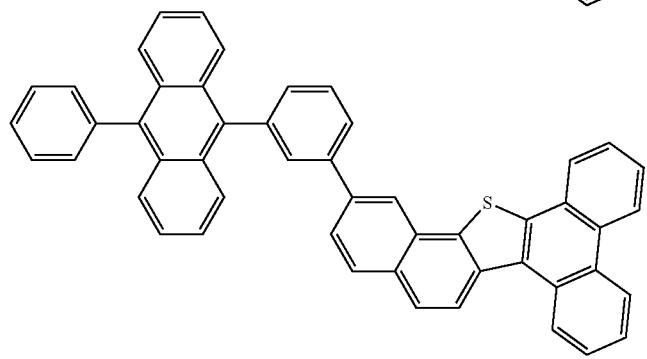

-continued
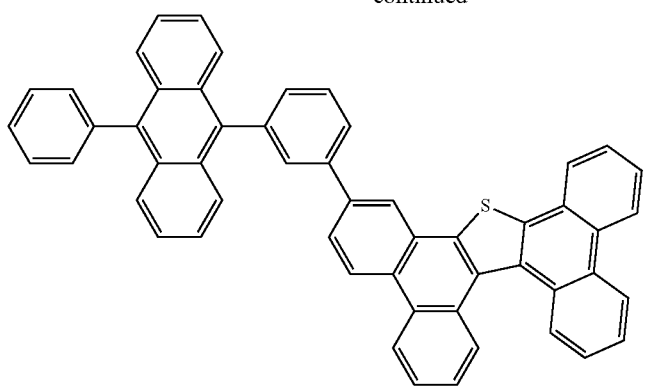
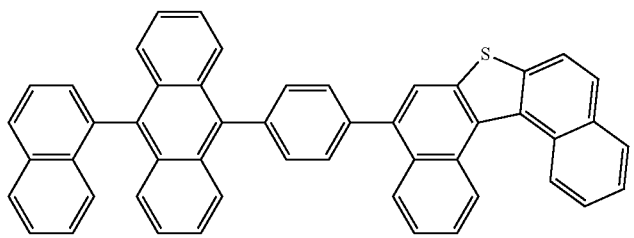
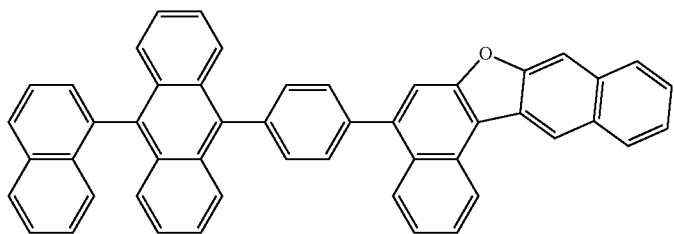
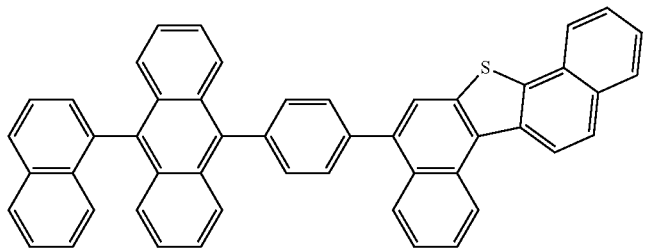
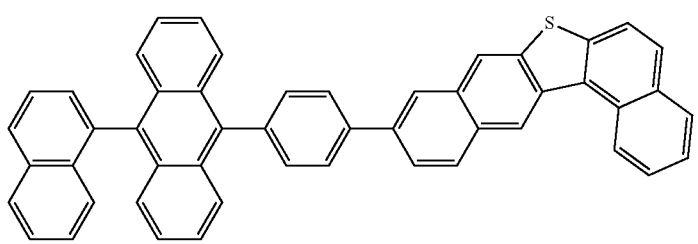
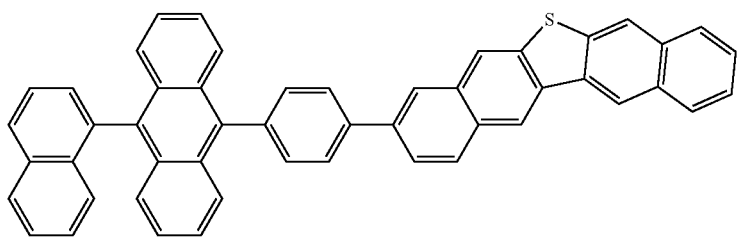

-continued
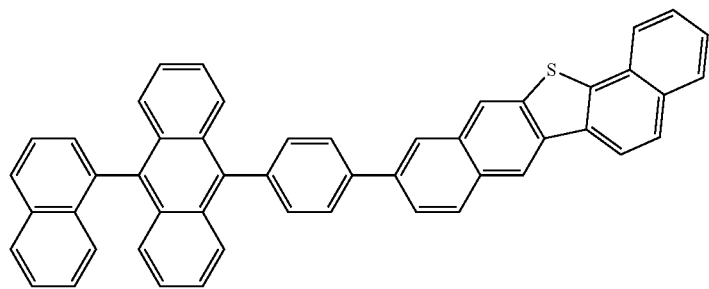
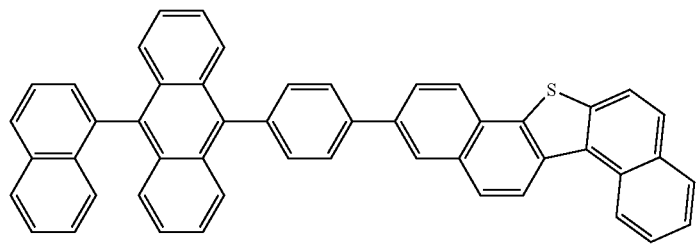
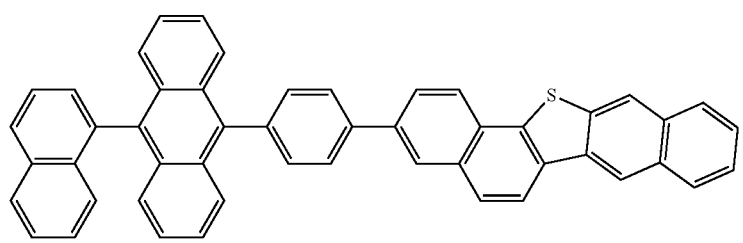
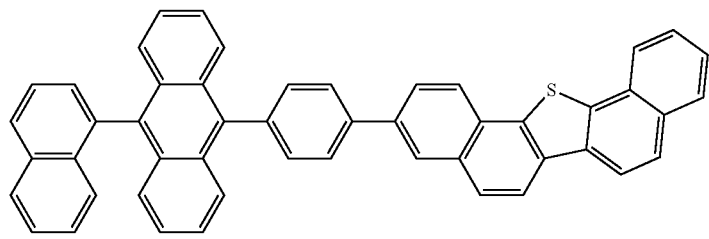
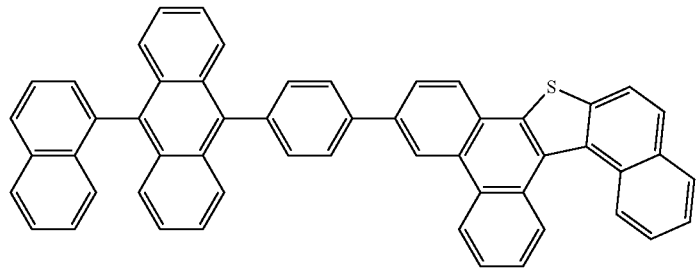
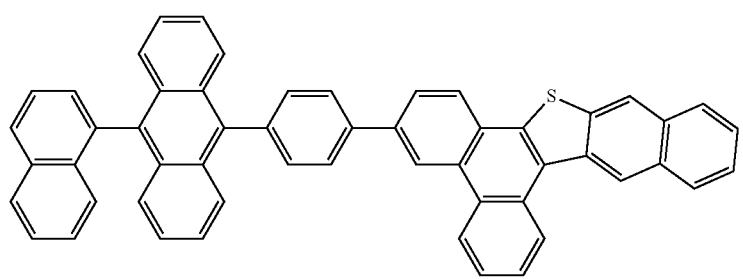

-continued
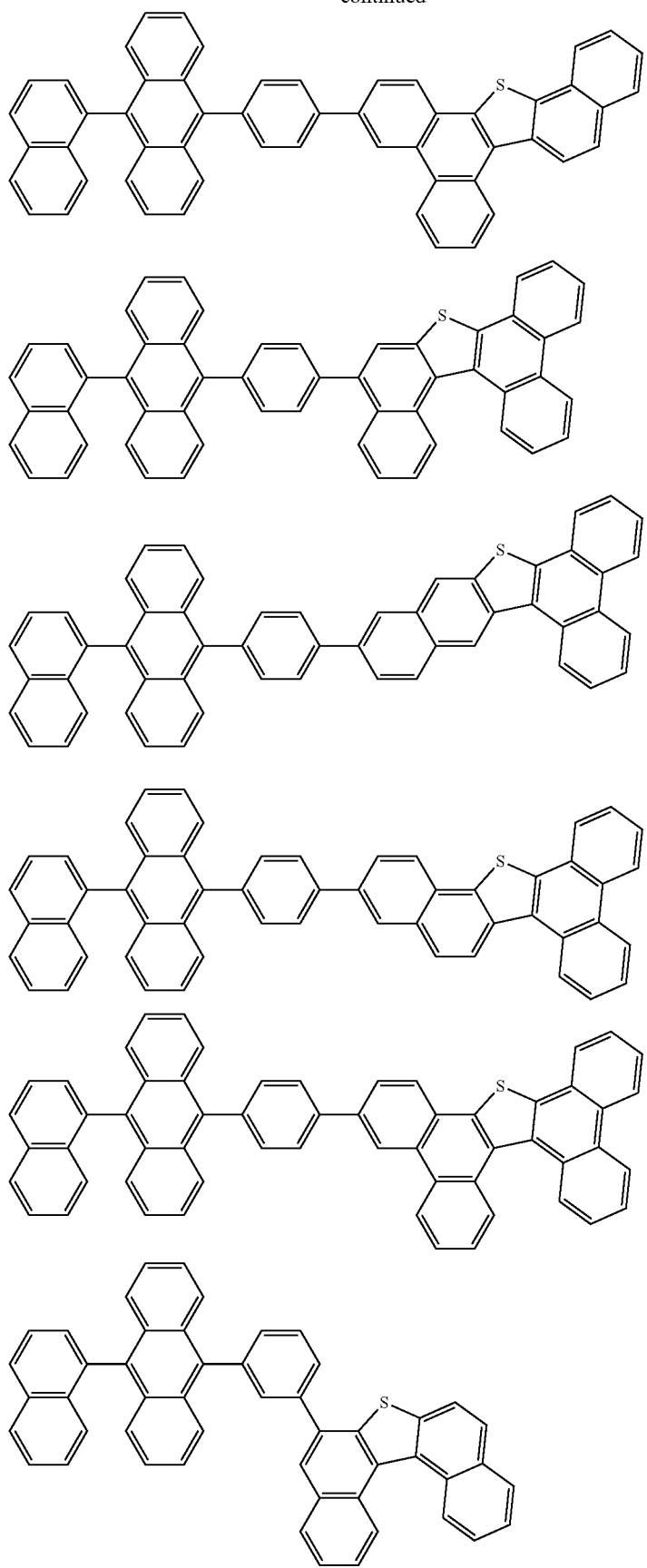

-continued
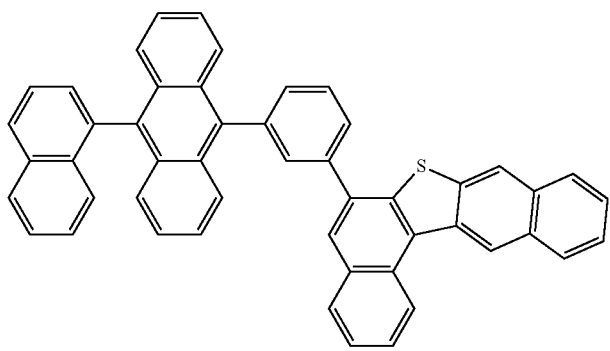
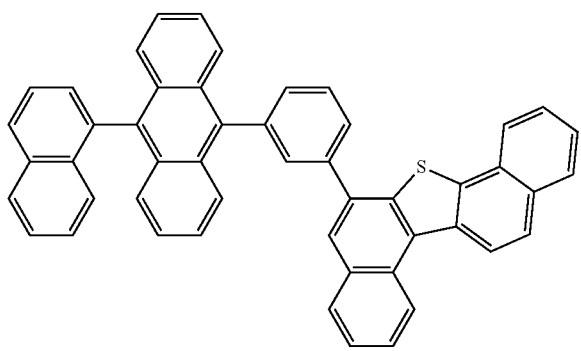
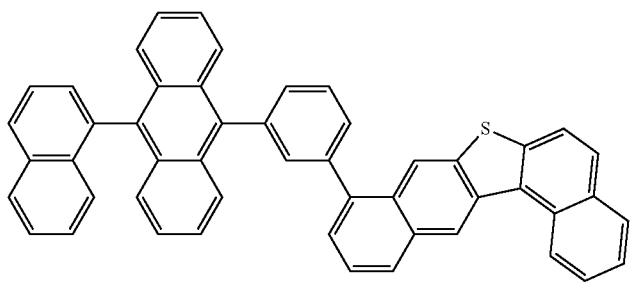
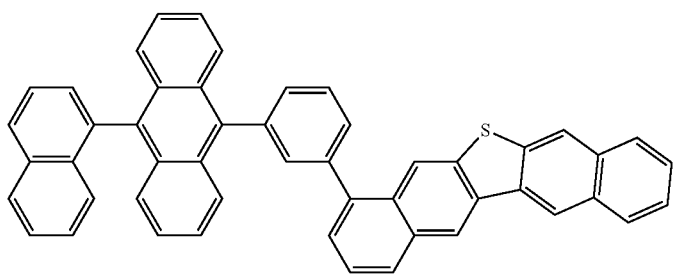
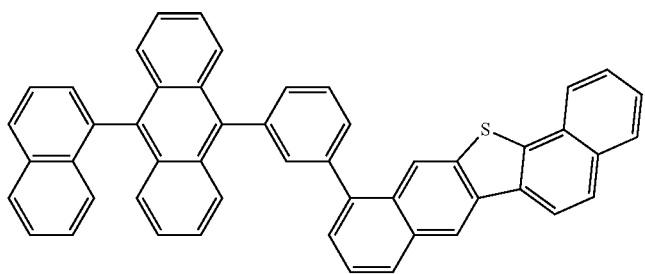

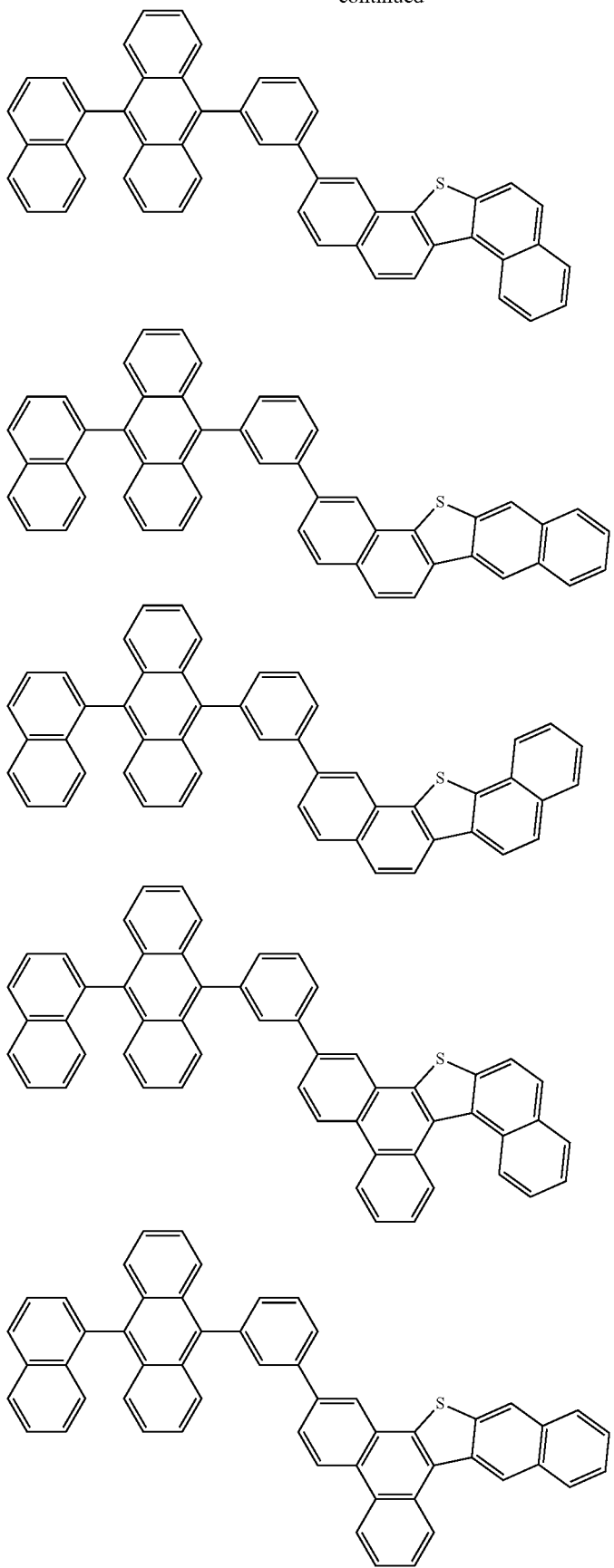

-continued
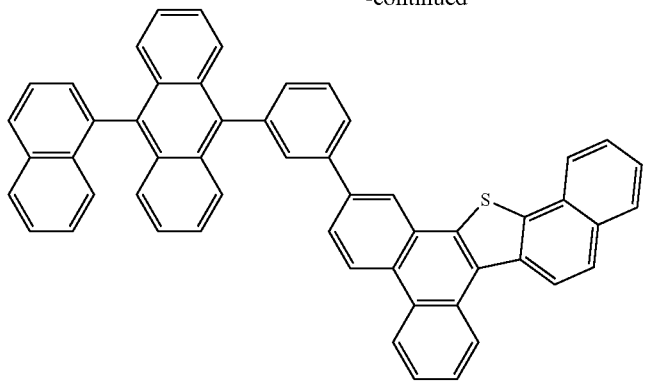
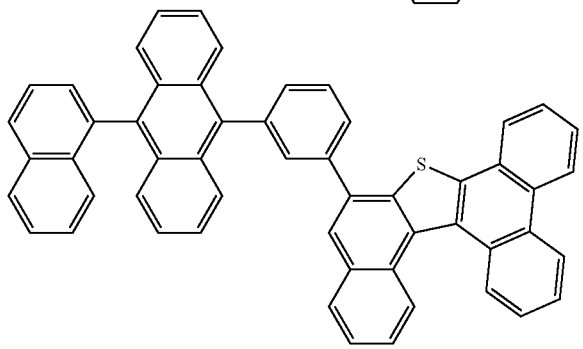
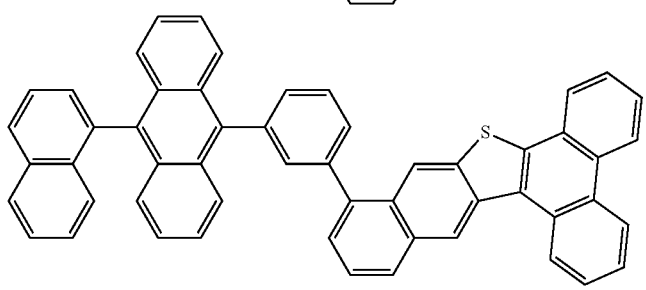
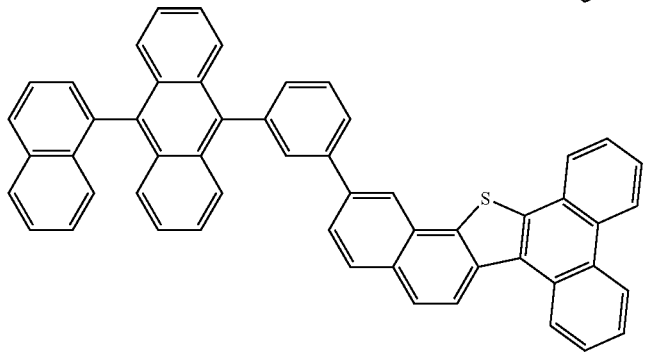
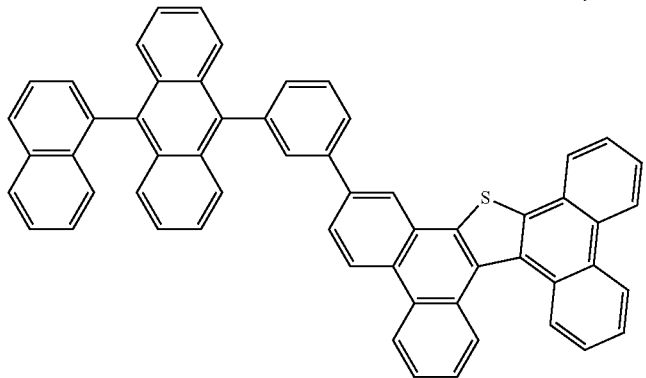

-continued
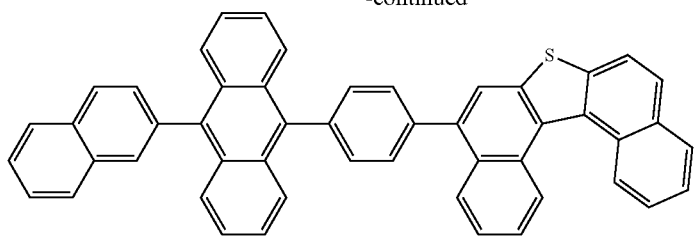
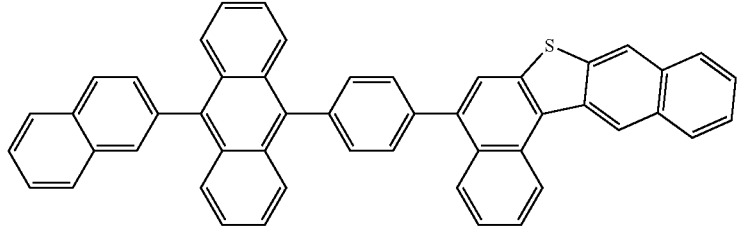
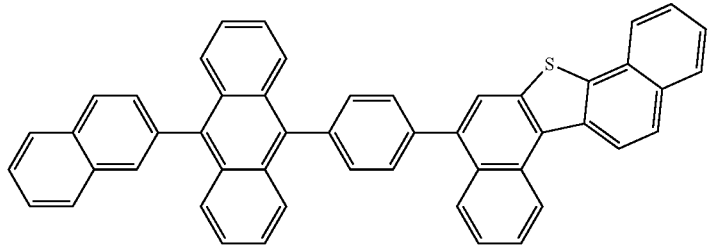
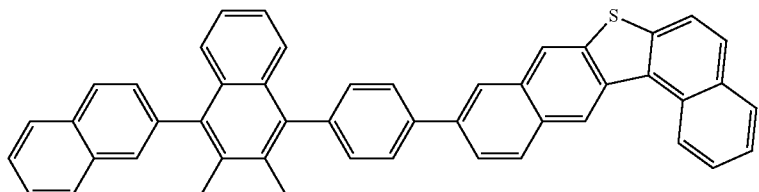
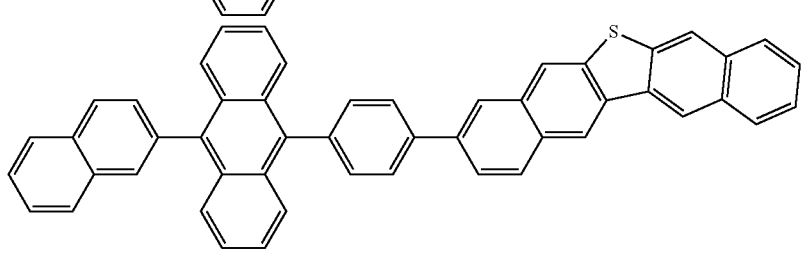
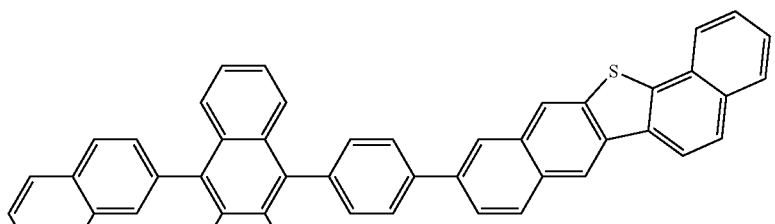
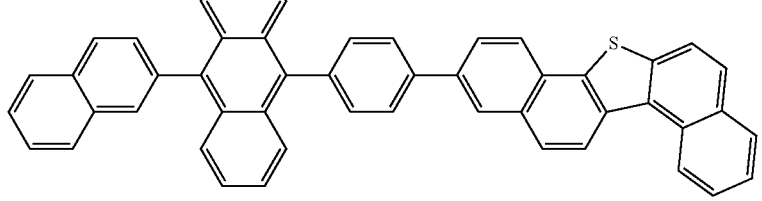

-continued
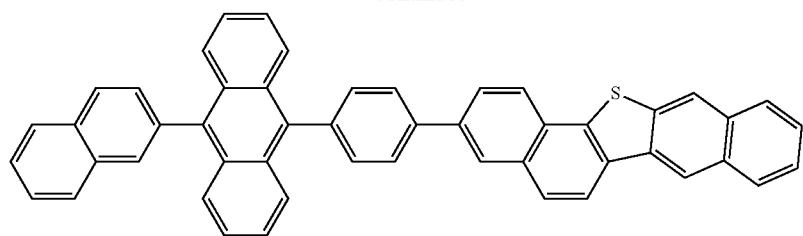
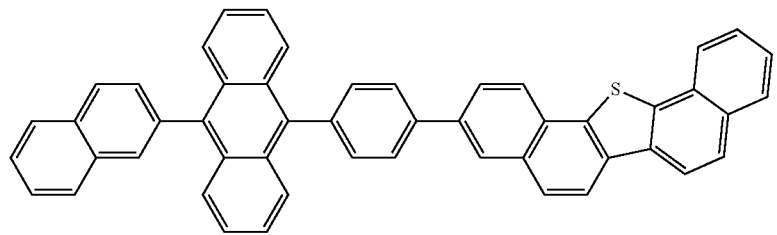
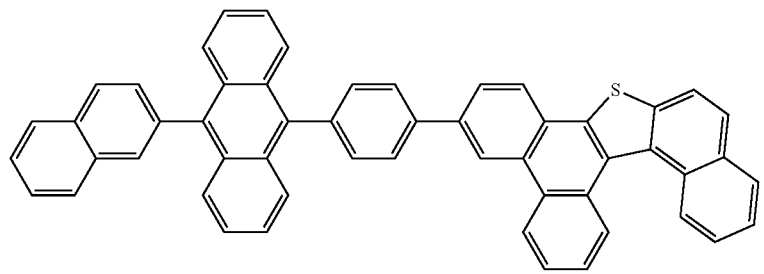
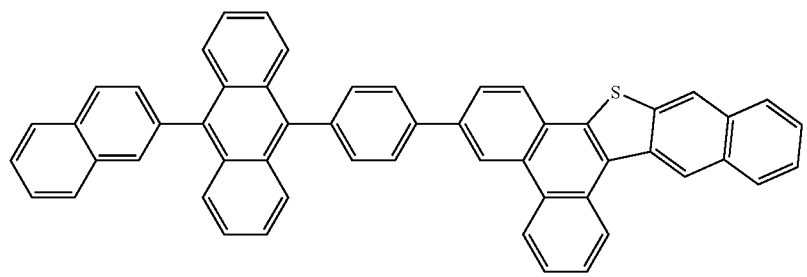
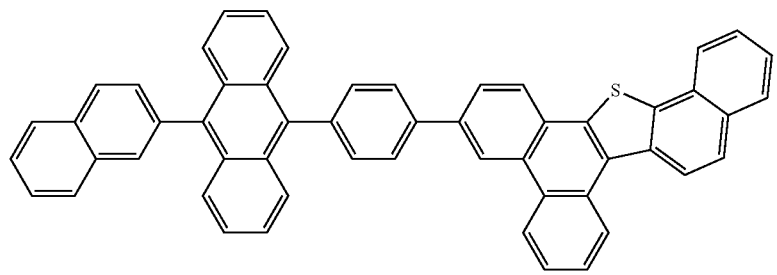
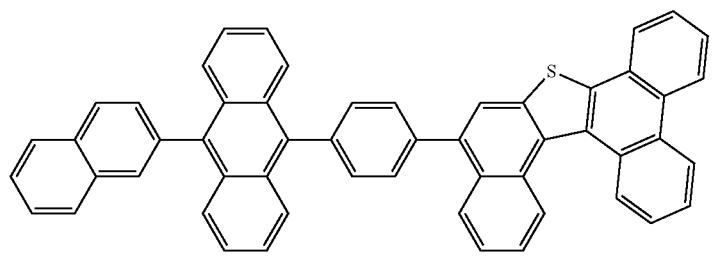

-continued
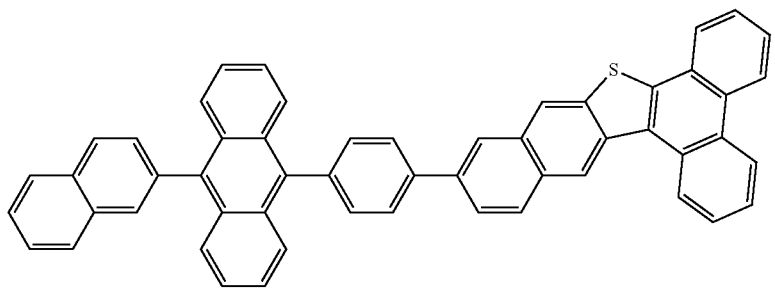
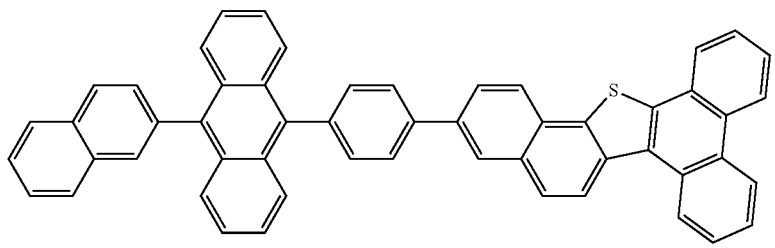
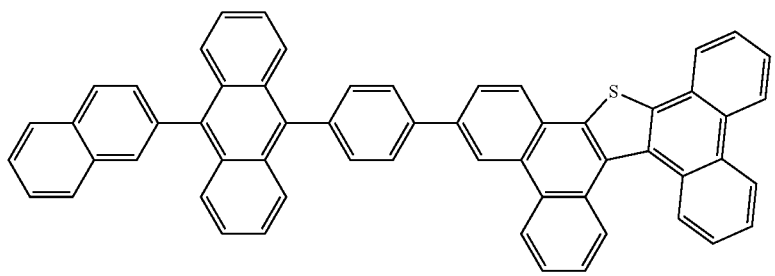
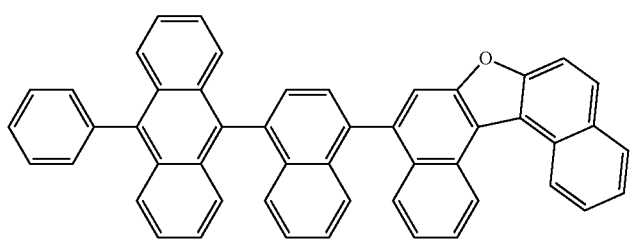
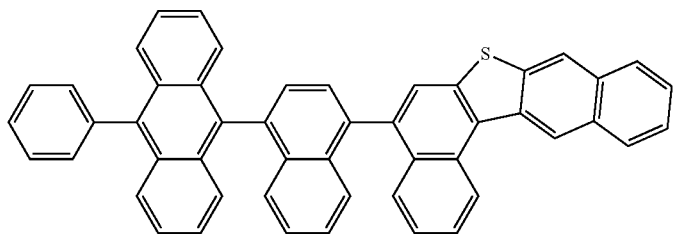
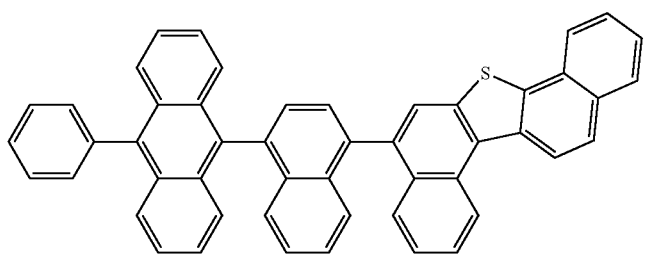

-continued
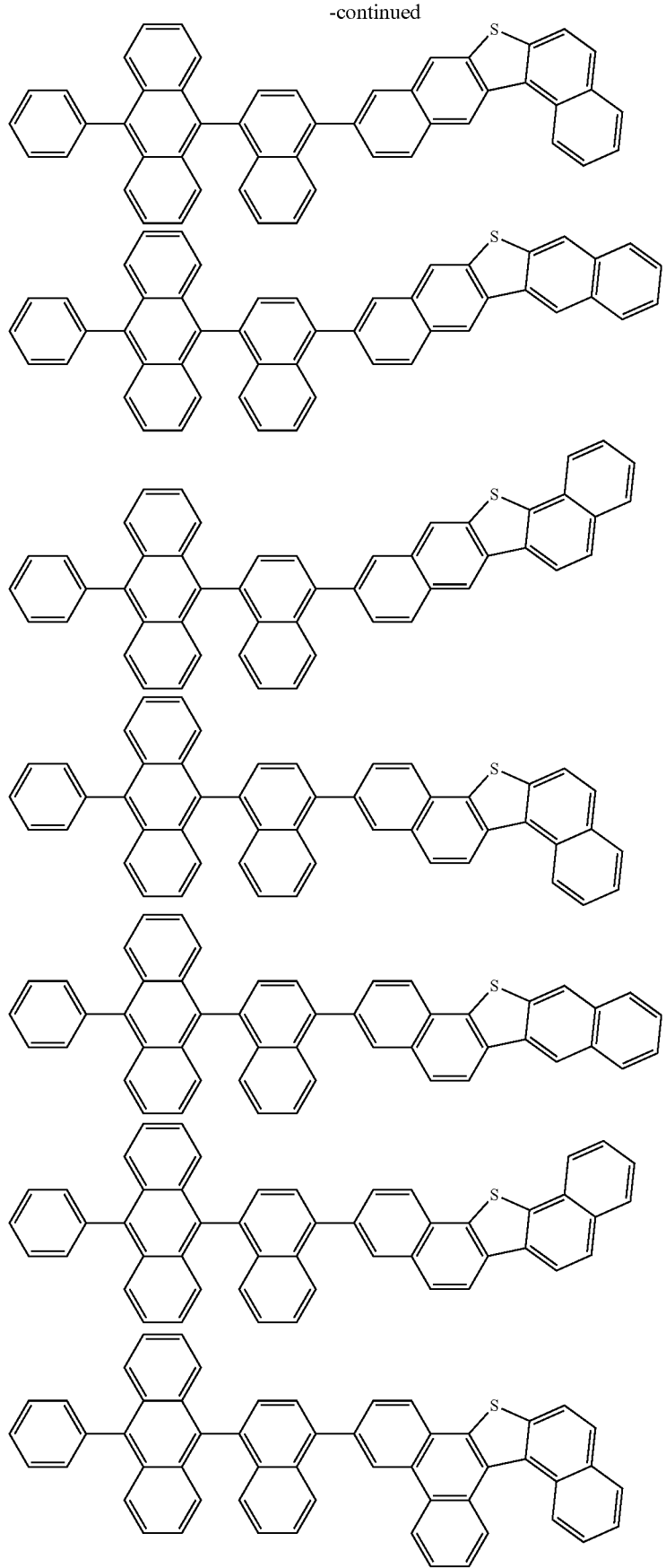

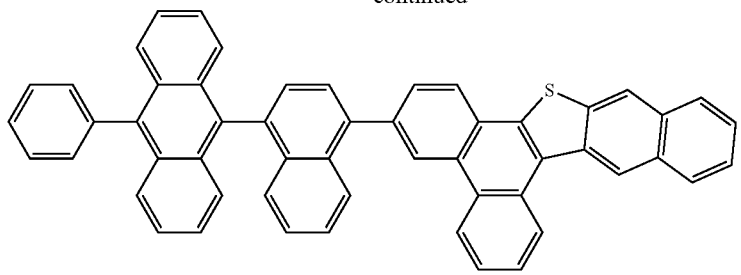
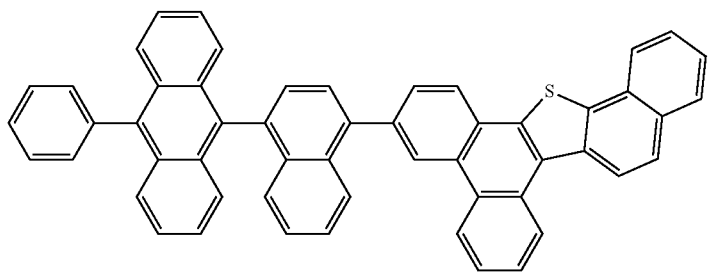
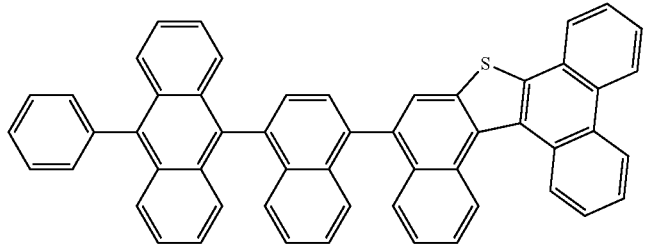
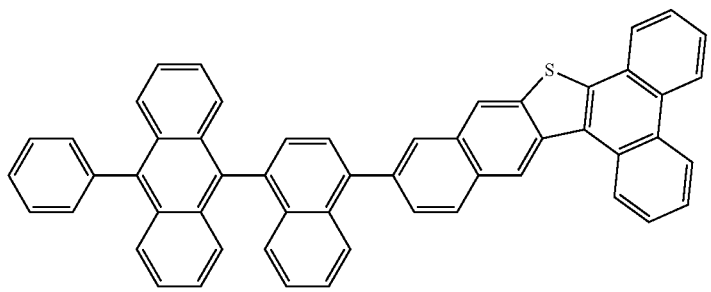
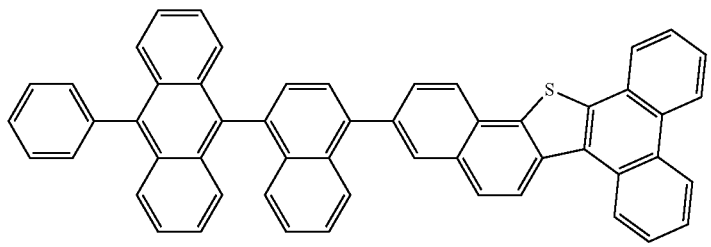
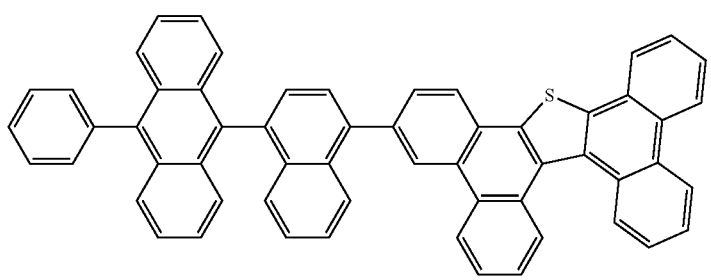

-continued
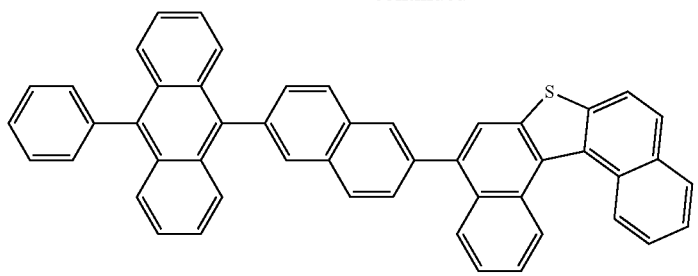
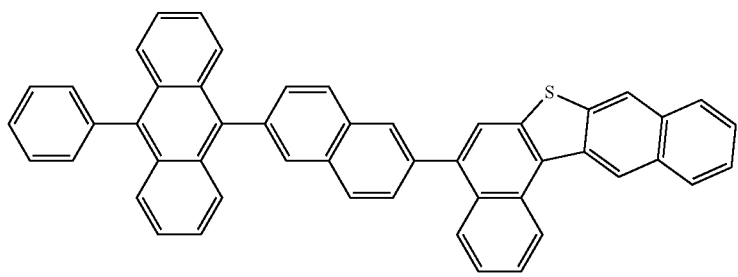
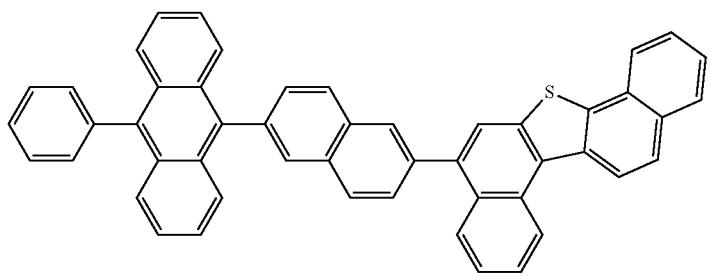
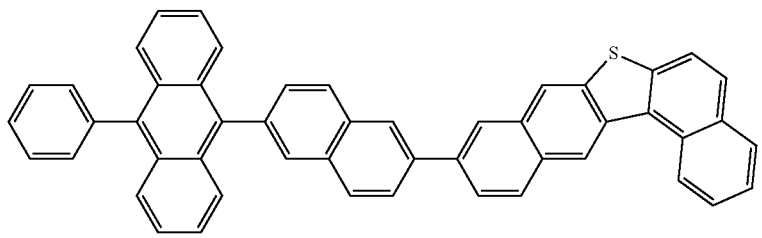
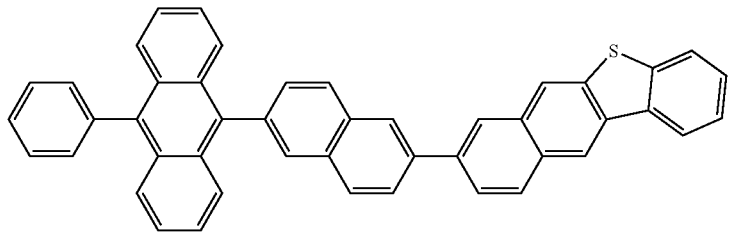
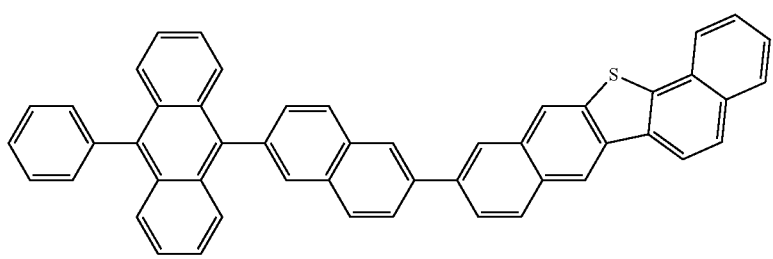

-continued
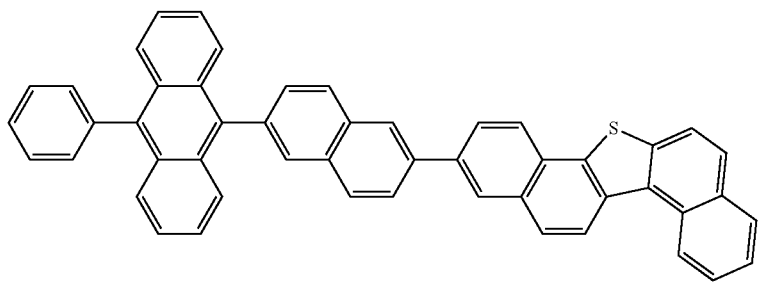
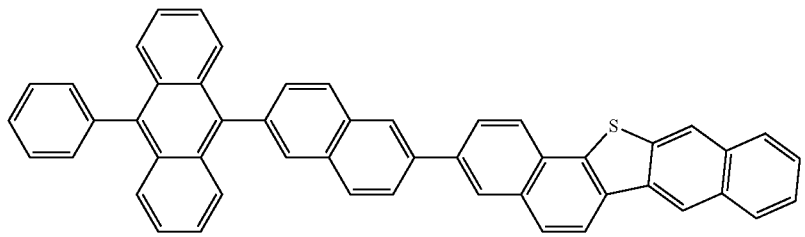
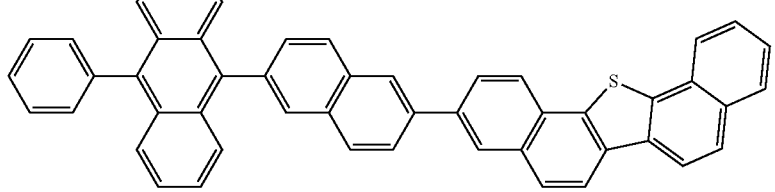
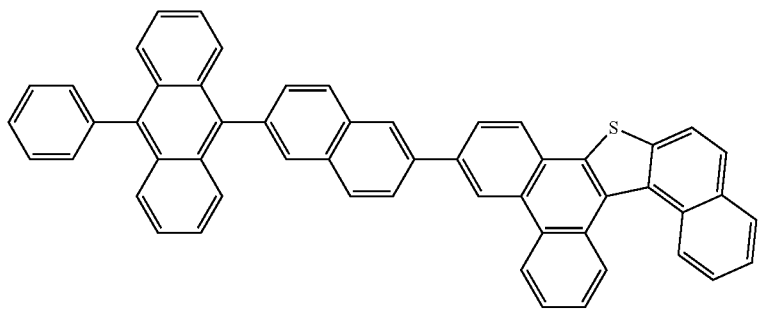
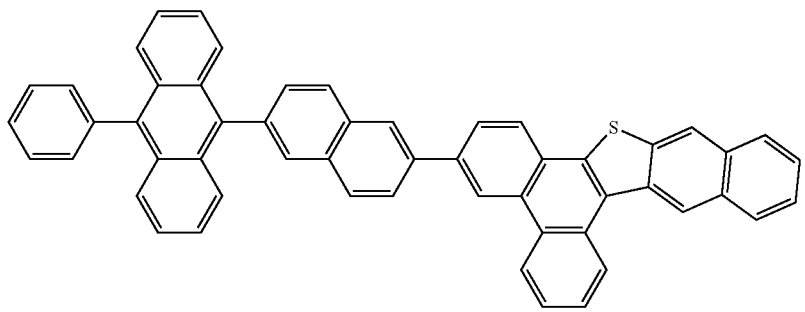
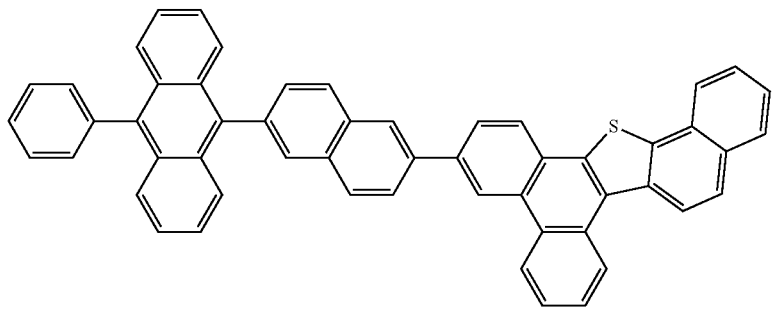

-continued
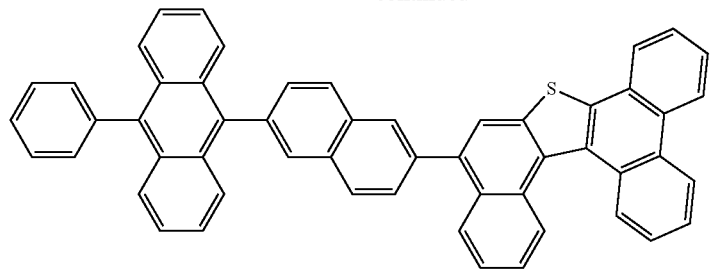
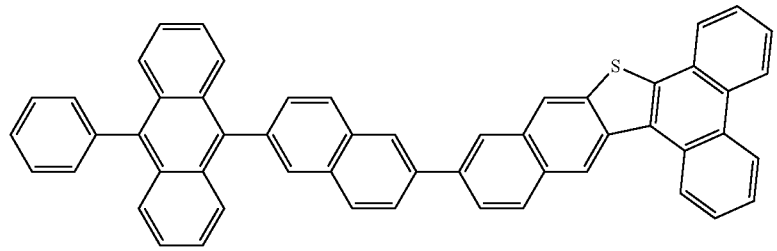
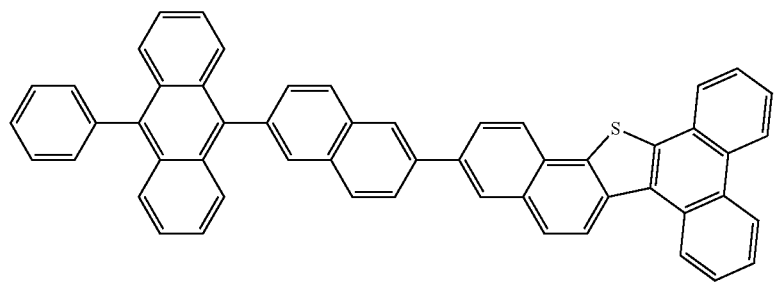
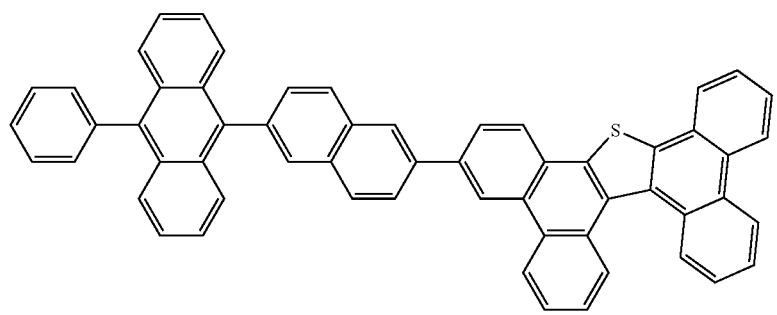
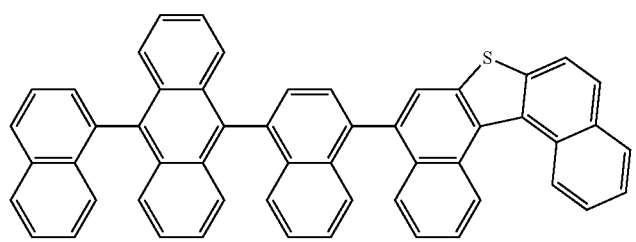
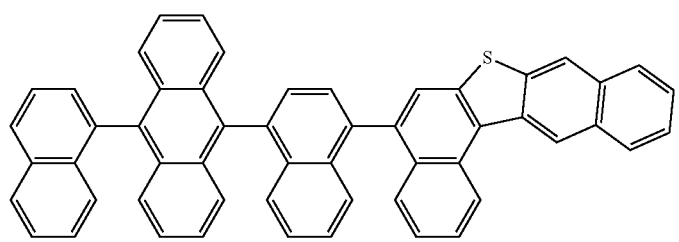

-continued
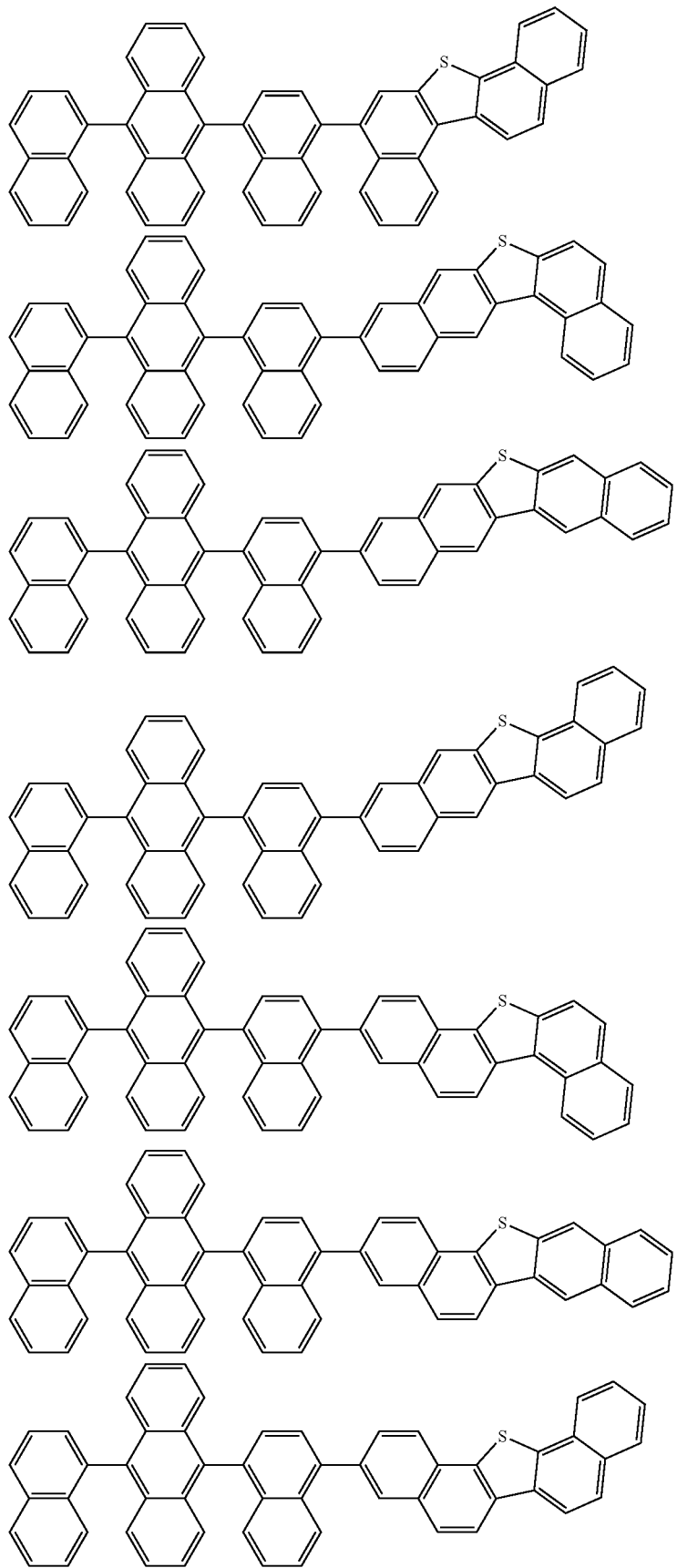

-continued
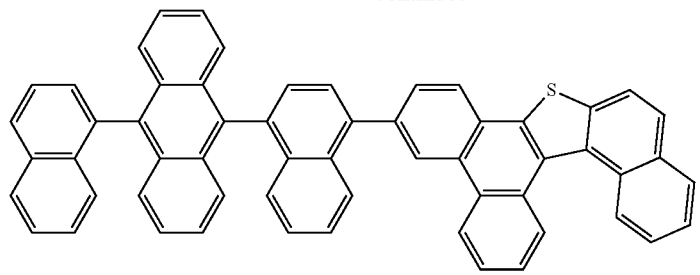
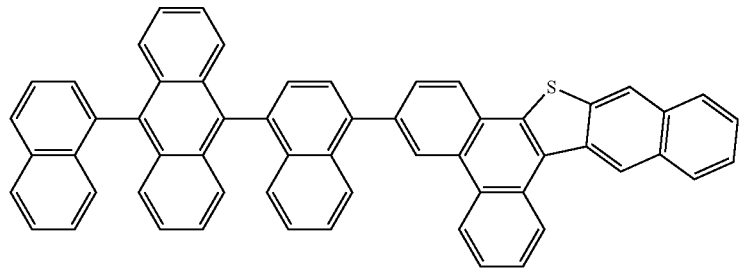
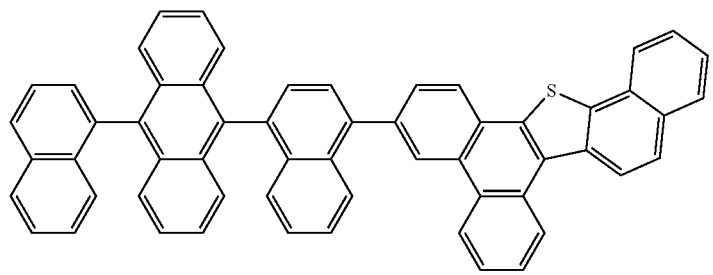
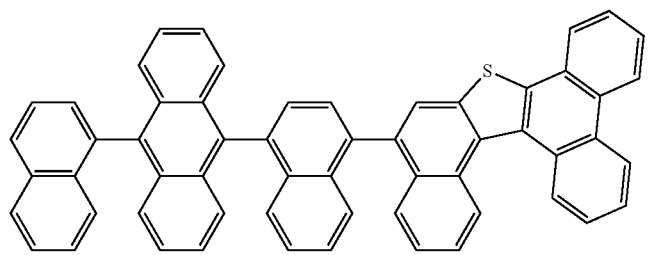
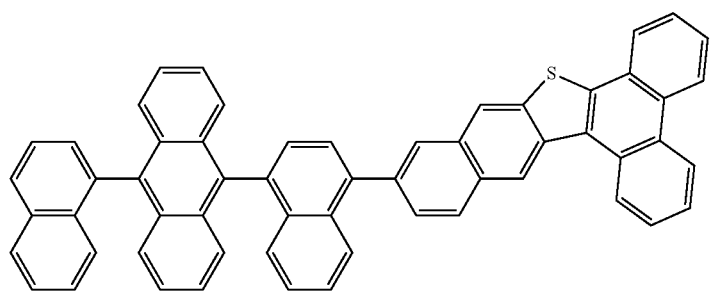
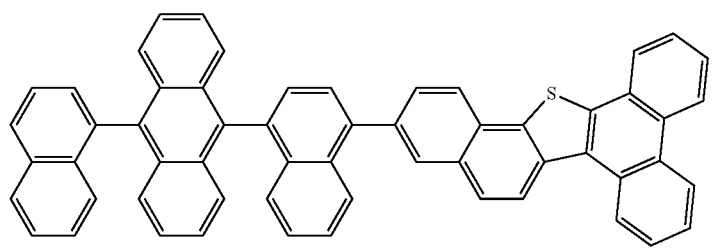

-continued
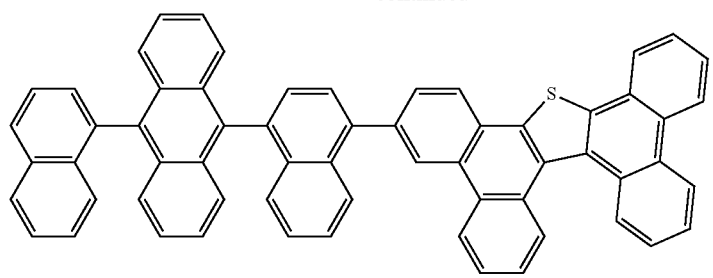

-continued
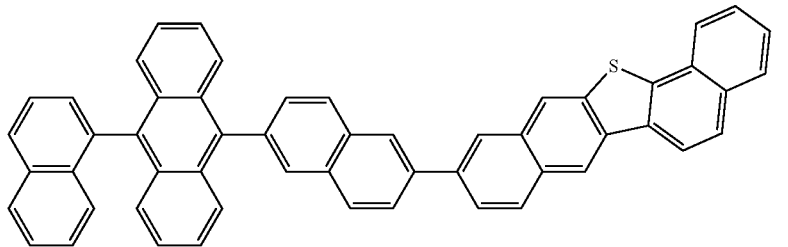
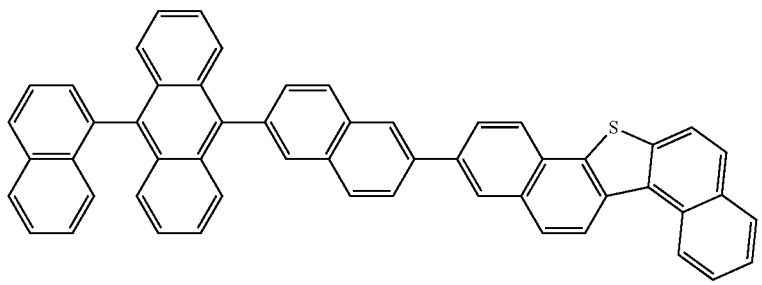
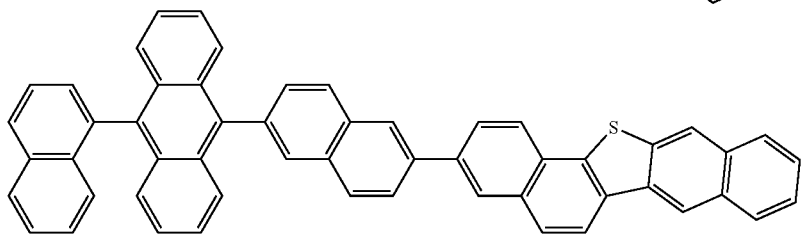
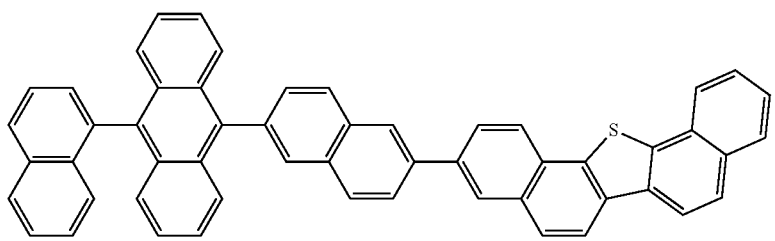
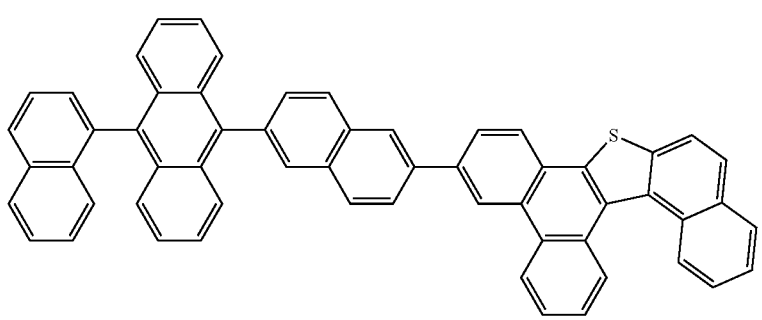
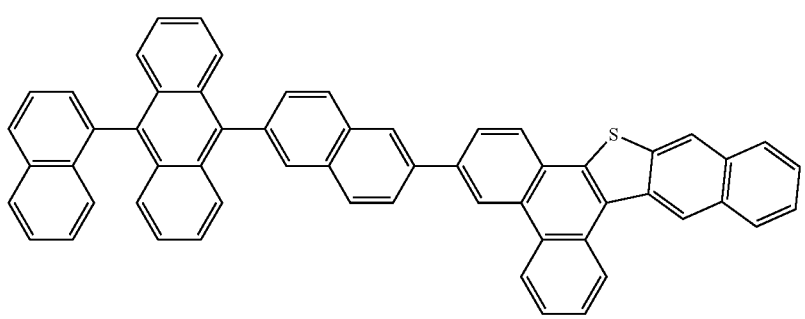

-continued
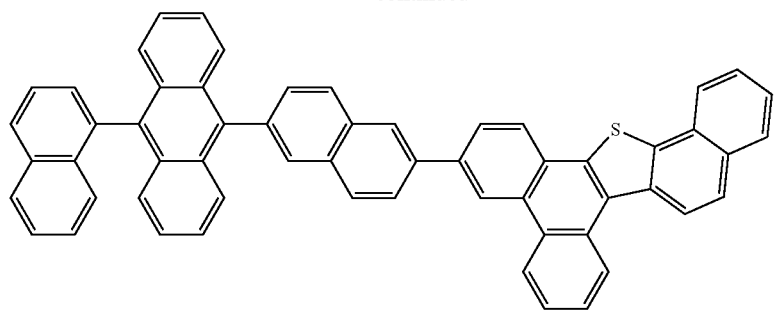
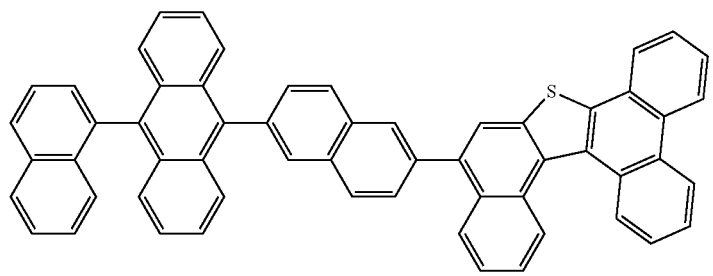
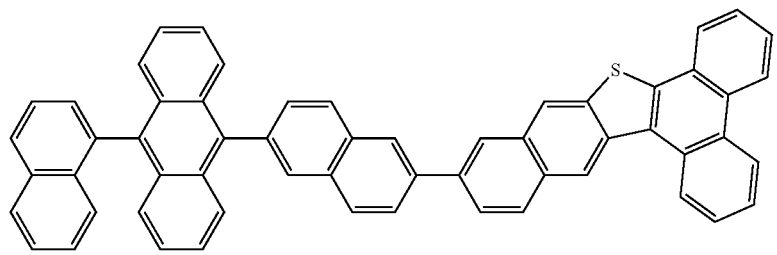
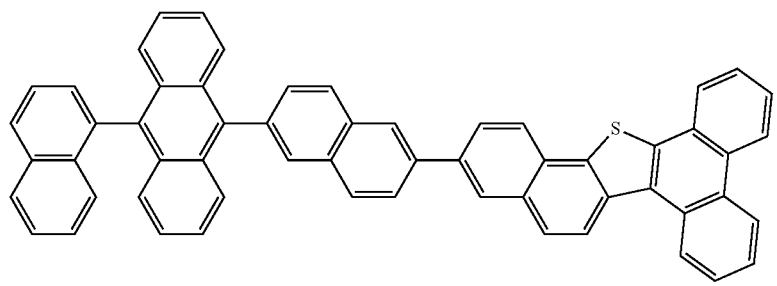
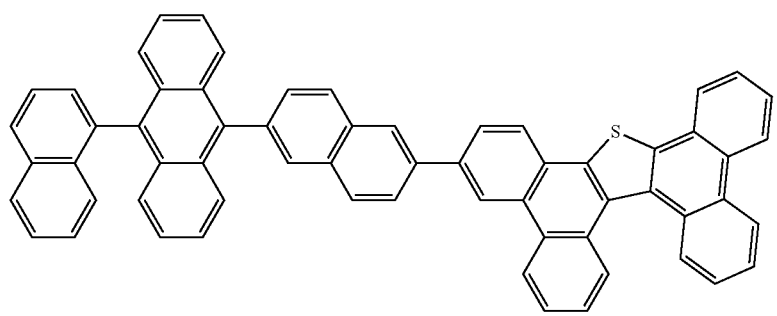

-continued
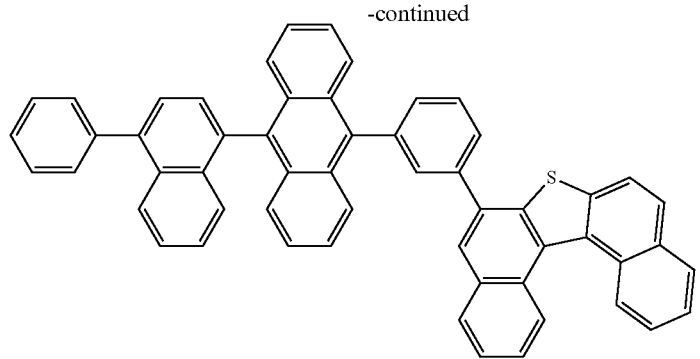
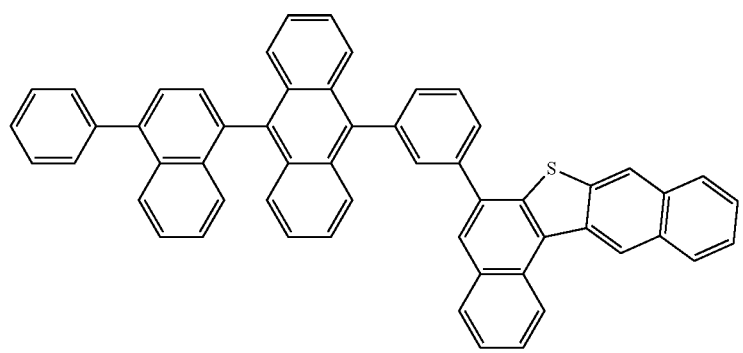
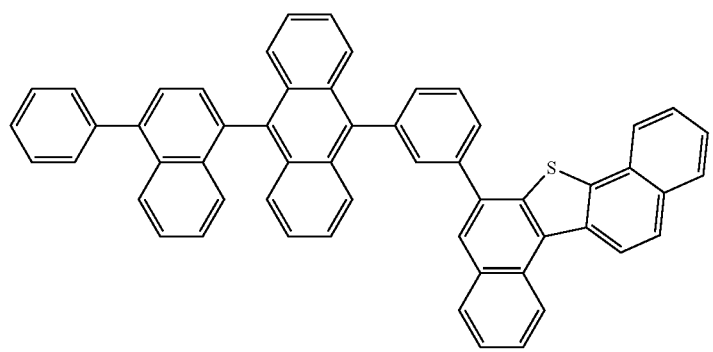
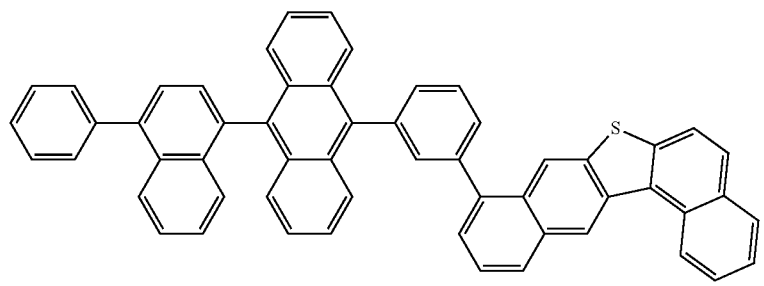
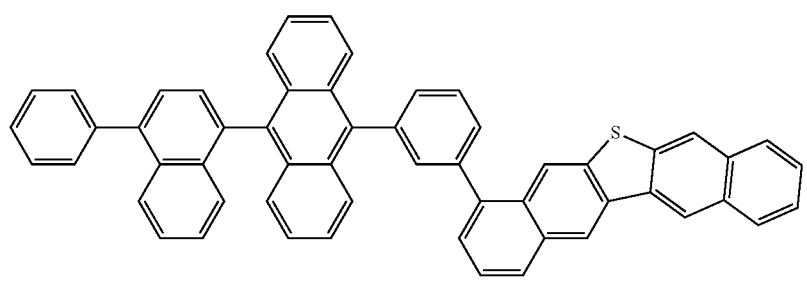

-continued
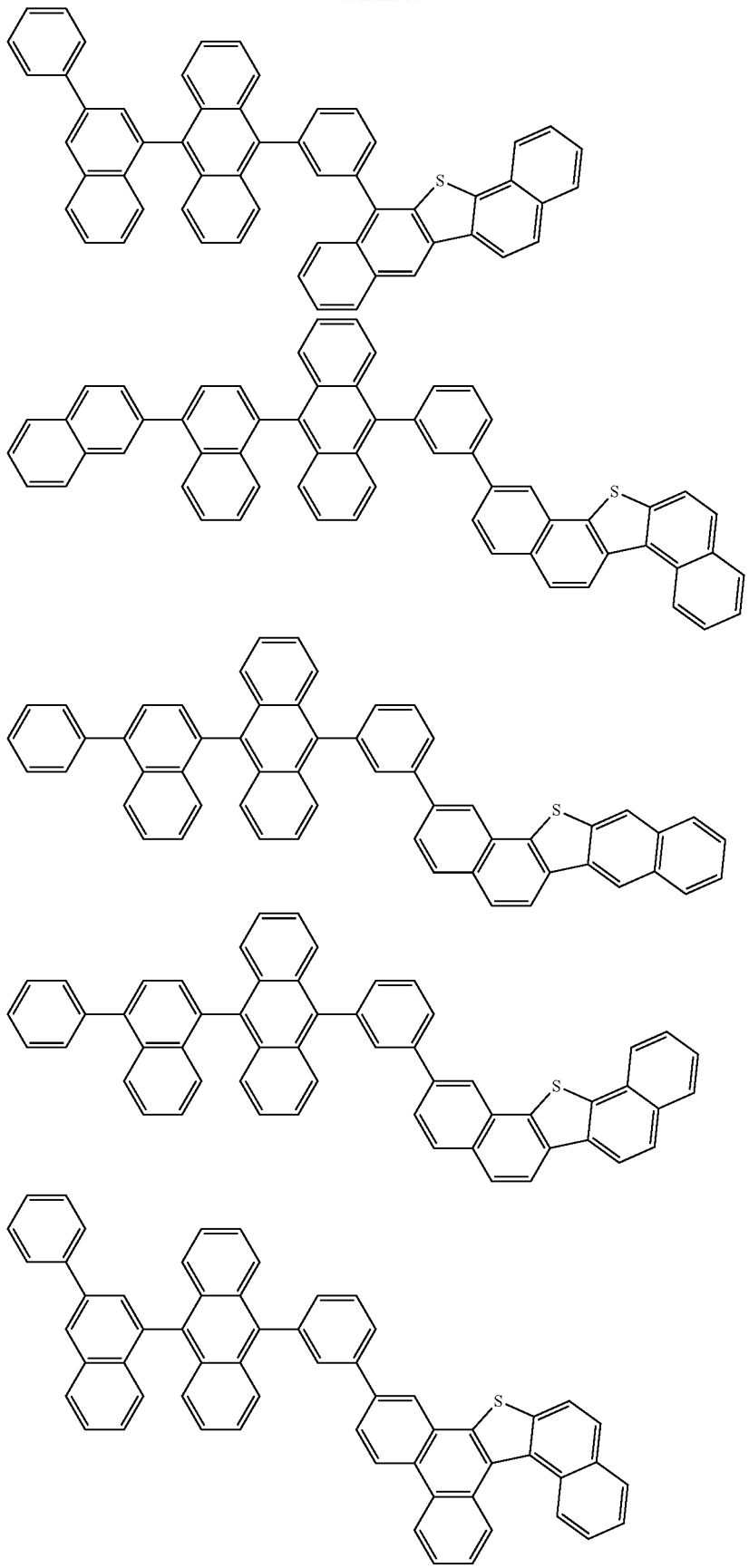

-continued
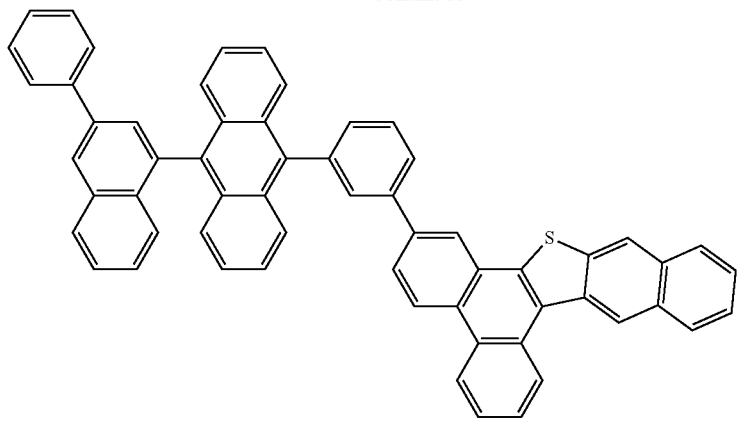
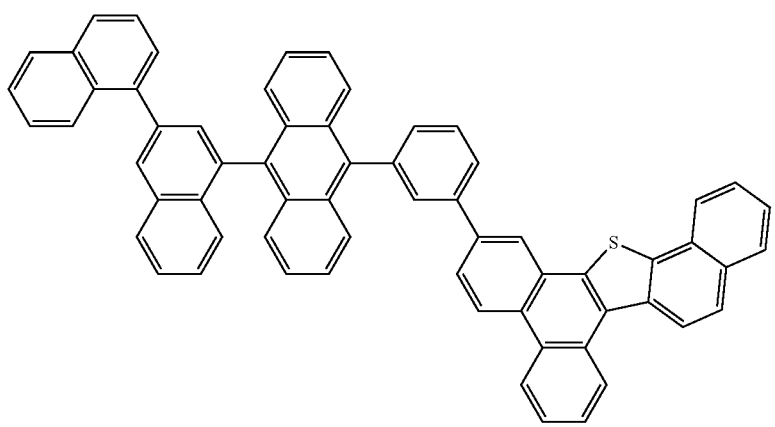
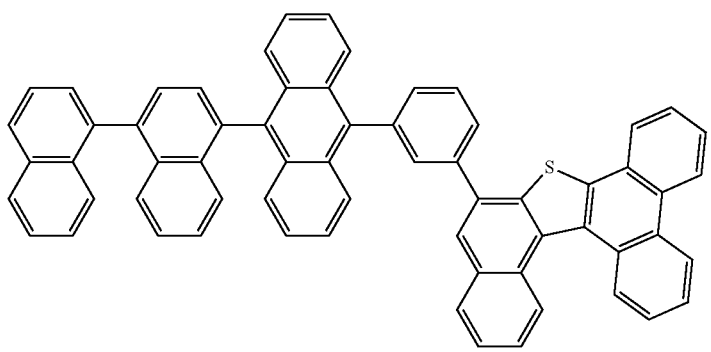
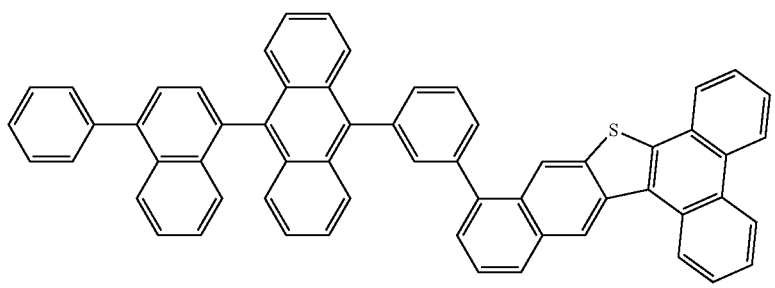

-continued
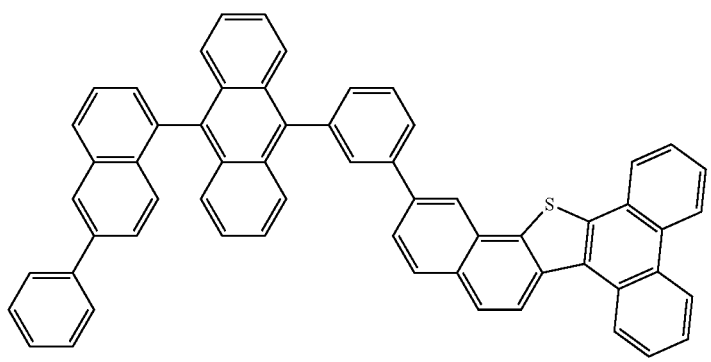
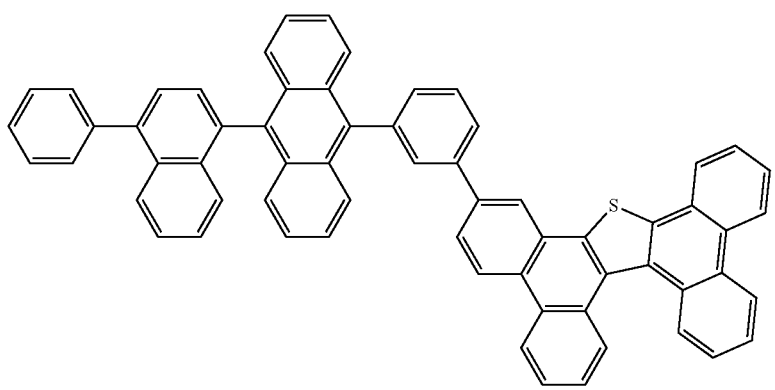
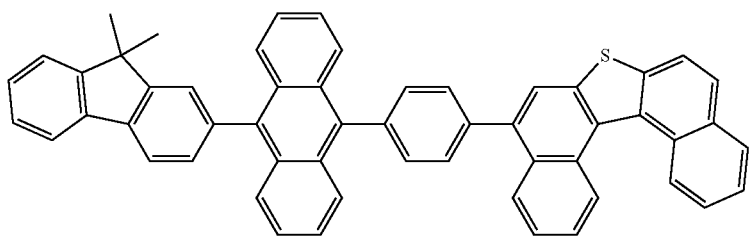
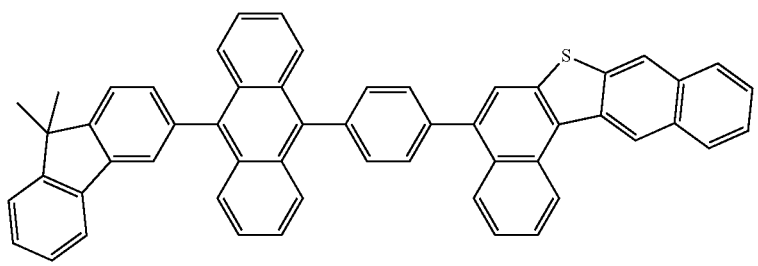
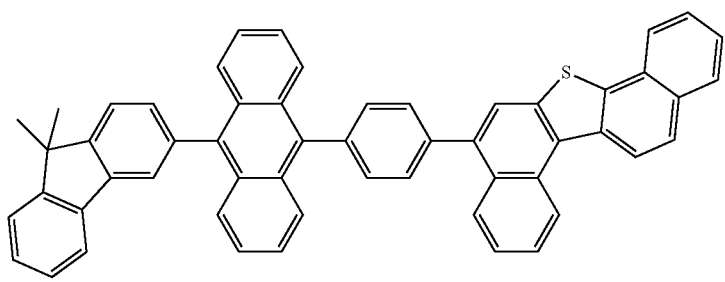

-continued
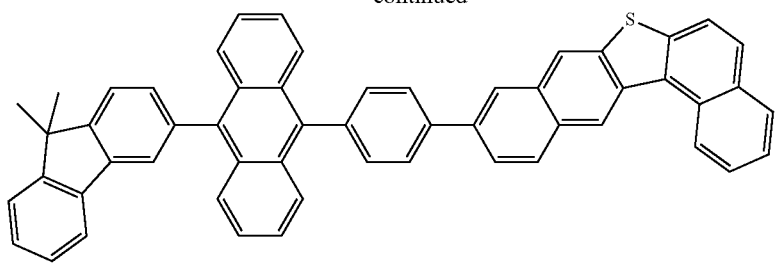
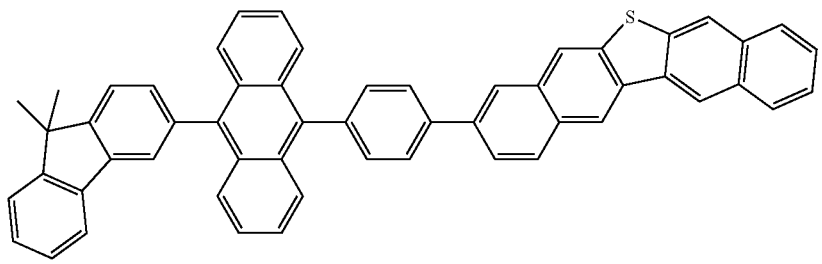
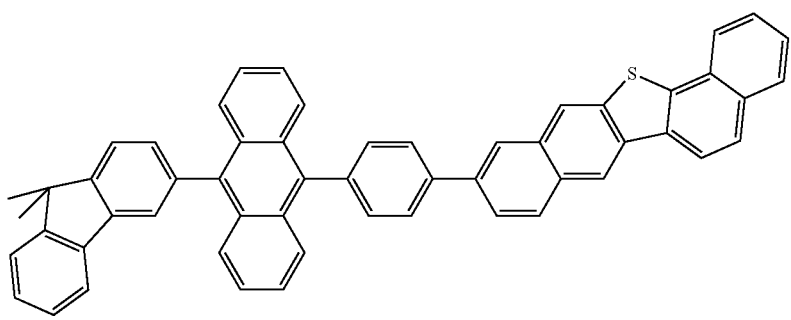
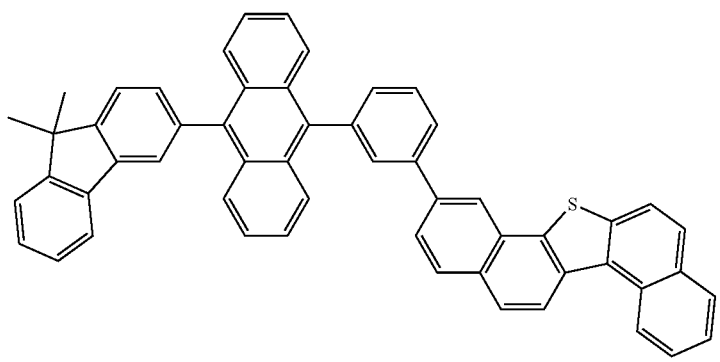
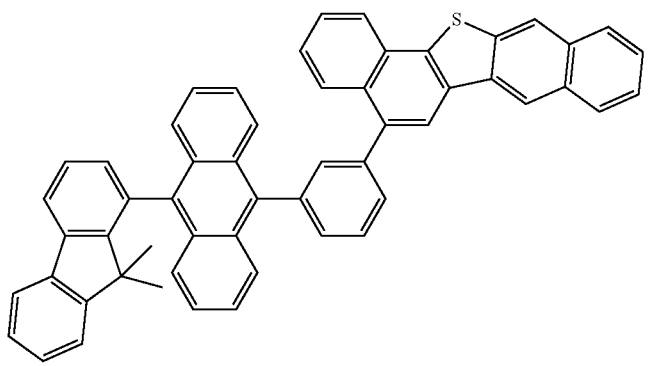

-continued
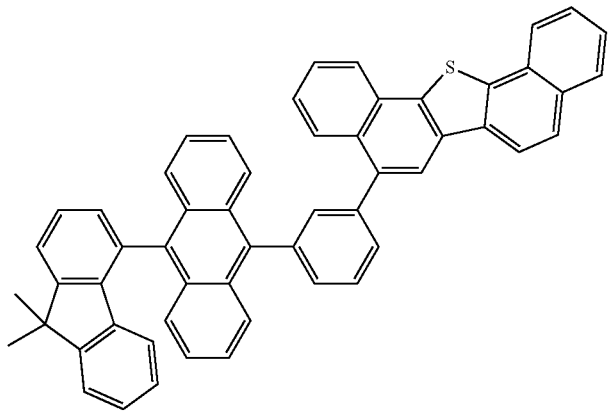
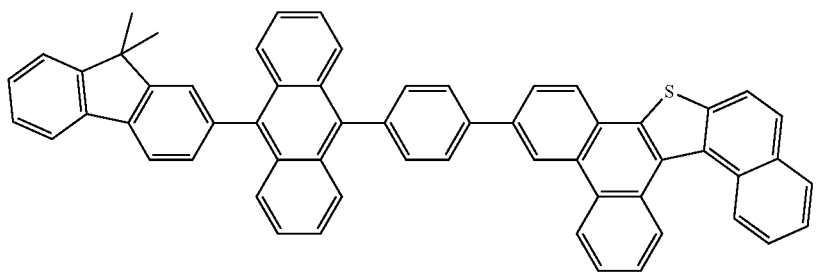
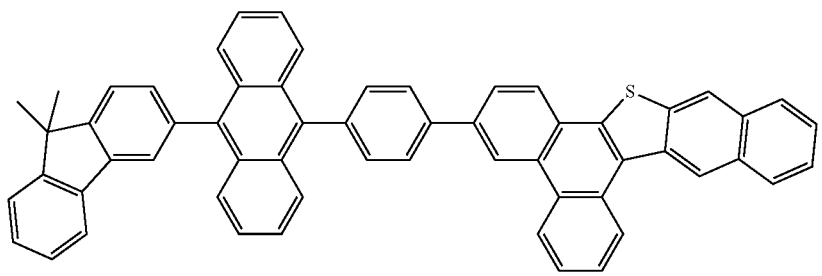
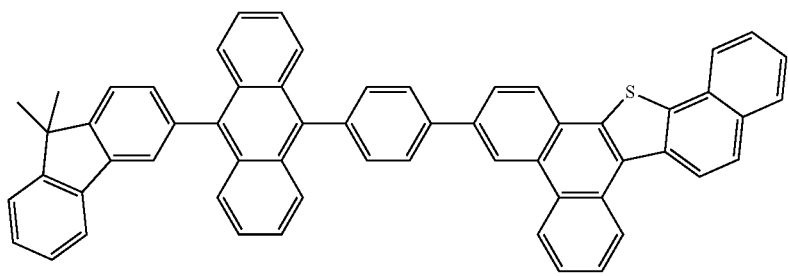
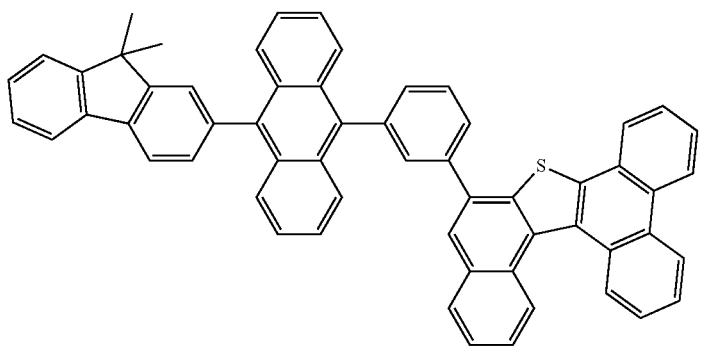

-continued
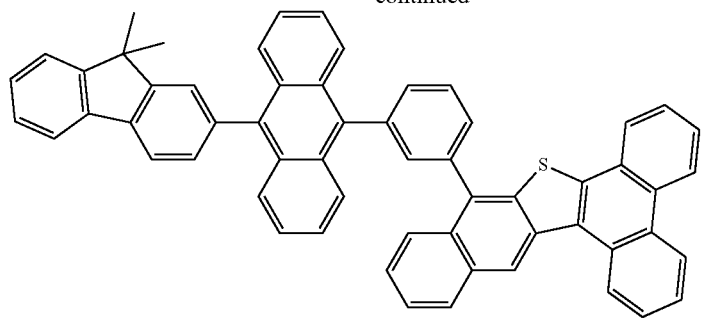
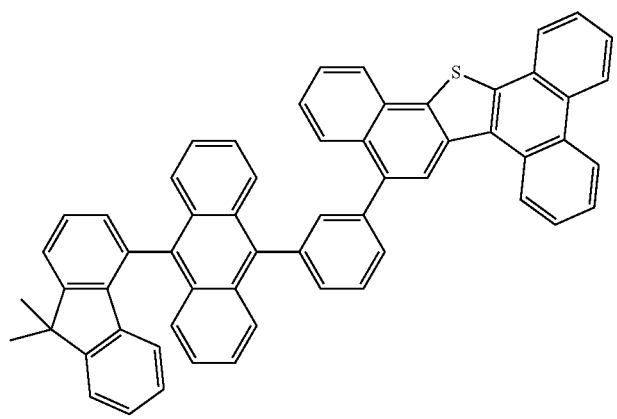
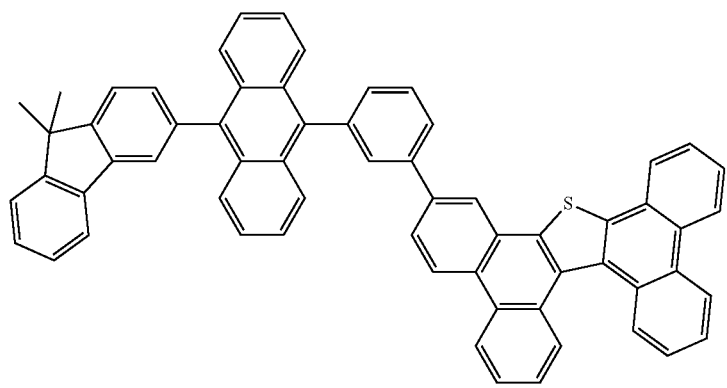
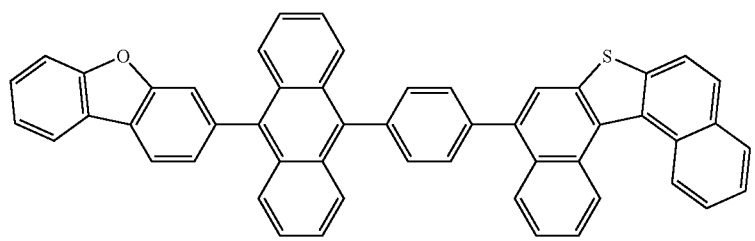
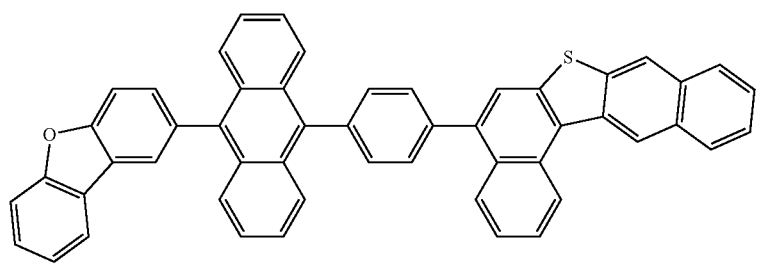

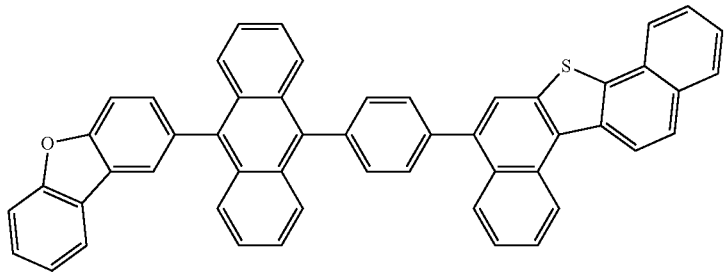
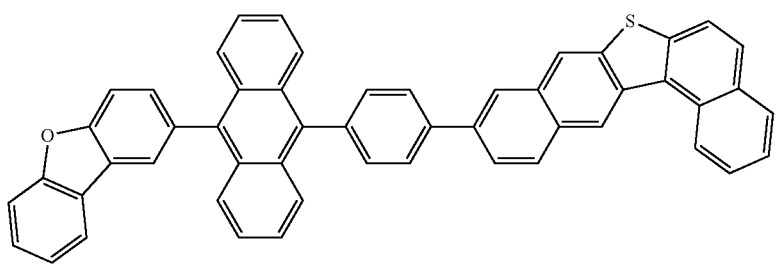
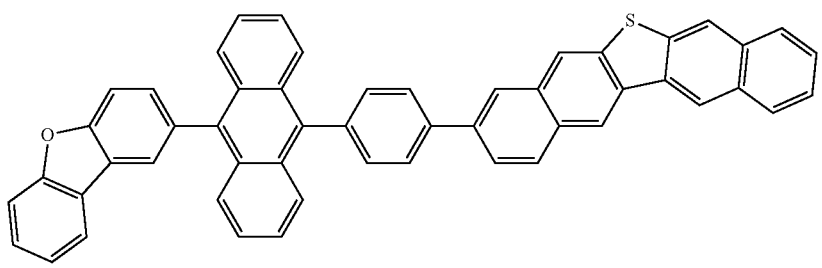
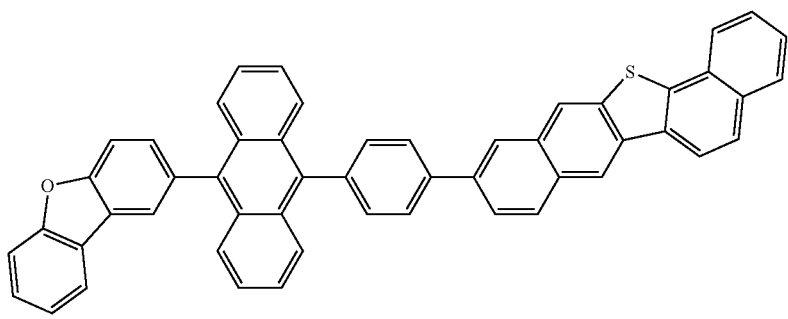
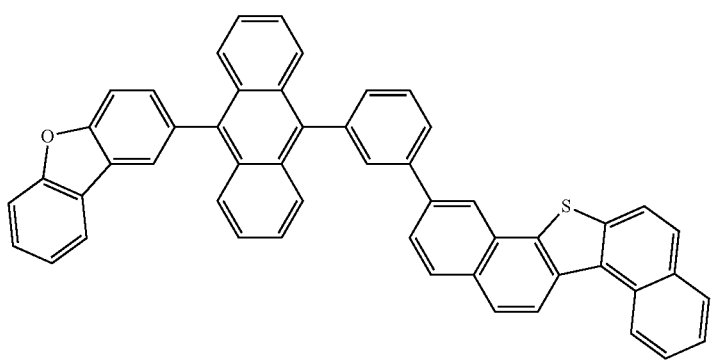

-continued
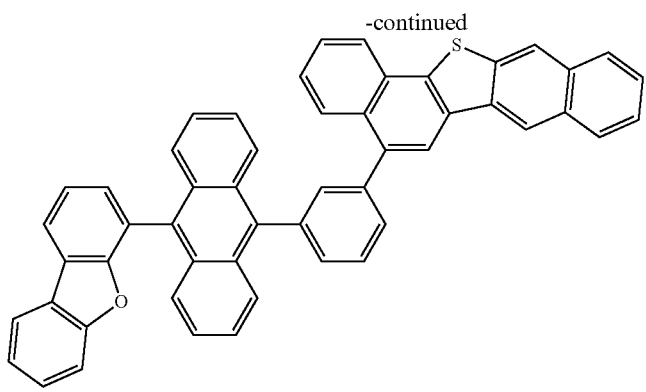
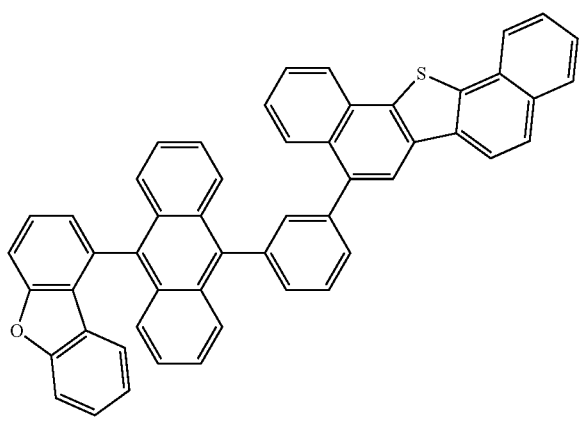
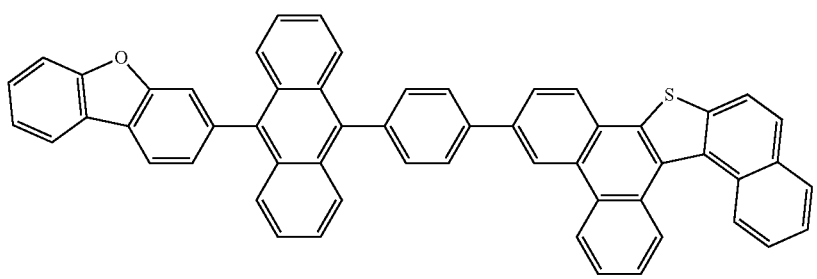
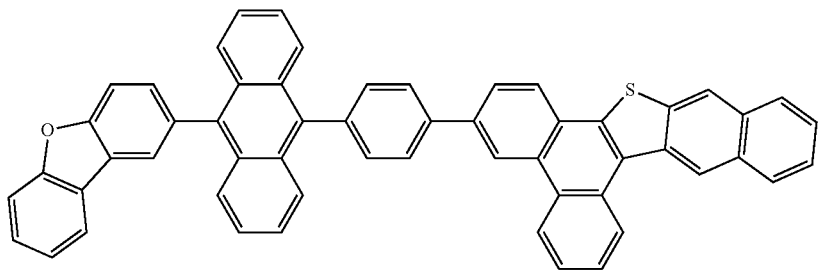
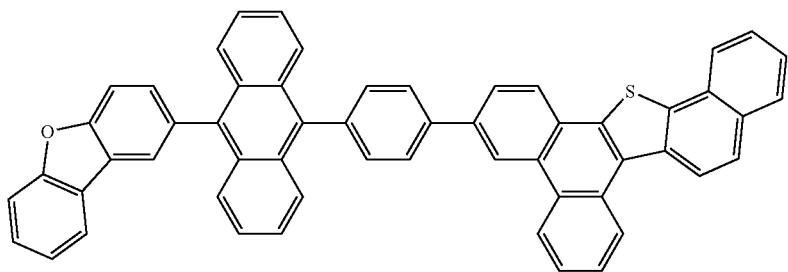

-continued
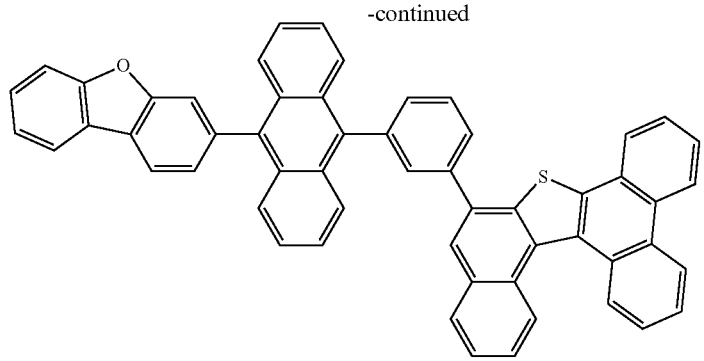
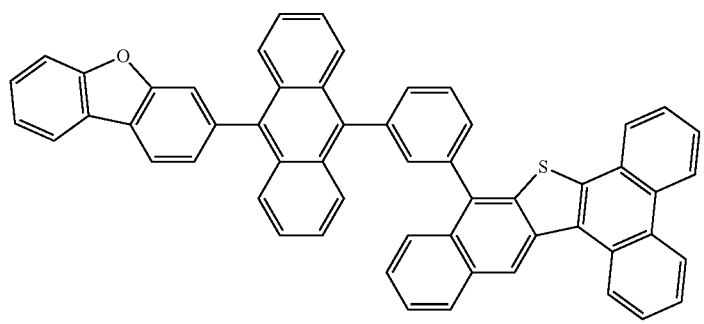
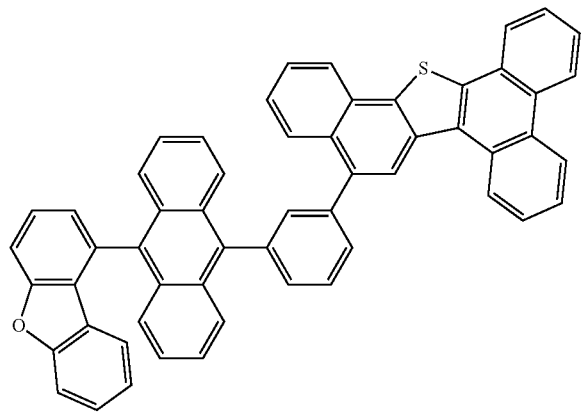
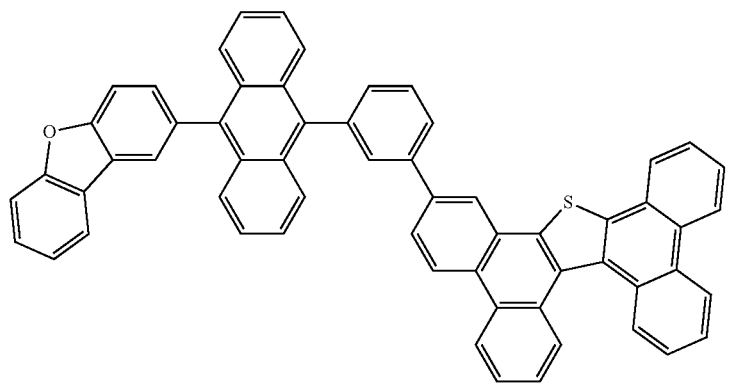

-continued
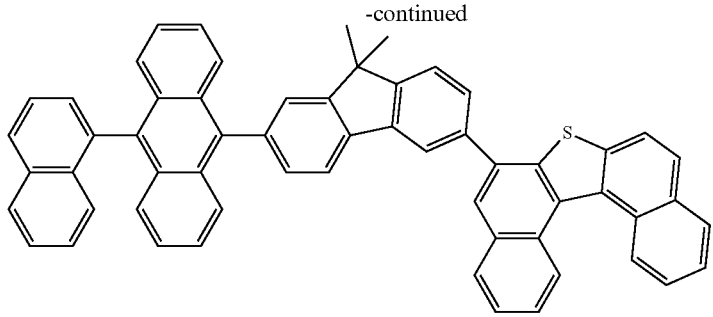
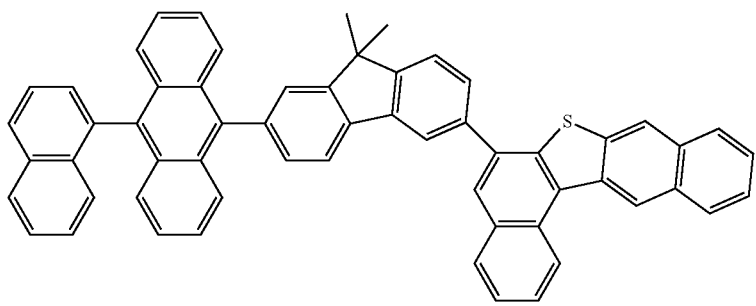
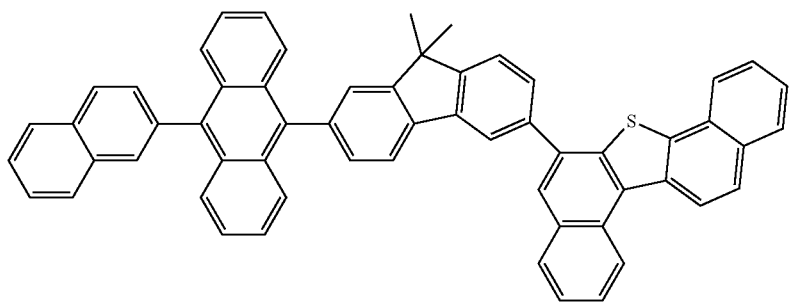
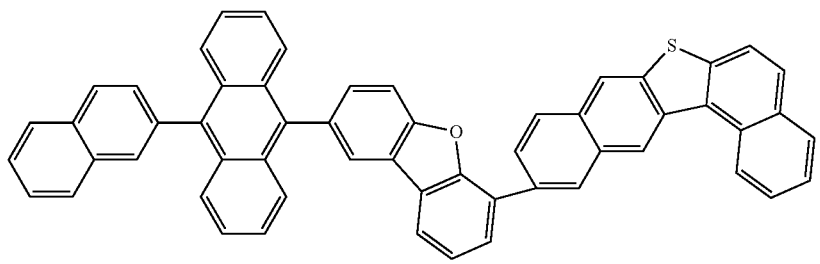
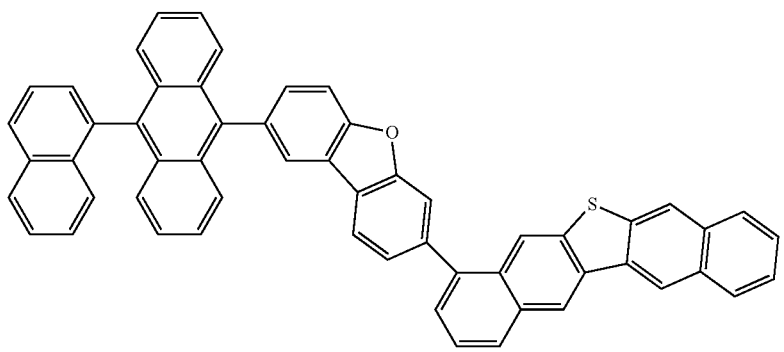

-continued
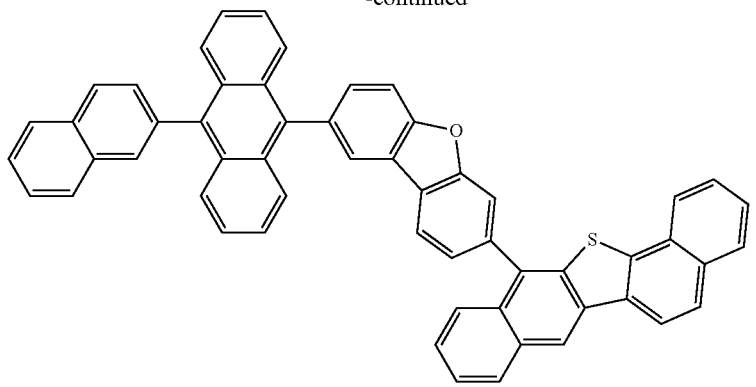
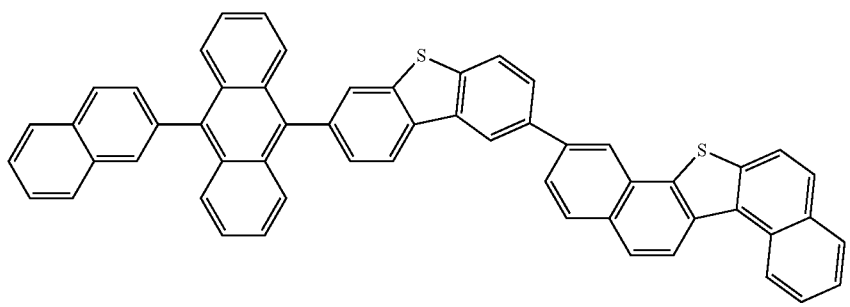
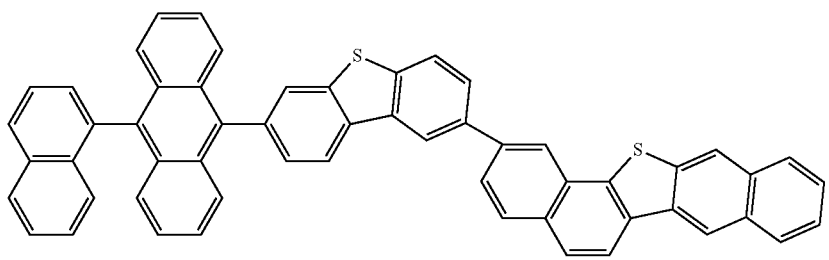
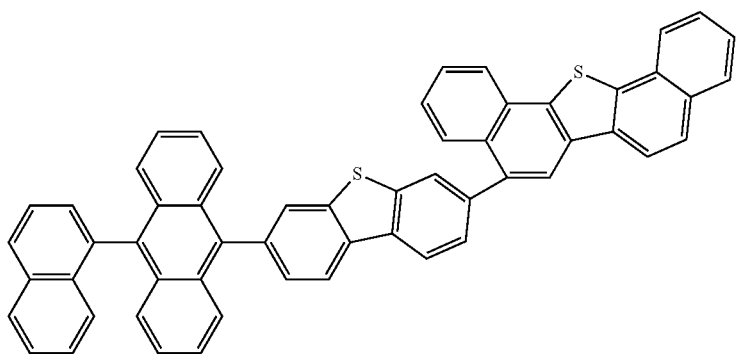
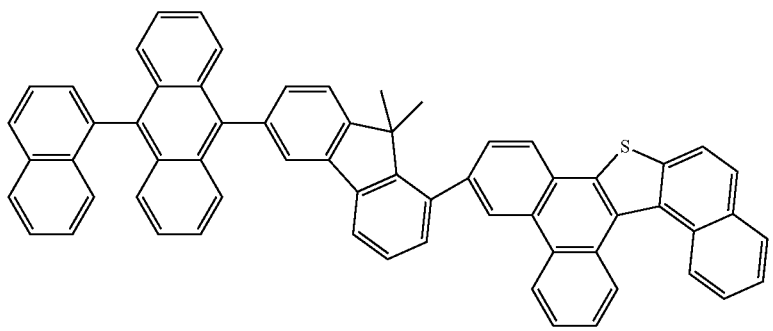

-continued
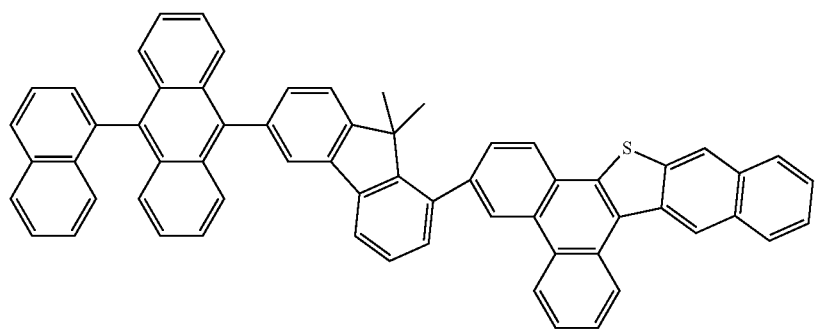
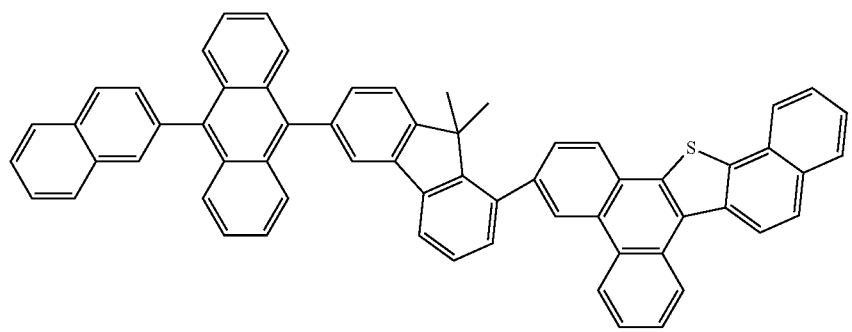
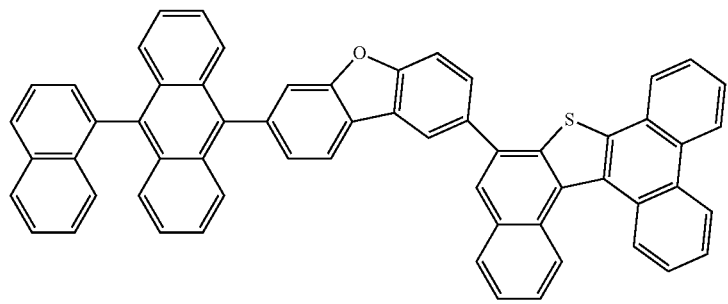
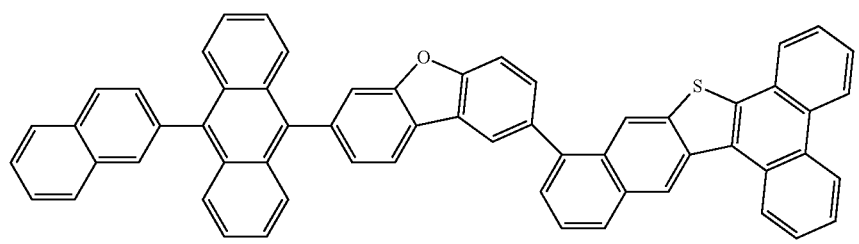
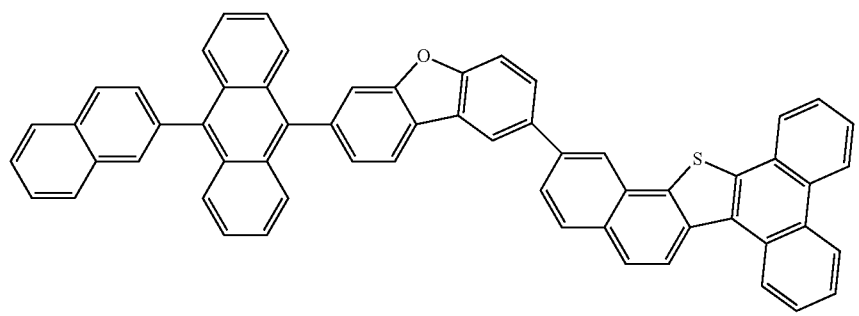

-continued

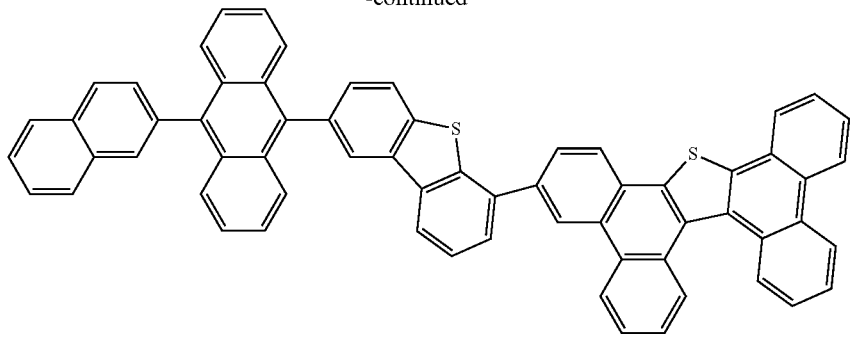

In Formula 1, ring $B_1$ and ring $B_2$ may each independently be selected from a $C_7$-$C_{60}$ aromatic ring and a $C_1$-$C_{60}$ heteroaromatic ring. Accordingly, the size of the entire molecular structure of the condensed cyclic compound represented by Formula 1 may increase to thereby easily disperse electrons of heteroatoms, for example, oxygen (O) or sulfur (S), and stabilize the entire molecular structure of the condensed cyclic compound represented by Formula 1. Therefore, an organic light-emitting device including the condensed cyclic compound represented by Formula 1 may have a relatively high efficiency and a relatively long lifespan.

In Formula 1, $L_1$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group. a1 may indicate the number of $L_1(s)$ might not be 0. Thus, a group represented by $*$-$(L_1)_{a1}$-$(A_1)_{n1}$ in Formula 1 may include $L_1$. Accordingly, electrons on the core of the anthracene group may be localized and may stabilize the entire molecular structure of the condensed cyclic compound represented by Formula 1. The entire molecular structure of the condensed cyclic compound represented by Formula 1 is a three-dimensional structure, which may be easily subjected to non-crystallization, thereby increasing film characteristics upon deposition. Therefore, an organic light-emitting device including the condensed cyclic compound represented by Formula 1 may have a relatively high efficiency and a relatively long lifespan.

As illustrated in Formula 1A', the condensed cyclic compound represented by Formula 1 may be combined with a group represented by Formula 1-1 on a particular position. Accordingly, the condensed cyclic compound represented by Formula 1 may be configured to serve as a host in an emission layer. Therefore, an organic light-emitting device including the condensed cyclic compound represented by Formula 1 may have a relatively high efficiency and a relatively long lifespan.

<Formula 1A'>

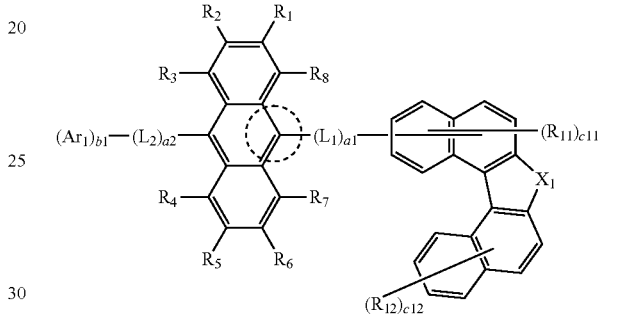

The condensed cyclic compound represented by Formula 1 may be synthesized by known suitable organic synthesis methods. A synthesis method of the condensed cyclic compound represented by Formula 1 may be recognizable by one of ordinary skill in the art in view of the following Examples.

According to an exemplary embodiment of the present invention, an organic light-emitting device may include a first electrode, a second electrode facing the first electrode, and an organic layer disposed between the first electrode and the second electrode. The organic layer may include an emission layer. The organic layer may include at least one condensed cyclic compound represented by Formula 1 as described herein.

The expression that "(an organic layer) includes at least one condensed cyclic compound" as used herein may refer to a case in which "(an organic layer) includes identical condensed cyclic compound represented by Formula 1" and a case in which "(an organic layer) includes two or more different condensed cyclic compounds represented by Formula 1".

For example, the organic layer may include, as the condensed cyclic compound, only Compound 1. In this regard, Compound 1 may be in an emission layer of the organic light-emitting device. According to an exemplary embodiment of the present invention, the organic layer may include, as the condensed cyclic compound, Compound 1 and Compound 2. According to an exemplary embodiment of the present invention, Compound 1 and Compound 2 may both be in an identical layer. For example, Compound 1 and Compound 2 may both be in an emission layer. Alternatively, Compound 1 and Compound 2 may be in different layers. For example, Compound 1 may be in a hole transport layer and Compound 2 may be in an emission layer.

According to an exemplary embodiment of the present invention, the first electrode of the organic light-emitting device may be an anode. The second electrode of the organic light-emitting device may be a cathode.

According to an exemplary embodiment of the present invention, the organic layer may include a hole transport region and an electron transport region. The hole transport region may be disposed between the first electrode and the emission layer. The hole transport region may include at least one of a hole injection layer, a hole transport layer, a buffer layer, or an electron blocking layer. The electron transport region may be disposed between the emission layer and the second electrode. The electron transport region may include at least one of a hole blocking layer, an electron transport layer, or an electron injection layer. At least one of the hole transport region or the emission layer may include at least one of the condensed cyclic compound represented by Formula 1. For example, the emission layer of the organic light-emitting device may include at least one of the condensed cyclic compounds represented by Formula 1. The condensed cyclic compound represented by Formula 1 included in the emission layer may be configured to serve as a host. The emission layer may include a dopant. The dopant may be a phosphorescent dopant or a fluorescent dopant. For example, the dopant may be a fluorescent dopant.

The term "organic layer" used herein may refer to a single layer and/or a plurality of layers disposed between the first electrode and the second electrode of the organic light-emitting device. A material included in the "organic layer" is not limited to an organic material.

Figure 1:
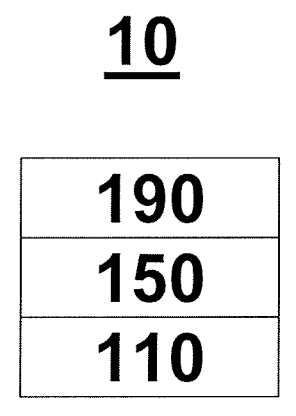

FIG. 1 is a schematic cross-sectional schematic diagram of an organic light-emitting device according to an exemplary embodiment of the present invention. An organic light-emitting device 10 may include a first electrode 110, an organic layer 150, and a second electrode 190.

A structure of an organic light-emitting device according to an exemplary embodiment of the present invention and a method of manufacturing an organic light-emitting device according to an exemplary embodiment of the present invention will be described in more detail below with reference to FIG. 1.

Referring to FIG. 1, a substrate may be disposed below the first electrode 110. Alternatively, the substrate may be disposed above the second electrode 190. The substrate may include a glass substrate or a plastic substrate. The glass substrate and the plastic substrate may each have a relatively high mechanical strength, thermal stability, transparency, surface smoothness, ease of handling, and water-resistance.

The first electrode 110 may be formed by, for example, depositing or sputtering a material included in the first electrode 110 on the substrate. When the first electrode 110 is an anode, the material included in the first electrode 110 may include materials with a relatively high work function, which may facilitate hole injection.

The first electrode 110 may be a reflective electrode, a semi-transmissive electrode, or a transmissive electrode. When the first electrode 110 is a transmissive electrode, a material included in the first electrode 110 may include indium tin oxide (ITO), indium zinc oxide (IZO), tin oxide ($SnO_2$), zinc oxide (ZnO), or any combination thereof; however, exemplary embodiments of the present invention are not limited thereto. When the first electrode 110 is a semi-transmissive electrode or a reflective electrode, a material included in the first electrode 110 may include magnesium (Mg), silver (Ag), aluminum (Al), aluminum-lithium (Al—Li), calcium (Ca), magnesium-indium (Mg—In), magnesium-silver (Mg—Ag), or any combination thereof; however, exemplary embodiments of the present invention are not limited thereto.

The first electrode 110 may have a single-layered structure. Alternatively, the first electrode 110 may have a multi-layered structure including two or more layers. For example, the first electrode 110 may have a three-layered structure of ITO/Ag/ITO; however, the structure of the first electrode 110 is not limited thereto.

The organic layer 150 may be disposed on the first electrode 110. The organic layer 150 may include an emission layer.

The organic layer 150 may include a hole transport region and an electron transport region. The hole transport region may be disposed between the first electrode 110 and the emission layer. The electron transport region may be disposed between the emission layer and the second electrode 190.

The hole transport region may have a single-layered structure including a single material. The hole transport region may have a single-layered structure including a plurality of different materials. The hole transport region may have a multi-layered structure having a plurality of layers including a plurality of different materials.

The hole transport region may include at least one layer selected from a hole injection layer (HIL), a hole transport layer (HTL), an emission auxiliary layer, and an electron blocking layer (EBL).

For example, the hole transport region may have a single-layered structure. The single layered structure may include a single layer including a plurality of different materials. Alternatively, the hole transport region may have a multi-layered structure. The multi-layered structure may include a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure. For each structure, the layers may be sequentially stacked on the first electrode 110; however, the structure of the hole transport region is not limited thereto.

The hole transport region may further include at least one selected from m-MTDATA, TDATA, 2-TNATA, NPB, β-NPB, TPD, Spiro-TPD, Spiro-NPB, methylated-NPB, TAPC, HMTPD, triphenylamine(4,4',4"-tris(N-carbazolyl) triphenylamine) (TCTA), polyaniline/dodecyl benzene sulfonic acid (Pani/DBSA), poly(3,4-ethylenedioxythiophene)/poly(4-styrenesulfonate) (PEDOT/PSS), polyaniline/camphor sulfonic acid (Pani/CSA), polyaniline/poly(4-styrenesulfonate) (Pani/PSS), a compound represented by Formula 201, and a compound represented by Formula 202:

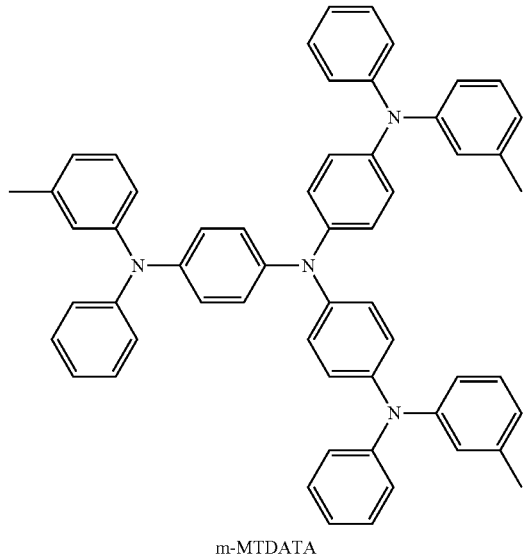

m-MTDATA

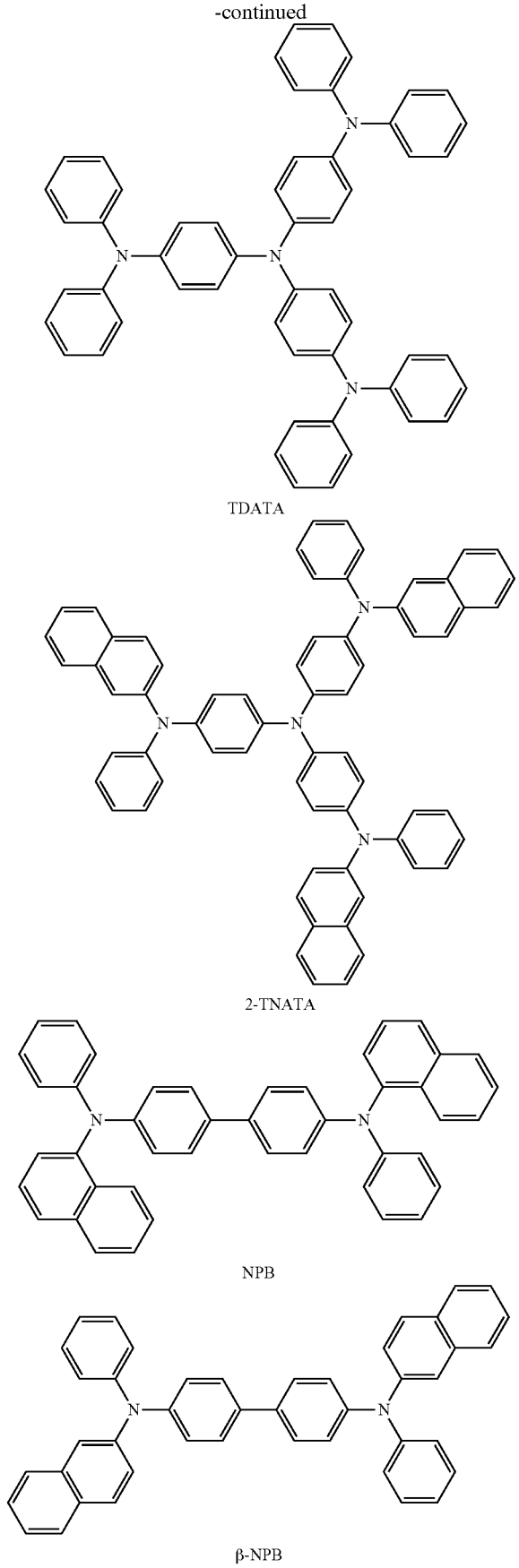
TDATA
2-TNATA
NPB
β-NPB
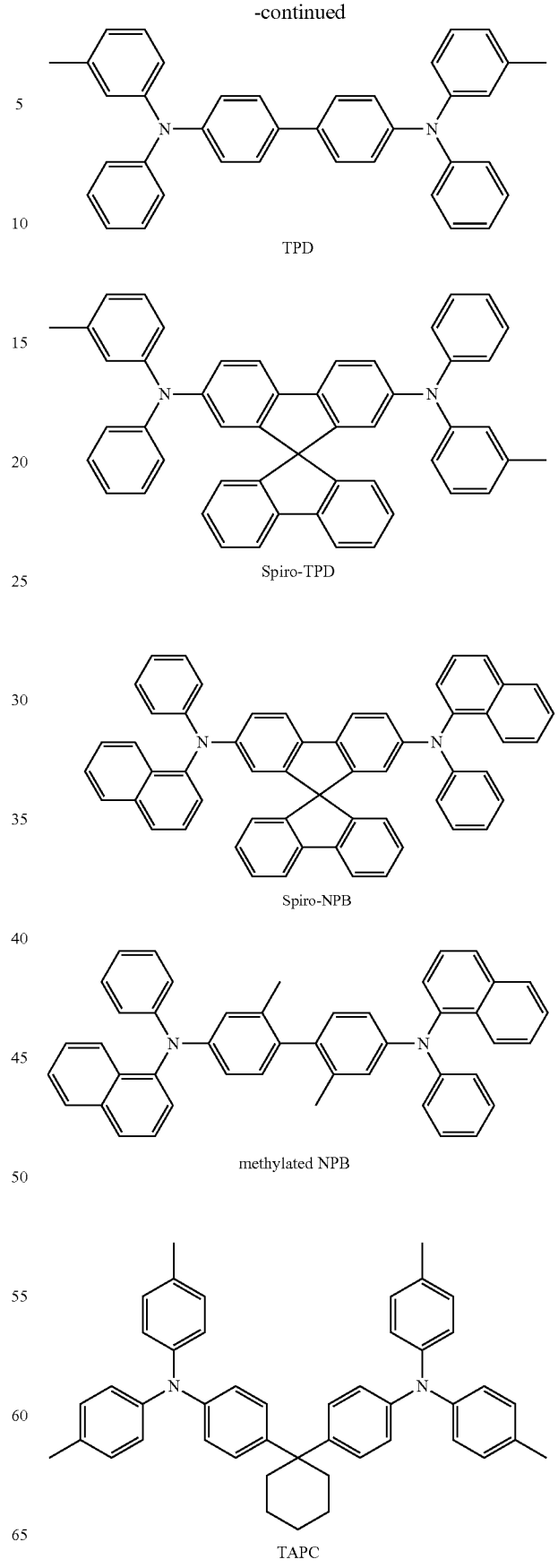
TPD
Spiro-TPD
Spiro-NPB
methylated NPB
TAPC -continued

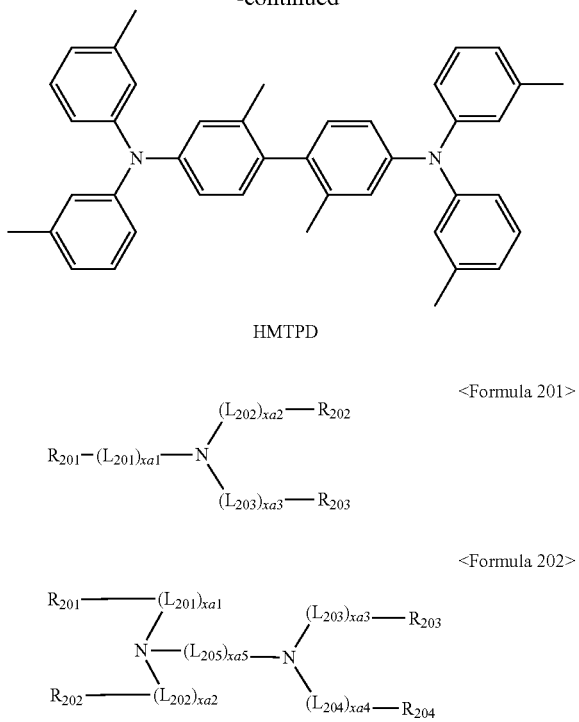

HMTPD

<Formula 201>

R$_{201}$—(L$_{201}$)$_{xa1}$—N(—(L$_{202}$)$_{xa2}$—R$_{202}$)(—(L$_{203}$)$_{xa3}$—R$_{203}$)

<Formula 202>

R$_{201}$—(L$_{201}$)$_{xa1}$\
R$_{202}$—(L$_{202}$)$_{xa2}$ N—(L$_{205}$)$_{xa5}$—N (L$_{203}$)$_{xa3}$—R$_{203}$\
(L$_{204}$)$_{xa4}$—R$_{204}$

In Formulae 201 and 202:

L$_{201}$ to L$_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

L$_{205}$ may be selected from *—O—*', *—S—*', *—N(Q$_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

xa1 to xa4 may each independently be an integer selected from 0 to 3.

xa5 may be an integer selected from 1 to 10.

R$_{201}$ to R$_{204}$ and Q$_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, in Formula 202, R$_{201}$ and R$_{202}$ may be connected to each other via a single bond, a dimethyl-methylene group, or a diphenyl-methylene group, and R$_{203}$ and R$_{204}$ may be connected to each other via a single bond, a dimethyl-methylene group, or a diphenyl-methylene group. However, exemplary embodiments of the present invention are not limited thereto.

According to an exemplary embodiment of the present invention, in Formulae 201 and 202, L$_{201}$ to L$_{205}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$).

$Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

According to an exemplary embodiment of the present invention, in Formulae 201 and 202, xa1 to xa4 may each independently be an integer selected from 0, 1, and 2.

According to an exemplary embodiment of the present invention, in Formula 202, xa5 may be an integer selected from 1, 2, 3, and 4.

According to an exemplary embodiment of the present invention, in Formulae 201 and 202, $R_{201}$ to $R_{204}$ and $Q_{201}$ may each independently be selected from:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$).

$Q_{31}$ to $Q_{33}$ may be the same as described above.

According to an exemplary embodiment of the present invention, in Formula 201, at least one of $R_{201}$ to $R_{203}$ may each independently be selected from:

a fluorenyl group, a spiro-bifluorenyl group, a carbazolyl group, a dibenzofuranyl group, or a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group; however, exemplary embodiments of the present invention are not limited thereto.

According to an exemplary embodiment of the present invention, in Formula 202, $R_{201}$ and $R_{202}$ may be linked via a single bond, and/or $R_{203}$ and $R_{204}$ may be linked via a single bond.

According to an exemplary embodiment of the present invention, in Formula 202, at least one of $R_{201}$ to $R_{204}$ may be selected from:

a carbazolyl group; and a carbazolyl group substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group; however, exemplary embodiments of the present invention are not limited thereto.

The compound represented by Formula 201 may be represented by Formula 201A:

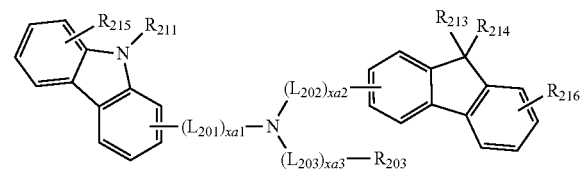

<Formula 201A>

The compound represented by Formula 201 may be represented by Formula 201A(1); however, exemplary embodiments of the present invention are not limited thereto:

<Formula 201A(1)>

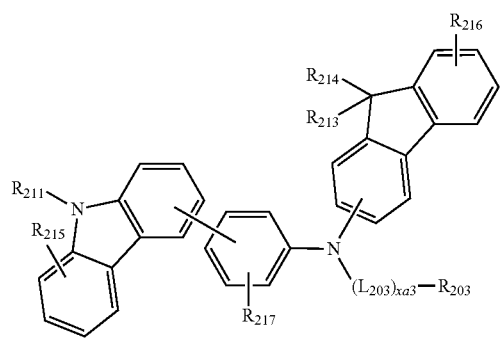

The compound represented by Formula 201 may be represented by Formula 201A-1; however, exemplary embodiments of the present invention are not limited thereto:

<Formula 201A-1>

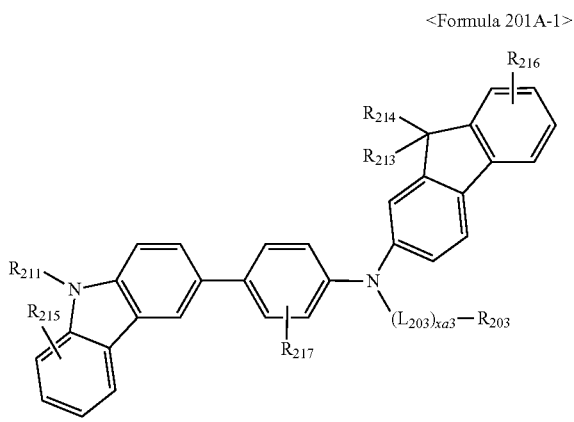

According to an exemplary embodiment of the present invention, the compound represented by Formula 202 may be represented by Formula 202A:

<Formula 202A>

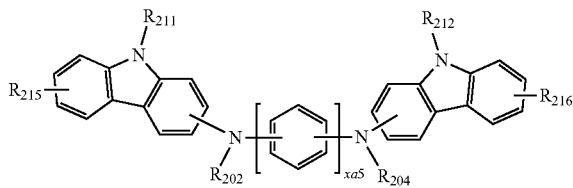

According to an exemplary embodiment of the present invention, the compound represented by Formula 202 may be represented by Formula 202A-1:

<Formula 202A-1>

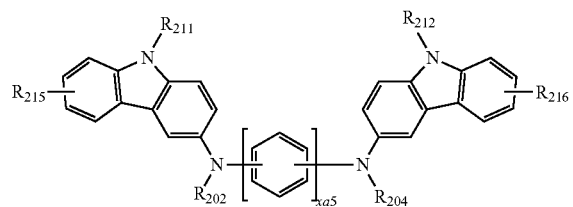

In Formulae 201A, 201A(1), 201A-1, 202A, and 202A-1, $L_{201}$ to $L_{203}$, xa1 to xa3, xa5, and $R_{202}$ to $R_{204}$ may each independently be the same as described above.

In Formulae 201A, 201A(1), 201A-1, 202A, and 202A-1, $R_{211}$ and $R_{212}$ may be the same as $R_{203}$.

In Formulae 201A, 201A(1), 201A-1, 202A, and 202A-1, $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT39; however, exemplary embodiments of the present invention are not limited thereto:

251 HT1  252 HT2
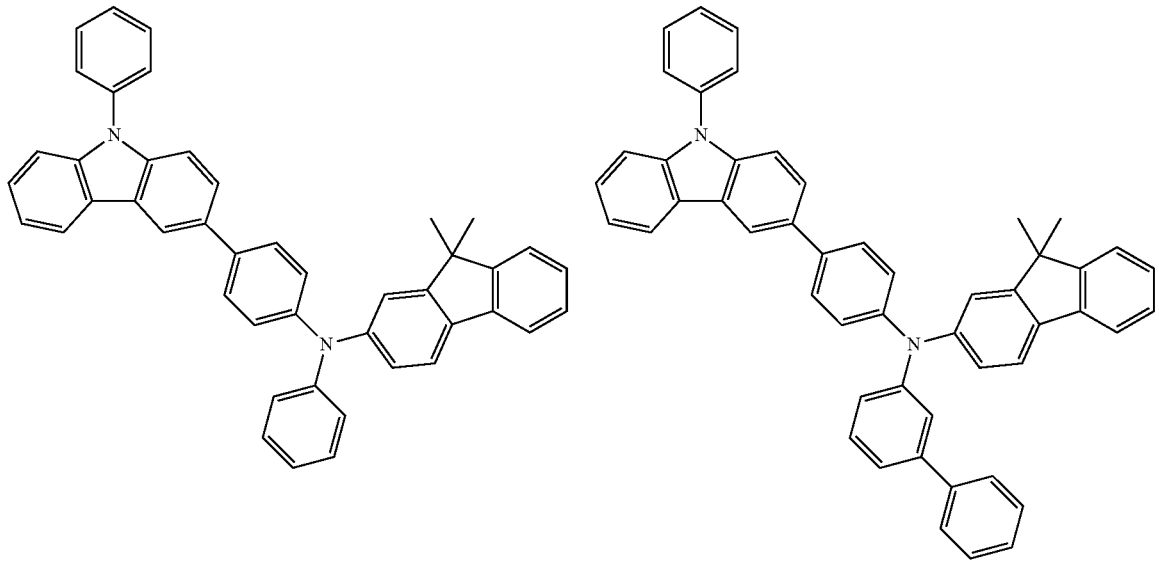
HT3  HT4
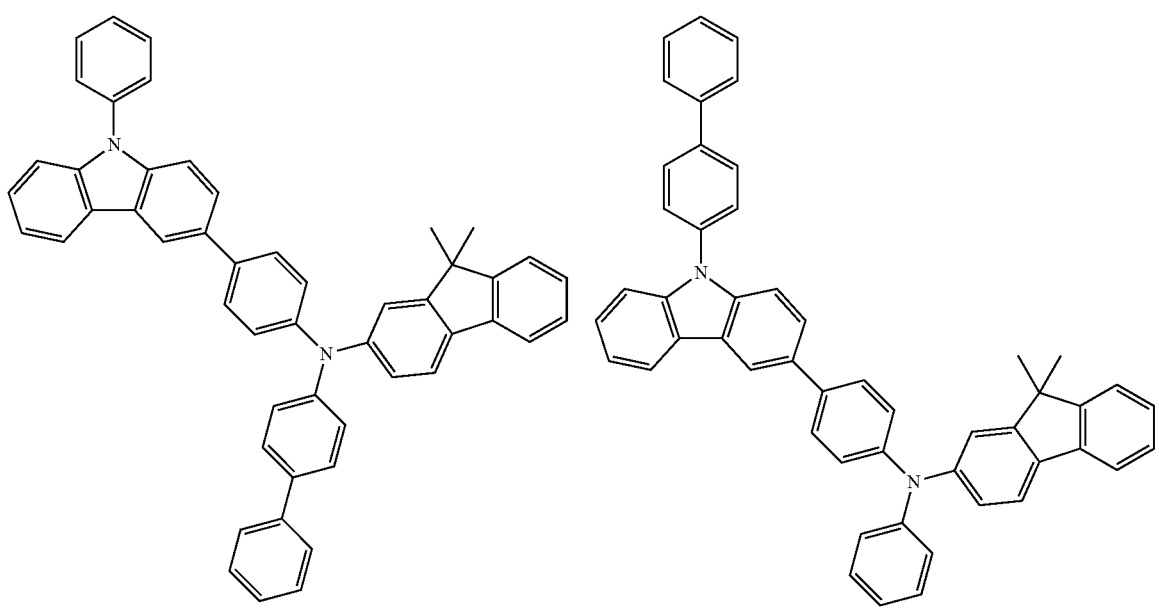

-continued
HT5
HT6
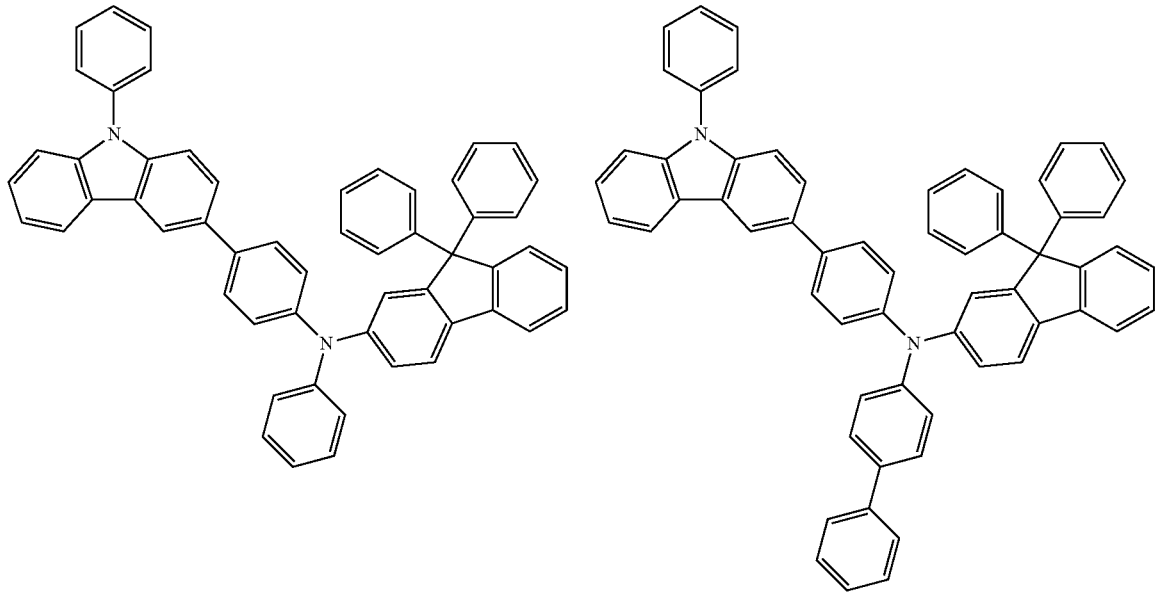
HT7
HT8
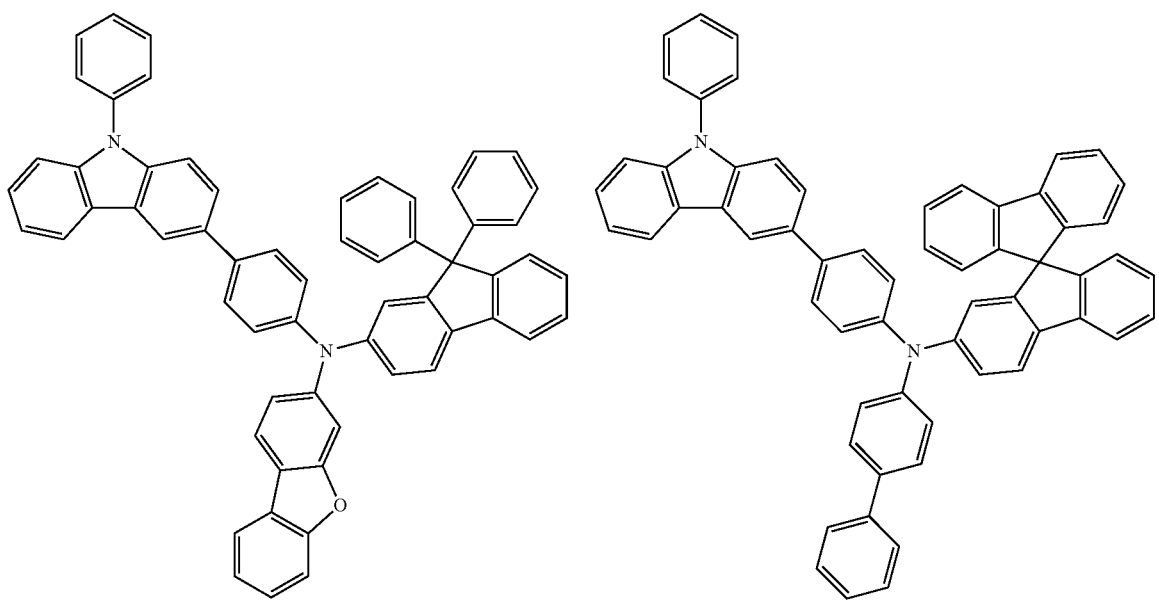

-continued
HT9
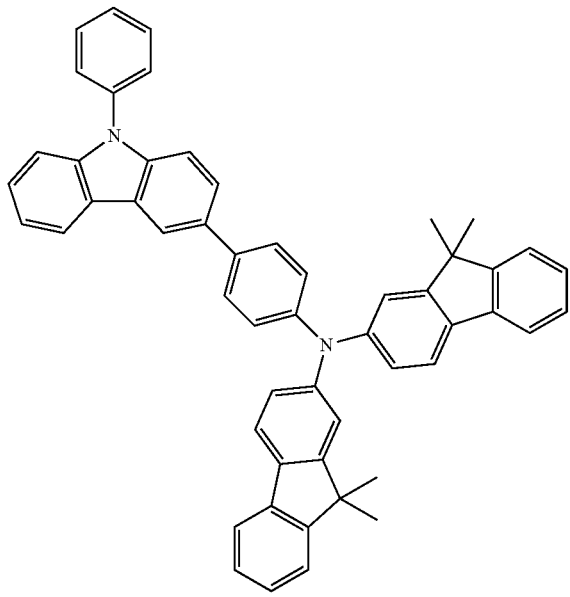
HT10
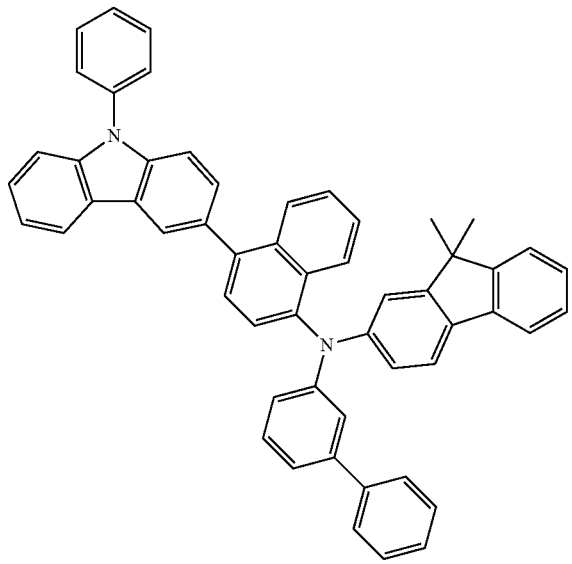
HT11
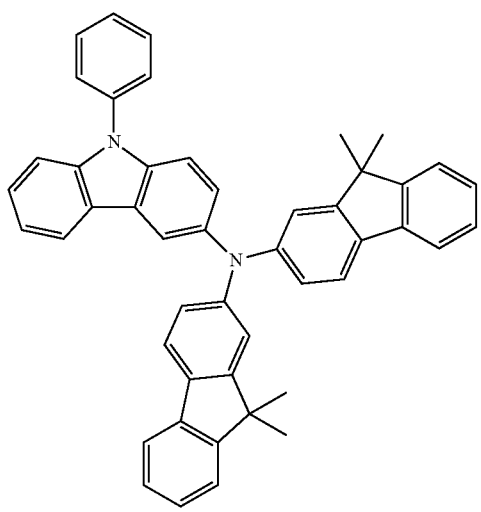
HT12
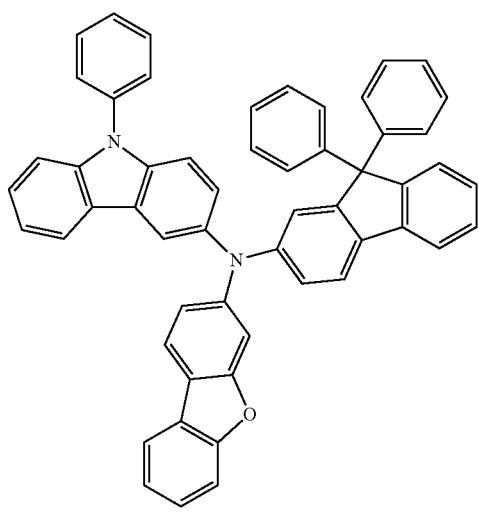

-continued
HT13
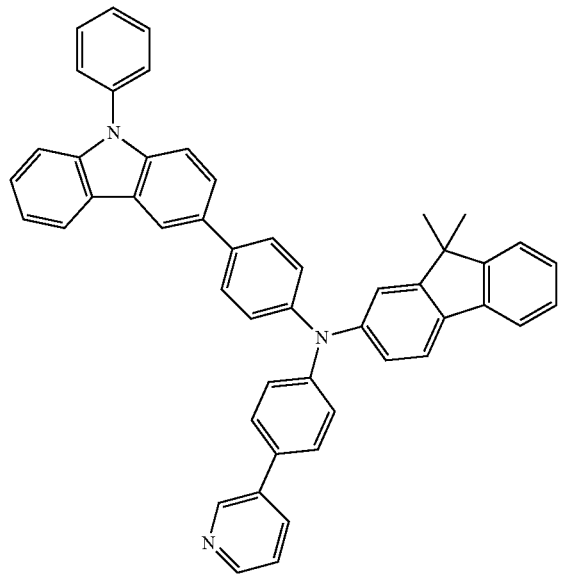
HT14
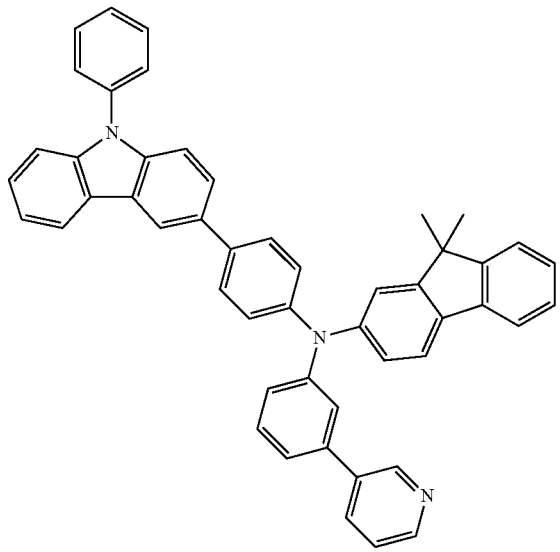
HT15
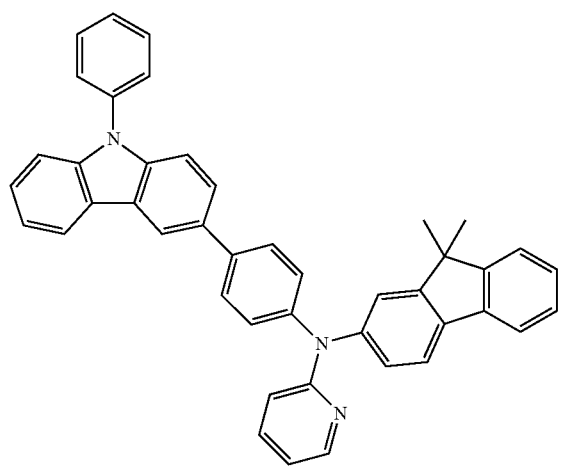
HT16
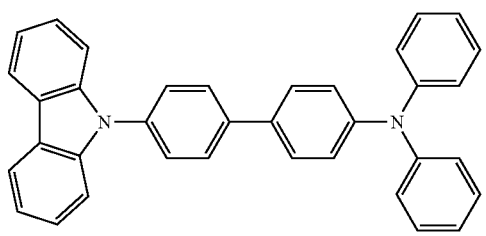
HT17
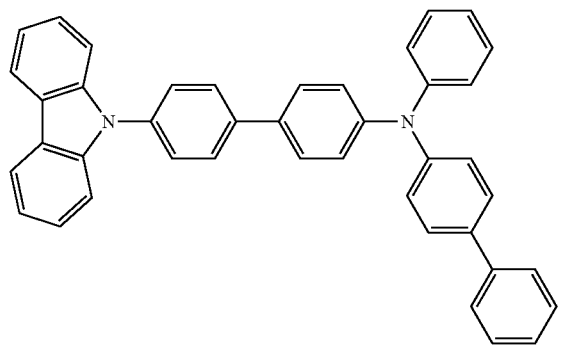
HT18
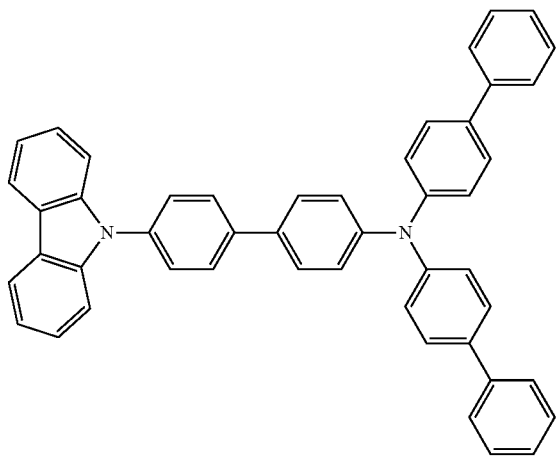

-continued
HT19
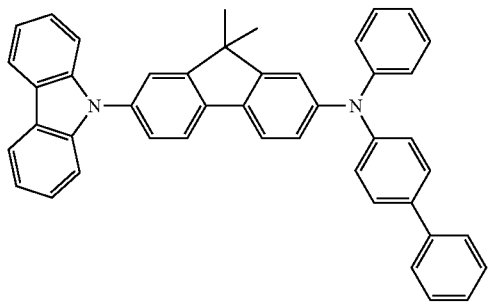
HT20
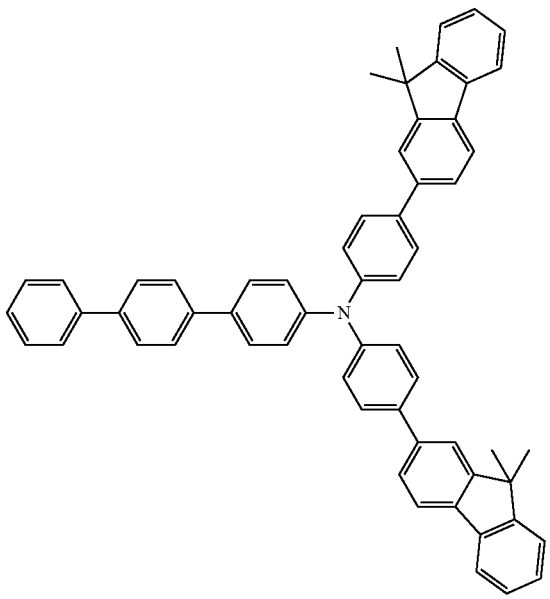
HT21
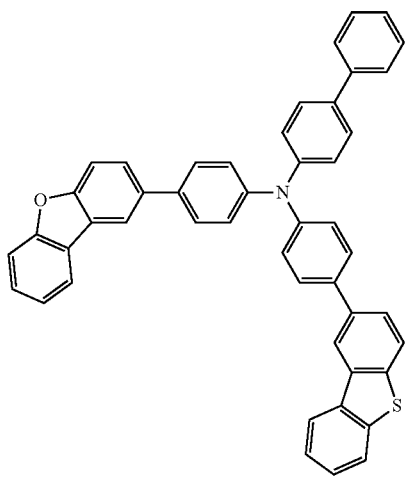
HT22
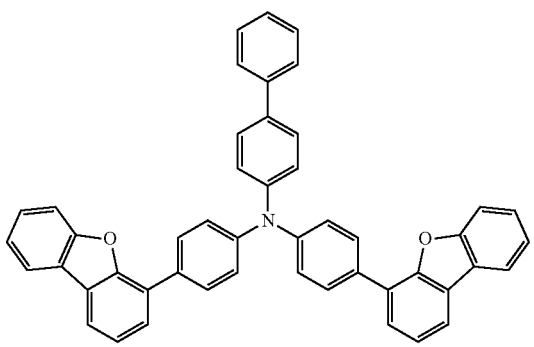
HT23
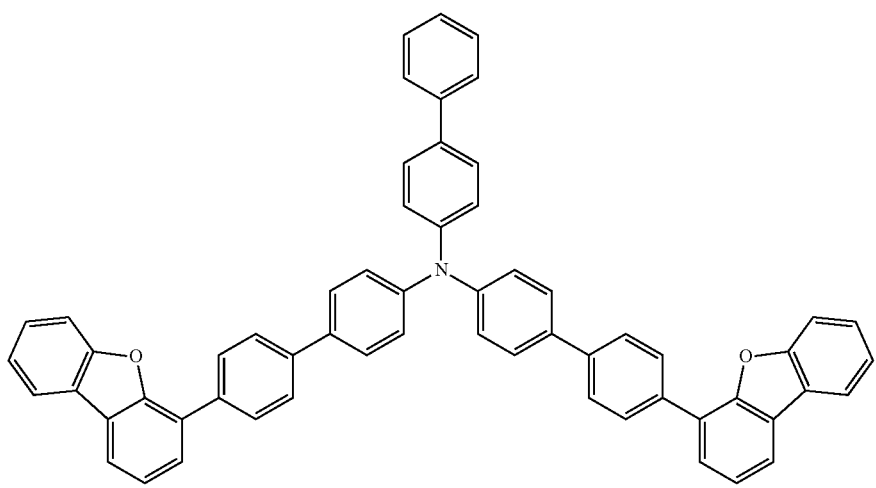

-continued
HT24
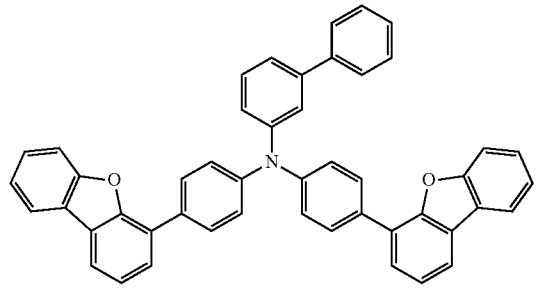
HT25
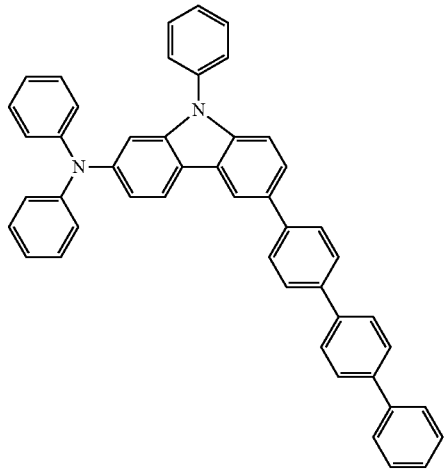
HT26
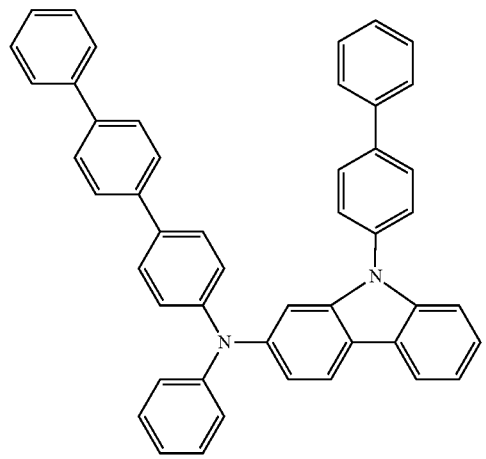
HT27
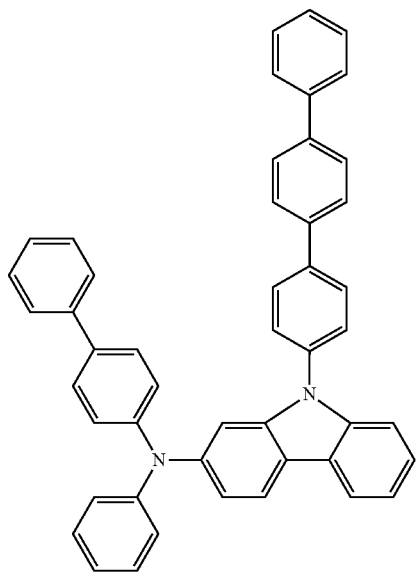
HT28
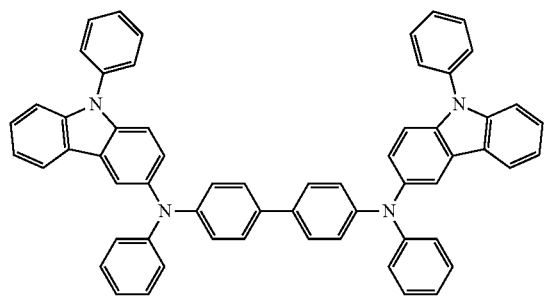
HT29
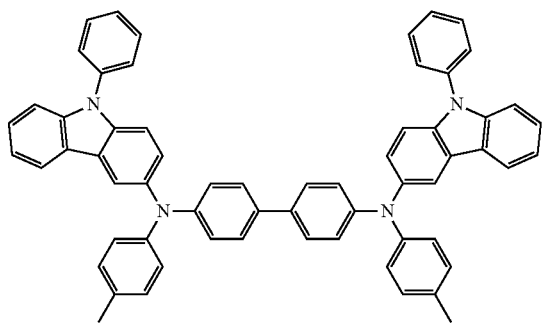

-continued
HT30
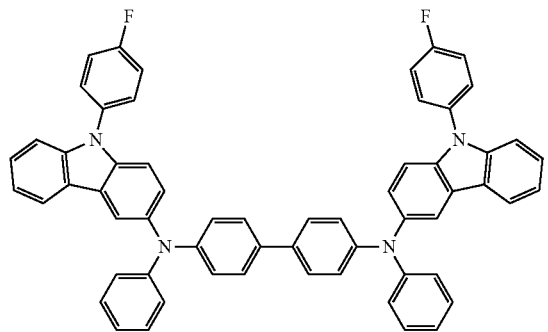
HT31
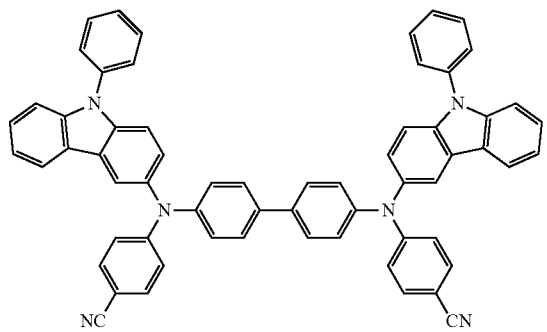
HT32
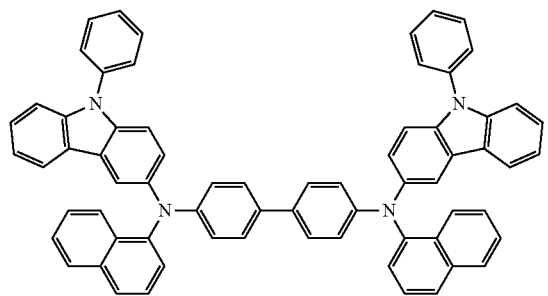
HT33
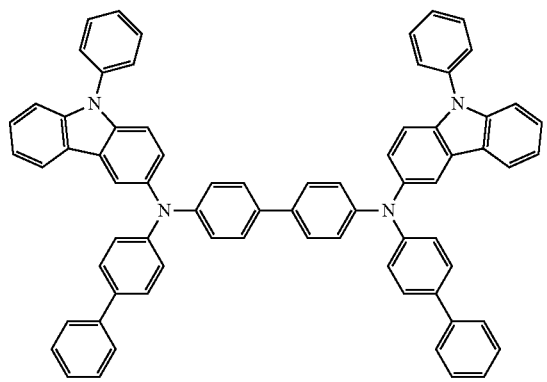
HT34
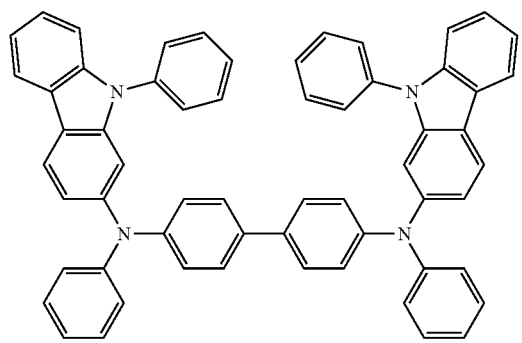
HT35
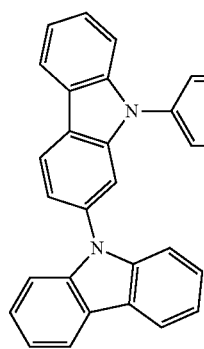

HT36

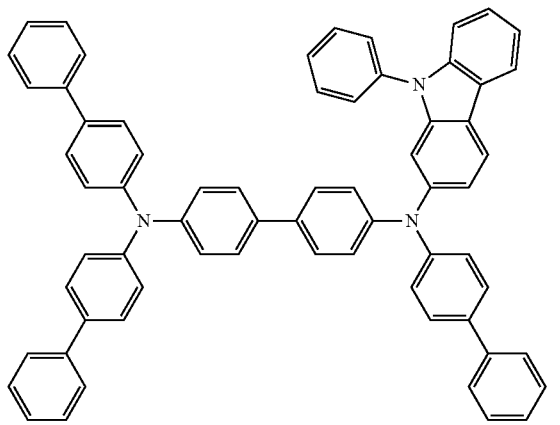

HT37

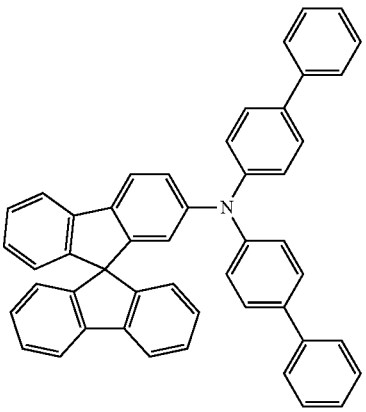

HT38

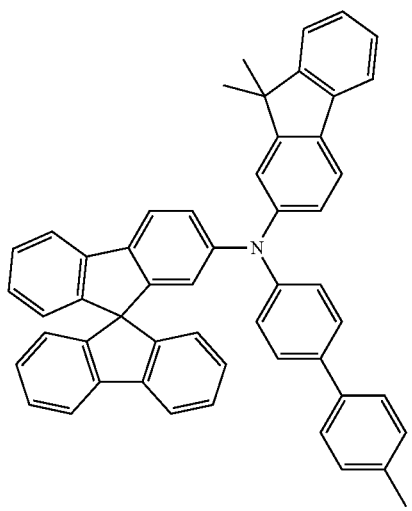

HT39

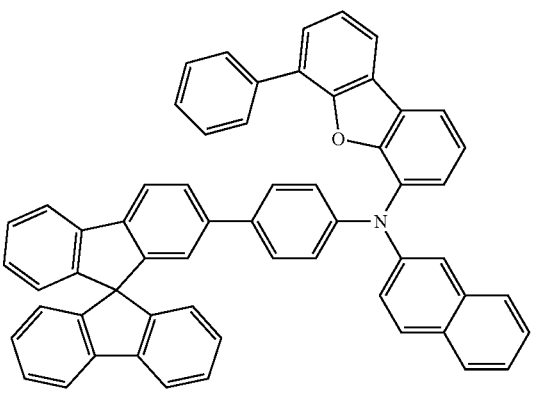

A thickness of the hole transport region may be in a range of from about 100 Å to about 10,000 Å, for example, from about 100 Å to about 1,000 Å. When the hole transport region includes at least one of a hole injection layer and a hole transport layer, a thickness of the hole injection layer may be in a range of from about 100 Å to about 9,000 Å, for example, from about 100 Å to about 1,000 Å, and a thickness of the hole transport layer may be in a range of from about 50 Å to about 2,000 Å, for example, from about 100 Å to about 1,500 Å. When the thicknesses of the hole transport region, the hole injection layer, and the hole transport layer are within any of these ranges, satisfactory hole transporting characteristics may be obtained without a substantial increase in driving voltage.

The emission auxiliary layer may compensate for an optical resonance distance according to a wavelength of light emitted from the emission layer. Thus, the light-emission efficiency of a formed organic light-emitting device may be increased. The electron blocking layer may decrease or prevent injection of electrons from the electron transport region. The emission auxiliary layer and the electron blocking layer may include materials as described herein.

The hole transport region may include a charge-generation material, which may increase conductive properties of the hole transport region. The charge-generation material may be substantially homogeneously or non-homogeneously dispersed in the hole transport region.

The charge-generation material may be, for example, a p-dopant.

According to an exemplary embodiment of the present invention, a lowest unoccupied molecular orbital (LUMO) of the p-dopant may be −3.5 eV or less.

The p-dopant may be one of a quinone derivative, a metal oxide, or a compound containing a cyano group; however, exemplary embodiments of the present invention are not limited thereto.

For example, p-dopant may include at least one selected from:

a quinone derivative, such as tetracyanoquinonedimethane (TCNQ) and 2,3,5,6-tetrafluoro-tetracyano-1,4-benzoquinonedimethane (F4-TCNQ);

a metal oxide, such as a tungsten oxide or a molybdenum oxide;

a compound containing a cyano group, such as 1,4,5,8,9,11-hexaazatriphenylene-hexacarbonitrile (HAT-CN); or a compound represented by Formula 221; however, exemplary embodiments of the present invention are not limited thereto:

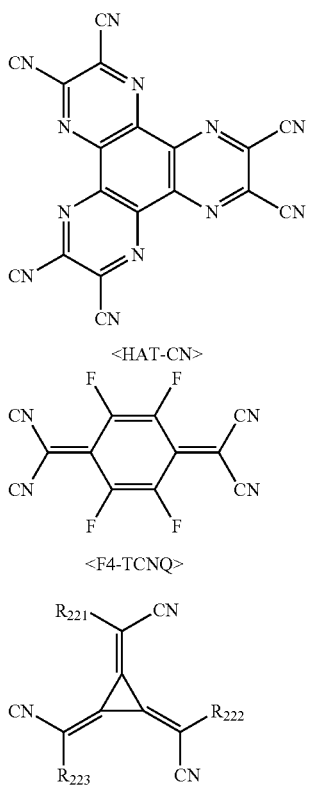

<HAT-CN>

<F4-TCNQ>

<Formula 221>

In Formula 221:

$R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, wherein at least one selected from $R_{221}$ to $R_{223}$ may include a substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

When the organic light-emitting device 10 is a full color organic light-emitting device, the emission layer may be patterned into a red emission layer, a green emission layer, and/or a blue emission layer, according to a sub-pixel. According to an exemplary embodiment of the present invention, the emission layer may have a stacked structure. The stacked structure may include two or more layers selected from a red emission layer, a green emission layer, and a blue emission layer. The two or more layers may be in direct contact with each other. Alternatively, the two or more layers may be separated from each other. According to an exemplary embodiment of the present invention, the emission layer may include two or more materials. The two or more materials may include a red-light emission material, a green-light emission material, or a blue-light emission material. The two or more materials may be mixed with each other in a single layer. The two or more materials mixed with each other in the single layer may emit white light.

The emission layer may include a host and a dopant. The dopant may include at least one of a phosphorescent dopant or a fluorescent dopant.

An amount of the above dopant in the emission layer may be in a range of from about 0.01 parts by weight to about 15 parts by weight based on 100 parts by weight of the host; however, exemplary embodiments of the present invention are not limited thereto.

A thickness of the emission layer may be in a range of from about 100 Å to about 1,000 Å, for example, from about 200 Å to about 600 Å. When the thickness of the emission layer is within any of these ranges, increased light-emission characteristics may be obtained without a substantial increase in driving voltage.

The host may include the condensed cyclic compound represented by Formula 1.

The phosphorescent dopant may include an organometallic complex represented by Formula 401:

<Formula 401>
$$M(L_{401})_{xc1}(L_{402})_{xc2}$$

<Formula 402>

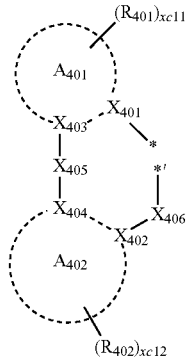

In Formulae 401 and 402, M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm).

$L_{401}$ may be selected from an organic ligand represented by Formula 402, and xc1 may be an integer selected from 1, 2, and 3. When xc1 is 2 or greater, at least two $L_{401}$(s) may be the same as or different from each other.

In Formulae 401 and 402, $L_{402}$ may be an organic ligand, and xc2 may be an integer selected from 0 to 4. When xc2 is 2 or greater, at least two or $L_{402}$(s) may be the same as or different from each other.

In Formulae 401 and 402, $X_{401}$ to $X_{404}$ may each independently be selected from nitrogen (N) and carbon (C).

In Formulae 401 and 402, $X_{401}$ and $X_{403}$ may be linked via a single bond or a double bond, and $X_{402}$ and $X_{404}$ may be linked via a single bond or a double bond.

In Formulae 401 and 402, $A_{401}$ and $A_{402}$ may each independently be selected from a $C_5$-$C_{60}$ carbocyclic group and a $C_1$-$C_{60}$ heterocyclic group.

In Formulae 401 and 402, $X_{405}$ may be a single bond, *—O—*', *—S—*', *—C(=O)—*', *—N($Q_{411}$)-*', *—C($Q_{411}$)($Q_{412}$)-*', *—C($Q_{411}$)=C($Q_{412}$)-*', *—C($Q_{411}$)=*', or *=C($Q_{411}$)=*'. $Q_{411}$ and $Q_{412}$ may each independently be selected from hydrogen, deuterium, a $C_1$-$C_{20}$ alkyl group, a $C_1$-$C_{20}$ alkoxy group, a phenyl group, a biphenyl group, a terphenyl group, and a naphthyl group.

In Formulae 401 and 402, $X_{406}$ may be selected from a single bond, oxygen (O), and sulfur (S).

In Formulae 401 and 402, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$).

$Q_{401}$ to $Q_{403}$ may each independently be selected from a $C_1$-$C_{10}$ alkyl group, a $C_1$-$C_{10}$ alkoxy group, a $C_6$-$C_{20}$ aryl group, or a $C_1$-$C_{20}$ heteroaryl group.

In Formulae 401 and 402, xc11 and xc12 may each independently an integer selected from 0 to 10.

in Formula 402, * and *' may each indicate a binding site to M of Formula 401.

According to an exemplary embodiment of the present invention, in Formula 402, $A_{401}$ and $A_{402}$ may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

According to an exemplary embodiment of the present invention, in Formula 402, $X_{401}$ may be N and $X_{402}$ may be carbon (C). Alternatively, $X_{401}$ and $X_{402}$ may each be nitrogen (N).

According to an exemplary embodiment of the present invention, in Formula 402, $R_{401}$ and $R_{402}$ may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantanyl group, a norbornanyl group, and a norbornenyl group;

a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantanyl group, a norbornanyl group, a norbornenyl group a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$).

$Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group; however, exemplary embodiments of the present invention are not limited thereto.

According to an exemplary embodiment of the present invention, in Formula 401, when xc1 is 2 or greater, two $A_{401}$(s) in at least two $L_{401}$(s) may be linked to each other via $X_{407}$, which is a linking group. Alternatively, two $A_{402}$(s) in at least two $L_{401}$(s) may be linked to each other via $X_{408}$, which is a linking group (see, e.g., Compounds PD1 to PD4 and PD7). $X_{407}$ and $X_{408}$ may each independently be selected from a single bond, *—O—*', *—S—*', *—C(=O)—*', *—N($Q_{413}$)-*', *—C($Q_{413}$)($Q_{414}$)-*', and *—C($Q_{413}$)=C($Q_{414}$)-*', in which $Q_{413}$ and $Q_{414}$ may each independently be hydrogen, deuterium, a $C_1$-$C_{20}$ alkyl group, a $C_1$-$C_{20}$ alkoxy group, a phenyl group, a biphenyl group, a terphenyl group, and a naphthyl group; however, exemplary embodiments of the present invention are not limited thereto.

In Formula 401, $L_{402}$ may be selected from a monovalent, divalent, or trivalent organic ligand. For example, $L_{402}$ may be selected from a halogen ligand, a diketone ligand (e.g., acetylacetonate), a carboxylic acid ligand (e.g., picolinate), —C(=O), an isonitrile ligand, —CN, and a phosphorus ligand (e.g., phosphine and phosphite); however, exemplary embodiments of the present invention are not limited thereto.

According to an exemplary embodiment of the present invention, the phosphorescent dopant may be, for example, selected from Compounds PD1 to PD25; however, exemplary embodiments of the present invention are not limited thereto:
PD1
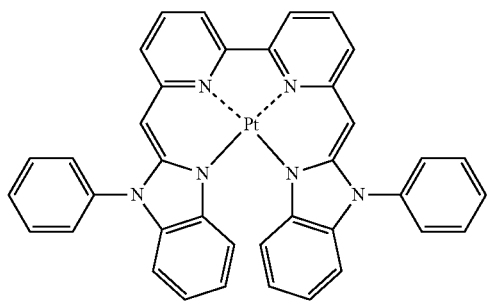
PD2
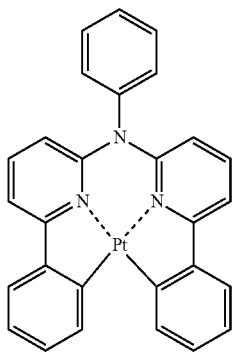
PD3
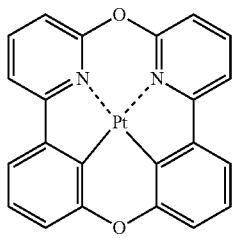
PD4
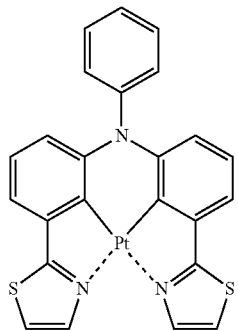
PD5
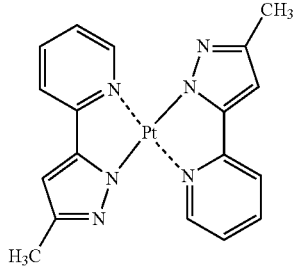
-continued
PD6
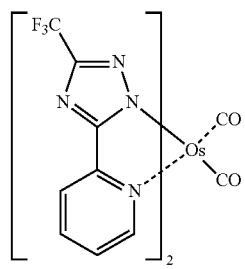
PD7
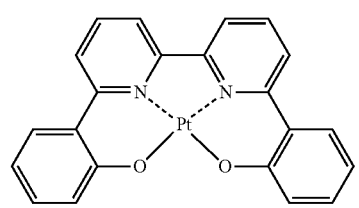
PD8
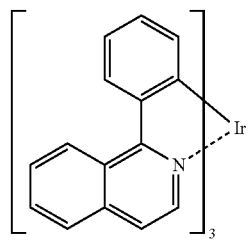
PD9
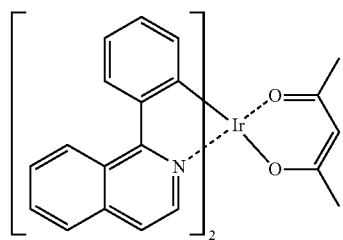
PD10
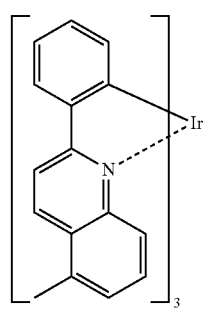
PD11
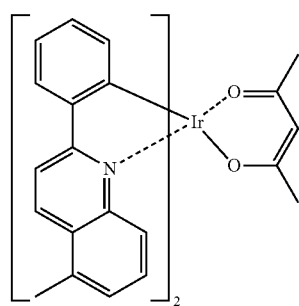

-continued
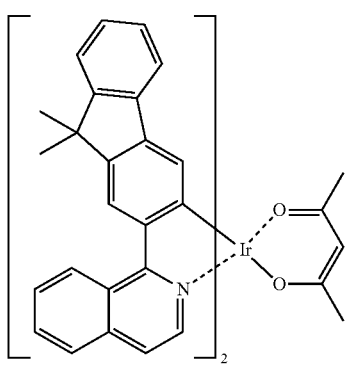
PD12
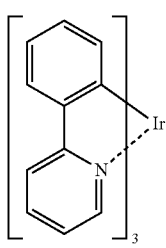
PD13
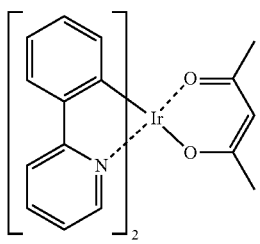
PD14
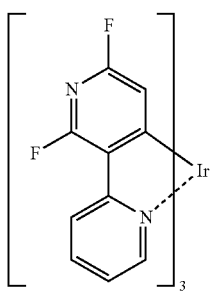
PD15
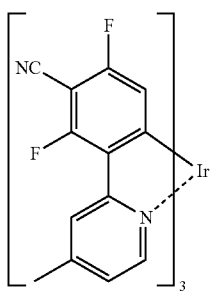
PD16
-continued
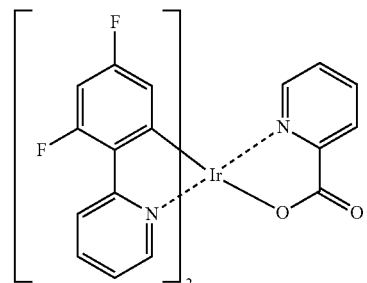
PD17
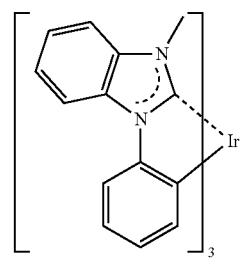
PD18
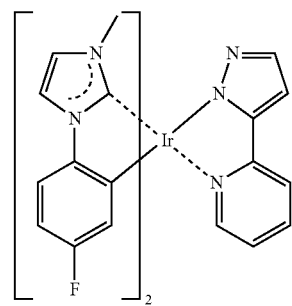
PD19
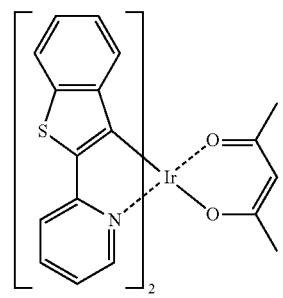
PD20
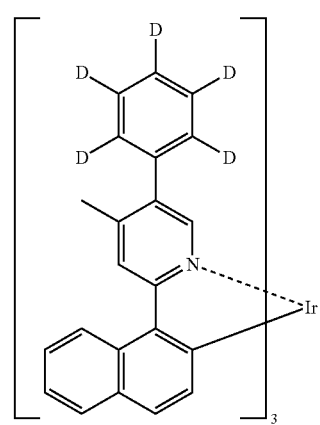
PD21

PD22

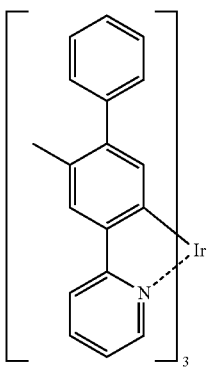

PD23

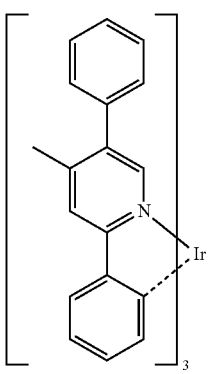

PD24

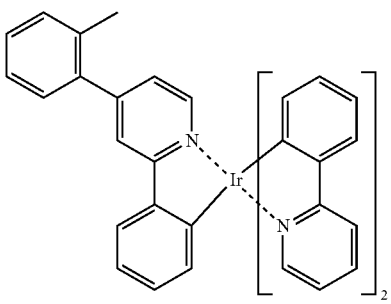

PD25

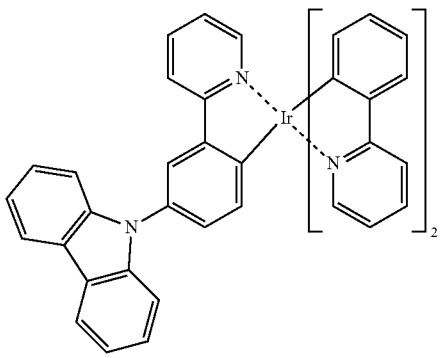

According to an exemplary embodiment of the present invention, the fluorescent dopant may include an arylamine compound or a stylamine compound.

The fluorescent dopant may include a compound represented by Formula 501:

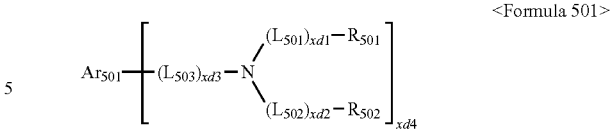

<Formula 501>

In Formula 501, $Ar_{501}$ may be selected from a substituted or unsubstituted $C_5$-$C_{60}$ carbocyclic group and a substituted or unsubstituted $C_1$-$C_{60}$ heterocyclic group.

In Formula 501, $L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

In Formula 501, xd1 to xd3 may each independently be an integer selected from 0 to 3.

In Formula 501, $R_{501}$ and $R_{502}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In Formula 501, xd4 may be an integer selected from 1 to 6.

According to an exemplary embodiment of the present invention, in Formula 501, $Ar_{501}$ may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

According to an exemplary embodiment of the present invention, in Formula 501, $L_{501}$ to $L_{503}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

According to an exemplary embodiment of the present invention, in Formula 501, $R_{501}$ and $R_{502}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$)

$Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

According to an exemplary embodiment of the present invention, in Formula 501, xd4 may be 2; however, exemplary embodiments of the present invention are not limited thereto.

As an example, the fluorescent dopant may be selected from Compounds FD1 to FD22:

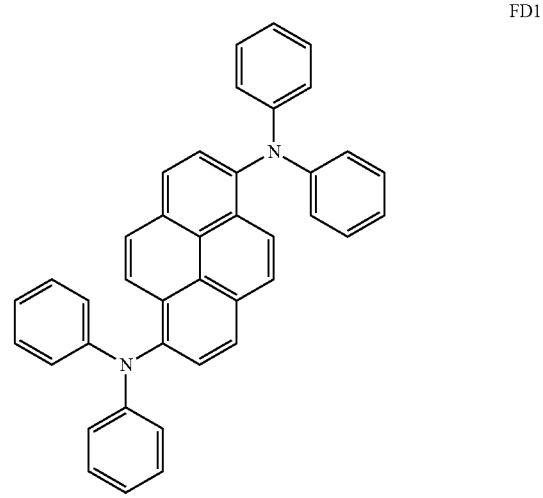

FD1

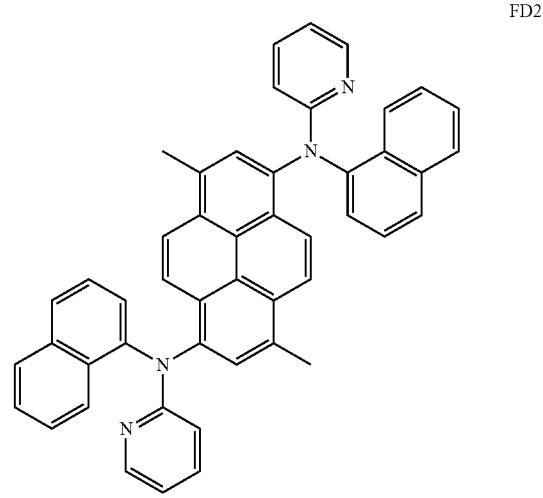

FD2

FD3
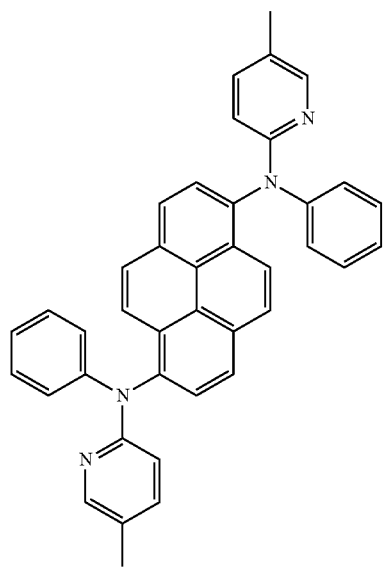
FD4
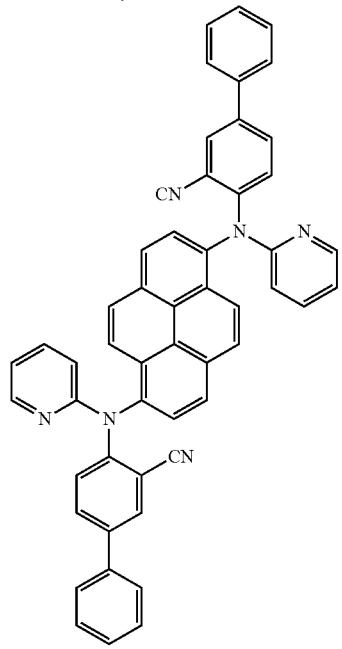
FD5
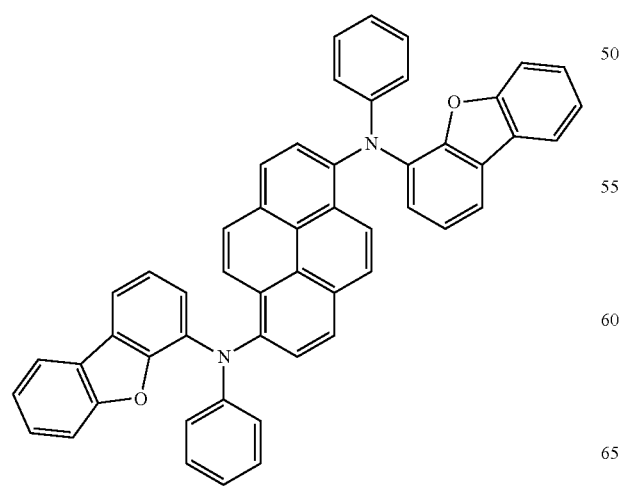
FD6
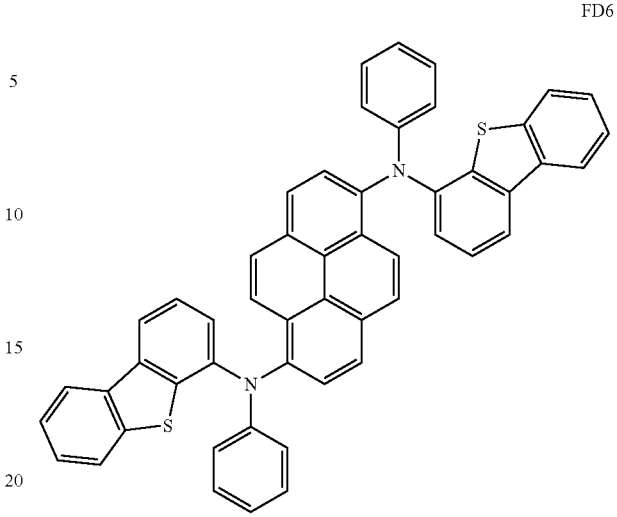
FD7
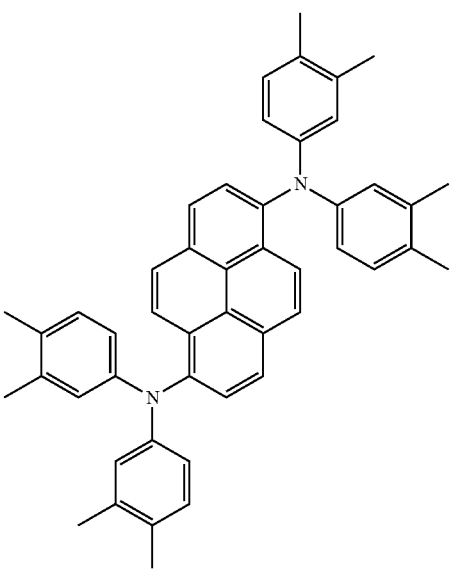
FD8
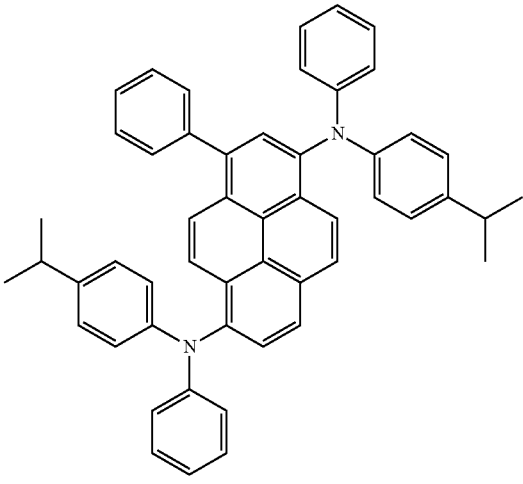

FD9
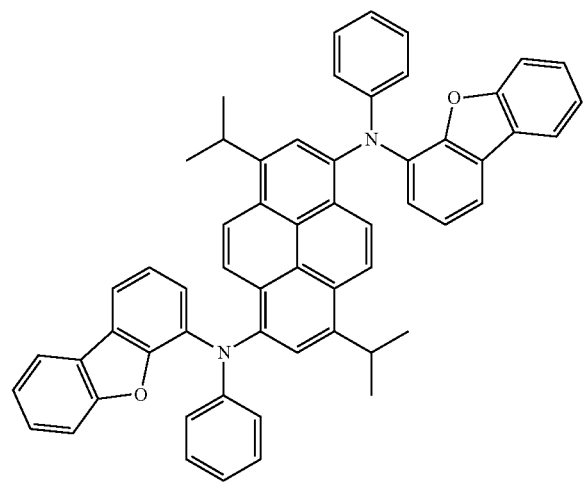
FD10
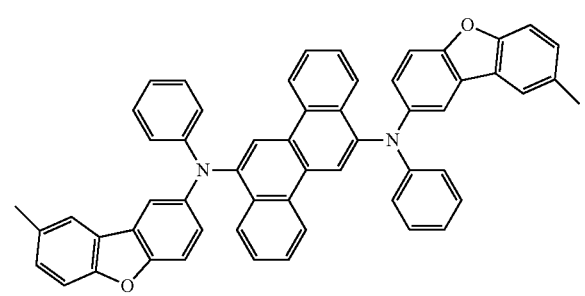
FD11
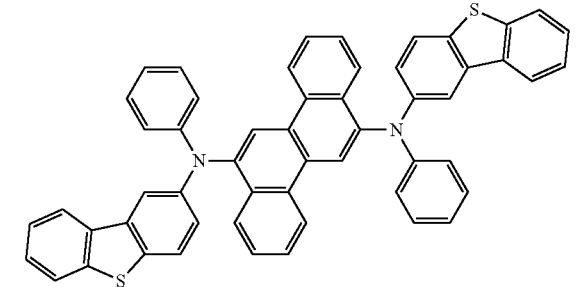
FD12
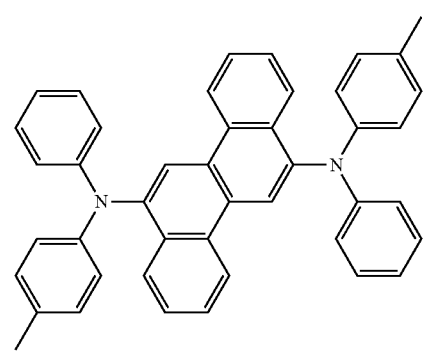
FD13
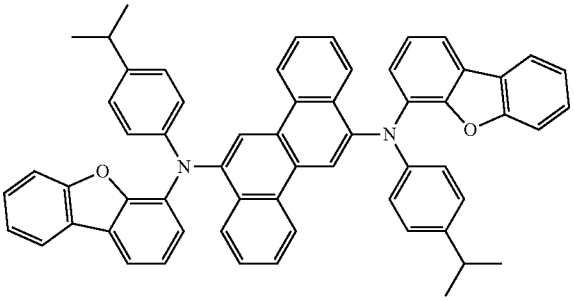
FD14
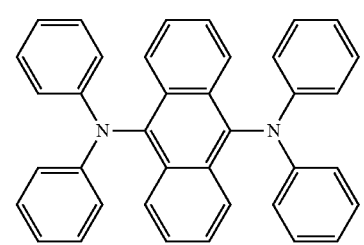
FD15
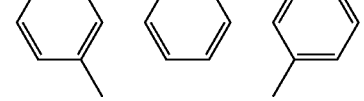
FD16
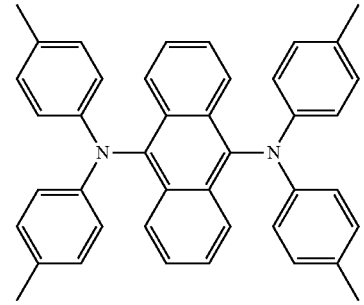

FD17
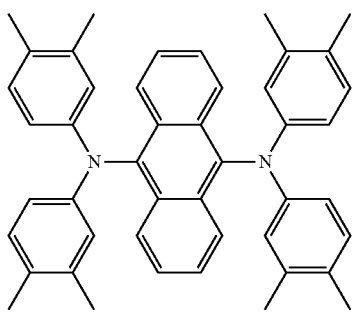
FD18
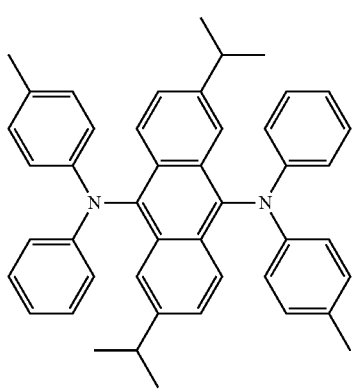
FD19
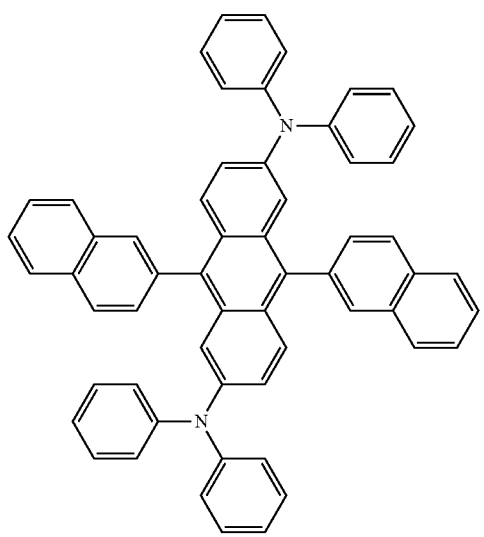
FD20
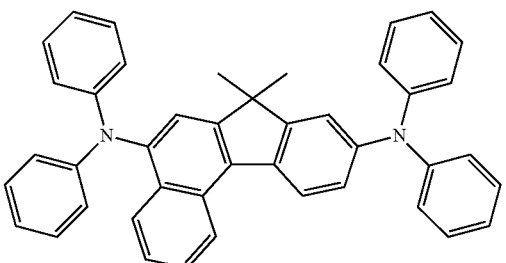
FD21
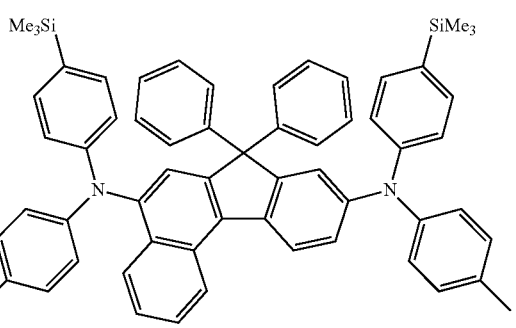
FD22
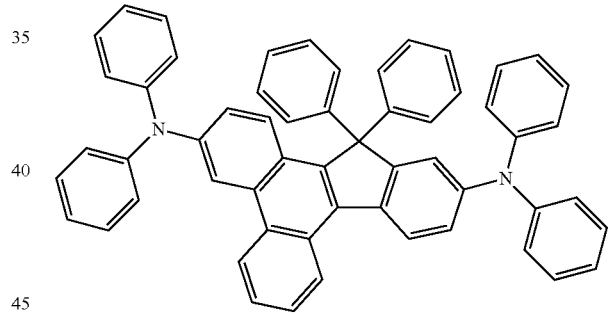
According to an exemplary embodiment of the present invention, the fluorescent dopant may be selected from the compounds illustrated below; however, exemplary embodiments of the present invention are not limited thereto:
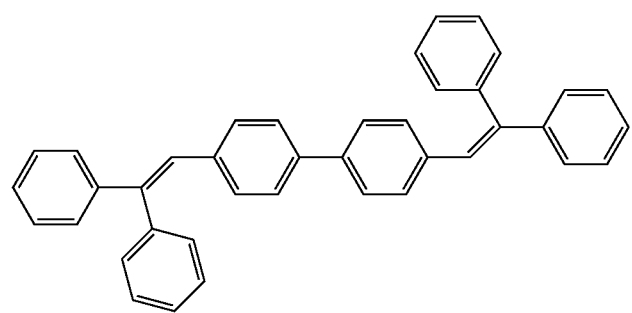
DPVBi -continued

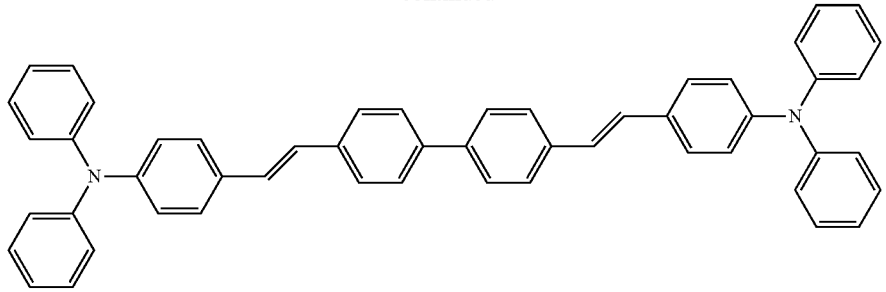
DPAVBi

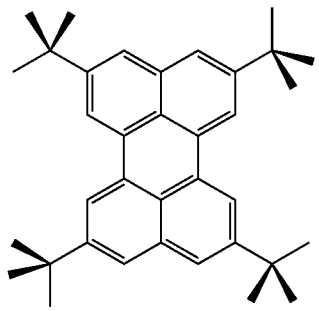
TBPe

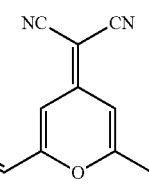
DCM

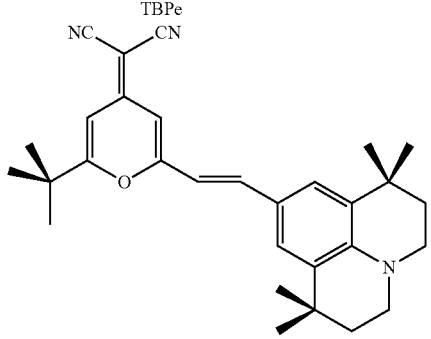
DCJTB

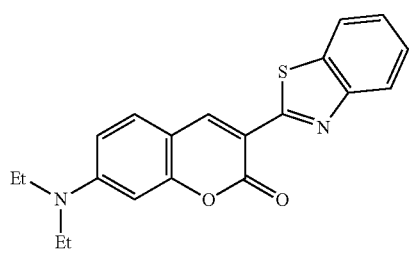
Coumarin 6

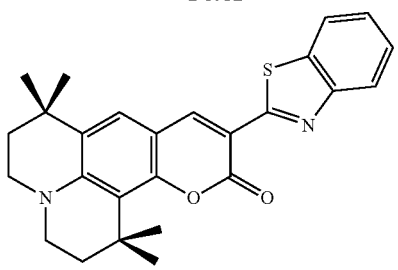
C545T

The electron transport region may have a single-layered structure including a single material. The electron transport region may have a single-layered structure including a plurality of different materials. The electron transport region may have a multi-layered structure having a plurality of layers each including a plurality of different materials.

The electron transport region may include at least one layer selected from a buffer layer, a hole blocking layer, an electron control layer, an electron transport layer, and an electron injection layer; however, exemplary embodiments of the present invention are not limited thereto.

For example, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure. For each structure, the layers may be sequentially stacked on an emission layer; however, exemplary embodiments of the structure of the electron transport region are not limited thereto.

The electron transport region, for example, a buffer layer, a hole blocking layer, an electron control layer, or an electron transport layer in the electron transport region, may include a metal-free compound including at least one π electron-depleted nitrogen-containing ring.

The π electron-depleted nitrogen-containing ring may indicate a $C_1$-$C_{60}$ heterocyclic group including at least one *—N=* moiety as a ring-forming moiety.

For example, the π electron-depleted nitrogen-containing ring may be a 5-membered to 7 membered heteromonocyclic group having at least one *—N=*' moiety. The π electron-depleted nitrogen-containing ring may be a heteropolycyclic group in which two or more 5-membered to 7 membered heteromonocyclic groups each having at least one *—N=*' moiety are condensed with each other. The π electron-depleted nitrogen-containing ring may be a heteropolycyclic group in which at least one 5-membered to 7-membered hetero monocyclic group having at least one *—N=*' moiety is condensed with at least one $C_5$-$C_{60}$ carbocyclic group.

Examples of the π electron-depleted nitrogen-containing ring may include an imidazole, a pyrazole, a thiazole, an isothiazole, an oxazole, an isoxazole, a pyridine, a pyrazine, a pyrimidine, a pyridazine, an indazole, a purine, a quinoline, an isoquinoline, a benzoquinoline, a phthalazine, naphthyridine, a quinoxaline, a quinazoline, a cinnoline, a phenanthridine, an acridine, phenanthroline, phenazine, a benzimidazole, an isobenzothiazole, a benzoxazole, an isobenzoxazole, a triazole, a tetrazole, an oxadiazole, a triazine, thiadiazol, an imidazopyridine, an imidazopyrimidine, or an azacarbazole; however, exemplary embodiments of the present invention are not limited thereto.

For example, the electron transport region may include a compound represented by Formula 601:

[Ar$_{601}$]$_{xe11}$-[(L$_{601}$)$_{xe1}$-R$_{601}$]$_{xe21}$.   <Formula 601>

In Formula 601, Ar$_{601}$ may be selected from a substituted or unsubstituted $C_5$-$C_{60}$ carbocyclic group and a substituted or unsubstituted $C_1$-$C_{60}$ heterocyclic group.

In Formula 601, xe11 may be an integer selected from 1, 2, and 3.

In Formula 601, L$_{601}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

In Formula 601, xe1 may be an integer selected from 0 to 5.

In Formula 601, R$_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si(Q$_{601}$)(Q$_{602}$)(Q$_{603}$), —C(=O)(Q$_{601}$), —S(=O)$_2$(Q$_{601}$), and —P(=O)(Q$_{601}$)(Q$_{602}$).

Q$_{601}$ to Q$_{603}$ may each independently be a $C_1$-$C_{10}$ alkyl group, a $C_1$-$C_{10}$ alkoxy group, a phenyl group, a biphenyl group, a terphenyl group, and a naphthyl group.

In Formula 601, xe21 may be an integer selected from 1 to 5.

According to an exemplary embodiment of the present invention, at least one selected from xe11, Ar$_{601}$(s) and/or at least one selected from xe21, R$_{601}$(s) may include the π electron-depleted nitrogen-containing ring.

According to an exemplary embodiment of the present invention, in Formula 601, ring Ar$_{601}$ may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazol group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazol group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si(Q$_{31}$)(Q$_{32}$)(Q$_{33}$), —S(=O)$_2$(Q$_{31}$), and —P(=O)(Q$_{31}$)(Q$_{32}$).

Q$_{31}$ to Q$_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In Formula 601, when xe11 is 2 or greater, at least Ar$_{601}$(s) may be linked via a single bond.

According to an exemplary embodiment of the present invention, in Formula 601, Ar$_{601}$ may be an anthracene group.

According to an exemplary embodiment of the present invention, the compound represented by Formula 601 may be represented by Formula 601-1:

<Formula 601-1>

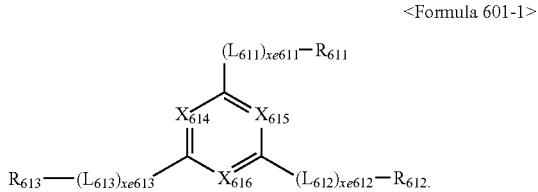

In Formula 601-1, $X_{614}$ may be nitrogen (N) or $C(R_{614})$, $X_{615}$ may be nitrogen (N) or $C(R_{615})$, $X_{616}$ may be nitrogen (N) or $C(R_{616})$, and at least one of $X_{614}$ to $X_{616}$ may be nitrogen (N).

In Formula 601-1, $L_{611}$ to $L_{613}$ may each independently be the same as $L_{601}$.

In Formula 601-1, xe611 to xe613 may each independently be the same as xe1,

In Formula 601-1, $R_{611}$ to $R_{613}$ may each independently be the same as $R_{601}$.

In Formula 601-1, $R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

According to an exemplary embodiment of the present invention, in Formulae 601 and 601-1, $L_{601}$ and $L_{611}$ to $L_{613}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; however, exemplary embodiments of the present invention are not limited thereto.

According to an exemplary embodiment of the present invention, in Formulae 601 and 601-1, xe1 and xe611 to xe613 may each independently be an integer selected from 0, 1, and 2.

According to an exemplary embodiment of the present invention, in Formulae 601 and 601-1, $R_{601}$ and $R_{611}$ to $R_{613}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S(=O)$_2$(Q$_{601}$) and —P(=O)(Q$_{601}$)(Q$_{602}$).

Q$_{601}$ and Q$_{602}$ may be the same as described above.

The electron transport region may include at least one compound selected from Compounds ET1 to ET36; however, exemplary embodiments of the present invention are not limited thereto:

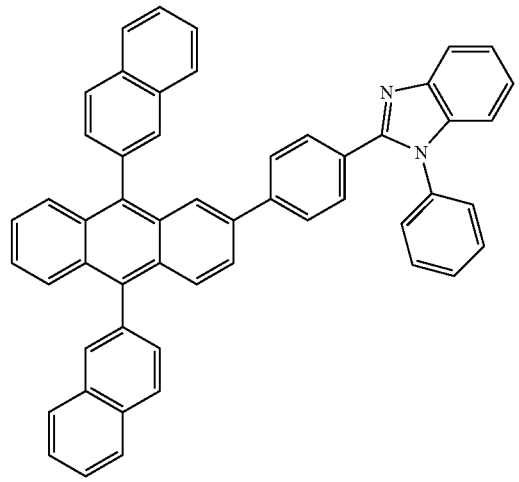
ET1

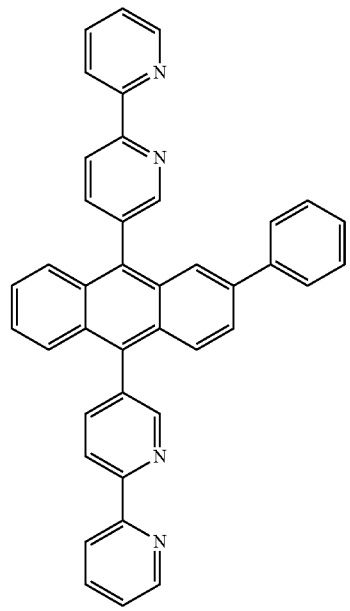
ET2

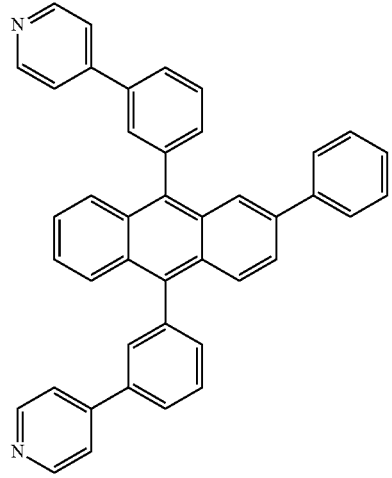
ET3

ET4
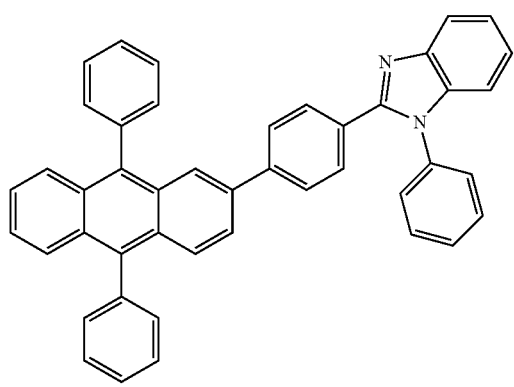
ET5
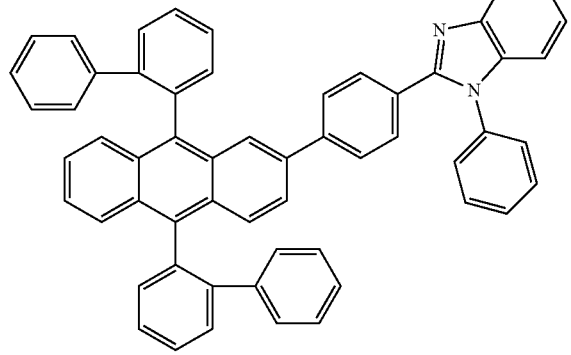
ET6
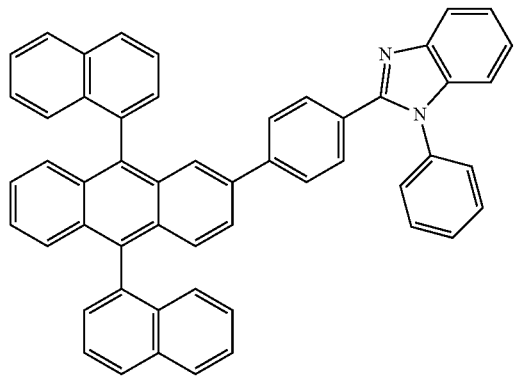
ET7
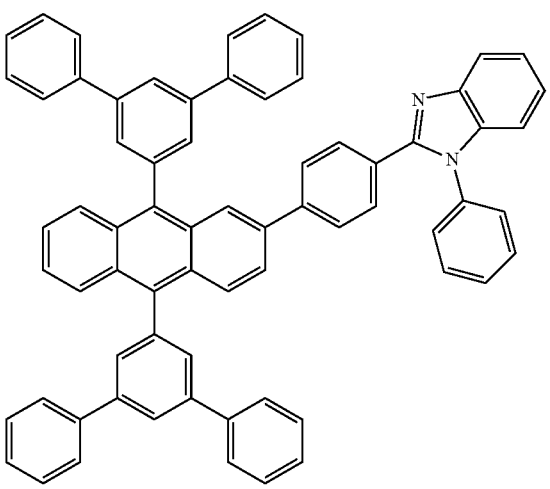
ET8
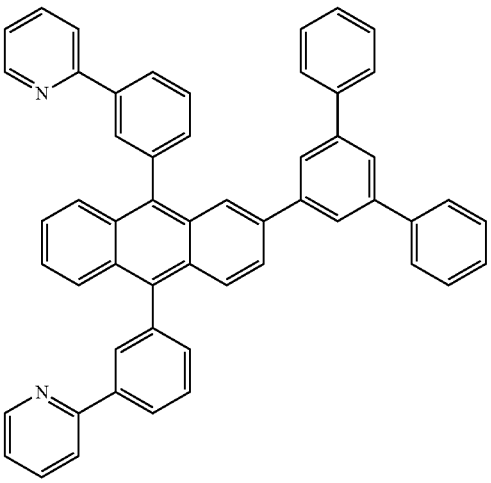
ET9
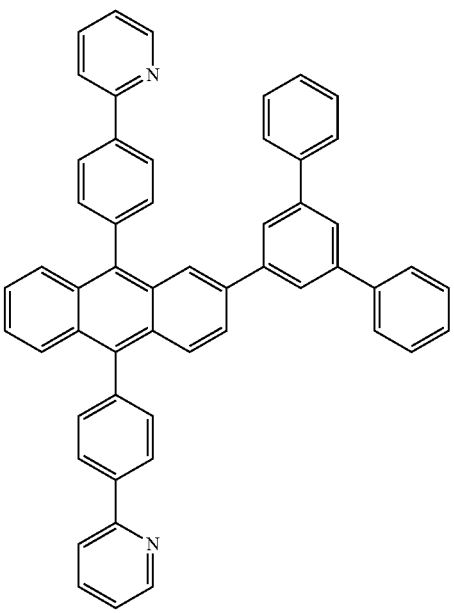

ET10
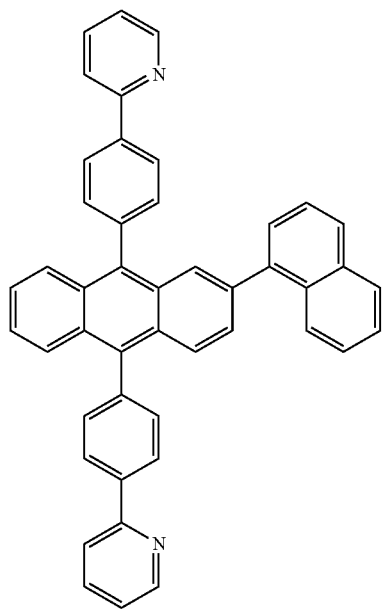
ET11
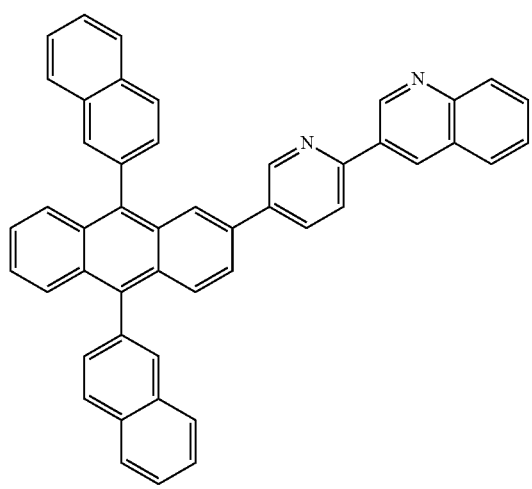
ET12
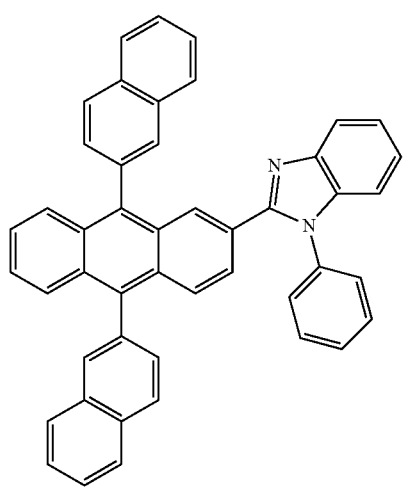
ET13
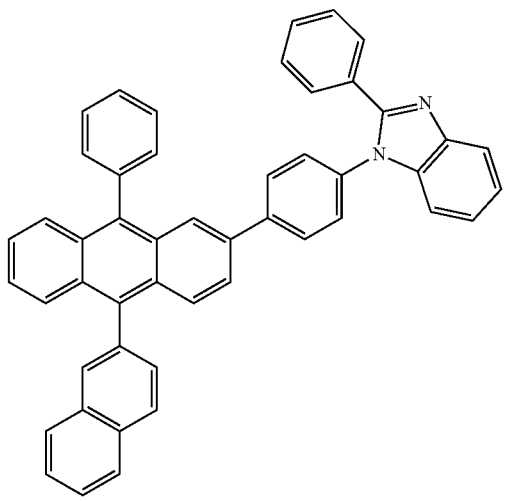
ET14
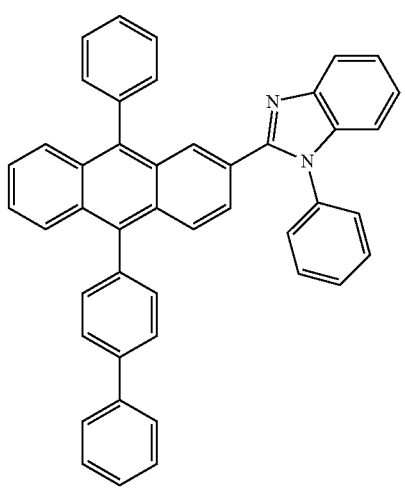
ET15
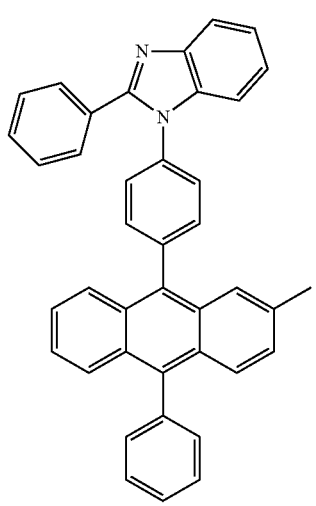

ET16
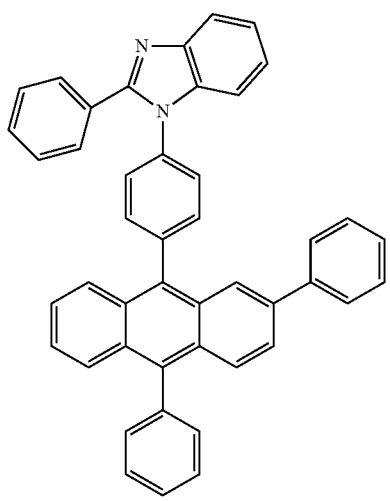
ET17
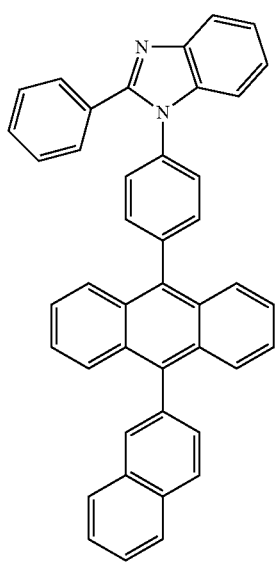
ET18
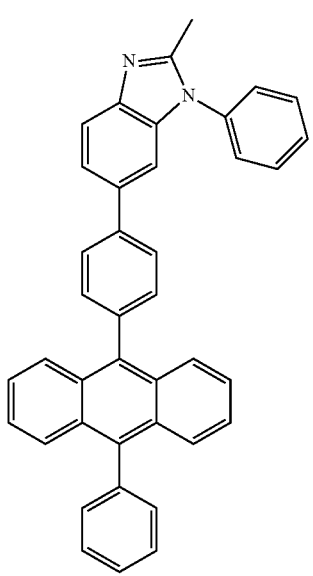
ET19
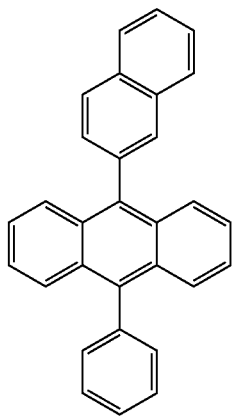
ET20
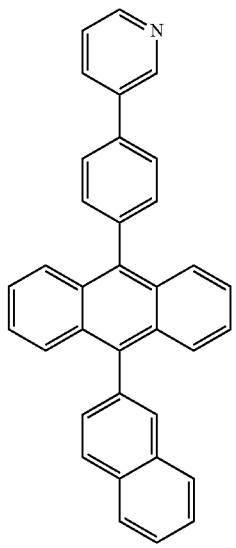
ET21
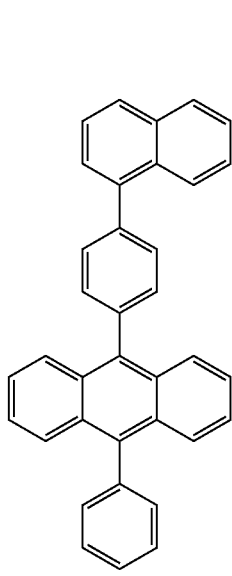

-continued
ET22
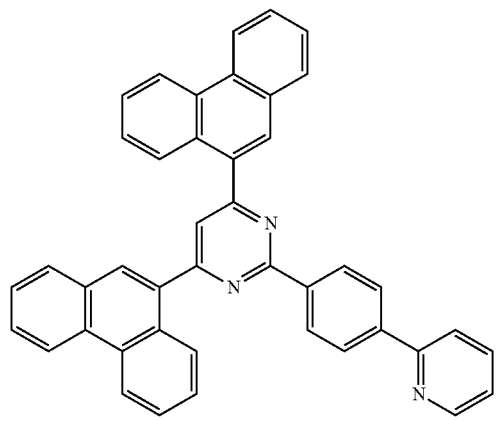
ET23
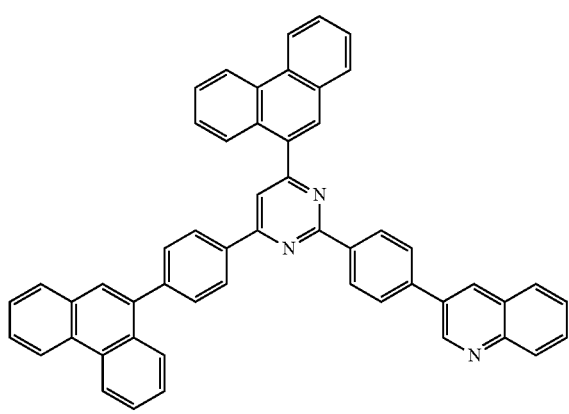
ET24
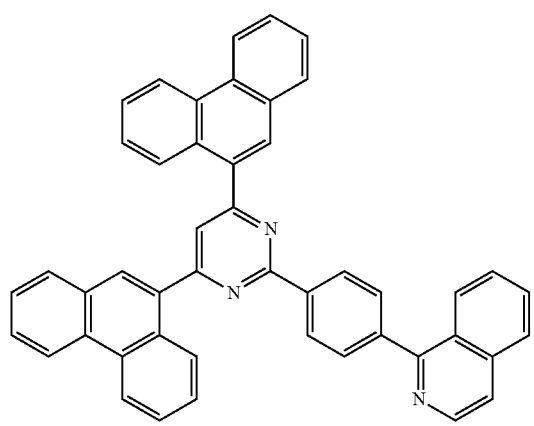
-continued
ET25
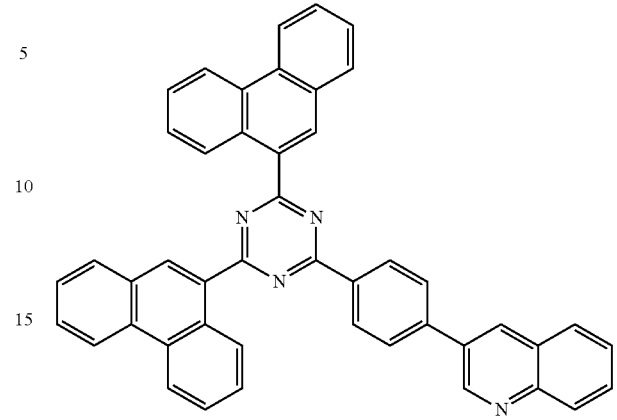
ET26
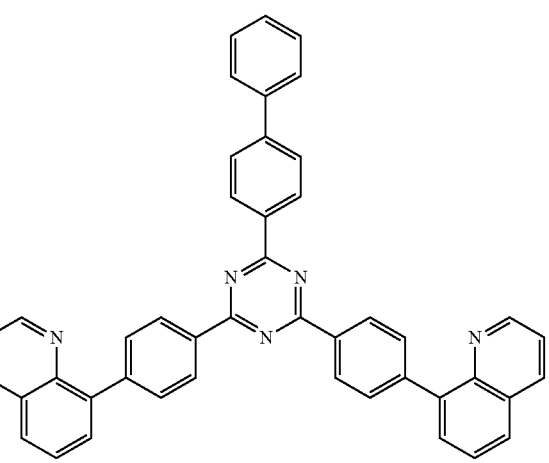
ET27
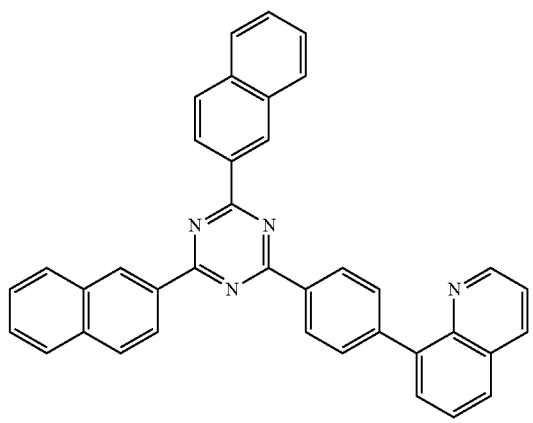

ET28
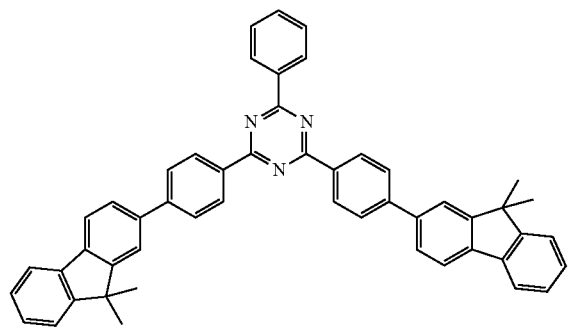
ET29
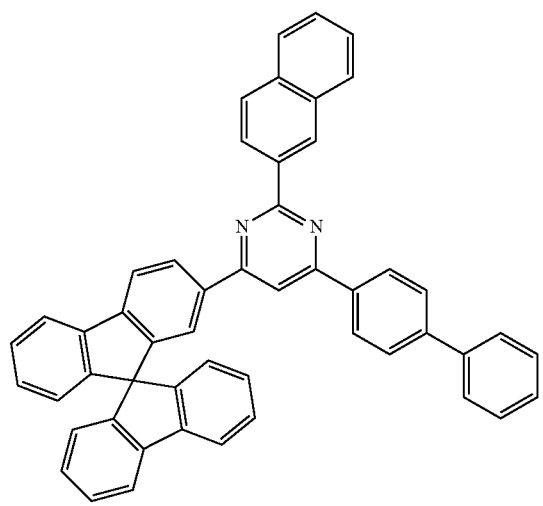
ET30
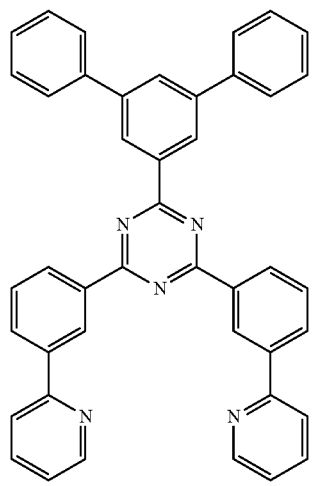
ET31
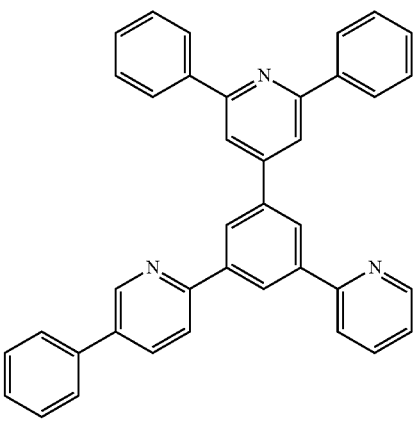
ET32
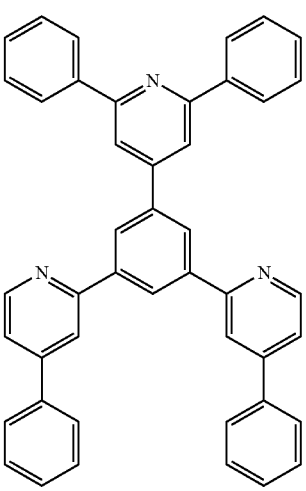
ET33
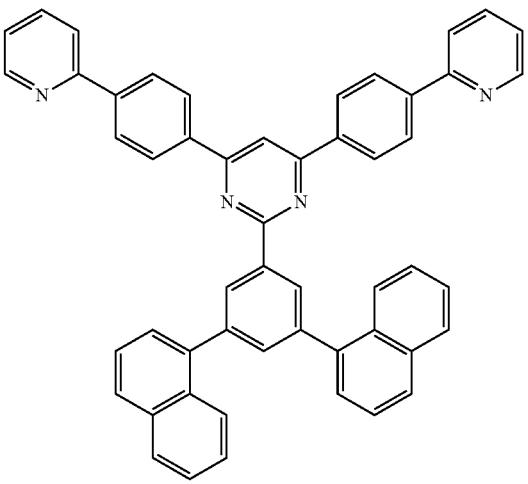

ET34

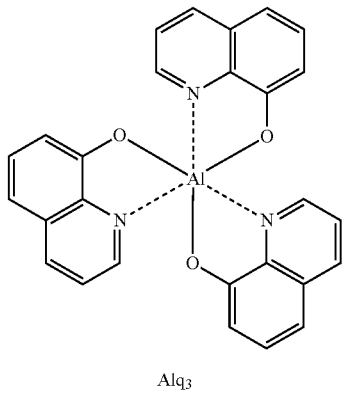

Alq₃

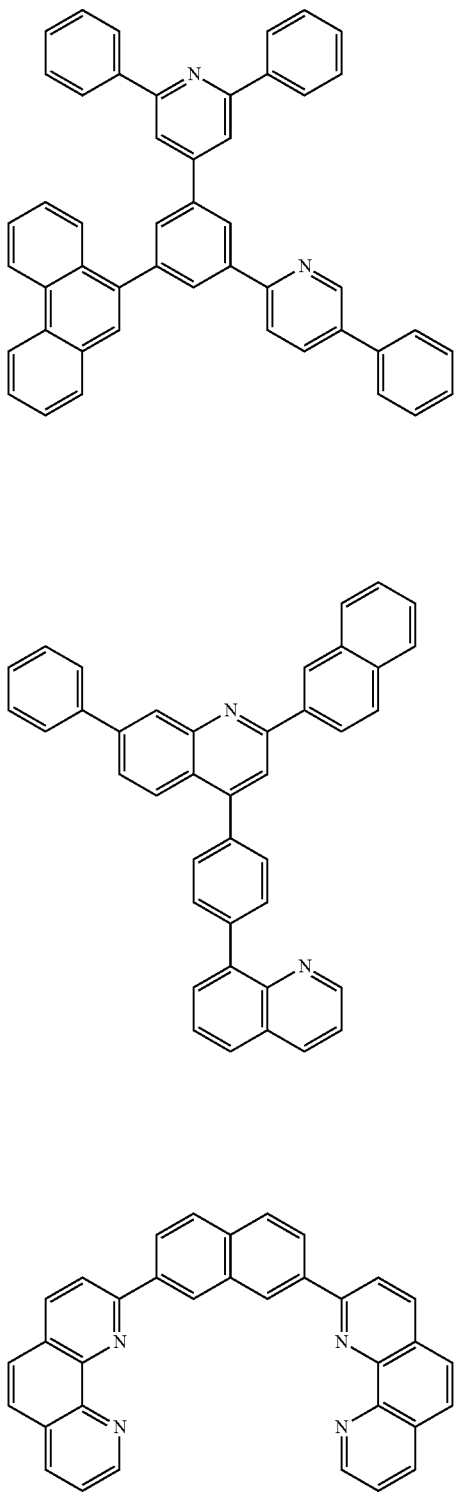

ET35

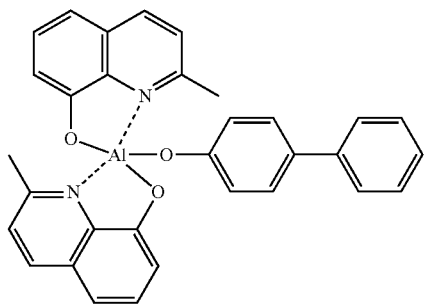

BAlq

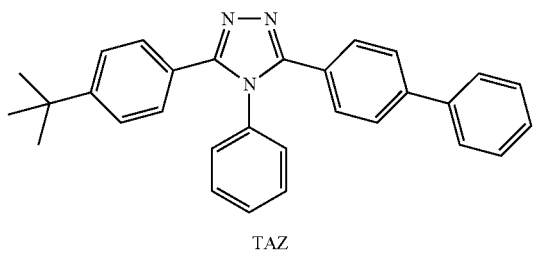

TAZ

ET36

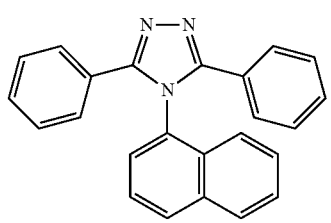

NTAZ

According to an exemplary embodiment of the present invention, the electron transport region may include at least one compound selected from 2,9-dimethyl-4,7-diphenyl-1,10-phenanthroline (BCP), 4,7-diphenyl-1,10-phenanthroline (Bphen), Alq₃, BAlq, 3-(biphenyl-4-yl)-5-(4-tert-butylphenyl)-4-phenyl-4H-1,2,4-triazole (TAZ), and NTAZ.

A thicknesses of the buffer layer, the hole blocking layer, and the electron control layer may each independently be in a range of from about 20 Å to about 1,000 Å, for example, from about 30 Å to about 300 Å. When the thicknesses of the buffer layer, the hole blocking layer, and the electron control layer are within any of these ranges, the electron blocking layer may have relatively high electron blocking characteristics and/or electron control characteristics, without a substantial increase in driving voltage.

A thickness of the electron transport layer may be in a range of from about 100 Å to about 1,000 Å, for example, from about 150 Å to about 500 Å. When the thickness of the electron transport layer is within any of these ranges, satisfactory electron transport characteristics may be obtained without a substantial increase in driving voltage.

The electron transport region, for example, an electron transport layer in the electron transport region, may include a material including metal.

The material including metal may include at least one selected from an alkali metal complex and an alkaline earth metal complex. The alkali metal complex may include a metal ion selected from a lithium (Li) ion, a sodium (Na) ion, a potassium (K) ion, a rubidium (Rb), or a cesium (Cs) ion. The alkaline earth metal complex may include a metal ion selected from a beryllium (Be) ion, a magnesium (Mg) ion, a calcium (Ca) ion, a strontium (Sr) ion, and a barium (Ba) ion. A ligand coordinated with the metal ion of the alkali metal complex or the alkaline earth metal complex may be selected from a hydroxyquinoline, a hydroxyisoquinoline, a hydroxybenzoquinoline, a hydroxyacridine, a hydroxyphenanthridine, a hydroxyphenyl oxazole, a hydroxyphenyl thiazole, a hydroxydiphenylan oxadiazole, a hydroxydiphenylthiadiazol, a hydroxyphenyl pyridine, a hydroxyphenyl benzimidazole, a hydroxyphenyl benzothiazole, a bipyridine, a phenanthroline, and a cyclopentadiene; however, exemplary embodiments of the present invention are not limited thereto.

For example, the material including metal may include a lithium (Li) complex. The lithium (Li) complex may include, for example, Compound ET-D1 (lithium quinolate, LiQ) and/or ET-D2:

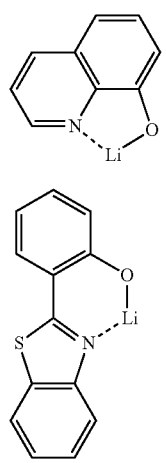

ET-D1

ET-D2

The electron transport region may include an electron injection layer. The electron injection layer may be configured to facilitate injection of electrons from the second electrode 190. The electron injection layer may be in direct contact with the second electrode 190.

The electron injection layer may have a single-layered structure including a single material. The electron injection layer may have a single-layered structure including a plurality of different materials. The electron injection layer may have a multi-layered structure having a plurality of layers including a plurality of different materials.

The electron injection layer may include an alkali metal, an alkaline earth metal, a rare earth metal, an alkali metal compound, an alkaline earth metal compound, a rare earth metal compound, an alkali metal complex, an alkaline earth metal complex, a rare earth metal complex, or any combination thereof.

The alkali metal may be selected from Li, Na, K, Rb, and Cs. According to an exemplary embodiment of the present invention, the alkali metal may be Li, Na, or Cs. According to an exemplary embodiment of the present invention, the alkali metal may be Li or Cs; however, exemplary embodiments of the present invention are not limited thereto.

The alkaline earth metal may be selected from Mg, Ca, Sr, and Ba.

The rare earth metal may be selected from scandium (Sc), yttrium (Y), cerium (Ce), ytterbium (Yb), gadolinium (Gd), and terbium (Tb).

The alkali metal compound, the alkaline earth metal compound, and the rare earth metal compound may be respectively selected from oxides and halides (e.g., fluorides, chlorides, bromides, and/or iodines) of the alkali metal, the alkaline earth metal, or the rare earth metal.

The alkali metal compound may be selected from alkali metal oxides, such as $Li_2O$, $Cs_2O$, and $K_2O$, and alkali metal halides, such as LiF, NaF, CsF, KF, LiI, NaI, CsI, and KI. According to an exemplary embodiment of the present invention, the alkali metal compound may be selected from LiF, $Li_2O$, NaF, LiI, NaI, CsI, and KI; however, exemplary embodiments of the present invention are not limited thereto.

The alkaline earth metal compound may be selected from alkaline earth metal compounds, such as BaO, SrO, CaO, $Ba_xSr_{1-x}O$ (0<x<1), and $Ba_xCa_{1-x}O$ (0<x<1). According to an exemplary embodiment of the present invention, the alkaline earth metal compound may be selected from BaO, SrO, and CaO; however, exemplary embodiments of the present invention are not limited thereto.

The rare earth metal compound may be selected from $YbF_3$, $ScF_3$, $ScO_3$, $Y_2O_3$, $Ce_2O_3$, $GdF_3$, and $TbF_3$. According to an exemplary embodiment of the present invention, the rare earth metal compound may be selected from $YbF_3$, $ScF_3$, $TbF_3$, $YbI_3$, $ScI_3$, and $TbI_3$; however, exemplary embodiments of the present invention are not limited thereto.

The alkali metal complex, the alkaline earth metal complex, and the rare earth metal complex may each include an alkali metal ion, an alkaline earth metal ion, or a rare earth metal ion as described above. A ligand coordinated with a metal ion of the alkali metal complex, the alkaline earth metal complex, or the rare earth metal complex may be selected from a hydroxyquinoline, a hydroxyisoquinoline, a hydroxybenzoquinoline, a hydroxyacridine, a hydroxyphenanthridine, a hydroxyphenyl oxazole, a hydroxyphenyl thiazole, a hydroxydiphenyl oxadiazole, a hydroxydiphenyl thiadiazol, a hydroxyphenyl pyridine, a hydroxyphenyl benzimidazole, a hydroxyphenyl benzothiazole, a bipyridine, a phenanthroline, and a cyclopentadiene; however, exemplary embodiments of the present invention are not limited thereto.

The electron injection layer may include the alkali metal, the alkaline earth metal, the rare earth metal, the alkali metal compound, the alkaline earth metal compound, the rare earth metal compound, the alkali metal complex, the alkaline earth metal complex, the rare earth metal complex, or any combination thereof. According to an exemplary embodiment of the present invention, the electron injection layer may include an organic material. When the electron injection layer includes the organic material, the alkali metal, the alkaline earth metal, the rare earth metal, the alkali metal compound, the alkaline earth metal compound, the rare earth metal compound, the alkali metal complex, the alkaline earth metal complex, the rare earth metal complex, or any combination thereof may be substantially homogeneously or non-homogeneously dispersed in a matrix including the organic material.

A thickness of the electron injection layer may be in a range of from about 1 Å to about 100 Å, for example, from about 3 Å to about 90 Å. When the thickness of the electron injection layer is any of these ranges, satisfactory electron injection characteristics may be obtained without a substantial increase in driving voltage.

The second electrode 190 may be disposed on the organic layer 150. The organic layer 150 may have a structure as described above. The second electrode 190 may be a cathode. The cathode may be an electron injection electrode. Thus, the second electrode 190 may include a metal, an alloy, an electrically conductive compound, or any combination thereof, which may have a relatively low work function.

The second electrode 190 may include at least one of magnesium (Mg), aluminum (Al), aluminum-lithium (Al—Li), calcium (Ca), magnesium-indium (Mg—In), magnesium-silver (Mg—Ag), indium tin oxide (ITO), or indium zinc oxide (IZO); however, exemplary embodiments of the present invention are not limited thereto. The second electrode 190 may be a semi-transmissive electrode or a transmissive electrode.

The second electrode 190 may have a single-layered structure. Alternatively, the second electrode 190 may have a multi-layered structure including two or more layers.

Figure 2:
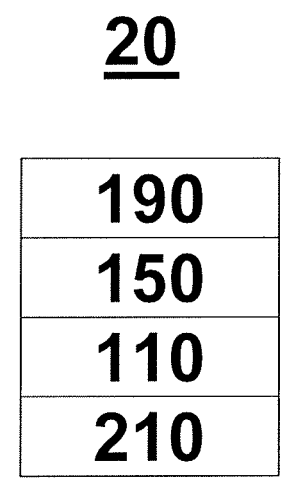

FIG. 2 is a schematic cross-sectional diagram illustrating an organic light-emitting device according to an exemplary embodiment of the present invention. Referring to FIG. 2, an organic light-emitting device 20 may include a first capping layer 210, the first electrode 110, the organic layer 150, and the second electrode 190. The first capping layer 210, the first electrode 110, the organic layer 150, and the second electrode 190 may be sequentially stacked.

Figure 3:
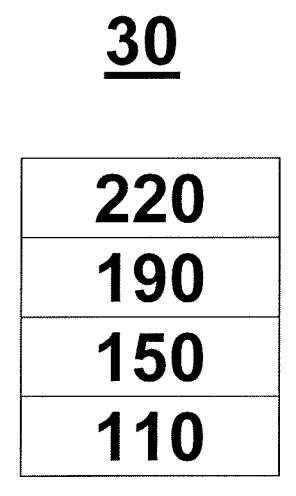

FIG. 3 is a schematic cross-sectional diagram illustrating an organic light-emitting device according to an exemplary embodiment of the present invention. Referring to FIG. 3, an organic light-emitting device 30 may include the first electrode 110, the organic layer 150, the second electrode 190, and a second capping layer 220. The first electrode 110, the organic layer 150, the second electrode 190, and the second capping layer 220 may be sequentially stacked.

Figure 4:
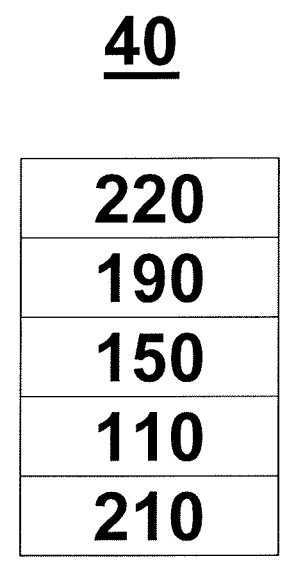

FIG. 4 is a schematic cross-sectional diagram illustrating an organic light-emitting device according to an exemplary embodiment of the present invention. Referring to FIG. 4, an organic light-emitting device 40 may include the first capping layer 210, the first electrode 110, the organic layer 150, the second electrode 190, and the second capping layer 220. The first capping layer 210, the first electrode 110, the organic layer 150, the second electrode 190, and the second capping layer 220 may be sequentially stacked.

In the organic layer 150 of each of the organic light-emitting devices 20 and 40, light generated in the emission layer may pass through the first electrode 110 and the first capping layer 210 toward the outside. The first electrode 110 may be a semi-transmissive electrode or a transmissive electrode. In the organic layer 150 of each of the organic light-emitting devices 30 and 40, light generated in the emission layer may pass through the second electrode 190 and the second capping layer 220 toward the outside. The second electrode 190 may be a semi-transmissive or a transmissive electrode.

The first capping layer 210 and the second capping layer 220 may increase external luminescent efficiency according to the principle of constructive interference.

The first capping layer 210 and the second capping layer 220 may each independently be an organic capping layer including an organic material, an inorganic capping layer including an inorganic material, or a composite capping layer including an organic material and an inorganic material.

At least one of the first capping layer 210 and the second capping layer 220 may include at least one material selected from a carbocyclic compound, a heterocyclic compound, an amine-based compound, a porphine derivative, a phthalocyanine derivative, a naphthalocyanine derivative, an alkaline metal complex, and an alkaline earth-based complex. The carbocyclic compound, the heterocyclic compound, and the amine-based compound may be substituted with a substituent at least one element selected from O, N, S, Se, Si, F, Cl, Br, and I.

According to an exemplary embodiment of the present invention, at least one of the first capping layer 210 and the second capping layer 220 may include an amine-based compound.

According to an exemplary embodiment of the present invention, at least one of the first capping layer 210 and the second capping layer 220 may include the compound represented by Formula 201 or the compound represented by Formula 202.

According to an exemplary embodiment of the present invention, at least one of the first capping layer 210 and the second capping layer 220 may include a compound selected from Compounds HT28 to HT33 and Compounds CP1 to CP5; however, exemplary embodiments of the present invention are not limited thereto:

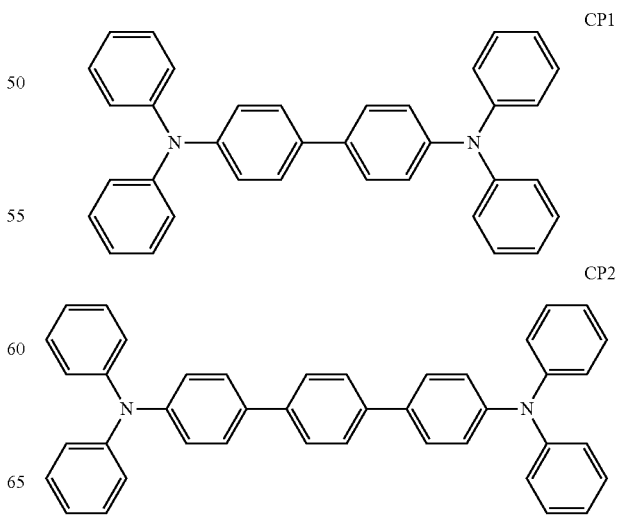

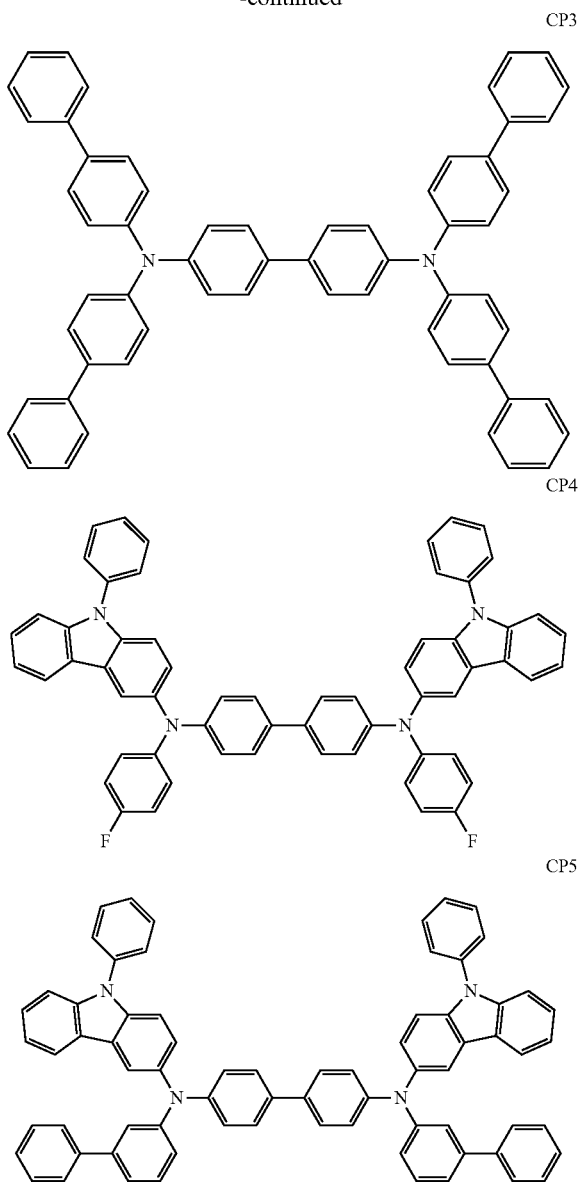

The organic light-emitting device according to an exemplary embodiment of the present invention has been described with reference to FIGS. 1 to 4. However, exemplary embodiments of the present invention are not limited thereto.

Layers included in the hole transport region, the emission layer, and the electron transport region may be formed by, for example, vacuum deposition, spin coating, casting, a Langmuir-Blodgett (LB) method, ink-jet printing, laser-printing, or laser induced thermal imaging (LITI).

When the respective layers of the hole transport region, the emission layer, and the electron transport region are formed by vacuum deposition, for example, the vacuum deposition may be performed at a deposition temperature of from about 100° C. to about 500° C., at a vacuum degree of from about $10^{-8}$ torr to about $10^{-3}$ torr, and at a deposition rate of from about 0.01 Å/sec to about 100 Å/sec, depending on the compound to be included in each layer, and the intended structure of each layer.

When the layers included in the hole transport region, the emission layer, and the layers included in electron transport region are formed by spin coating, for example, the spin coating may be performed at a coating speed of from about 2,000 rpm to about 5,000 rpm, and at a temperature of from about 80° C. to 200° C., depending on the compound to be included in each layer, and the structure of the layer to be formed.

The term "$C_1$-$C_{60}$ alkyl group" as used herein refers to a linear or branched monovalent aliphatic saturated hydrocarbon group having 1 to 60 carbon atoms, and non-limiting examples thereof may include a methyl group, an ethyl group, a propyl group, an isobutyl group, a sec-butyl group, a ter-butyl group, a pentyl group, an iso-amyl group, or a hexyl group. The term "$C_1$-$C_{60}$ alkylene group" as used herein refers to a divalent group having the same structure as the $C_1$-$C_{60}$ alkyl group.

The term "$C_2$-$C_{60}$ alkenyl group" as used herein refers to a hydrocarbon group having at least one carbon-carbon double bond at one or more positions along the hydrocarbon chain of the $C_2$-$C_{60}$ alkyl group (e.g., in the middle and/or at either terminus of the $C_2$-$C_{60}$ alkyl group), and non-limiting examples thereof may include an ethenyl group, a propenyl group, or a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group having at least one carbon-carbon triple bond at one or more positions along the hydrocarbon chain of the $C_2$-$C_{60}$ alkyl group (e.g., in the middle and/or at either terminus of the $C_2$-$C_{60}$ alkyl group), and non-limiting examples thereof may include an ethynyl group or a propynyl group. The term "$C_2$-$C_{60}$ alkynylene group" as used herein refers to a divalent group having the same structure as the $C_2$-$C_{60}$ alkynyl group.

The term "$C_1$-$C_{60}$ alkoxy group" as used herein refers to a monovalent group represented by —$OA_{101}$, in which $A_{101}$ is the $C_1$-$C_{60}$ alkyl group, and non-limiting examples thereof may include a methoxy group, an ethoxy group, or an isopropoxy group.

The term "$C_3$-$C_{10}$ cycloalkyl group" as used herein refers to a monovalent saturated hydrocarbon monocyclic group having 3 to 10 carbon atoms, and non-limiting examples thereof may include a cyclopropyl group, a cyclobutyl group, a cyclopentyl group, a cyclohexyl group, or a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent saturated monocyclic group having at least one heteroatom selected from N, O, Si, P, and S as a ring-forming atom and 1 to 10 carbon atoms, and non-limiting examples thereof may include a 1,2,3,4-oxatriazolidinyl group, a tetrahydrofuranyl group, or a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof, and does not have aromaticity. Non-limiting examples of the $C_3$-$C_{10}$ cycloalkenyl group may include a cyclopentenyl group, a cyclohexenyl group, or a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, Si, P, and S as a ring-forming atom, 1 to 10 carbon atoms, and at least one double bond in its ring. Non-limiting examples thereof may include a 4,5-dihydro-1,2,3,4-oxatriazolyl group, a 2,3-dihydrofuranyl group, or a 2,3-dihydrothiophenyl group. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms. The term "$C_6$-$C_{60}$ arylene group" as used herein refers to a divalent group having a carbocyclic aromatic system having 6 to 60 carbon atoms. Non-limiting examples of the $C_6$-$C_{60}$ aryl group may include a phenyl group, a naphthyl group, an anthracenyl group, a phenanthrenyl group, a pyrenyl group, or a chrysenyl group. When the $C_6$-$C_{60}$ aryl group and the $C_6$-$C_{60}$ arylene group each include two or more rings, the respective rings may be chemically bonded to each other.

The term "$C_1$-$C_{60}$ heteroaryl group" as used herein refers to a monovalent group having an aromatic system that has at least one heteroatom selected from N, O, Si, P, and S as a ring-forming atom and 1 to 60 carbon atoms. The term "$C_1$-$C_{60}$ heteroarylene group" as used herein refers to a divalent group having an aromatic system that has at least one heteroatom selected from N, O, Si, P, and S as a ring-forming atom, and 1 to 60 carbon atoms. Non-limiting examples of the $C_1$-$C_{60}$ heteroaryl group may include a pyridinyl group, a pyrimidinyl group, a pyrazinyl group, a pyridazinyl group, a triazinyl group, a quinolinyl group, or an isoquinolinyl group. When the $C_1$-$C_{60}$ heteroaryl group and the $C_1$-$C_{60}$ heteroarylene group each include two or more rings, the respective rings may be chemically bonded to each other.

The term "$C_6$-$C_{60}$ aryloxy group" as used herein refers to a monovalent group represented by —O$A_{102}$, in which $A_{102}$ is the $C_6$-$C_{60}$ aryl group. The term "$C_6$-$C_{60}$ arylthio group" as used herein refers to a monovalent group represented by —S$A_{103}$, in which $A_{103}$ is the $C_6$-$C_{60}$ aryl group.

The term "monovalent non-aromatic condensed polycyclic group" as used herein refers to a monovalent group, for example, having 8 to 60 carbon atoms. The monovalent group has two or more rings condensed with each other. Additionally, only carbon atoms are used as ring-forming atoms. The entire molecular structure has non-aromaticity. A non-limiting example of the monovalent non-aromatic condensed polycyclic group may include a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group, for example, having 1 to 60 carbon atoms. The monovalent group has two or more rings condensed with each other. The monovalent group has at least one heteroatom selected from N, O, Si, P, and S. Additionally, atoms other than carbon atoms are used as ring-forming atoms. The entire molecular structure has non-aromaticity. A non-limiting example of the monovalent non-aromatic condensed heteropolycyclic group may include a carbazolyl group. The term "divalent non-aromatic condensed heteropolycyclic group" as used herein refers to a divalent group having the same structure as the monovalent non-aromatic hetero-condensed polycyclic group.

The term "$C_5$-$C_{60}$ carbocyclic group" as used herein refers to a monocyclic or polycyclic group having only carbon atoms as ring-forming atoms (e.g., 5 to 60 carbon atoms). The $C_5$-$C_{60}$ cyclic group may be a carbocyclic group or a non-aromatic carbocyclic group. The $C_5$-$C_{60}$ carbocyclic group may be a ring same as a benzene, a monovalent group such as a phenyl group, or a divalent group such as a phenylene group. According to an exemplary embodiment of the present invention, depending on the number of substituents connected to the $C_5$-$C_{60}$ carbocyclic group, the $C_5$-$C_{60}$ carbocyclic group may be a trivalent quadrant group.

The term "$C_1$-$C_{60}$ heterocyclic group" as used herein refers to a group having the same structure as the $C_5$-$C_{60}$ carbocyclic group, but including at least one heteroatom selected from N, O, Si, P, and S, other than carbon atoms (e.g., 1 to 60 carbon atoms), as ring-forming atoms.

At least one substituent selected from the substituted $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —B(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($O_{31}$), —S(=O)$_2$($Q_{31}$), and —P(=O)($Q_{31}$)($Q_{32}$).

$Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The term "Ph" as used herein refers to a phenyl group; the term "Me" as used herein refers to a methyl group; the term "Et" as used herein refers to an ethyl group; the term "ter-Bu" or "Bu$^t$" as used herein refers to a tert-butyl group; and the term "OMe" as used herein refers to a methoxy group.

The term "biphenyl group" as used herein refers to "a phenyl group substituted with a phenyl group." As an example, a biphenyl group is a substituted phenyl group having a $C_6$-$C_{60}$ aryl group as a substituent.

The term "terphenyl group" as used herein may refer to "a phenyl group substituted with a biphenyl group." As an example, a terphenyl group is a substituted phenyl group having a $C_6$-$C_{60}$ aryl group as a substituent.

The symbols * and *' as used herein, unless defined otherwise, refer to a binding site to a neighboring atom in a corresponding formula.

A compound according to one or more exemplary embodiments of the present invention and an organic light-emitting device according one or more exemplary embodiments of the present invention will be described in more detail below with reference to Synthesis Examples and Examples. The wording "B was used instead of A" as used in describing Synthesis Examples refers to an example in which a molar equivalent of B was used in place of A.

EXAMPLES

Synthesis Examples

Synthesis Example 1

Synthesis of Intermediate A

Intermediate A was synthesized according to Reaction Scheme 1-1:

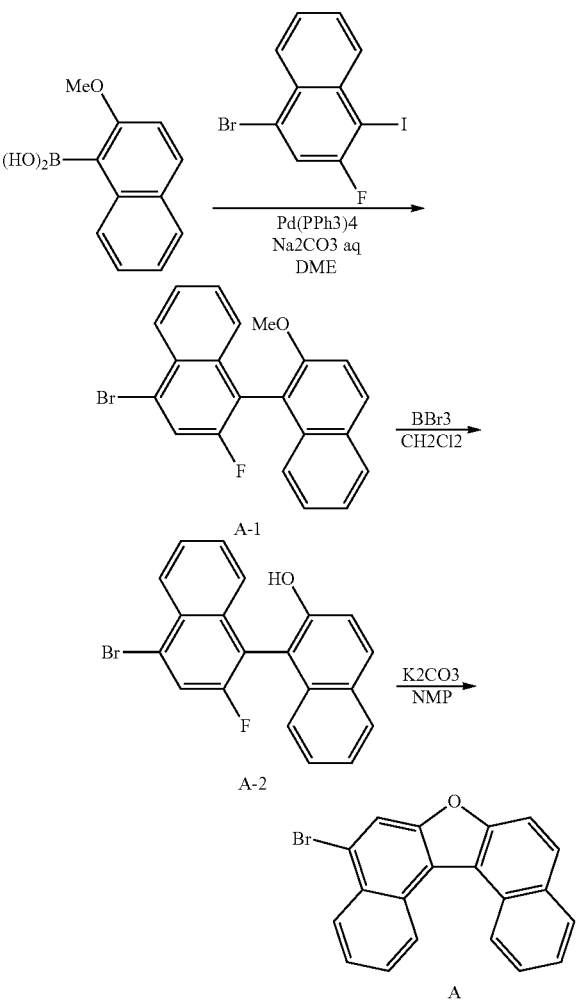

<Reaction Scheme 1-1>

(1) Synthesis of Intermediate A-1

In an argon gas atmosphere, 19.2 g of (2-methoxynaphthalen-1-yl) boronic acid, 35.1 g of 4-bromo-2-fluoro-1-iodonaphthalene, 1.28 g of tetrakis(triphenylphosphine) palladium (0), 180 mL of toluene, and 90 mL of a 2 M sodium carbonate solution were added to a flask. The mixed solution was heated for about 8 hours while being stirred under reflux. After the reaction solution was cooled to room temperature, an extraction process using toluene was performed thereon to remove a water layer. An organic layer collected therefrom was then washed using sodium thiosulfate, dried using MgSO$_4$, and concentrated. The resulting residue was purified by silica gel column chromatography, thus preparing 32.3 g (yield: 84.6%) of 4-bromo-2-fluoro-2'-methoxy-1,1'-binaphthalene (Intermediate A-1).

(2) Synthesis of Intermediate A-2

32.3 g of Intermediate A-1 and 250 mL of dichloromethane (dehydrated) were added to a flask, followed by being cooled to a temperature of 0° C. 27.5 g of 1M boron tribromide (BBr$_3$) was added thereto, and the mixed solution was stirred for about 24 hours at room temperature. After the completion of the reaction, the reaction solution was cooled to a temperature of −78° C., and the excited state thereof was inactivated with methanol and a sufficient amount of water in a sequential manner. The resulting solution was transferred into a separatory funnel, and an extraction process was performed thereon using dichloromethane. The extracted solution was then dried using MgSO₄, and passed through a short column using silica gel to remove impurities. The product was concentrated, and the resulting sample was vacuum-dried, thus preparing 30.9 g (yield: 99.5%) of 4-bromo-2-fluoro-2'-methoxy-1,1'-binaphthalene (Intermediate A-2).

(3) Synthesis of Intermediate A 30.9 g of Intermediate A-2, 300 mL of N-methyl-2-pyrrolidinone (dehydrated), 24.5 g of K₂CO₃ were added to a flask, followed by being stirred for about 2 hours at a temperature of 200° C. After the completion of the reaction, the reaction solution was cooled to room temperature, 2 l of toluene was added thereto. The reaction solution was transferred into a separatory funnel, followed by being washed using water. Then, the resulting solution was dried using MgSO₄, and passed through a short column using silica gel to remove impurities. The product was concentrated and subjected to recrystallization using a mixed solvent including toluene and methanol, thus preparing 20.0 g (yield: 68.3%) of Intermediate A.

Synthesis Example 2

Synthesis of Intermediate B

Intermediate B was synthesized according to Reaction Scheme 1-2:

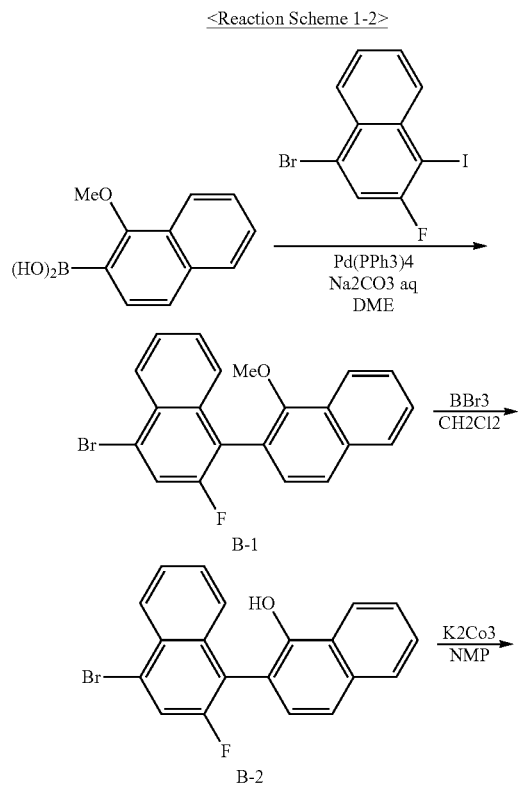

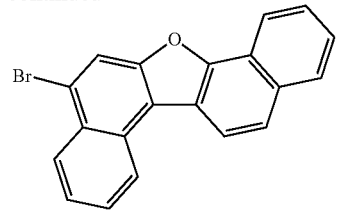

B (1) Synthesis of Intermediate B-1

In an argon gas atmosphere, 19.2 g of (1-methoxynaphthalen-2-yl) boronic acid, 35.1 g of 4-bromo-2-fluoro-1-iodonaphthalene, 1.28 g of tetrakis(triphenylphosphine) palladium (0), 180 mL of toluene, and 90 mL of a 2M sodium carbonate solution were added to a flask. The mixed solution was heated for about 8 hours while being stirred under reflux. After the reaction solution was cooled to room temperature, an extraction process using toluene was performed thereon to remove a water layer. An organic layer collected therefrom was then washed using sodium thiosulfate, dried using MgSO₄, and concentrated. The resulting residue was purified by silica gel column chromatography, thus preparing 32.5 g (yield: 85.3%) of 4-bromo-2-fluoro-1'-methoxy-1,2'-binaphthalene (Intermediate B-1).

(2) Synthesis of Intermediate B-2

32.5 g of Intermediate B-1 and 250 mL of dichloromethane (dehydrated) were added to a flask, followed by being cooled to a temperature of 0° C. 27.5 g of BBr₃ was added thereto, and the mixed solution was stirred for about 24 hours at room temperature. After the completion of the reaction, the reaction solution was cooled to a temperature of −78° C., and the excited state thereof was inactivated with methanol and a sufficient amount of water in a sequential manner. The resulting solution was transferred into a separatory funnel, and an extraction process was performed thereon using dichloromethane. The extracted solution was then dried using MgSO₄, and passed through a short column using silica gel to remove impurities. The product was concentrated, and the resulting sample was vacuum-dried, thus preparing 31.2 g (yield: 99.5%) of 4-bromo-2-fluoro-(1,2'-binaphthalen)-1'-ol (Intermediate B-2).

(3) Synthesis of Intermediate B 31.2 g of Intermediate B-2, 300 mL of N-methyl-2-pyrrolidinone (dehydrated), and 24.5 g of K₂CO₃ were added to a flask, followed by being stirred for about 2 hours at a temperature of 200° C. After the completion of the reaction, the reaction solution was cooled to room temperature, and 2 l of toluene was added thereto. The reaction solution was transferred into a separatory funnel, followed by being washed using water. Then, the resulting solution was dried using MgSO₄, and passed through a short column using silica gel to remove impurities. The product was concentrated and subjected to recrystallization using a mixed solvent including toluene and methanol, thus preparing 18.9 g (yield: 64.3%) of Intermediate B.

Synthesis Example 3

Synthesis of Intermediate C

Intermediate C was synthesized according to Reaction Scheme 3:

317

<Reaction Scheme 3>

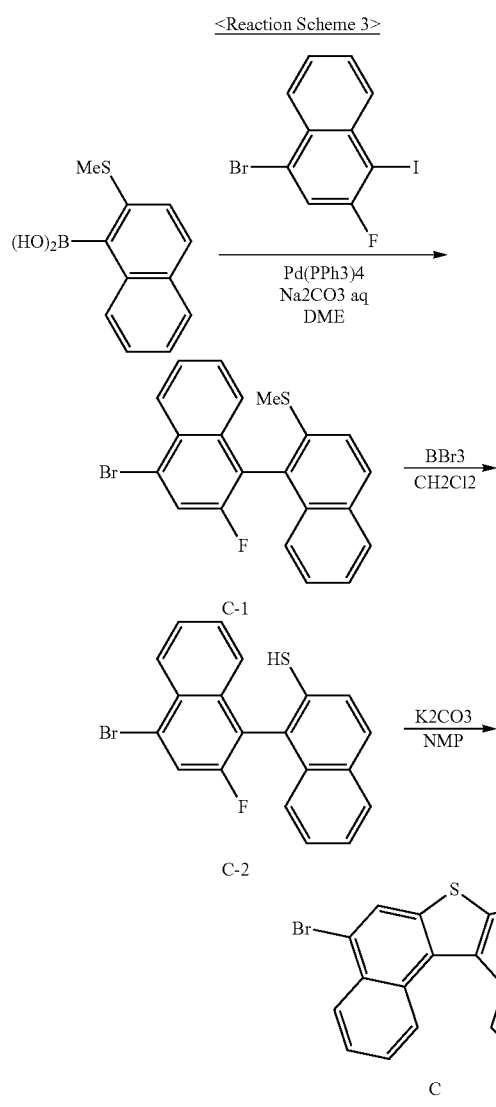

C (1) Synthesis of Intermediate C-1

In an argon gas atmosphere, 20.7 g of (2-[methylthio] naphthalen-1-yl) boronic acid, 35.1 g of 4-bromo-2-fluoro-1-iodonaphthalene, 1.28 g of tetrakis(triphenylphosphine) palladium (0), 180 mL of toluene, and 90 mL of a 2M sodium carbonate solution were added to a flask. The mixed solution was heated for about 8 hours while being stirred under reflux. After the reaction solution was cooled to room temperature, an extraction process using toluene was performed thereon to remove a water layer. An organic layer collected therefrom was then washed using sodium thiosulfate, dried using MgSO₄, and concentrated. The resulting residue was purified by silica gel column chromatography, thus preparing 33.6 g (yield: 84.5%) of 4'-bromo-2'-fluoro-[1,1'-binaphthalen]-2-yl(methyl)sulfane (Intermediate C-1).

(2) Synthesis of Intermediate C-2

33.6 g of Intermediate C-1 and 250 mL of dichloromethane (dehydrated) were added to a flask, followed by being cooled to a temperature of 0° C. 27.5 g of BBr₃ was added thereto, and the mixed solution was stirred for about 24 hours at room temperature. After the completion of the reaction, the reaction solution was cooled to a temperature of −78° C., and the excited state thereof was inactivated with methanol and a sufficient amount of water in a sequential manner. The resulting solution was transferred into a separatory funnel, and an extraction process was performed thereon using dichloromethane. The extracted solution was then dried using MgSO₄, and passed through a short column using silica gel to remove impurities. The product was concentrated, and the resulting sample was vacuum-dried, thus preparing 32.2 g (yield: 99.3%) of 4'-bromo-2'-fluoro-(1,1'-binaphthalene)-2-thiol (Intermediate C-2).

(3) Synthesis of Intermediate C 32.2 g of Intermediate C-2, 300 mL of N-methyl-2-pyrrolidinone (dehydrated), and 24.5 g of K₂CO₃ were added to a flask, followed by being stirred for about 2 hours at a tmperautre of 200° C. After the completion of the reaction, the reaction solution was cooled to room temperature, and 2 l of toluene was added thereto. The reaction solution was transferred into a separatory funnel, followed by being washed using water. Then, the resulting solution was dried using MgSO₄, and passed through a short column using silica gel to remove impurities. The product was concentrated and subjected to recrystallization using a mixed solvent including toluene and methanol, thus preparing 19.7 g (yield: 64.6%) of Intermediate C.

Synthesis Example 4

Synthesis of Intermediate D

Intermediate D was synthesized according to Reaction Scheme 4:

<Reaction Scheme 4>

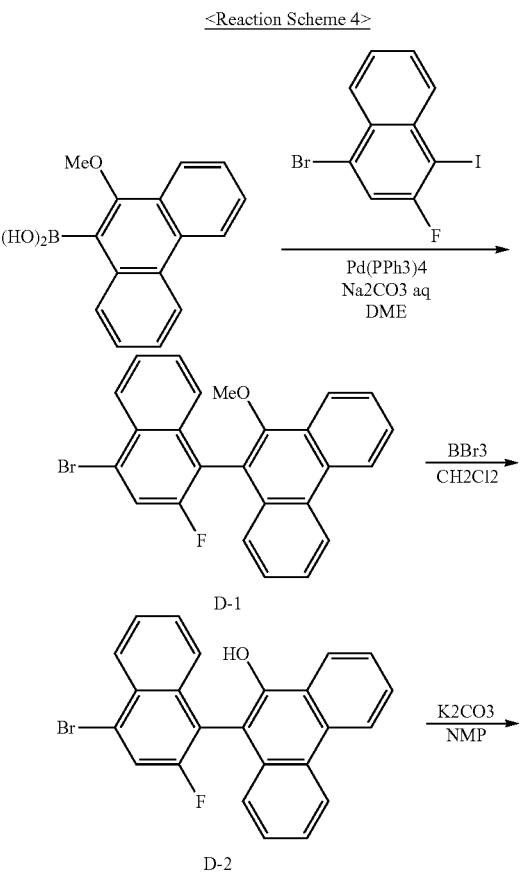

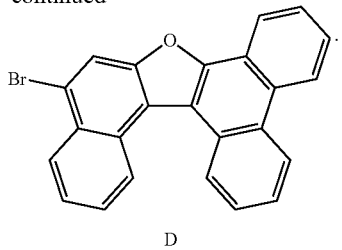

D (1) Synthesis of Intermediate D-1

In an argon gas atmosphere, 23.9 g of (10-methoxyphenanthren-9-yl) boronic acid, 35.1 g of 4-bromo-2-fluoro-1-iodonaphthalene, 1.28 g of tetrakis(triphenylphosphine) palladium (0), 180 mL of toluene, and 90 mL of a 2M sodium carbonate solution were added to a flask. The mixed solution was heated for about 8 hours while being stirred under reflux. After the reaction solution was cooled to room temperature, an extraction process using toluene was performed thereon to remove a water layer. An organic layer collected therefrom was then washed using sodium thiosulfate, dried using $MgSO_4$, and concentrated. The resulting residue was purified by silica gel column chromatography, thus preparing 36.4 g (molecular weight: 431.30 g/mol, yield: 84.5%) of 9-(4-bromo-2-fluoronaphthalen-1-yl)-10-methoxyphenanthrene (Intermediate D-1).

(2) Synthesis of Intermediate D-2

36.4 g of Intermediate D-2 and 250 mL of dichloromethane (dehydrated) were added to a flask, followed by being cooled to a temperature of 0° C. 27.5 g of $BBr_3$ was added thereto, and the mixed solution was stirred for about 24 hours at room temperature. After the completion of the reaction, the reaction solution was cooled to a temperature of −78° C., and the excited state thereof was inactivated with methanol and a sufficient amount of water in a sequential manner. The resulting solution was transferred into a separatory funnel, and an extraction process was performed thereon using dichloromethane. The extracted solution was then dried using $MgSO_4$, and passed through a short column using silica gel to remove impurities. The product was concentrated, and the resulting sample was vacuum-dried, thus preparing 35.0 g (yield: 99.4%) of 10-(4-bromo-2-fluoronaphthalen-1-yl) phenanthren-9-ol (Intermediate D-2).

(3) Synthesis of Intermediate D 35.0 g of Intermediate D-2, 300 mL of N-methyl-2-pyrrolidinone (dehydrated), and 24.5 g of $K_2CO_3$ were added to a flask, followed by being stirred for about 2 hours at a tmperautre of 200° C. After the completion of the reaction, the reaction solution was cooled to room temperature, and 2 l of toluene was added thereto. The reaction solution was transferred into a separatory funnel, followed by being washed using water. Then, the resulting solution was dried using $MgSO_4$, and passed through a short column using silica gel to remove impurities. The product was concentrated and subjected to recrystallization using a mixed solvent including toluene and methanol, thus preparing 21.6 g (yield: 64.8%) of Intermediate D.

Synthesis Example 5

Synthesis of Intermediate E

Intermediate E was synthesized according to Reaction Scheme 5:

<Reaction Scheme 5>

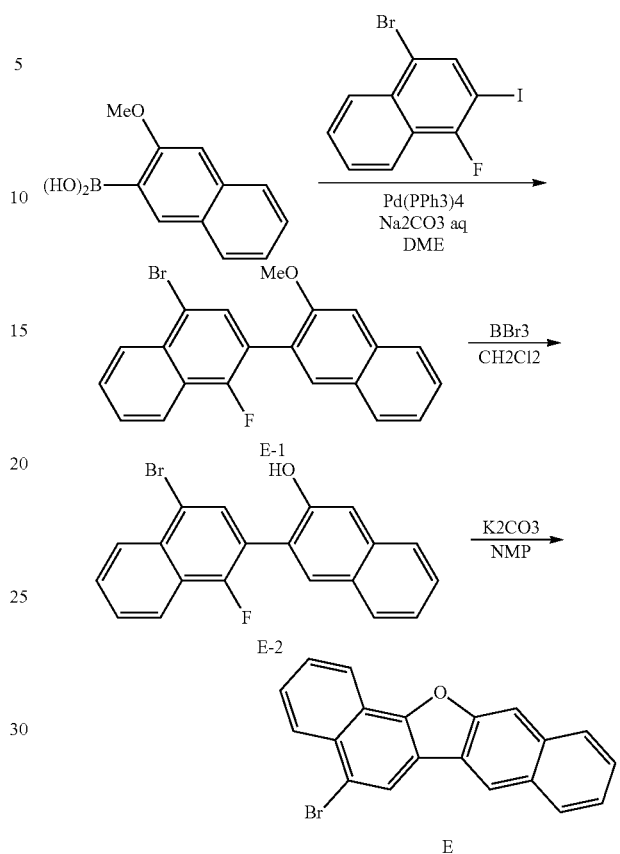

(1) Synthesis of Intermediate E-1

In an argon gas atmosphere, 19.2 g of (3-methoxynaphthalen-2-yl) boronic acid, 35.1 g of 4-bromo-1-fluoro-2-iodonaphthalene, 1.28 g of tetrakis(triphenylphosphine) palladium (0), 180 mL of toluene, and 90 mL of a 2M sodium carbonate solution added to a flask. The mixed solution was heated for about 8 hours while being stirred under reflux. After the reaction solution was cooled to room temperature, an extraction process using toluene was performed thereon to remove a water layer. An organic layer collected therefrom was then washed using sodium thiosulfate, dried using $MgSO_4$, and concentrated. The resulting residue was purified by silica gel column chromatography, thus preparing 32.4 g (yield: 85.1%) of 4-bromo-1-fluoro-3'-methoxy-2,2'-binaphthalene (Intermediate E-1).

(2) Synthesis of Intermediate E-2

32.4 g of Intermediate E-1 and 250 mL of dichloromethane (dehydrated) were added to a flask, followed by being cooled to a temperature of 0° C. 27.5 g of $BBr_3$ was added thereto, and the mixed solution was stirred for about 24 hours at room temperature. After the completion of the reaction, the reaction solution was cooled to a temperature of −78° C., and the excited state thereof was inactivated with methanol and a sufficient amount of water in a sequential manner. The resulting solution was transferred into a separatory funnel, and an extraction process was performed thereon using dichloromethane. The extracted solution was then dried using $MgSO_4$, and passed through a short column using silica gel to remove impurities. The product was concentrated, and the resulting sample was vacuum-dried, thus preparing 31.1 g (yield: 99.5%) of 4'-bromo-1'-fluoro-(2,2'-binaphthalen)-3-ol (Intermediate E-2).

(3) Synthesis of Intermediate E 31.1 g of Intermediate E-2, 300 mL of N-methyl-2-pyrrolidinone (dehydrated), and 24.5 g of K$_2$CO$_3$ were added to a flask, followed by being stirred for about 2 hours at a temperature of 200° C. After the completion of the reaction, the reaction solution was cooled to room temperature, 2 l of toluene was added thereto. The reaction solution was transferred into a separatory funnel, followed by being washed using water. Then, the resulting solution was dried using MgSO$_4$, and passed through a short column using silica gel to remove impurities. The product was concentrated and subjected to recrystallization using a mixed solvent including toluene and methanol, thus preparing 19.9 g (yield: 67.6%) of Intermediate E.

Synthesis Example 6

Synthesis of Intermediate F

Intermediate F was synthesized according to Reaction Scheme 6:

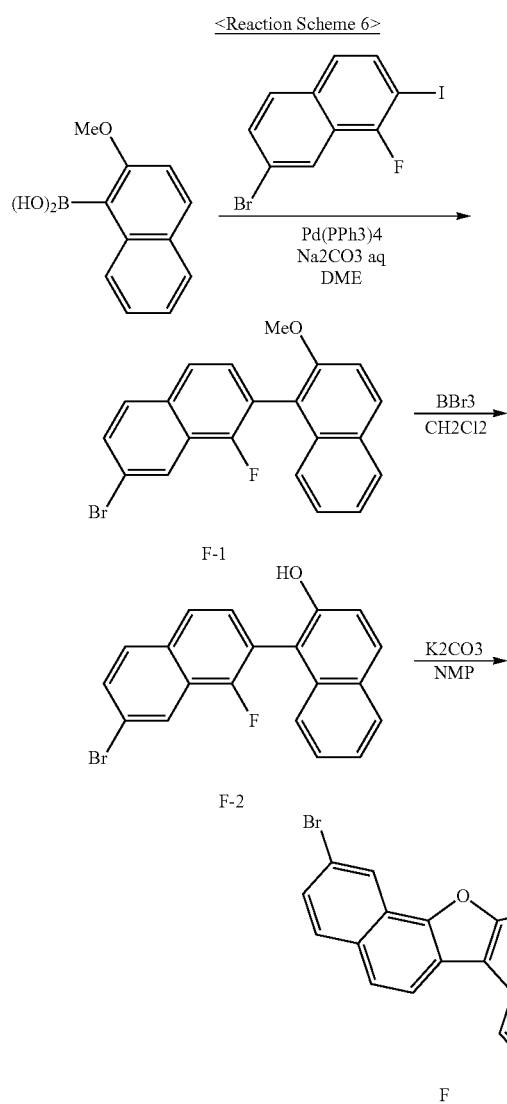

(1) Synthesis of Intermediate F-1

In an argon gas atmosphere, 17.3 g of (2,3-dimethoxyphenyl) boronic acid, 17.5 g of 1-bromo-2-fluorobenzene, 2.34 g of tetrakis(triphenylphosphine) palladium (0), 300 mL of 1,2-dimethoxyethane, and 150 mL of a 2M sodium carbonate solution were added to a flask. The mixed solution was heated for about 8 hours while being stirred under reflux. After the reaction solution was cooled to room temperature, an extraction process using toluene was performed thereon to remove a water layer. An organic layer collected therefrom was then washed using sodium thiosulfate, dried using MgSO$_4$, and concentrated. The resulting residue was purified by silica gel column chromatography, thus preparing 18.9 g (yield: 85.8%) of 2'-fluoro-2,3-dimethoxy-1,1'-biphenyl (Intermediate F-1).

(2) Synthesis of Intermediate F-2

In an argon gas atmosphere, 18.9 g of Intermediate F-1 and 500 mL of anhydrous THF were added to a flask, and 55 mL of a hexane solution containing 1.6 M n-butyllithium was added thereto. The reaction solution was stirred for about 4 hours at room temperature, followed by being cooled to a temperature of −78° C. Then, 30 mL of THF containing 28.1 g of trimethyl borate was added thereto drop by drop. A temperature at which the reaction occurs was raised up to room temperature while stirring was performed for about 8 hours. 200 mL of a 10% HCl solution was added to the reaction solution, followed by being stirred for about 2 hours. After removal of a water solution from the resulting reaction through an extraction process using ether, an organic layer collected therefrom was then washed using sodium thiosulfate and dried using MgSO$_4$. The product was concentrated, and the resulting residue was washed using hexane, thus preparing 14.3 g (yield: 63.9%) of (2'-fluoro-2,3-dimethoxy-[1,1'-biphenyl]-4-yl) boronic acid (Intermediate F-2).

(3) Synthesis of Intermediate F 31.1 g of Intermediate F-2, 300 mL of N-methyl-2-pyrrolidinone (dehydrated), and 24.5 g of K$_2$CO$_3$ were added to a flask, followed by being stirred for about 2 hours at a tmperautre of 200° C. After the completion of the reaction, the reaction solution was cooled to room temperature, and 2 l of toluene was added thereto. The reaction solution was transferred into a separatory funnel, followed by being washed using water. Then, the resulting solution was dried using MgSO$_4$, and passed through a short column using silica gel to remove impurities. The product was concentrated and subjected to recrystallization using a mixed solvent including toluene and methanol, thus preparing 19.4 g (yield: 65.9%) of Intermediate F.

Synthesis Example 7

Synthesis of Intermediate G

Intermediate G was synthesized according to Reaction Scheme 7:

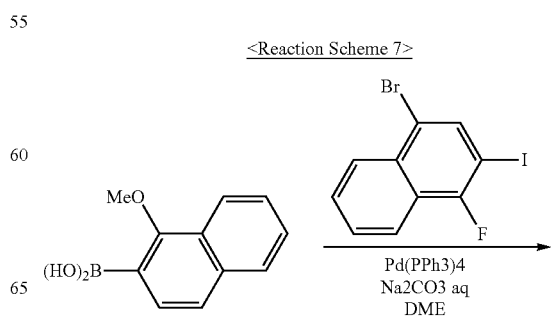

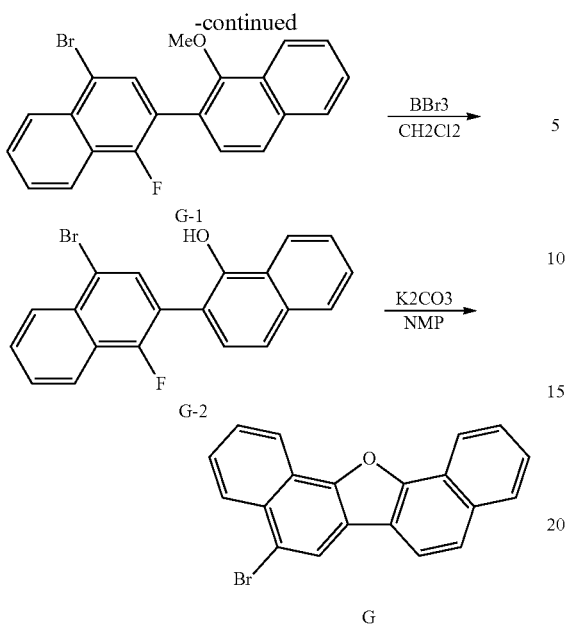

(1) Synthesis of Intermediate G-1

In an argon gas atmosphere, 19.2 g of (1-methoxynaphthalen-2-yl) boronic acid, 35.1 g of 4-bromo-1-fluoro-2-iodonaphthalene, 1.28 g of tetrakis(triphenylphosphine) palladium (0), 180 mL of toluene, and 90 mL of a 2M sodium carbonate solution were added to a flask. The mixed solution was heated for about 8 hours while being stirred under reflux. After the reaction solution was cooled to room temperature, an extraction process using toluene was performed thereon to remove a water layer. An organic layer collected therefrom was then washed using sodium thiosulfate, dried using MgSO$_4$, and concentrated. The resulting residue was purified by silica gel column chromatography, thus preparing 32.5 g (yield: 85.3%) of 4-bromo-1-fluoro-1'-methoxy-2,2'-binaphthalene (Intermediate G-1).

(2) Synthesis of Intermediate G-2

32.5 g of Intermediate G-1 and 250 mL of dichloromethane (dehydrated) were added to a flask, followed by being cooled to a temperature of 0° C. 27.5 g of BBr$_3$ was added thereto, and the mixed solution was stirred for about 24 hours at room temperature. After the completion of the reaction, the reaction solution was cooled to a temperature of −78° C., and the excited state thereof was inactivated with methanol and a sufficient amount of water in a sequential manner. The resulting solution was transferred into a separatory funnel, and an extraction process was performed thereon using dichloromethane. The extracted solution was then dried using MgSO$_4$, and passed through a short column using silica gel to remove impurities. The product was concentrated, and the resulting sample was vacuum-dried, thus preparing 31.2 g (yield: 99.5%) of 4'-bromo-1'-fluoro-(2,2'-binaphthalen)-1-ol (Intermediate G-2).

(3) Synthesis of Intermediate G 31.2 g of Intermediate G-2, 300 mL of N-methyl-2-pyrrolidinone (dehydrated), and 24.5 g of K$_2$CO$_3$ were added to a flask, followed by being stirred for about 2 hours at a temperature of 200° C. After the completion of the reaction, the reaction solution was cooled to room temperature, and 2 l of toluene was added thereto. The reaction solution was transferred into a separatory funnel, followed by being washed using water. Then, the resulting solution was dried using MgSO$_4$, and passed through a short column using silica gel to remove impurities. The product was concentrated and subjected to recrystallization using a mixed solvent including toluene and methanol, thus preparing 19.3 g (yield: 65.4%) of Intermediate G.

Synthesis Example 8

Synthesis of Intermediate H

Intermediate H was synthesized according to Reaction Scheme 8:

(1) Synthesis of Intermediate H-1

In an argon gas atmosphere, 20.7 g of (1-(methylthio) naphthalen-2-yl) boronic acid, 35.1 g of 1-bromo-2-fluoro-3-iodonaphthalene, 1.28 g of tetrakis(triphenylphosphine) palladium (0), 180 mL of toluene, and 90 mL of a 2M sodium carbonate solution were added to a flask. The mixed solution was heated for about 8 hours while being stirred under reflux. After the reaction solution was cooled to room temperature, an extraction process using toluene was performed thereon to remove a water layer. An organic layer collected therefrom was then washed using sodium thiosulfate, dried using MgSO$_4$, and concentrated. The resulting residue was purified by silica gel column chromatography, thereby completing the preparation of 33.6 g (yield: 84.6%) of 4'-bromo-3'-fluoro-[2,2'-binaphthalen]-1-yl(methyl) sulfane (Intermediate H-1).

(2) Synthesis of Intermediate H-2

33.6 g of Intermediate H-1 250 mL of and dichloromethane (dehydrated) were added to a flask, followed by being cooled to a temperature of 0° C. 27.5 g of BBr$_3$ was added thereto, and the mixed solution was stirred for about 24 hours at room temperature. After the completion of the reaction, the reaction solution was cooled to a temperature of −78° C., and the excited state thereof was inactivated with methanol and a sufficient amount of water in a sequential manner. The resulting solution was transferred into a separatory funnel, and an extraction process was performed thereon using dichloromethane. The extracted solution was then dried using MgSO$_4$, and passed through a short column using silica gel to remove impurities. The product was concentrated, and the resulting sample was vacuum-dried, thus preparing 32.3 g (yield: 99.5%) of 4′-bromo-3′-fluoro-(2,2′-binaphthalene)-1-thiol (Intermediate H-2).

(3) Synthesis of Intermediate H 32.3 g of Intermediate H-2, 300 mL of N-methyl-2-pyrrolidinone (dehydrated), and 24.5 g of K$_2$CO$_3$ were added to a flask, followed by being stirred for about 2 hours at a tmperautre of 200° C. After the completion of the reaction, the reaction solution was cooled to room temperature, and 2 l of toluene was added thereto. The reaction solution was transferred into a separatory funnel, followed by being washed using water. Then, the resulting solution was dried using MgSO$_4$, and passed through a short column using silica gel to remove impurities. The product was concentrated and subjected to recrystallization using a mixed solvent including toluene and methanol, thus preparing 19.6 g (yield: 64.1%) of Intermediate H.

Synthesis Example 9

Synthesis of Intermediate I

Intermediate I was synthesized according to Reaction Scheme 9:

<Reaction Scheme 9>

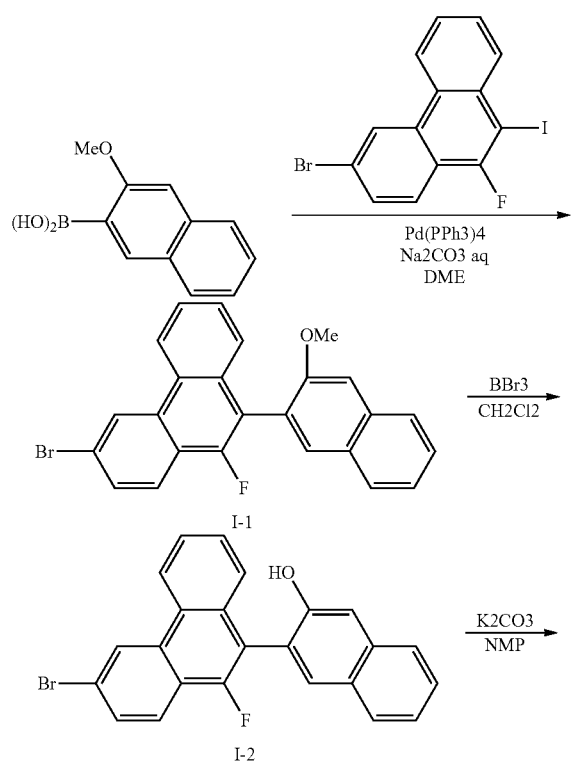

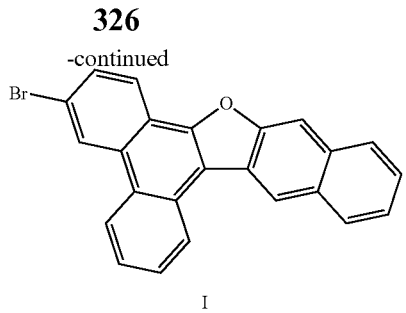

I (1) Synthesis of Intermediate I-1

In an argon gas atmosphere, 19.2 g of (3-methoxynaphthalen-2-yl) boronic acid, 40.1 g of 3-bromo-10-fluoro-9-iodophenanthrene, 1.28 g of tetrakis(triphenylphosphine) palladium (0), 180 mL of toluene, 90 mL of a 2M sodium carbonate solution were added to a flask. The mixed solution was heated for about 8 hours while being stirred under reflux. After the reaction solution was cooled to room temperature, an extraction process using toluene was performed thereon to remove a water layer. An organic layer collected therefrom was then washed using sodium thiosulfate, dried using MgSO$_4$, and concentrated. The resulting residue was purified by silica gel column chromatography, thus preparing 36.3 g (yield: 84.2%) of 3-bromo-10-fluoro-9-(3-methoxynaphthalen-2-yl)phenanthrene (Intermediate I-1).

(2) Synthesis of Intermediate I-2

36.3 g of Intermediate I-1 and 250 mL of dichloromethane (dehydrated) were added to a flask, followed by being cooled to a temperature of 0° C. 27.5 g of BBr$_3$ was added thereto, and the mixed solution was stirred for about 24 hours at room temperature. After the completion of the reaction, the reaction solution was cooled to a temperature of −78° C., and the excited state thereof was inactivated with methanol and a sufficient amount of water in a sequential manner. The resulting solution was transferred into a separatory funnel, and an extraction process was performed thereon using dichloromethane. The extracted solution was then dried using MgSO$_4$, and passed through a short column using silica gel to remove impurities. The product was concentrated, and the resulting sample was vacuum-dried, thus preparing 35.0 g (yield: 99.5%) of 3-(3-bromo-10-fluorophenanthren-9-yl) naphthalen-2-ol (Intermediate I-2).

(3) Synthesis of Intermediate I 35.0 g of Intermediate I-2, 300 mL of N-methyl-2-pyrrolidinone (dehydrated), and 24.5 g of K$_2$CO$_3$ were added to a flask, followed by being stirred for about 2 hours at a temperature of 200° C. After the completion of the reaction, the reaction solution was cooled to room temperature, and 2 l of toluene was added thereto. The reaction solution was transferred into a separatory funnel, followed by being washed using water. Then, the resulting solution was dried using MgSO$_4$, and passed through a short column using silica gel to remove impurities. The product was concentrated and subjected to recrystallization using a mixed solvent including toluene and methanol, thus preparing 21.2 g (yield: 63.8%) of Intermediate I.

Synthesis Example 10

Synthesis of Compound H1

Compound H1 was synthesized according to Reaction Scheme 10:

<Reaction Scheme 10>

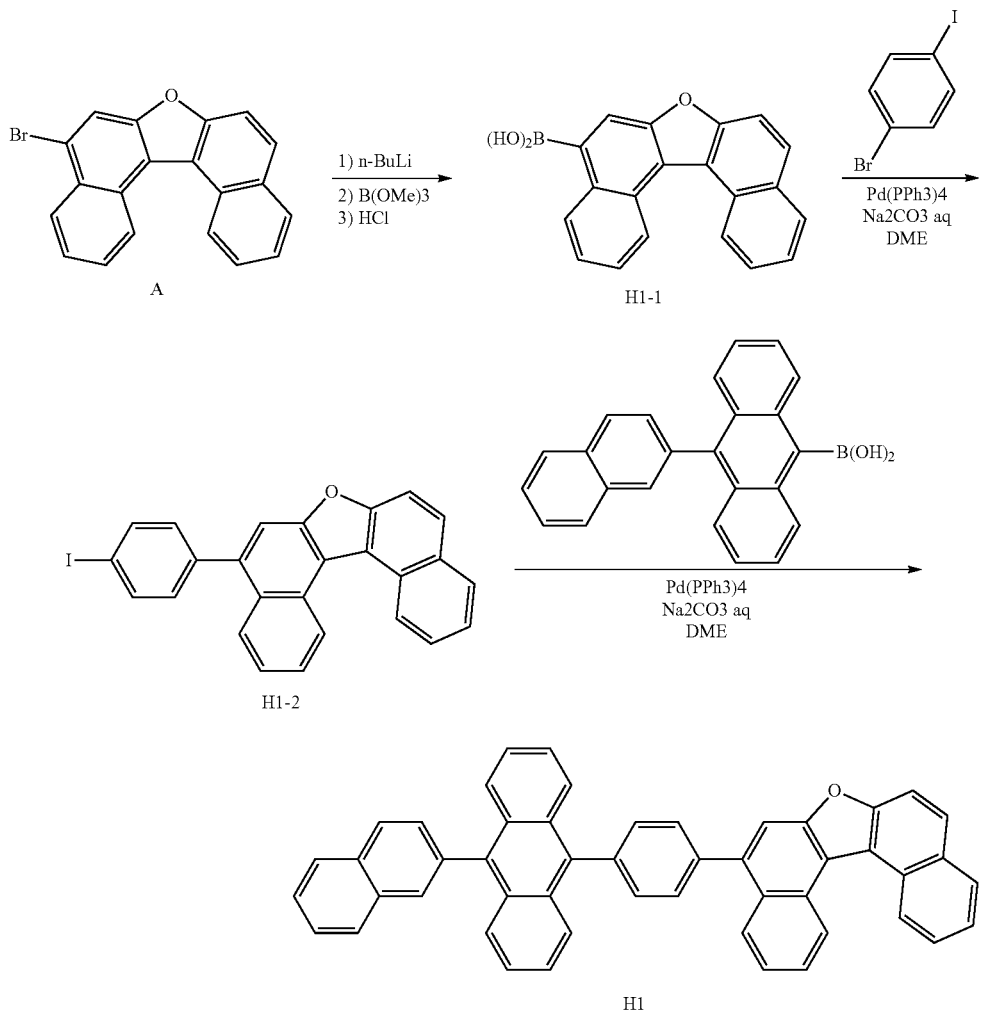

(1) Synthesis of Intermediate H1-1

34.7 g of Intermediate A and 500 mL of tetrahydrofuran (dehydrated) were added to a flask, and the mixed solution was cooled to a temperature of −78° C. 66 mL of n-BuLi (1.6 M in hexane) was added thereto, and a temperature at which the reaction occurs was increased to 0° C. while stirring was performed on the reaction solution for about 2 hours. Then, the reaction solution was cooled to a temperature of −78° C., 327.5 g of B(OMe)$_3$ was added thereto, and the resulting solution was stirred for about 10 minutes at a temperature of −78° C. and for about 5 hours at room temperature in a sequential manner. After the completion of the reaction, 200 mL of 1N HCl aq. was added thereto, followed by being stirred for about 1 hour at room temperature. Afterwards, the resulting solution was transferred into a separatory funnel, and an extration process was performed thereon using ethyl acetate. The extracted solution was then dried using MgSO$_4$, and the product was concentrated and washed using n-hexane, thus preparing 19.9 g (yield: 63.5%) of Intermediate H1-1.

(2) Synthesis of Intermediate H1-2

In an argon gas atmosphere, 19.9 g of Intermediate H1-1, 19.8 g of 1-bromo-4-iodobenzene, 1.52 g of tetrakis(triphenylphosphine) palladium (0), 200 mL of toluene, and 100 mL of a 2M sodium carbonate solution were added to a flask. The mixed solution was heated for about 8 hours while being stirred under reflux. After the reaction solution was cooled to room temperature, an extraction process using toluene was performed thereon to remove a water layer. An organic layer collected therefrom was then washed using sodium thiosulfate, dried using MgSO$_4$, and concentrated. The resulting residue was purified by silica gel column chromatography, thus preparing 21.8 g (yield: 72.5%) of Intermediate H1-2.

(3) Synthesis of Compound H1

In an argon gas atmosphere, 21.8 g of Intermediate H1-2, 16.4 g of (10-(naphthalen-2-yl) anthracen-9-yl) boronic acid, 0.232 g of tetrakis(triphenylphosphine) palladium (0), 40 mL of 1,2-dimethoxyethane, and 20 mL of a 2 M sodium carbonate solution were added to a flask. The mixed solution was stirred under reflux for about 8 hours. After the reaction solution was cooled to room temperature, a precipitated solid was filtered. Then, the solid was washed using a mixture including water and methanol, and subjected to recrystallization using toluene, thus preparing 19.2 g (yield: 64.1%) of Compound H1. The obtained compound was identified using MS/FAB.

cald: 646.23, found: 646.79.

Synthesis Example 11

Synthesis of Compound H2

Compound H2 was synthesized according to Reaction Scheme 11:

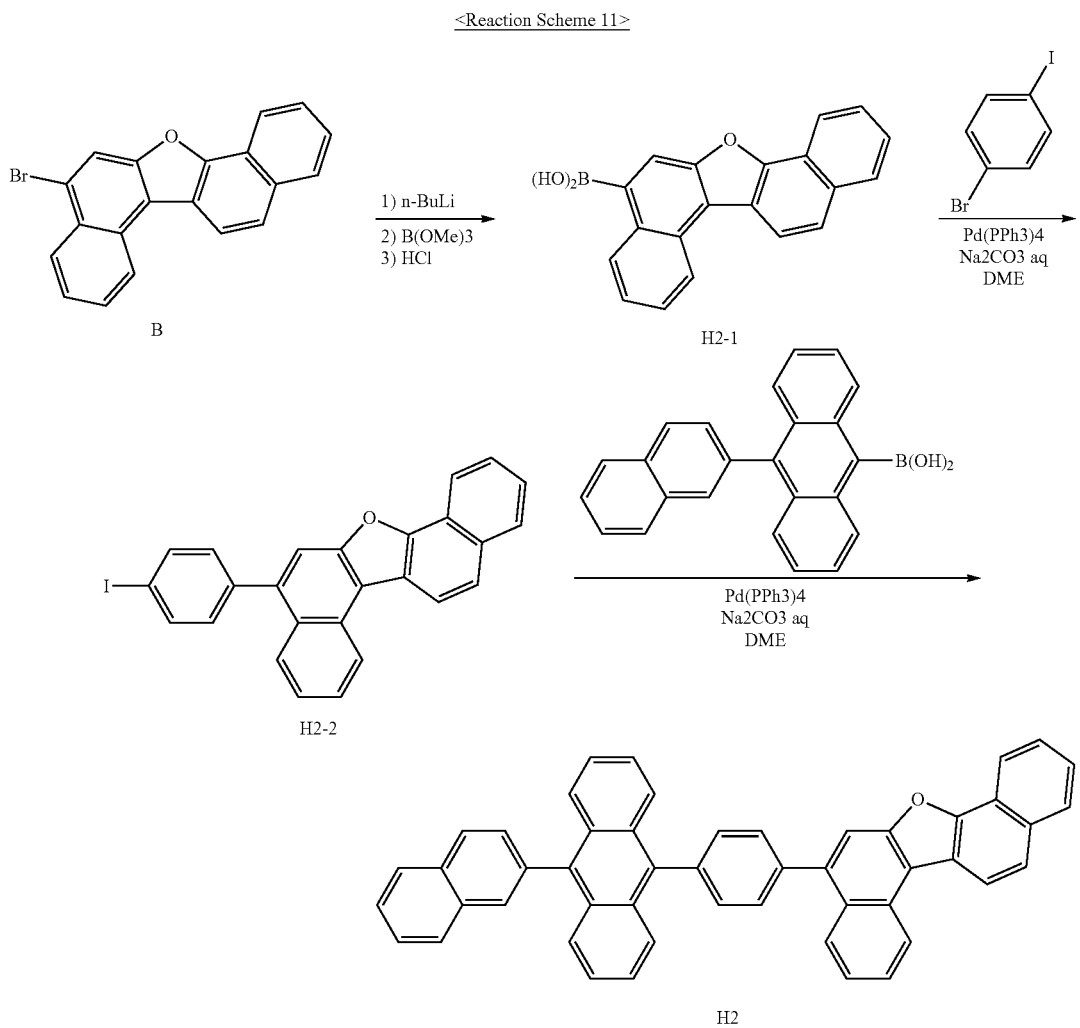

(1) Synthesis of Intermediate H2-1

20.0 g (yield: 64.0%) of Intermediate H2-1 was obtained in substantially the same manner as in preparing Intermediate H1-1 according to Synthesis Example 10, except that Intermediate B was used instead of Intermediate A.

(2) Synthesis of Intermediate H2-2

22.2 g (yield: 73.1%) of Intermediate H2-2 was obtained in substantially the same manner as in preparing Intermediate H1-1 according to Synthesis Example 10, except that Intermediate H2-1 was used instead of Intermediate H1-1.

(3) Synthesis of Compound H2

19.3 g (yield: 63.9%) of Compound H2 was obtained in substantially the same manner as in preparing Compound H1 according to Synthesis Example 10, except that Intermediate H2-2 was used instead of Intermediate H1-2. The obtained compound was identified using MS/FAB.

cald: 646.23, found: 646.79.

Synthesis Example 12

Synthesis of Compound H3

Compound H3 was synthesized according to Reaction Scheme 12:

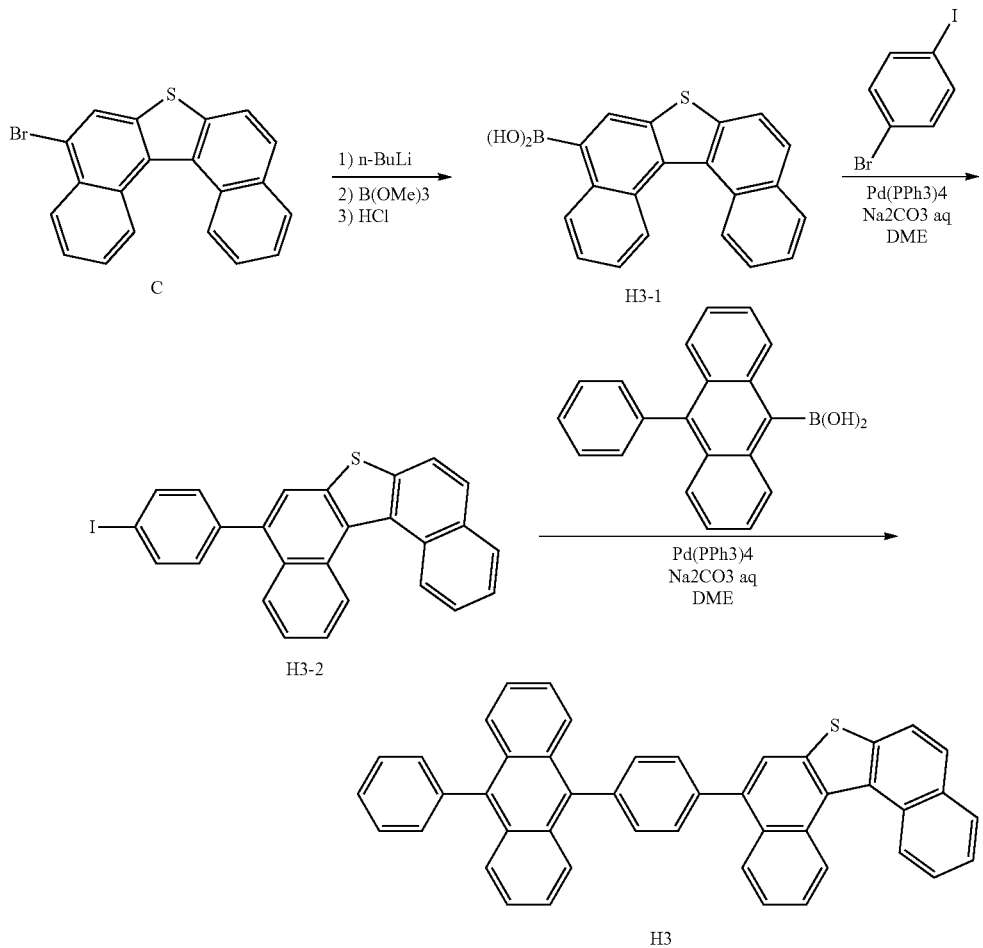

(1) Synthesis of Intermediate H3-1

20.9 g (yield: 63.6%) of Intermediate H3-1 was obtained in substantially the same manner as in preparing Intermediate H1-1 according to Synthesis Example 10, except that Intermediate C was used instead of Intermediate A.

(2) Synthesis of Intermediate H3-2

22.3 g (yield: 72.2%) of Intermediate H3-2 was obtained in substantially the same manner as in preparing Intermediate H1-2 according to Synthesis Example 10, except that Intermediate H3-1 was used instead of Intermediate H1-1.

(3) Synthesis of Compound H3

18.0 g (yield: 64.0%) of Compound H3 was obtained in substantially the same manner as in preparing Compound H1 according to Synthesis Example 10, except that Intermediate H3-2 and (10-phenylanthracen-9-yl) boronic acid were used instead of Intermediate H1-2 and 10-(naphthalen-2-yl) anthracen-9-yl) boronic acid, respectively. The obtained compound was identified using MS/FAB.

cald: 612.79, found: 612.19.

Synthesis Example 13

Synthesis of Compound H4

Compound H4 was synthesized according to Reaction Scheme 13:

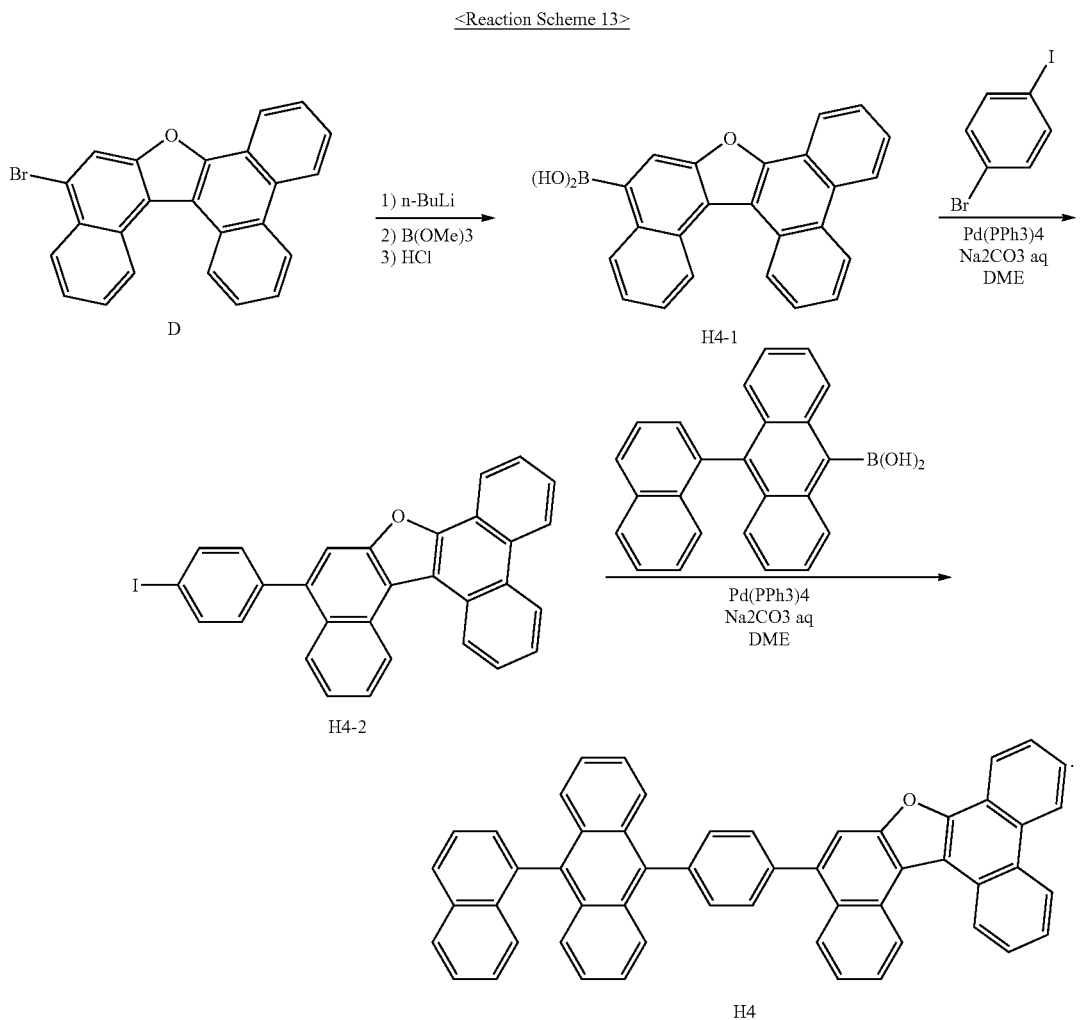

(1) Synthesis of Intermediate H4-1

23.0 g (yield: 63.6%) of Intermediate H4-1 was obtained in substantially the same manner as in preparing Intermediate H1-1 according to Synthesis Example 10, except that Intermediate D was used instead of Intermediate A.

(2) Synthesis of Intermediate H4-2

24.0 g (yield: 72.4%) of Intermediate H4-2 was obtained in substantially the same manner as in preparing Intermediate H1-1 according to Synthesis Example 10, except that Intermediate H4-1 was used instead of Intermediate H1-1.

(3) Synthesis of Compound H4

20.2 g (yield: 62.8%) of Compound H4 was obtained in substantially the same manner as in preparing Compound H1 according to Synthesis Example 10, except that Intermediate H4-2 and (10-(naphthalen-1-yl) anthracen-9-yl) boronic acid were used instead of Intermediate H1-2 and 10-(naphthalen-2-yl) anthracen-9-yl) boronic acid, respectively. The obtained compound was identified using MS/FAB.

cald: 696.85, found: 696.25.

Synthesis Example 14

Synthesis of Compound H5

Compound H5 was synthesized according to Reaction Scheme 14:

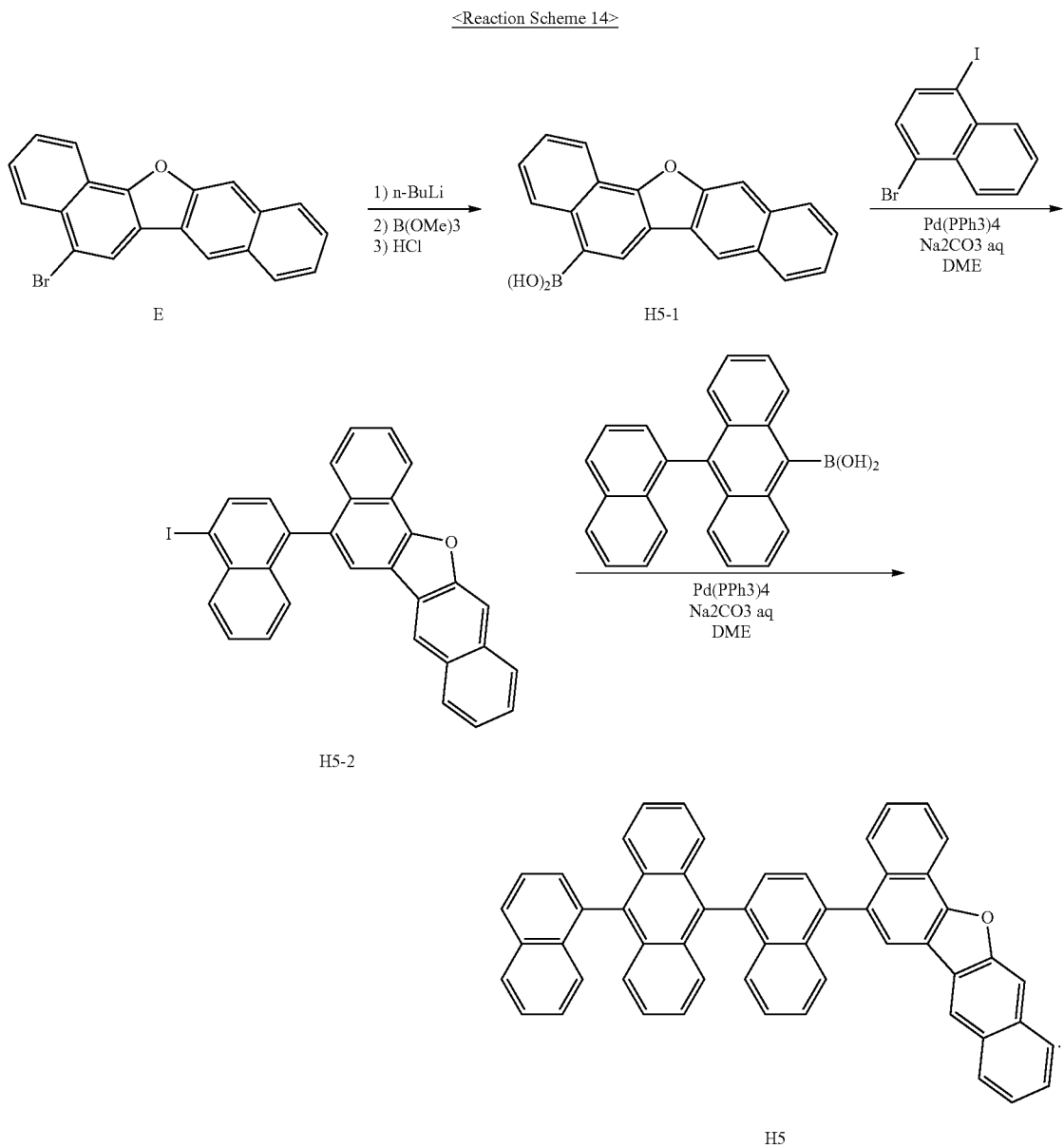

<Reaction Scheme 14>

(1) Synthesis of Intermediate H5-1

19.9 g (yield: 63.6%) of Intermediate H5-1 was obtained in substantially the same manner as in preparing Intermediate H1-1 according to Synthesis Example 10, except that Intermediate E was used instead of Intermediate A.

(2) Synthesis of Intermediate H5-2

23.2 g (yield: 70.2%) of Intermediate H5-2 was obtained in substantially the same manner as in preparing Intermediate H1-2 according to Synthesis Example 10, except that Intermediate H5-1 was used instead of Intermediate H1-1.

(3) Synthesis of Compound H5

19.4 g (yield: 62.5%) of Compound H5 was obtained in substantially the same manner as in preparing Intermediate Compound H1 according to Synthesis Example 10, except that Intermediate H5-2 and (10-(naphthalen-1-yl) anthracen-9-yl) boronic acid were used instead of Intermediate H1-2 and (10-(naphthalen-2-yl) anthracen-9-yl) boronic acid, respectively. The obtained compound was identified using MS/FAB.

cald: 696.85, found: 696.25.

Synthesis Example 15

Synthesis of Compound H6

Compound H6 was synthesized according to Reaction Scheme 15:

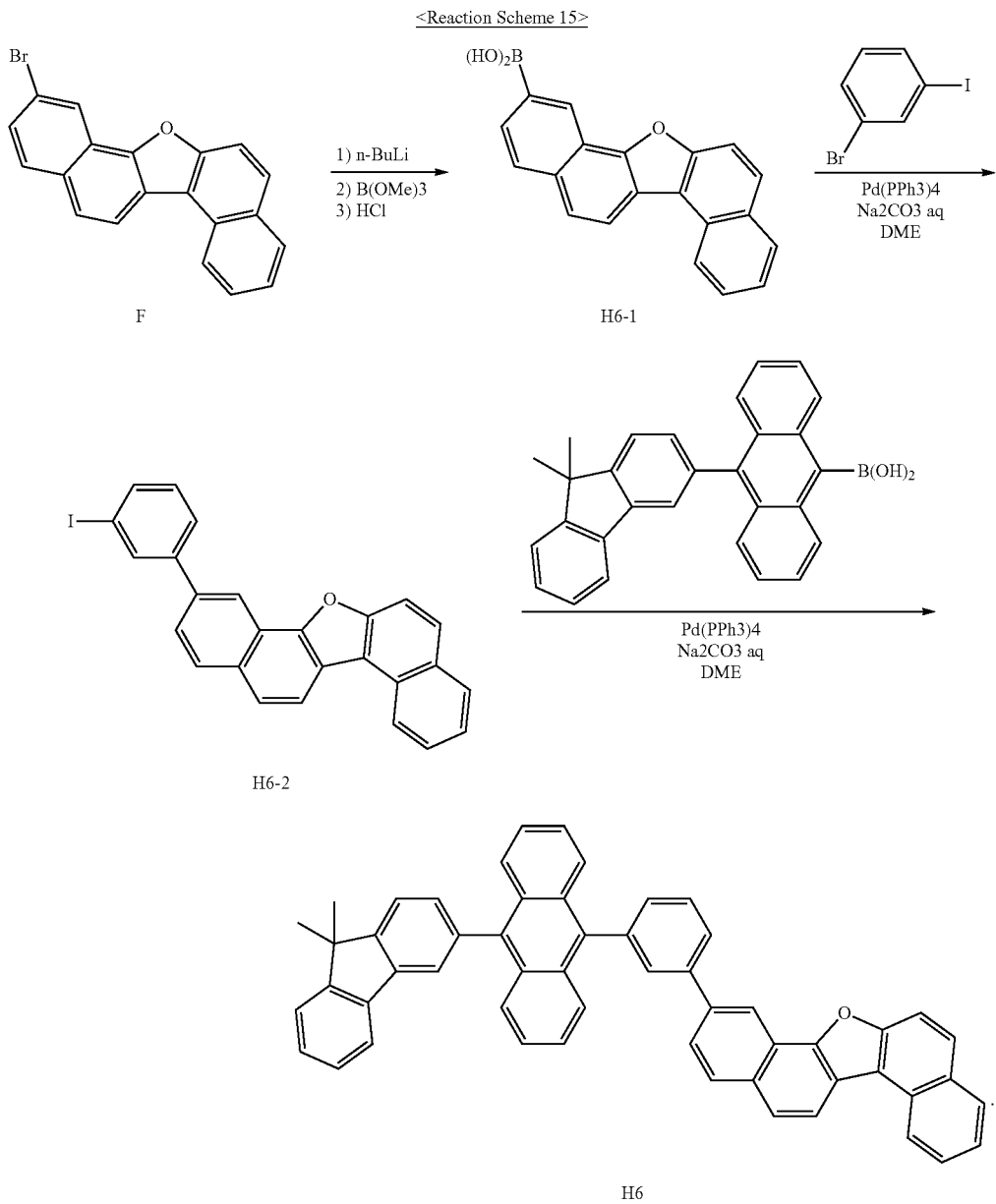

(1) Synthesis of Intermediate H6-1

20.0 g (yield: 64.0%) of Intermediate H6-1 was obtained in substantially the same manner as in preparing Intermediate H1-1 according to Synthesis Example 10, except that Intermediate F was used instead of Intermediate A.

(2) Synthesis of Intermediate H6-2

21.9 g (yield: 72.7%) of Intermediate H6-2 was obtained in substantially the same manner as in preparing Intermediate H1-2 according to Synthesis Example 10, except that Intermediate H6-1 was used instead of Intermediate H1-1.

(3) Synthesis of Compound H6

21.0 g (yield: 63.2%) of Compound H6 was obtained in substantially the same manner as in preparing Compound H1 according to Synthesis Example 10, except that Intermediate H6-2 and (10-(9,9-dimethyl-9H-fluoren-3-yl) anthracen-9-yl) boronic acid were used instead of Intermediate H1-2 and 10-(naphthalen-2-yl) anthracen-9-yl) boronic acid, respectively. The obtained compound was identified using MS/FAB.

cald: 712.89, found: 712.28.

Synthesis Example 16

Synthesis of Compound H7

Compound H7 was synthesized according to Reaction Scheme 16:

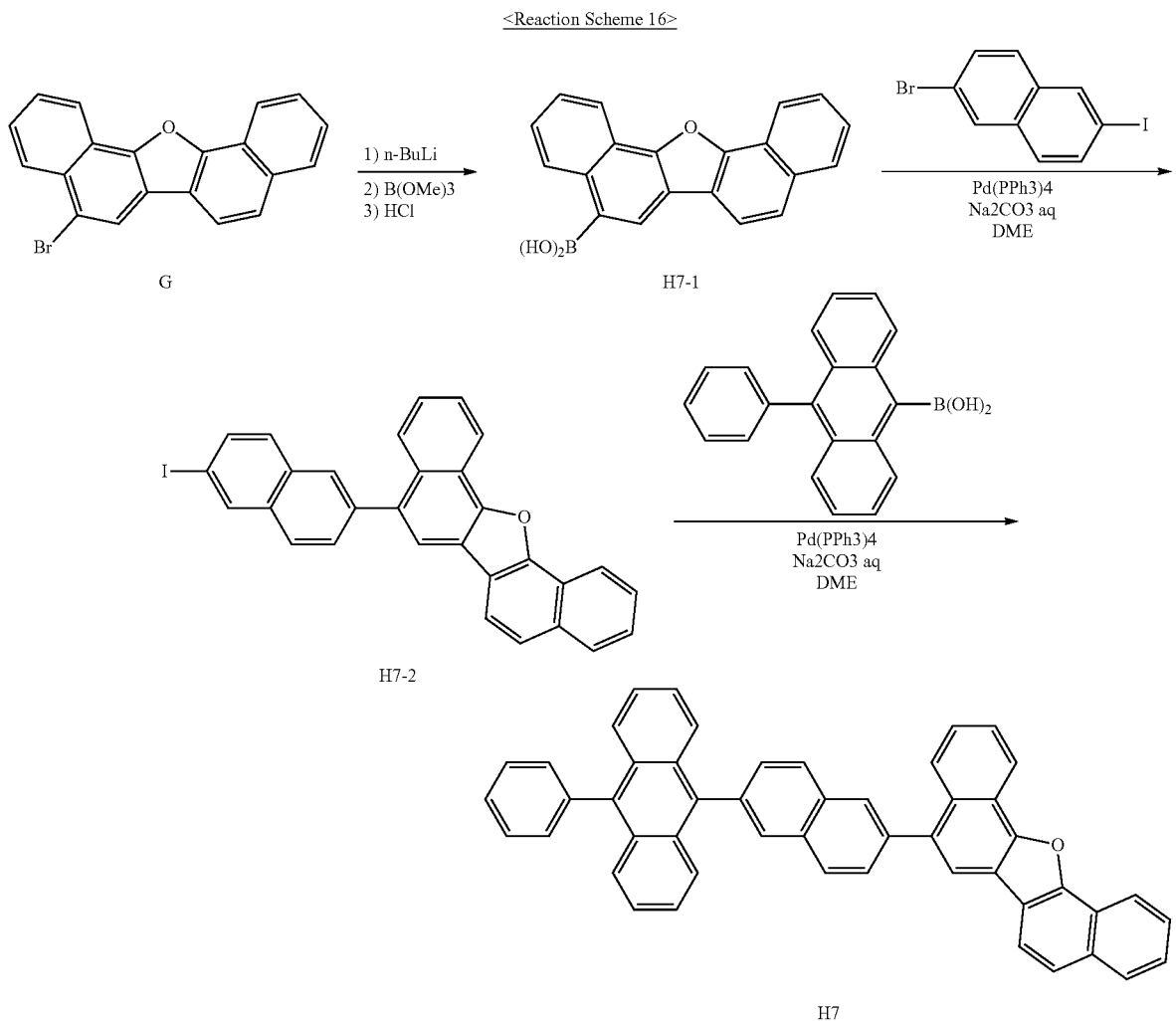

<Reaction Scheme 16>

(1) Synthesis of Intermediate H7-1

19.9 g (yield: 63.6%) of Intermediate H7-1 was obtained in substantially the same manner as in preparing Intermediate H1-1 according to Synthesis Example 10, except that Intermediate G was used instead of Intermediate A.

(2) Synthesis of Intermediate H7-2

23.8 g (yield: 71.8%) of Intermediate H7-2 was obtained in substantially the same manner as in preparing Intermediate H1-2 according to Synthesis Example 10, except that Intermediate H7-1 was used instead of Intermediate H1-1.

(3) Synthesis of Compound H7

18.7 g (yield: 63.3%) of Compound H7 was obtained in substantially the same manner as in preparing Intermediate Compound H1 according to Synthesis Example 10, except that Intermediate H7-2 and (10-phenylanthracen-9-yl) boronic acid were used instead of Intermediate H1-2 and (10-(naphthalen-2-yl) anthracen-9-yl) boronic acid, respectively. The obtained compound was identified using MS/FAB.

cald: 646.79, found: 646.23.

Synthesis Example 17

Synthesis of Compound H8

Compound H8 was synthesized according to Reaction Scheme 17:

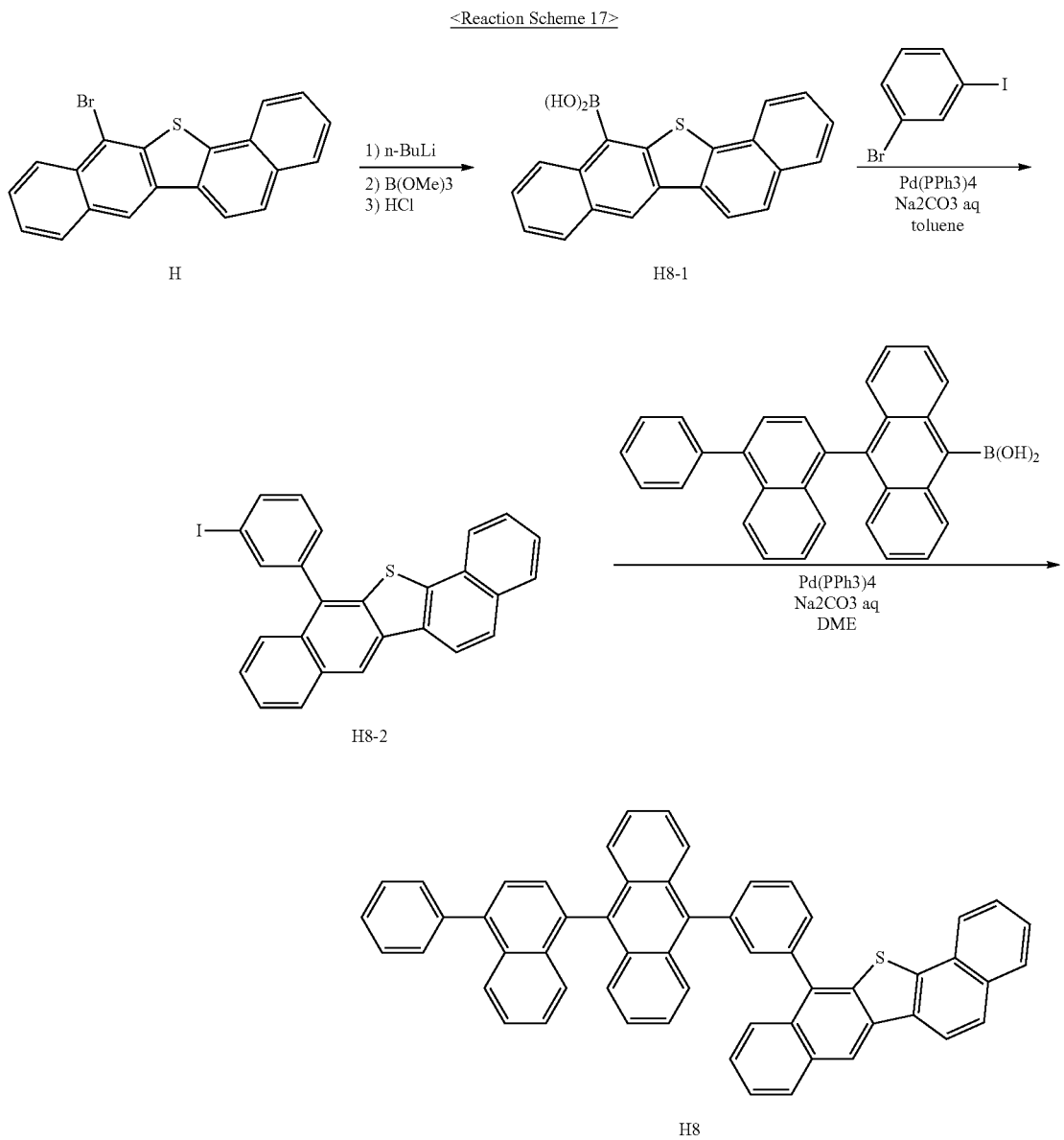

(1) Synthesis of Intermediate H8-1

20.2 g (yield: 61.5%) of Intermediate H8-1 was obtained in substantially the same manner as in preparing Intermediate H1-1 according to Synthesis Example 10, except that Intermediate H was used instead of Intermediate A.

(2) Synthesis of Intermediate H8-2

21.4 g (yield: 71.4%) of Intermediate H8-2 was obtained in substantially the same manner as in preparing Intermediate H1-2 according to Synthesis Example 10, except that Intermediate H8-1 was used instead of Intermediate H1-1.

(3) Synthesis of Compound H8

20.4 g (yield: 62.8%) of Compound H8 was obtained in substantially the same manner as in preparing Intermediate Compound H1 according to Synthesis Example 10, except that Intermediate H8-2 and (10-(4-phenylnaphthalen-1-yl)anthracen-9-yl) boronic acid were used instead of Intermediate H1-2 and (10-(naphthalen-2-yl) anthracen-9-yl) boronic acid, respectively. The obtained compound was identified using MS/FAB.

cald: 738.95, found: 738.24.

Synthesis Example 18

Synthesis of Compound H9

Compound H9 was synthesized according to Reaction Scheme 18:

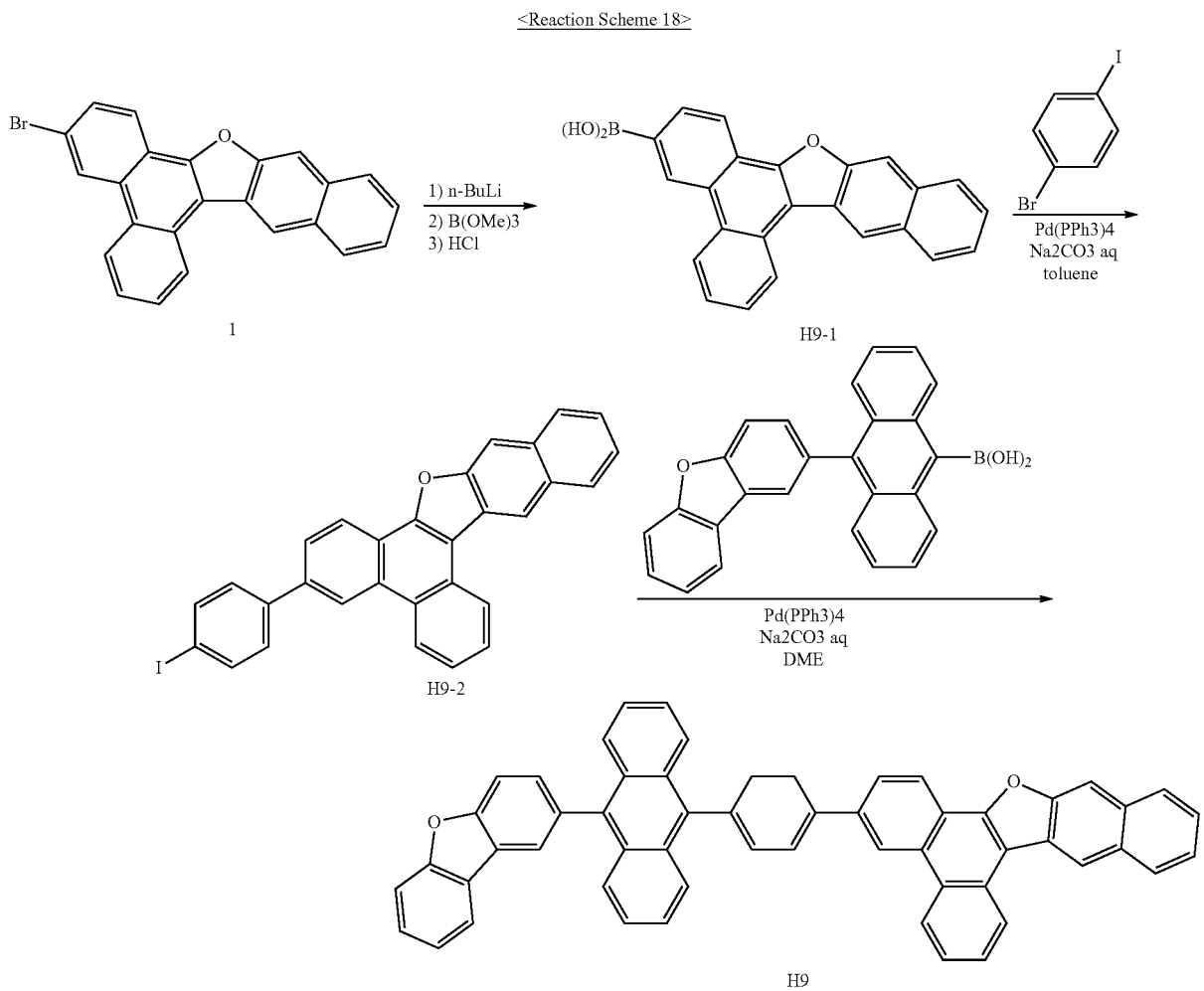

(1) Synthesis of Intermediate H9-1

23.0 g (yield: 63.6%) of Intermediate H9-1 was obtained in substantially the same manner as in preparing Intermediate H1-1 according to Synthesis Example 10, except that Intermediate I was used instead of Intermediate A.

(2) Synthesis of Intermediate H9-2

24.0 g (yield: 72.6%) of Intermediate H9-2 was obtained in substantially the same manner as in preparing Intermediate H1-2 according to Synthesis Example 10, except that Intermediate H9-1 was used instead of Intermediate H1-1.

(3) Synthesis of Compound H9

21.0 g (yield: 61.7°) of Compound H9 was obtained in substantially the same manner as in preparing Intermediate Compound H1 according to Synthesis Example 10, except that Intermediate H9-2 and (10-(dibenzo[b, d]furan-2-yl)anthracen-9-yl) boronic acid were used instead of Intermediate H1-2 and (10-(naphthalen-2-yl) anthracen-9-yl) boronic acid, respectively. The obtained compound was identified using MS/FAB.

cald: 736.87, found: 736.24.

Example 1

As a substrate and an anode, an ITO glass substrate having a thickness of 15 $\Omega/cm^2$ (1,200 Å) was cut to a size of 50 mm×50 mm×0.7 mm, sonicated by using isopropyl alcohol and pure water for about 5 minutes each, and cleaned by the exposure to ultraviolet rays for about 30 minutes, and then ozone, and the resulting ITO glass substrate was mounted on a vacuum deposition apparatus.

Compound HT28 was vacuum deposited on the ITO glass substrate to form a hole injection layer having a thickness of about 500 Å, and then, Compound HT3 was vacuum deposited on the hole injection layer to form a hole transport layer having a thickness of about 450 Å.

Then, Compound H1 (as a host) and FD1 (as a dopant) were co-deposited on the hole transport layer at a weight ratio of 95:5 to form an emission layer having a thickness of about 300 Å.

Compound ET1 was deposited on the emission layer to form an electron transport layer having a thickness of about 250 Å. LiF was deposited on the electron transport layer to form an electron injection layer having a thickness of about 50 Å. Al was vacuum deposited on the electron injection layer to form a cathode having a thickness of about 1,500 Å. Thus, an organic light-emitting device was formed.

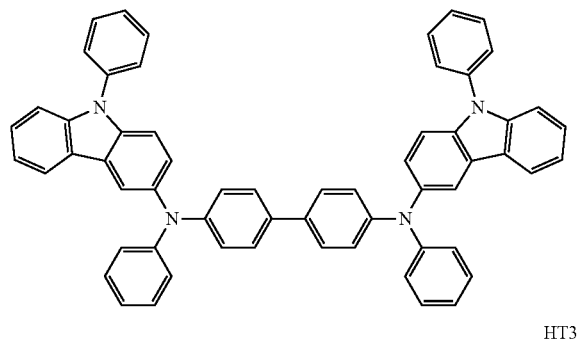

HT28

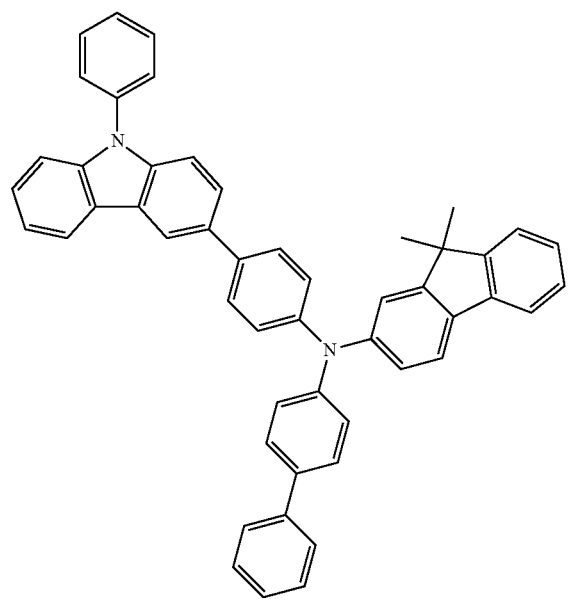

HT3

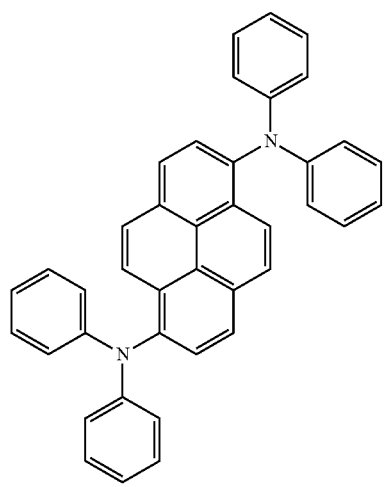

FD1

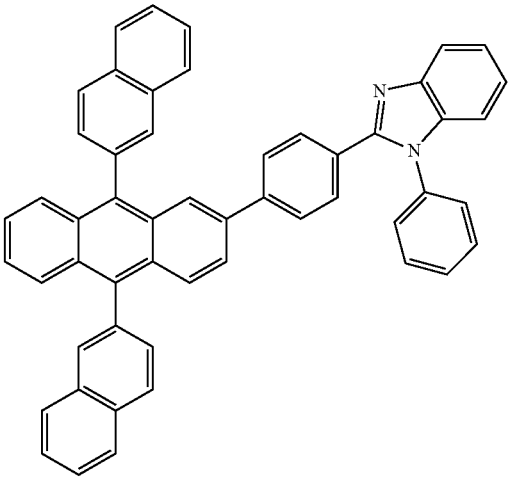

ET1

Examples 2 to 9 and a Comparatives Example 1 to 5

Organic light-emitting devices were each manufactured in substantially the same manner as in Example 1, except that compounds listed in Table 1 were used as hosts in forming the emission layer, instead of Compound H1.

Evaluation Example 1

Efficiency (cd/A) of each of the organic light-emitting devices of Examples 1 to 9 and a Comparative Examples 1 to 5 was measured by using a Kethley SMU 236 at current density of 10 mA/cm$^2$, and results thereof are shown in Table 1.

Half lifespan ($T_{80}$) of each of the organic light-emitting devices of Examples 1 to 9 and a Comparative Examples 1 to 5 were measured by using a PR650 luminance measuring unit at current density of 50 mA/cm$^2$, and results thereof are shown in Table 1. The half lifespan ($T_{80}$) is the time taken after being driven for the organic light-emitting device to reach about 80% of the initial luminance (100%).

TABLE 1

|  | Host | Efficiency (cd/A) | Half lifespan ($T_{80}$, hr) |
| --- | --- | --- | --- |
| Example 1 | Compound H1 | 5.0 | 100 |
| Example 2 | Compound H2 | 5.1 | 90 |
| Example 3 | Compound H3 | 4.9 | 90 |
| Example 4 | Compound H4 | 5.0 | 110 |
| Example 5 | Compound H5 | 4.9 | 120 |
| Example 6 | Compound H6 | 5.1 | 100 |
| Example 7 | Compound H7 | 5.1 | 110 |
| Example 8 | Compound H8 | 4.9 | 100 |
| Example 9 | Compound H9 | 5.1 | 110 |
| Comparative Example 1 | Compound A | 4.5 | 50 |
| Comparative Example 2 | Compound B | 4.7 | 80 |
| Comparative Example 3 | Compound C | 4.8 | 90 |

TABLE 1-continued
| | Host | Efficiency (cd/A) | Half lifespan ($T_{80}$, hr) |
|---|---|---|---|
| Comparative Example 4 | Compound D | 4.7 | 70 |
| Comparative Example 5 | Compound E | 4.6 | 60 |
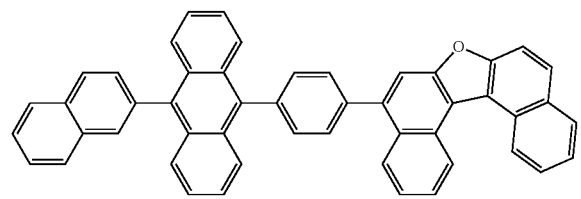
H1
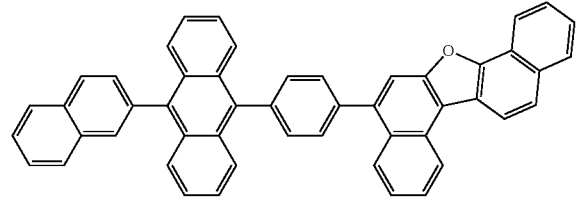
H2
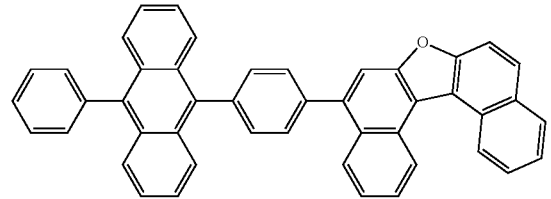
H3
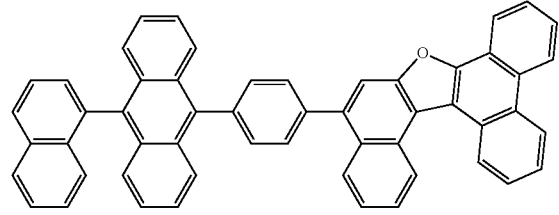
H4
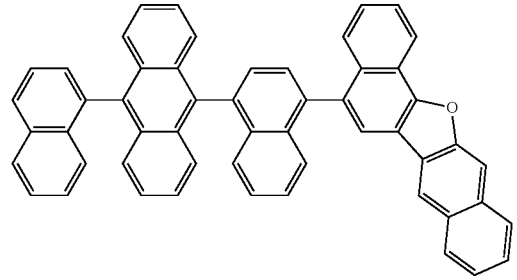
H5
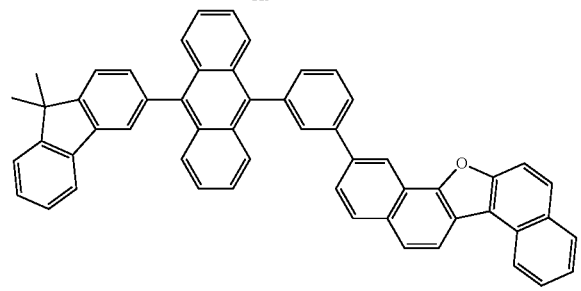
H6
TABLE 1-continued
| | Host | Efficiency (cd/A) | Half lifespan ($T_{80}$, hr) |
|---|---|---|---|
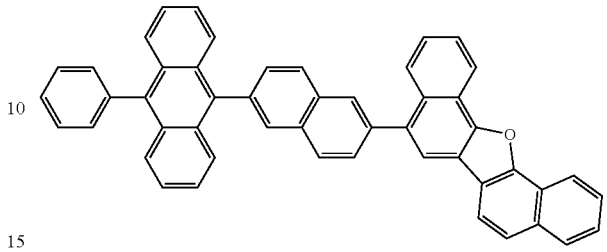
H7
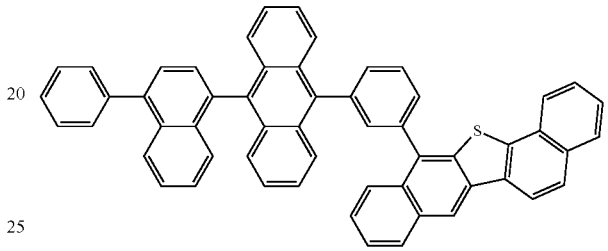
H8
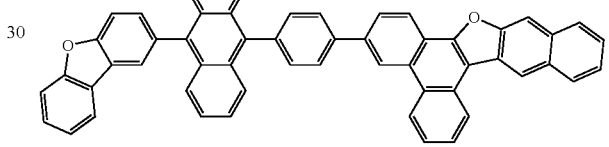
H9
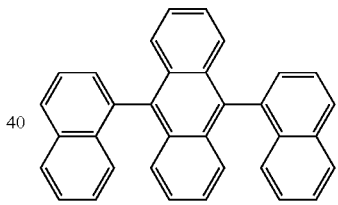
Compound A
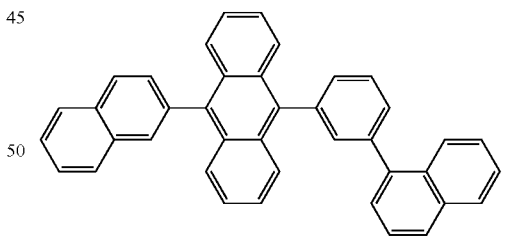
Compound B
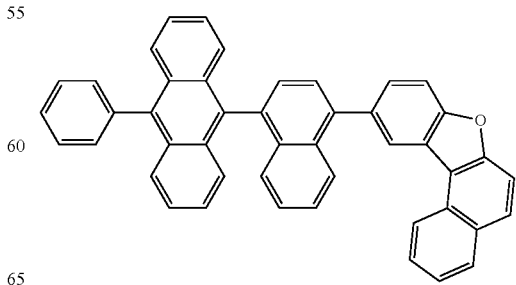
Compound C TABLE 1-continued

| Host | Efficiency (cd/A) | Half lifespan ($T_{80}$, hr) |
|---|---|---|
| 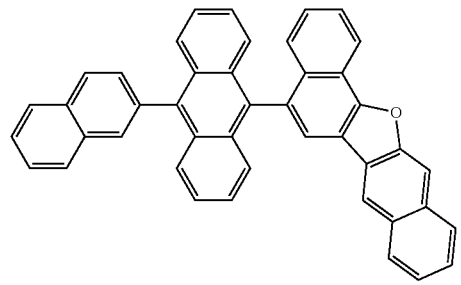 Compound D | | |
| 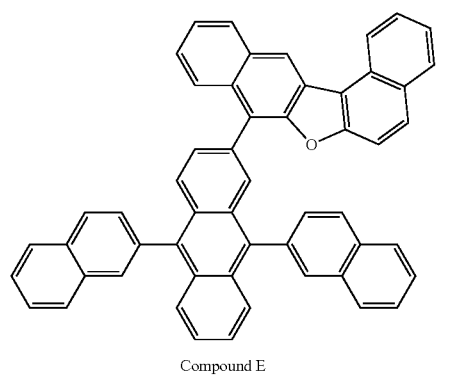 [SMILES: c1ccc2cc(-c3c4ccccc4c(-c4ccc5ccccc5c4)c4cc(-c5c6ccccc6cc6c5oc5ccc7ccccc7c56)ccc34)ccc2c1] Compound E | | |

Referring to Table 1, the organic light-emitting devices of Examples 1 to 9 had relatively high efficiency and half lifespan, compared to those of the organic light-emitting devices of Comparative Examples 1 to 5.

As described above, an organic light-emitting device including the condensed cyclic compound represented by Formula 1 may have a relatively high efficiency and a relatively long lifespan.

It should be understood that one or more exemplary embodiments of the present invention described herein should be considered in a descriptive sense only and not for purposes of limitation. Descriptions of features or aspects within each exemplary embodiment of the present invention should typically be considered as available for other similar features or aspects in other exemplary embodiments of the present invention.

While one or more exemplary embodiments of the present invention have been described with reference to the figures, it will be understood by those of ordinary skill in the art that various changes in form and details may be made therein without departing from the spirit and scope of the present invention.

What is claimed is:

1. A condensed cyclic compound represented by Formula 1:

<Formula 1>

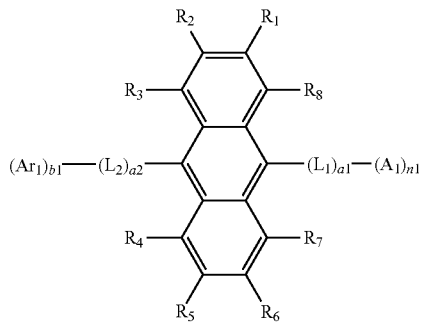

<Formula 1-1>

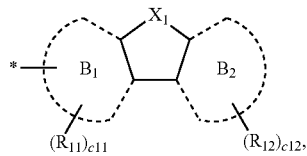

wherein, in Formulae 1 and 1-1, $A_1$ is selected from groups represented by Formula 1-1, n1 is an integer selected from 1 to 5, $X_1$ is selected from oxygen (O) and sulfur (S), ring $B_1$ is a naphthalene group and ring $B_2$ is a phenanthrene group; or ring $B_1$ is a phenanthrene group and ring $B_2$ is a naphthalene group, $L_1$ and $L_2$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a1 is an integer selected from 1 to 3, a2 is an integer selected from 0 to 3, $Ar_1$ is selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, b1 is an integer selected from 1 to 5,

* indicates a binding site to a neighboring atom, $R_1$ to $R_8$, $R_{11}$, and $R_{12}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), c11 is an integer selected from 0 to 7, c12 is an integer selected from 0 to 8, at least one substituent selected from the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycylic group is selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$), and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_6$-$C_{60}$ aryl group substituted with a $C_6$-$C_{60}$ aryl group, a terphenyl group, a $C_1$-$C_{60}$ heteroaryl group, a $C_1$-$C_{60}$ heteroaryl group substituted with a $C_1$-$C_{60}$ alkyl group, a $C_1$-$C_{60}$ heteroaryl group substituted with a $C_6$-$C_{60}$ aryl group, a monovalent non-aromatic condensed polycyclic group, and a monovalent non-aromatic condensed heteropolycylic group.

2. The condensed cyclic compound of claim 1, wherein $A_1$ is selected from groups represented by Formulae 1-1(10) to 1-1(18):

Formula 1-1(10)

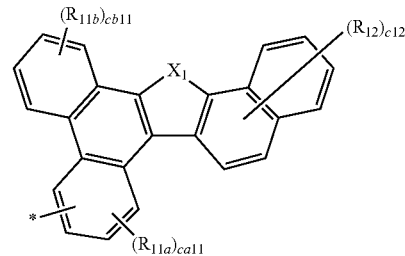

Formula 1-1(11)

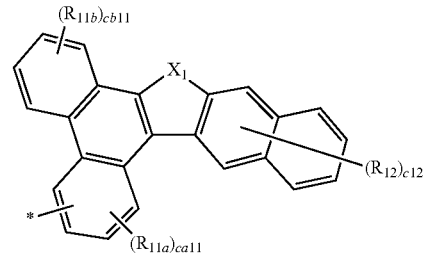

-continued

Formula 1-1(12)
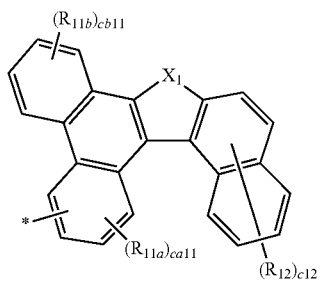

Formula 1-1(13)
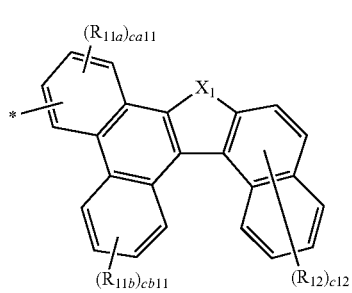

Formula 1-1(14)
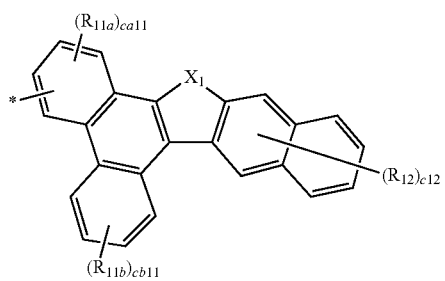

Formula 1-1(15)
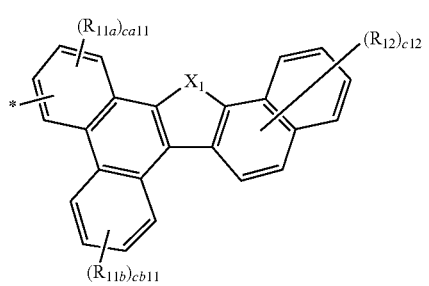

Formula 1-1(16)
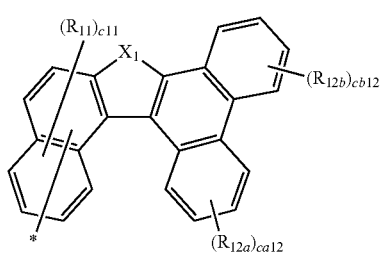

-continued

Formula 1-1(17)
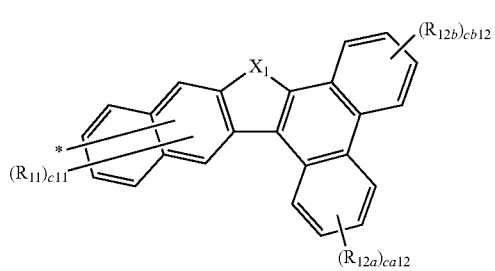

Formula 1-1(18)
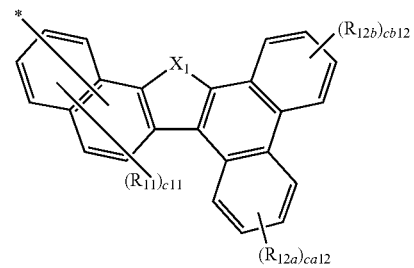

wherein, in Formulae 1-1(10) to 1-1(18), $X_1$, $R_{11}$, R12, c11, c12, and * are each independently the same as in claim 1, $R_{11a}$ and $R_{11b}$ are each independently the same as $R_{11}$ in claim 1, $R_{12a}$ and $R_{12b}$ are each independently the same as $R_{12}$ in claim 1, ca11 is an integer selected from 0 to 3, and ca12, cb11, and cb12 are each independently an integer selected from 0 to 4.

3. The condensed cyclic compound of claim 1, wherein $L_1$ and $L_2$ are each independently selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$), and $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group.

4. The condensed cyclic compound of claim 1, wherein $L_1$ and $L_2$ are each independently selected from groups represented by Formulae 3-1 to 3-41:

Formula 3-1

Formula 3-2

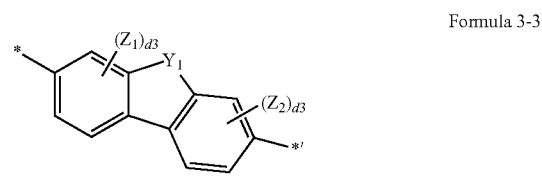

Formula 3-3

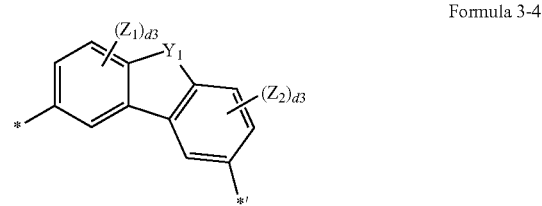

Formula 3-4

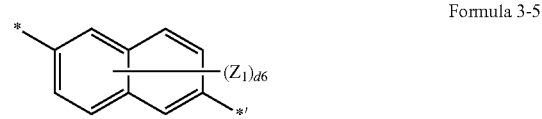

Formula 3-5

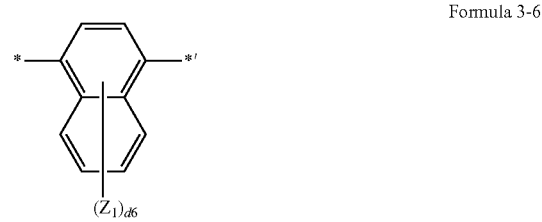

Formula 3-6

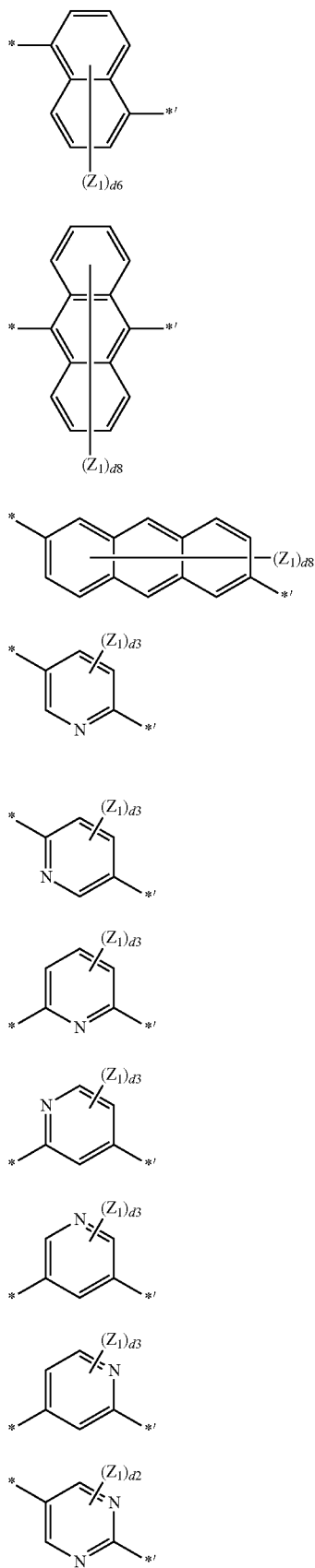
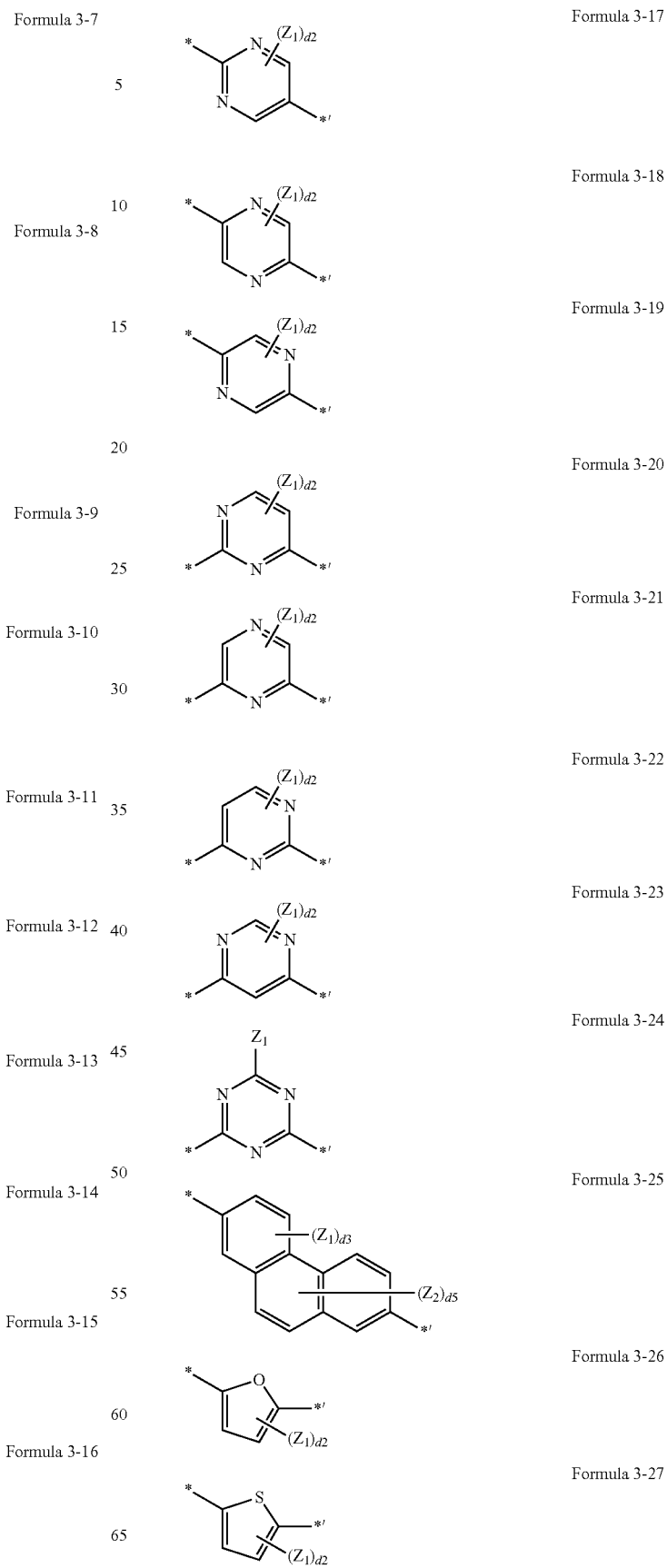

-continued
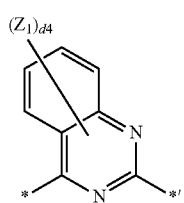
Formula 3-28
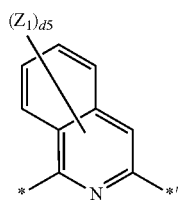
Formula 3-29
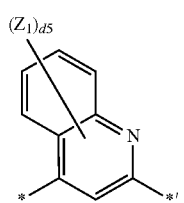
Formula 3-30
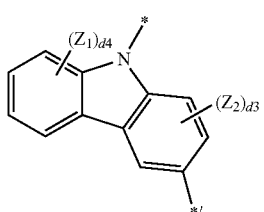
Formula 3-31
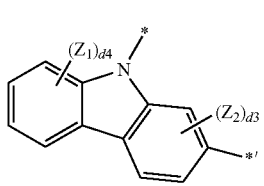
Formula 3-32
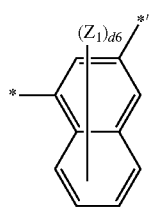
Formula 3-33
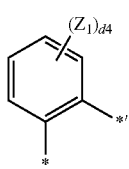
Formula 3-34
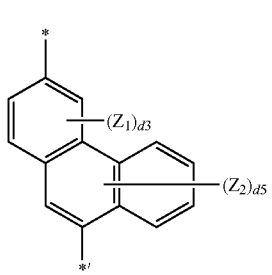
Formula 3-35
-continued
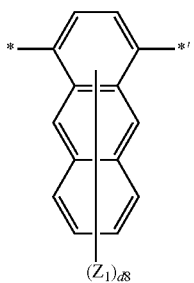
Formula 3-36
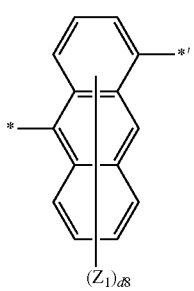
Formula 3-37
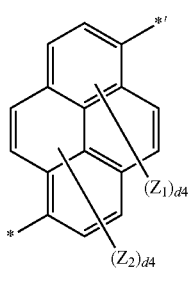
Formula 3-38
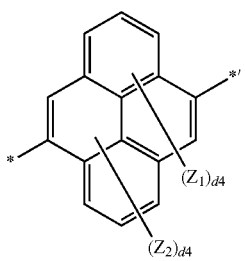
Formula 3-39
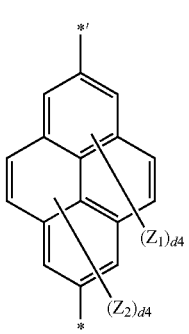
Formula 3-40

-continued

Formula 3-41

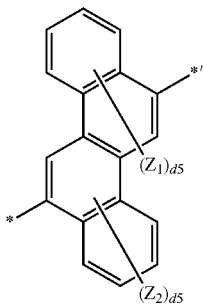

wherein, in Formulae 3-1 to 3-41,

Y$_1$ is selected from O, S, C(Z$_3$)(Z$_4$), N(Z$_5$), and Si(Z$_6$)(Z$_7$),

Z$_1$ to Z$_7$ are each independently selected from hydrogen, deuterium, —F, —Cl,—Br, —I, a hydroxyl group, a cyano group, a nitro group, an amidino group, a hydrazino group, a hydrazono group, a C$_1$-C$_{20}$ alkyl group, a C$_1$-C$_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a dibenzofuranyl group, a dibenzothiophenyl group, a triazinyl group, a benzimidazolyl group, a phenanthrolinyl group, and —Si(Q$_{31}$)(Q$_{32}$)(Q$_{33}$), Q$_{31}$ to Q$_{33}$ are each independently selected from a C$_1$-C$_{10}$ alkyl group, a C$_1$-C$_{10}$ alkoxy group, a phenyl group, a biphenyl group, a terphenyl group, and a naphthyl group, d2 is an integer selected from 1 and 2,
d3 is an integer selected from 1 to 3,
d4 is an integer selected from 1 to 4,
d5 is an integer selected from 1 to 5,
d6 is an integer selected from 1 to 6,
d8 is an integer selected from 1 to 8, and
* and *' each independently indicate a binding site to a neighboring atom.

5. The condensed cyclic compound of claim 1, wherein L$_1$ and L$_2$ are each independently selected from groups represented by Formulae 4-1 to 4-35:

Formula 4-1

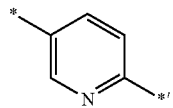

Formula 4-2

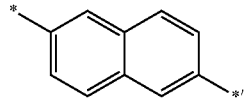

Formula 4-3

-continued

Formula 4-4

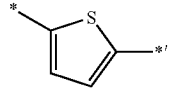

Formula 4-5

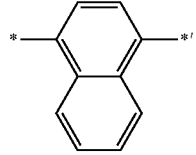

Formula 4-6

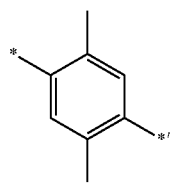

Formula 4-7

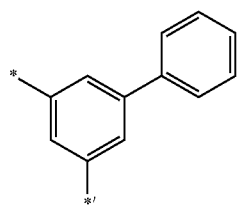

Formula 4-8

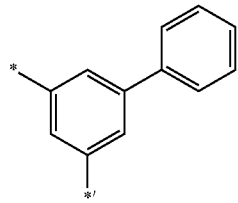

Formula 4-9

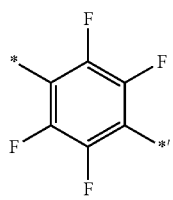

Formula 4-10

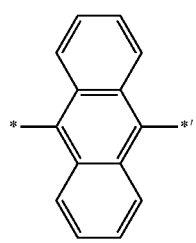

Formula 4-11

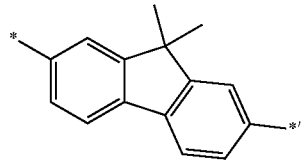

Formula 4-12

-continued
Formula 4-13
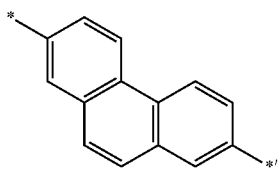
Formula 4-14
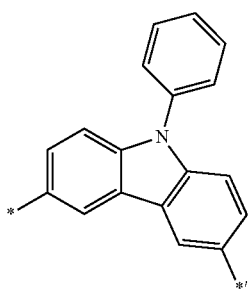
Formula 4-15
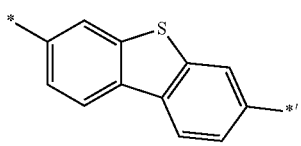
Formula 4-16
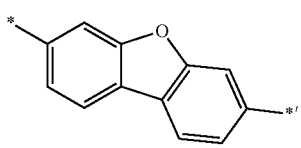
Formula 4-17
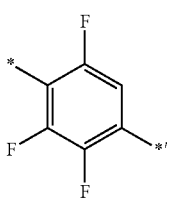
Formula 4-18
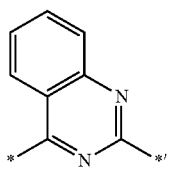
Formula 4-19
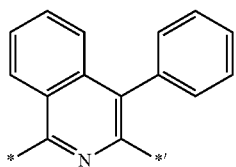
Formula 4-20
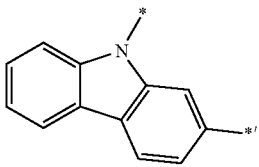
-continued
Formula 4-21
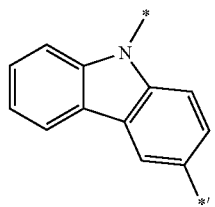
Formula 4-22
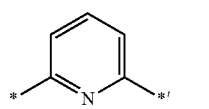
Formula 4-23
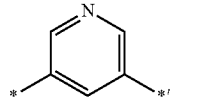
Formula 4-24
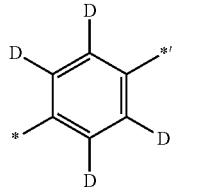
Formula 4-25
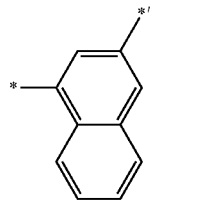
Formula 4-26
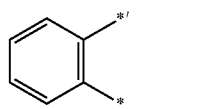
Formula 4-27
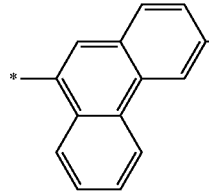
Formula 4-28
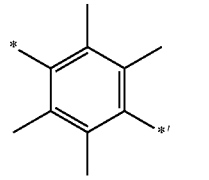
Formula 4-29
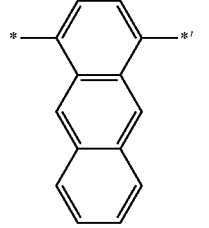

-continued

Formula 4-30

Formula 4-31

Formula 4-32

Formula 4-33

Formula 4-34

Formula 4-35 wherein, in Formulae 4-1 to 4-35, * and *' each independently indicate a binding site to a neighboring atom.

6. The condensed cyclic compound of claim 1, wherein a1 is 1, and a2 is an integer selected from 0 and 1.

7. The condensed cyclic compound of claim 1, wherein Ar₁ is selected from:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, a benzothiazolyl group, an isobenzothiazolyl group, a benzoxazolyl group, an isobenzoxazolyl group, a triazolyl group, a tetrazolyl group, an oxadiazolyl group, a triazinyl group, a benzocarbazolyl group, a dibenzocarbazolyl group, a thiadiazolyl group, an imidazopyridinyl group, and an imidazopyrimidinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, a benzothiazolyl group, an isobenzothiazolyl group, a benzoxazolyl group, an isobenzoxazolyl group, a triazolyl group, a tetrazolyl group, an oxadiazolyl group, a triazinyl group, a benzocarbazolyl group, a dibenzocarbazolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$), and $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group.

8. The condensed cyclic compound of claim 1, wherein $Ar_1$ is selected from groups represented by Formulae 5-1 to 5-79:

Formula 5-1

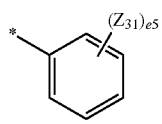

Formula 5-2

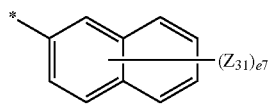

Formula 5-3

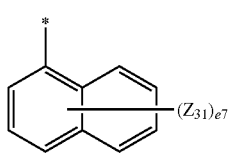

Formula 5-4

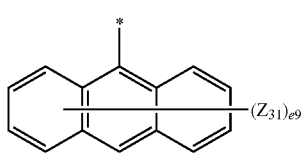

Formula 5-5

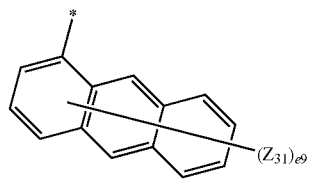

Formula 5-6

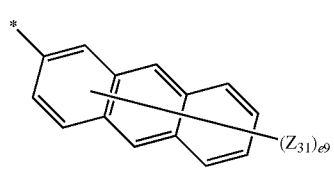

Formula 5-7

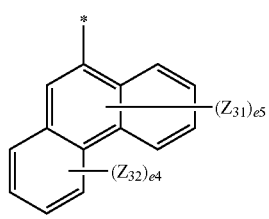

Formula 5-8

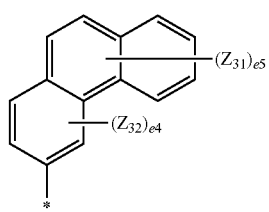

Formula 5-9

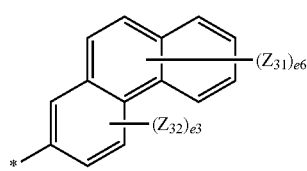

Formula 5-10

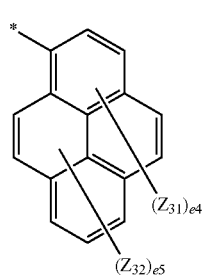

Formula 5-11

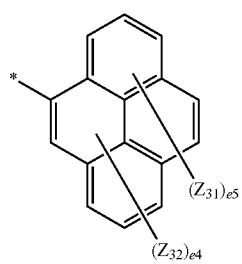

US 10,580,999 B2
369
-continued
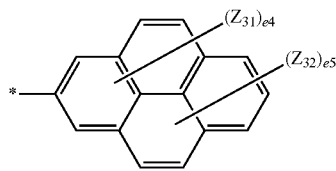
Formula 5-12
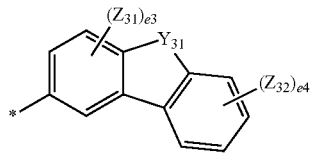
Formula 5-13
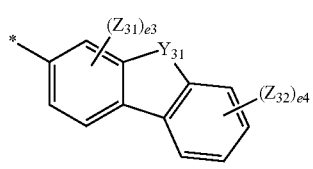
Formula 5-14
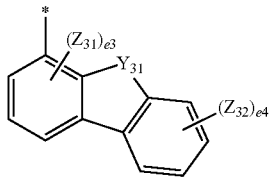
Formula 5-15
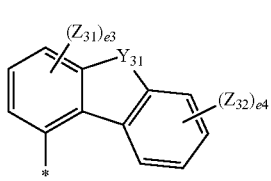
Formula 5-16
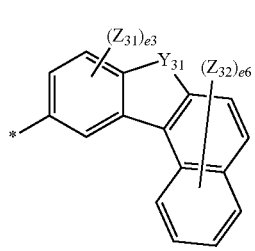
Formula 5-17
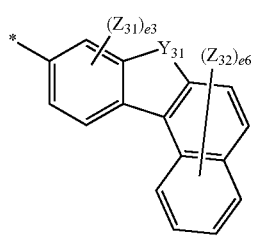
Formula 5-18
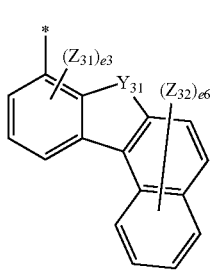
Formula 5-19
370
-continued
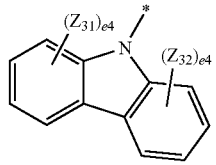
Formula 5-20
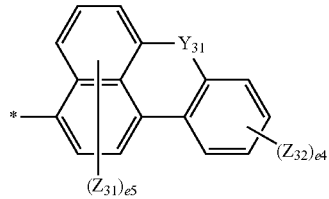
Formula 5-21
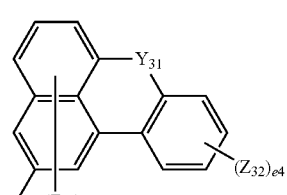
Formula 5-22
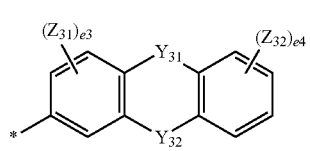
Formula 5-23
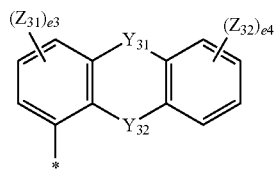
Formula 5-24
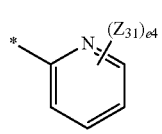
Formula 5-25
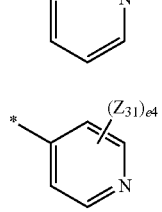
Formula 5-26
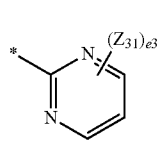
Formula 5-27
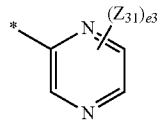
Formula 5-28
Formula 5-29

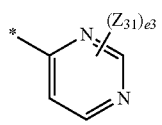
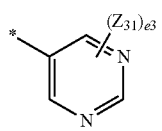
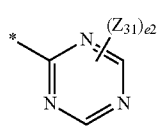
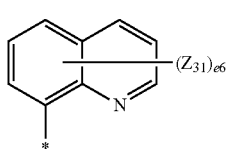
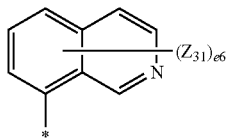
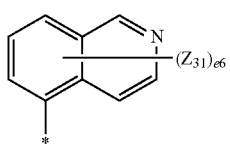
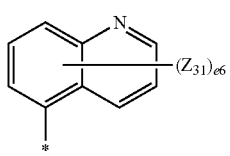
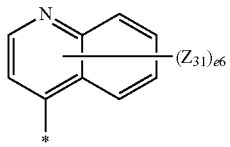
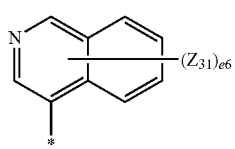
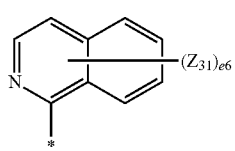
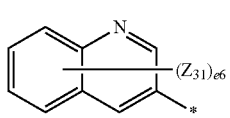
Formula 5-30
Formula 5-31
Formula 5-32
Formula 5-33
Formula 5-34
Formula 5-35
Formula 5-36
Formula 5-37
Formula 5-38
Formula 5-39
Formula 5-40
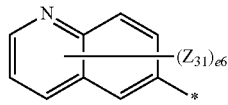
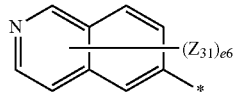
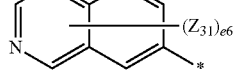
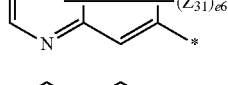
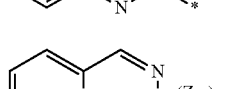
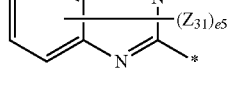
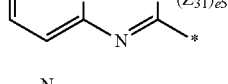
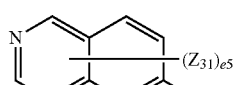
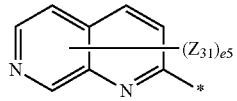
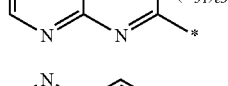
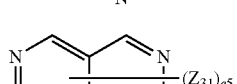
Formula 5-41
Formula 5-42
Formula 5-43
Formula 5-44
Formula 5-45
Formula 5-46
Formula 5-47
Formula 5-48
Formula 5-49
Formula 5-50
Formula 5-51
Formula 5-52
Formula 5-53
Formula 5-54

-continued
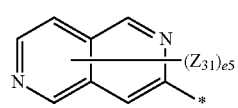
Formula 5-55
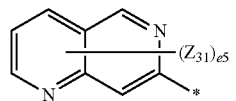
Formula 5-56
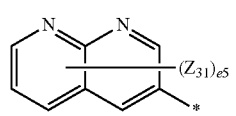
Formula 5-57
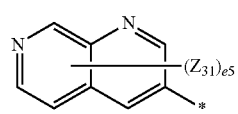
Formula 5-58
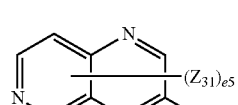
Formula 5-59
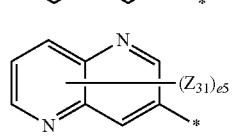
Formula 5-60
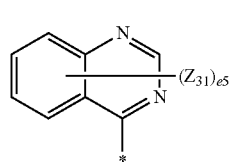
Formula 5-61
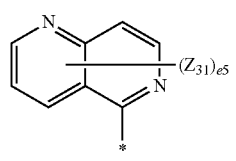
Formula 5-62
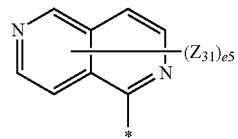
Formula 5-63
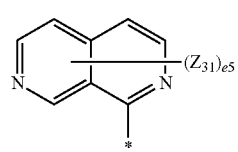
Formula 5-64
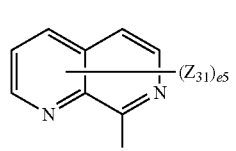
Formula 5-65
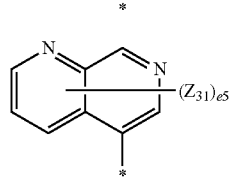
Formula 5-66
-continued
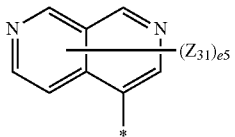
Formula 5-67
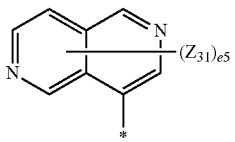
Formula 5-68
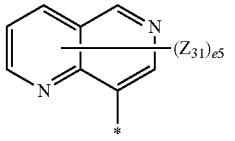
Formula 5-69
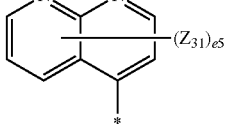
Formula 5-70
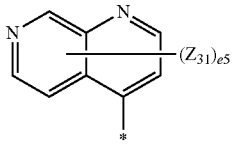
Formula 5-71
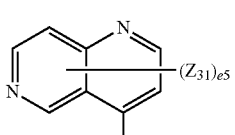
Formula 5-72
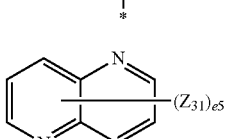
Formula 5-73
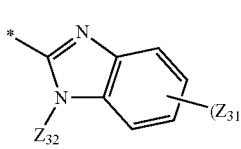
Formula 5-74
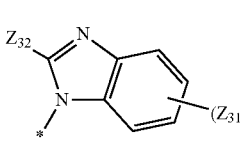
Formula 5-75
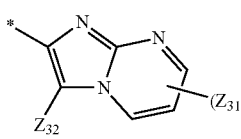
Formula 5-76
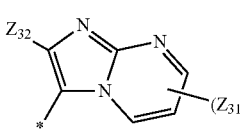
Formula 5-77

-continued

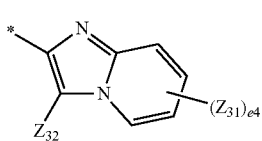
Formula 5-78

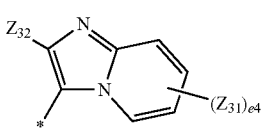
Formula 5-79 wherein, in Formulae 5-1 to 5-79,
$Y_{31}$ and $Y_{32}$ are each independently selected from O, S, $C(Z_{33})(Z_{34})$, $N(Z_{35})$, and $Si(Z_{36})(Z_{37})$,
$Z_{31}$ to $Z_{37}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a dibenzofuranyl group, a dibenzothiophenyl group, a benzimidazolyl group, a phenanthrolinyl group, a triazinyl group, and —$Si(Q_{31})(Q_{32})(Q_{33})$,
$Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group,
e2 is an integer selected from 1 and 2,
e3 is an integer selected from 1 to 3,
e4 is an integer selected from 1 to 4,
e5 is an integer selected from 1 to 5,
e6 is an integer selected from 1 to 6,
e8 is an integer selected from 1 to 8, and
* indicates a binding site to a neighboring atom.

9. The condensed cyclic compound of claim 1, wherein $Ar_1$ is selected from groups represented by Formulae 6-1 to 6-44:

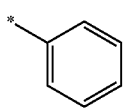
Formula 6-1

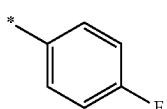
Formula 6-2

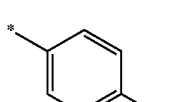
Formula 6-3

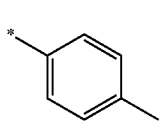
Formula 6-4

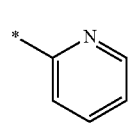
Formula 6-5

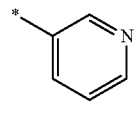
Formula 6-6

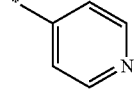
Formula 6-7

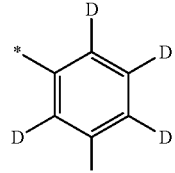
Formula 6-8

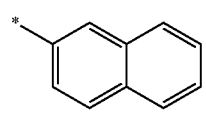
Formula 6-9

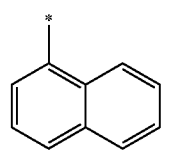
Formula 6-10

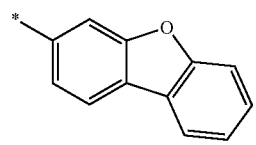
Formula 6-11

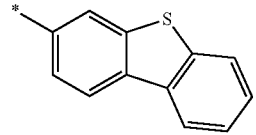
Formula 6-12

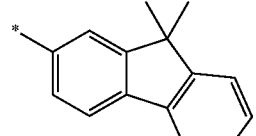
Formula 6-13

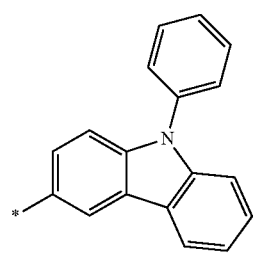
Formula 6-14

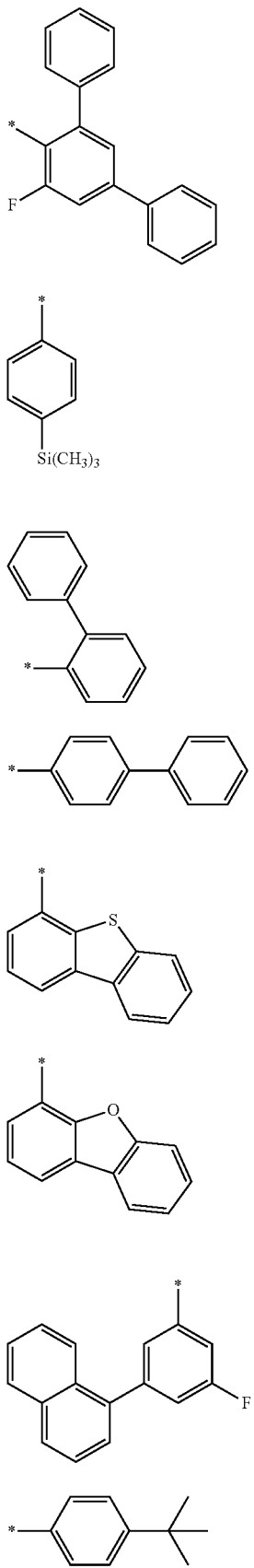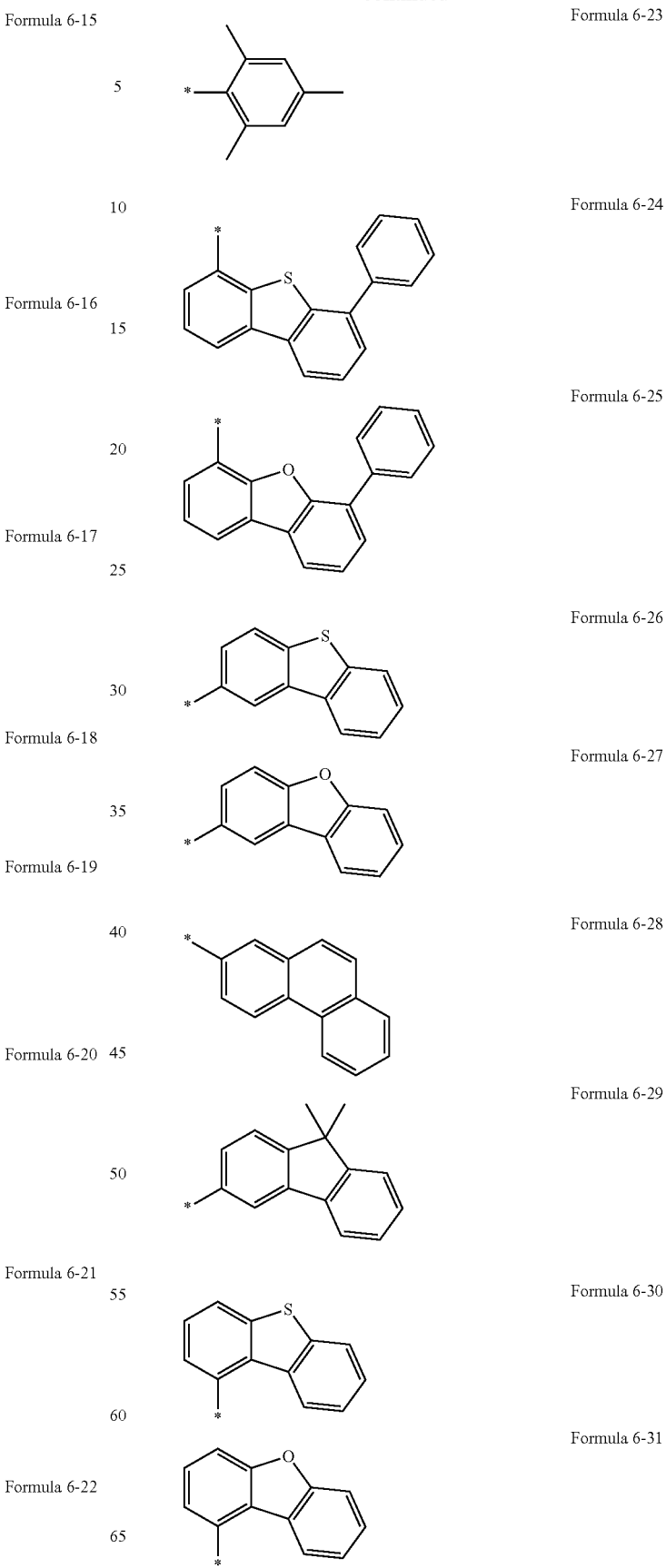

-continued

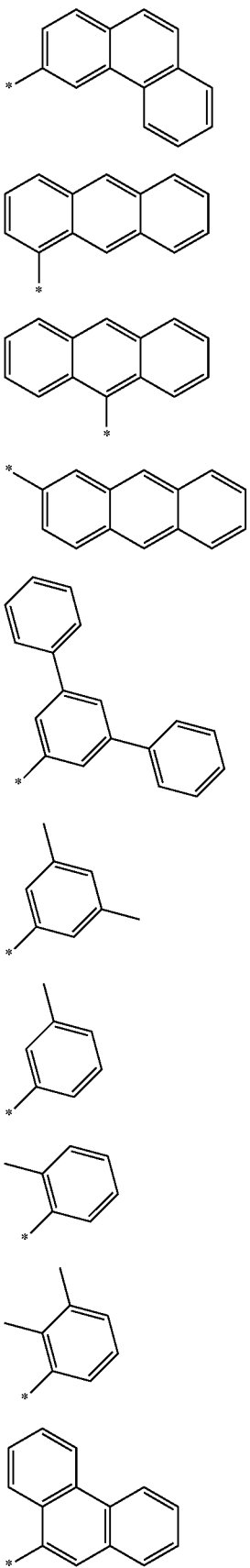

Formula 6-32
Formula 6-33
Formula 6-34
Formula 6-35
Formula 6-36
Formula 6-37
Formula 6-38
Formula 6-39
Formula 6-40
Formula 6-41

-continued

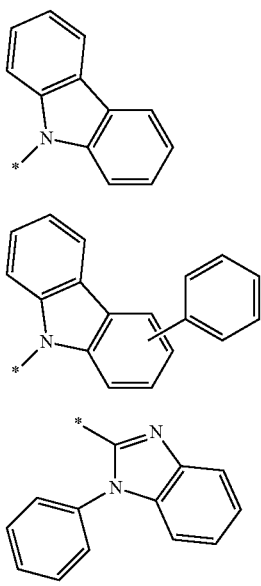

Formula 6-42
Formula 6-43
Formula 6-44 wherein, in Formulae 6-1 to 6-44, * indicates a binding site to a neighboring atom.

10. The condensed cyclic compound of claim 1, wherein $R_1$ to $R_8$, $R_{11}$, and $R_{12}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$).

11. The condensed cyclic compound of claim 1, wherein $R_1$ to $R_8$, $R_{11}$, and $R_{12}$ are each independently selected from:
hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;
a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, and a hydrazono group;
a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group;

a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, an imidazopyrimidinyl group, and —Si($Q_{31}$)($Q_{32}$)($Q_{33}$); and —Si($Q_1$)($Q_2$)($Q_3$), and $Q_1$ to $Q_3$ and $Q_{31}$ to $Q_{33}$ are each independently selected from a $C_1$-$C_{10}$ alkyl group, a $C_1$-$C_{10}$ alkoxy group, a phenyl group, a biphenyl group, a terphenyl group, and a naphthyl group.

12. The condensed cyclic compound of claim 1, wherein $R_1$ to $R_8$, $R_{11}$, and $R_{12}$ are each independently selected from:
hydrogen, deuterium, —F, —Cl, —Br, —I, a hydroxyl group, a cyano group, a nitro group, an amidino group, a hydrazino group, a hydrazono group, a $C_1$-$C_{10}$ alkyl group, and a $C_1$-$C_{10}$ alkoxy group;

a $C_1$-$C_{10}$ alkyl group and a $C_1$-$C_{10}$ alkoxy group, each substituted with at least one selected from deuterium, —F, —Cl, —Br, —I, a hydroxyl group, a cyano group, a nitro group, an amidino group, a hydrazino group, and a hydrazono group;

a phenyl group, a biphenyl group, a terphenyl group, a naphthyl group, a pyridinyl group, a pyrimidinyl group, and a triazinyl group; and a phenyl group, a naphthyl group, a pyridinyl group, a pyrimidinyl group, and a triazinyl group deuterium, each substituted with at least one selected from —F, —Cl, —Br, —I, a hydroxyl group, a cyano group, a nitro group, an amidino group, a hydrazino group, a hydrazono group, a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, and a triazinyl group.

13. The condensed cyclic compound of claim 1, wherein the condensed cyclic compound is represented by one selected from Formulae 1J to 1R:

<Formula 1J>

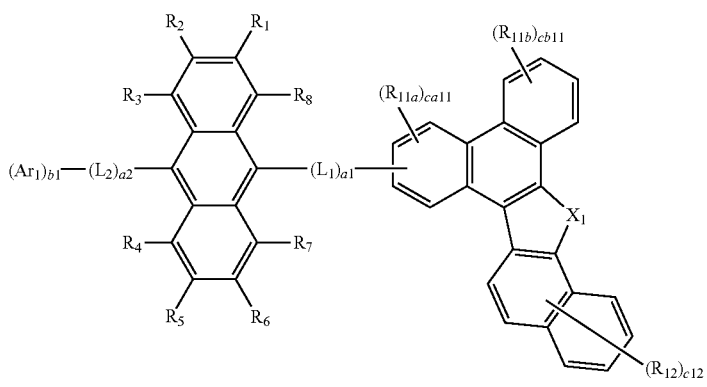

<Formula 1K>

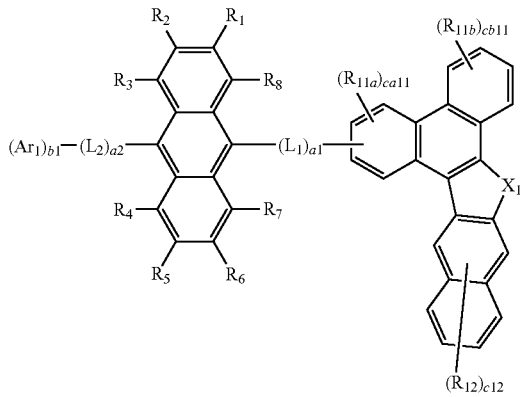

<Formula 1L>

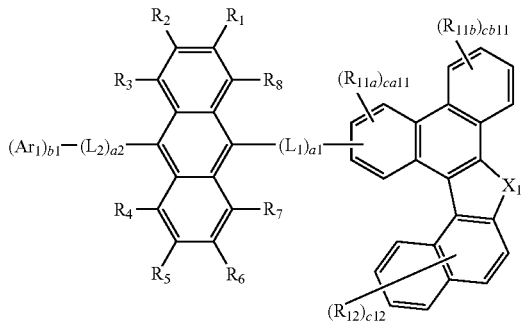

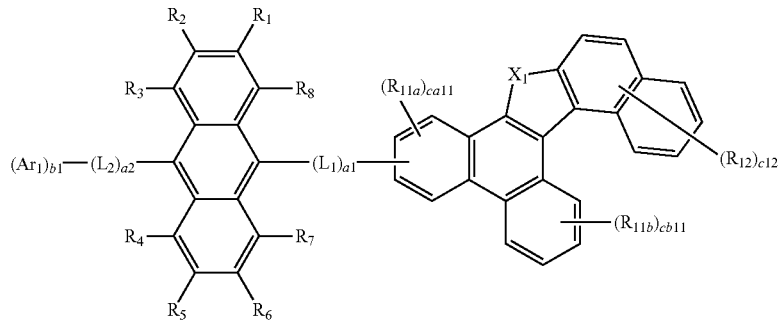
<Formula 1M>
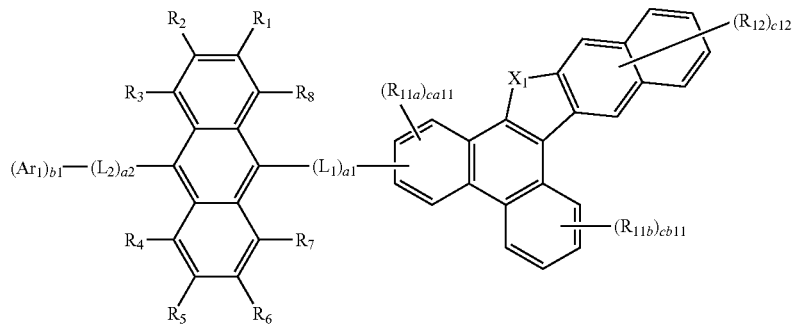
<Formula 1N>
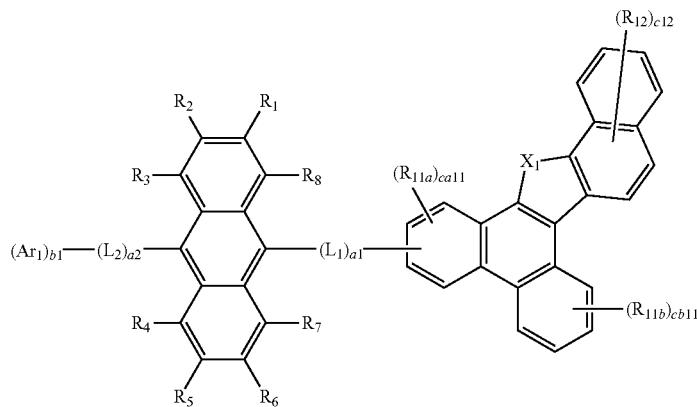
<Formula 1O>
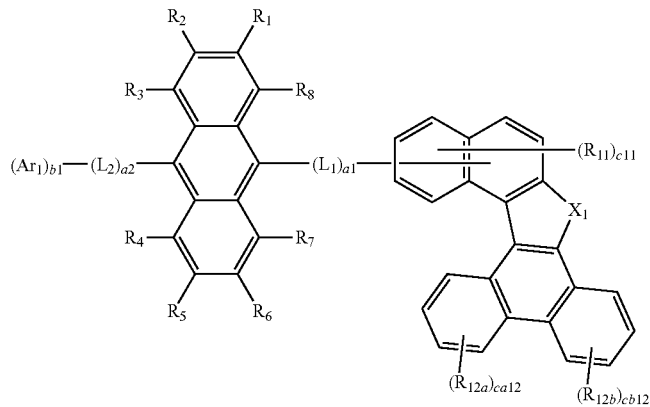
<Formula 1P>

<Formula 1Q>

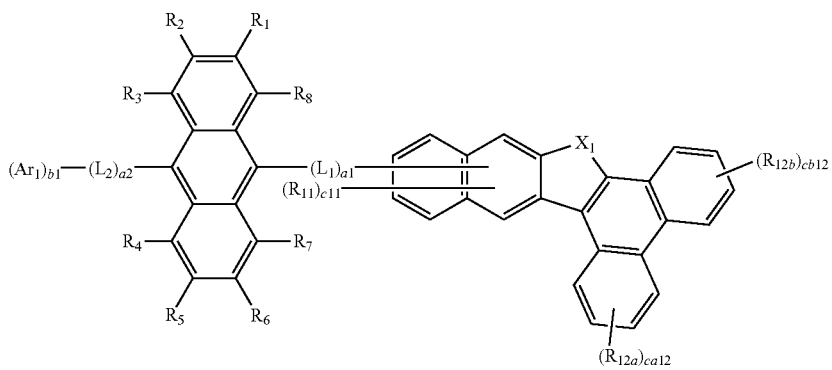

<Formula 1R>

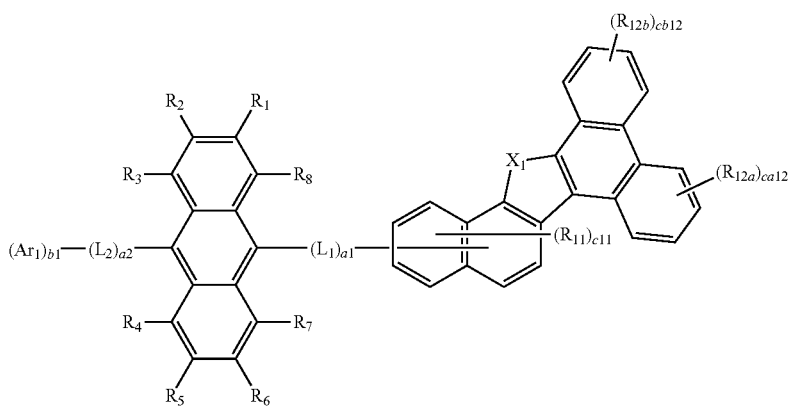

wherein, in Formulae 1J to 1R, $X_1$, $L_1$, $L_2$, a1, a2, $Ar_1$, b1, $R_1$ to $R_8$, $R_{11}$, $R_{12}$, c11, and c12 are each independently the same as in claim 1, $R_{11a}$ and $R_{11b}$ are each independently the same as $R_{11}$ in claim 1, $R_{12a}$ and $R_{12b}$ are each independently the same as $R_{12}$ in claim 1, ca11 is an integer selected from 0 to 3, and ca12, cb11, and cb12 are each independently an integer selected from 0 to 4.

14. The condensed cyclic compound of claim 1, wherein the condensed cyclic compound is represented by one selected from Formulae 1J(1) to 1R(1):

<Formula 1J(1)>

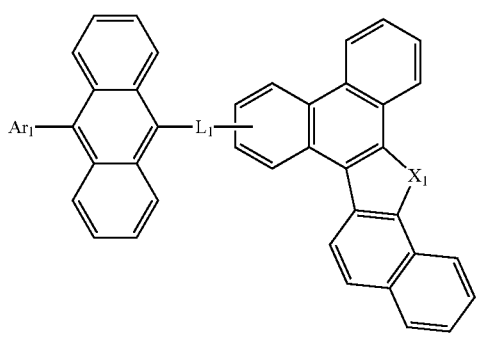

-continued

<Formula 1K(1)>

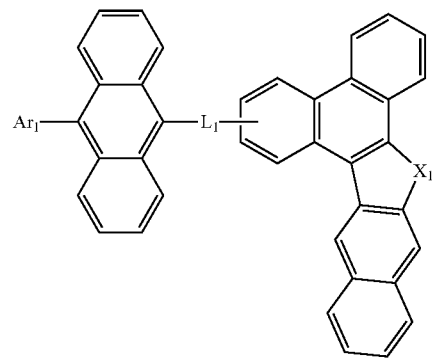

<Formula 1L(1)>

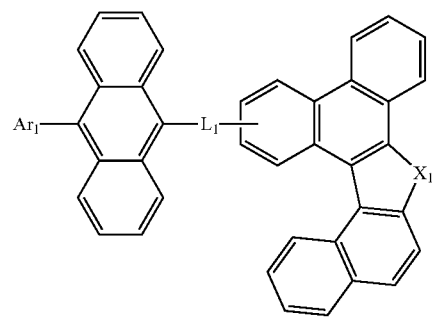

-continued

<Formula 1M(1)>

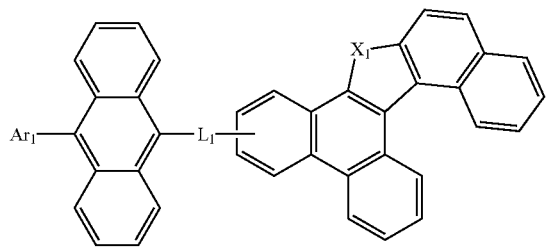

<Formula 1N(1)>

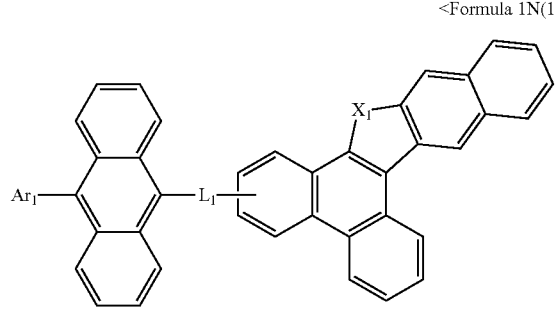

<Formula 1O(1)>

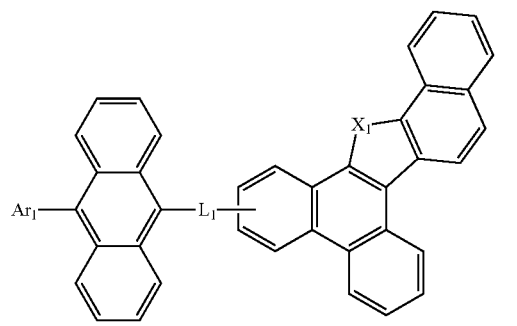

<Formula 1P(1)>

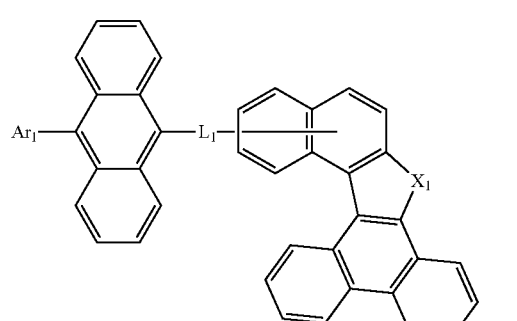

<Formula 1Q(1)>

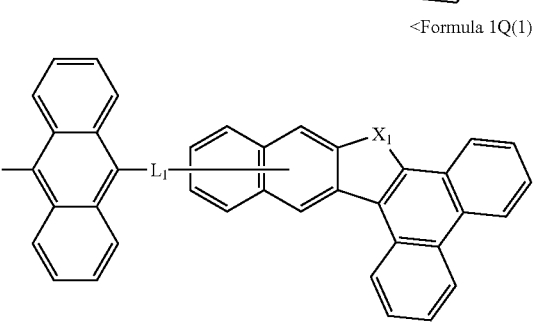

-continued

<Formula 1R(1)>

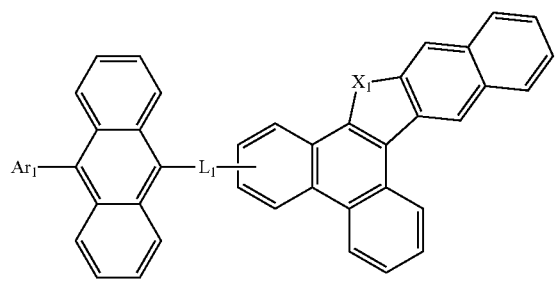

wherein, in Formulae 1J(1) to 1R(1), $X_1$, $L_1$, and $Ar_1$ are each independently the same as in claim 1.

15. The condensed cyclic compound of claim 14, wherein $X_1$ is selected from O and S, $L_1$ and $L_2$ are each independently selected from groups represented by Formulae 4-1 to 4-35, and $Ar_1$ is selected from groups represented by Formulae 6-1 to 6-44:

Formula 4-1

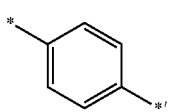

Formula 4-2

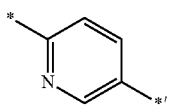

Formula 4-3

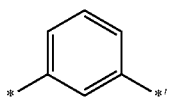

Formula 4-4

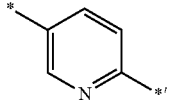

Formula 4-5

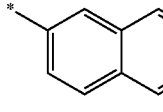

Formula 4-6

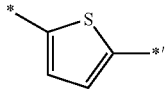

Formula 4-7

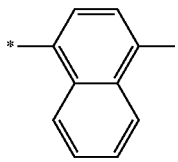

-continued
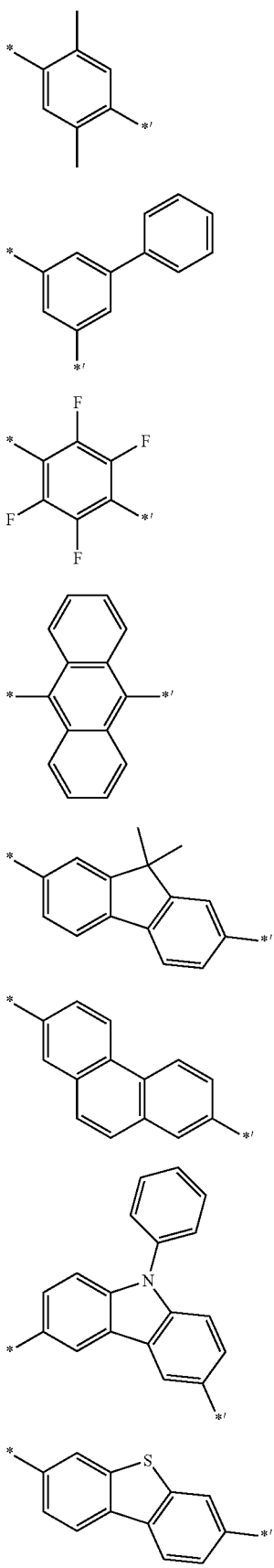
-continued
Formula 4-8
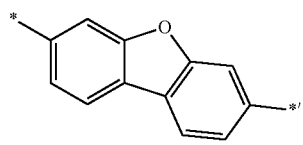
Formula 4-16
Formula 4-9
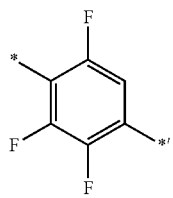
Formula 4-17
Formula 4-10
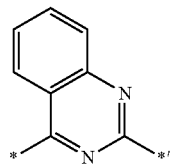
Formula 4-18
Formula 4-11
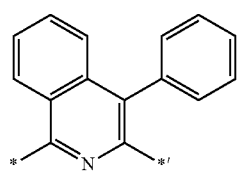
Formula 4-19
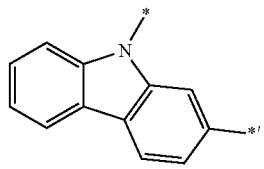
Formula 4-20
Formula 4-12
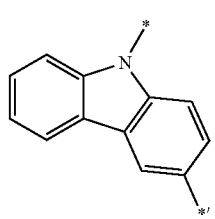
Formula 4-21
Formula 4-13
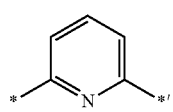
Formula 4-22
Formula 4-14
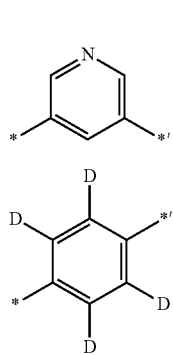
Formula 4-23
Formula 4-15
Formula 4-24

Formula 4-25
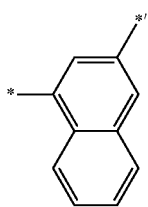
Formula 4-26
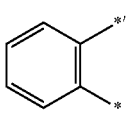
Formula 4-27
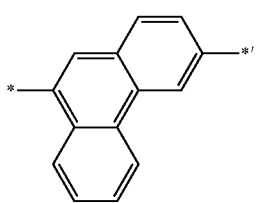
Formula 4-28
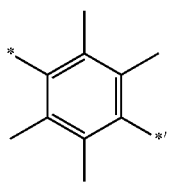
Formula 4-29
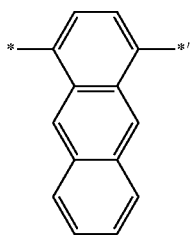
Formula 4-30
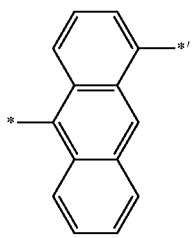
Formula 4-31
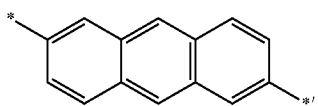
Formula 4-32
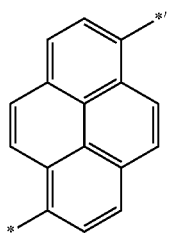
Formula 4-33
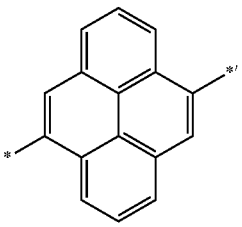
Formula 4-34
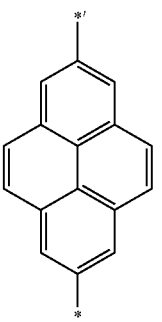
Formula 4-35
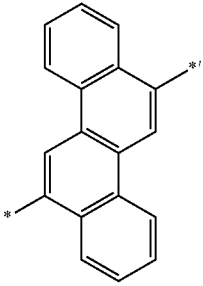
Formula 6-1
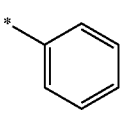
Formula 6-2
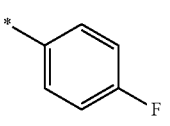
Formula 6-3
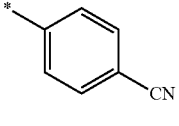
Formula 6-4
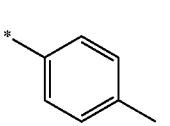
Formula 6-5
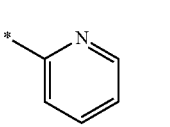
Formula 6-6
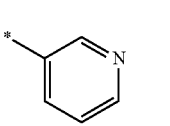

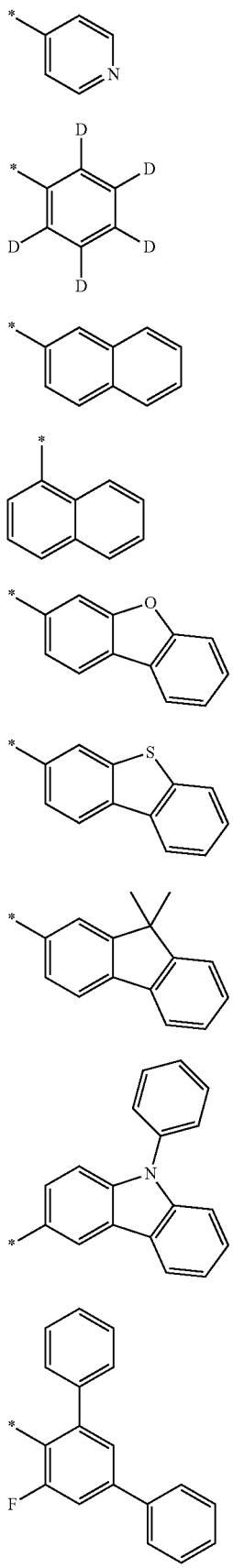
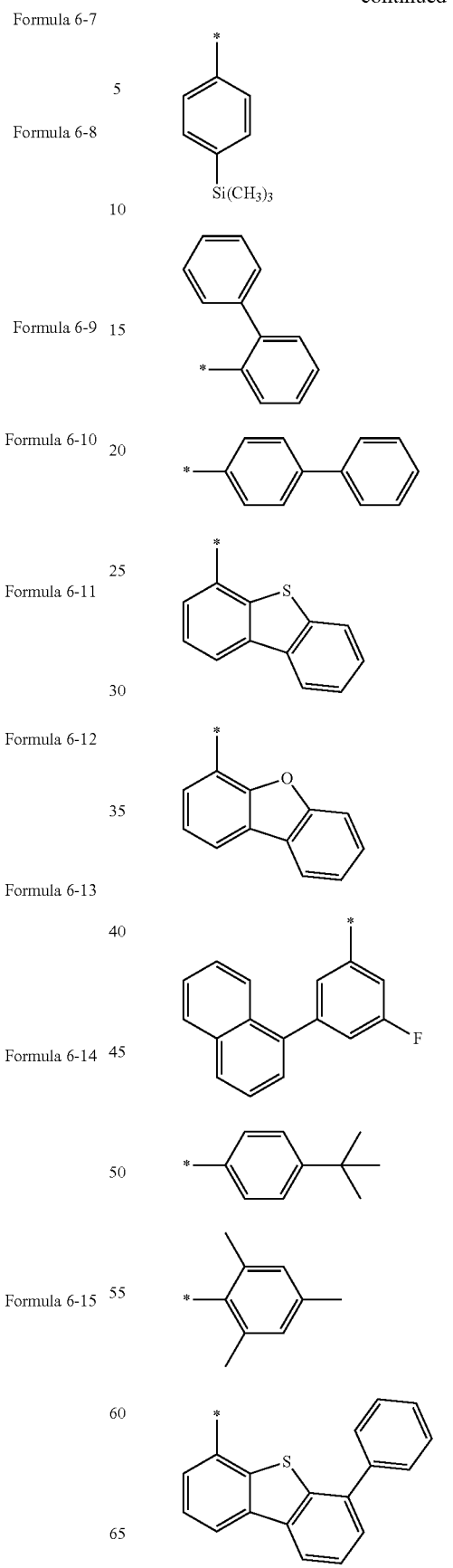

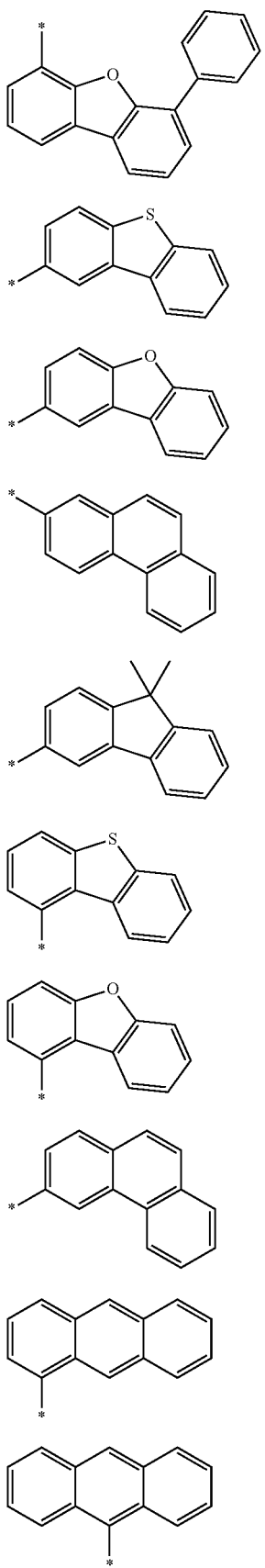
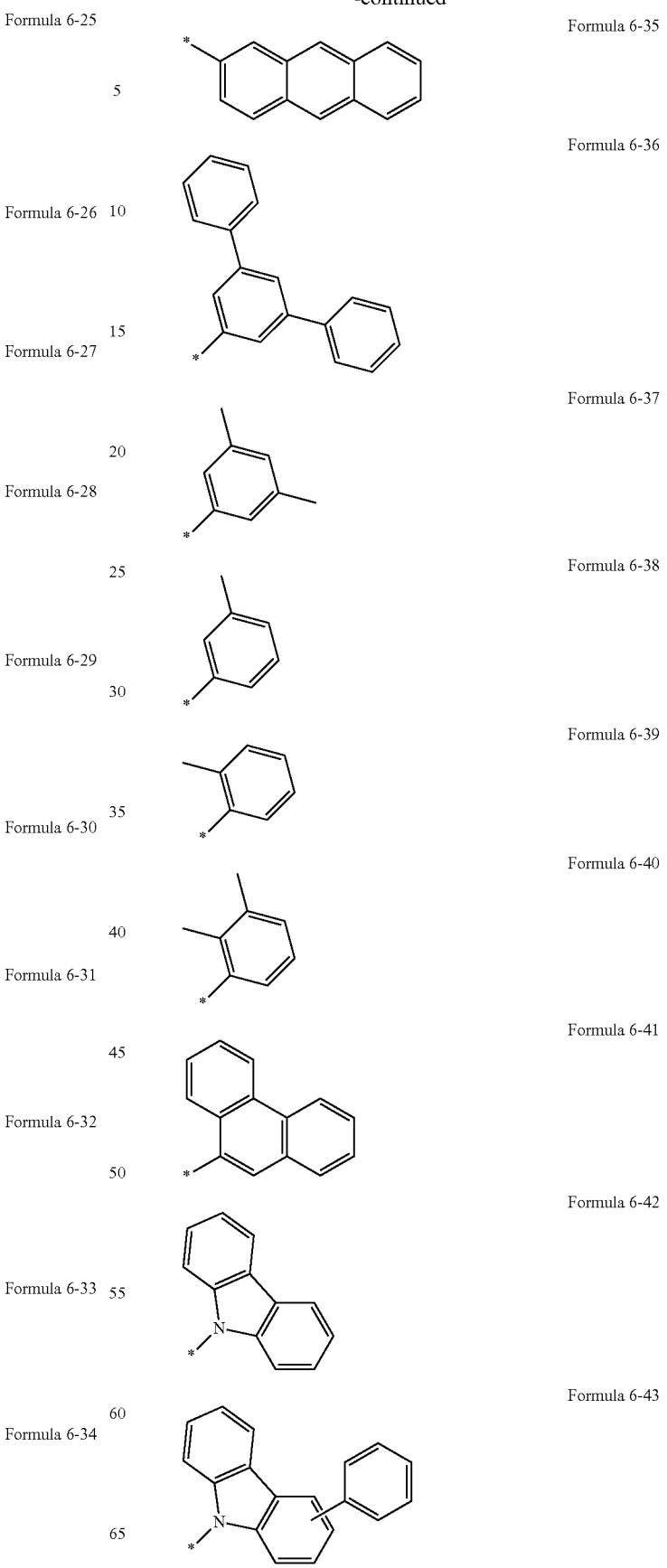

-continued

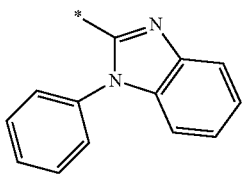

Formula 6-44 wherein, in Formulae 4-1 to 4-35 and 6-1 to 6-44, * and *' each independently indicate a binding site to a neighboring atom.

16. An organic light-emitting device comprising:
a first electrode;
a second electrode facing the first electrode; and
an organic layer disposed between the first electrode and the second electrode, the organic layer comprising an emission layer,
wherein the organic layer comprises at least one condensed cyclic compound represented by Formula 1 of claim 1.

17. The organic light-emitting device of claim 16, wherein
the first electrode is an anode,
the second electrode is a cathode, and
the organic layer comprises a hole transport region disposed between the first electrode and the emission layer and an electron transport region disposed between the emission layer and the second electrode.

18. The organic light-emitting device of claim 16, wherein the emission layer comprises at least one condensed cyclic compound represented by Formula 1 of claim 1.

19. The organic light-emitting device of claim 16, wherein the emission layer further comprises a fluorescent dopant.

* * * * *